United States Patent
King et al.

(10) Patent No.: US 10,183,001 B1
(45) Date of Patent: Jan. 22, 2019

(54) OPIOID AND ATTENTION DEFICIT HYPERACTIVITY DISORDER MEDICATIONS POSSESSING ABUSE DETERRENT AND ANTI-DOSE DUMPING SAFETY FEATURES

(71) Applicant: Pisgah Laboratories, Inc., Pisgah Forest, NC (US)

(72) Inventors: Clifford Riley King, Pisgah Forest, NC (US); Stephen G. D'Ambrosio, Pisgah Forest, NC (US); David W. Bristol, Pisgah Forest, NC (US)

(73) Assignee: Pisgah Laboratories, Inc., Pisgah Forest, NC (US)

( * ) Notice: Subject to any disclaimer, the term of this patent is extended or adjusted under 35 U.S.C. 154(b) by 144 days.

(21) Appl. No.: 14/974,339

(22) Filed: Dec. 18, 2015

Related U.S. Application Data

(60) Continuation-in-part of application No. 14/628,344, filed on Feb. 23, 2015, which is a continuation-in-part of application No. 13/723,370, filed on Dec. 21, 2012, now Pat. No. 9,421,266, and a continuation-in-part of application No. 13/334,842, filed on Dec. 22, 2011, now Pat. No. 8,334,322, and a continuation-in-part of application No. 13/313,870, filed on Dec. 7, 2011, now abandoned, and a continuation-in-part of application No. 12/537,664, filed on Aug. 7, 2009, now abandoned, and a continuation-in-part of application No. 12/080,531, filed on Apr. 3, 2008, now Pat. No. 8,575,151, and a continuation-in-part of application No. 11/805,225, filed on May 22, 2007, now abandoned, and a division of application No. 11/973,252, filed on Oct. 5, 2007, and a division of application No. 11/805,225, filed on May 22, 2007, now abandoned, application No. 14/974,339, which is a continuation-in-part of application No. 13/444,191, filed on Apr. 11, 2012, now Pat. No. 9,226,925, which is a division of application No. 12/846,936, filed on Jul. 30, 2010, now Pat. No. 8,653,106.

(51) Int. Cl.

| A61K 31/194 | (2006.01) |
|---|---|
| A61K 9/00 | (2006.01) |
| A61K 31/485 | (2006.01) |
| A61K 31/4515 | (2006.01) |
| A61K 31/4458 | (2006.01) |
| A61K 31/55 | (2006.01) |
| A61K 31/137 | (2006.01) |
| A61K 31/198 | (2006.01) |

(52) U.S. Cl.
CPC .......... *A61K 31/194* (2013.01); *A61K 9/0053* (2013.01); *A61K 31/137* (2013.01); *A61K 31/198* (2013.01); *A61K 31/4458* (2013.01); *A61K 31/4515* (2013.01); *A61K 31/485* (2013.01); *A61K 31/55* (2013.01)

(58) Field of Classification Search
CPC ............... A61K 31/194; A61K 31/485; A61K 31/4515; A61K 31/4458; A61K 31/55; A61K 31/137; A61K 31/198; A61K 9/0053

See application file for complete search history.

(56) References Cited

U.S. PATENT DOCUMENTS

| 2,935,417 | A | 5/1960 | Biskup et al. | |
|---|---|---|---|---|
| 3,502,661 | A | 3/1970 | Kasubick et al. | |
| 4,622,244 | A * | 11/1986 | Lapka | A61K 9/1647 424/497 |
| 5,225,205 | A | 7/1993 | Orsolini | |
| 5,232,919 | A | 8/1993 | Scheffler et al. | |
| 5,271,946 | A | 12/1993 | Hettche | |
| 5,439,688 | A | 8/1995 | Orsolini et al. | |
| 5,445,832 | A | 8/1995 | Orsolini et al. | |
| 5,601,839 | A * | 2/1997 | Quan | A61K 9/0014 424/448 |
| 5,776,885 | A | 7/1998 | Orsolini et al. | |
| 5,916,590 | A | 6/1999 | Cody et al. | |
| 6,203,813 | B1 | 3/2001 | Gooberman | |
| 6,673,856 | B1 | 1/2004 | Mentink | |
| 6,987,111 | B2 * | 1/2006 | Greco | C07D 211/52 424/422 |
| 7,105,486 | B2 | 9/2006 | Mickle et al. | |
| 2004/0058946 | A1 | 3/2004 | Buchwald et al. | |
| 2004/0131552 | A1 | 7/2004 | Boehm | |
| 2005/0158382 | A1 | 7/2005 | Cruz et al. | |
| 2005/0176645 | A1 | 8/2005 | Mickle et al. | |

(Continued)

FOREIGN PATENT DOCUMENTS

| EP | 0137600 A1 * | 4/1985 |
|---|---|---|
| EP | 0137600 | 7/1994 |

(Continued)

OTHER PUBLICATIONS

Haynes et al., A Systemic Study of Lutidine Salts Formed with the Pharmaceutically Acceptable Salt-Forming Agent, Pamoic Acid, Aug. 9, 2005, The Royal Society of Chemistry, vol. 5, pp. 538-543.*
Hamlin, William E.; Northam, Jack I., and Wagner, John G—"Relationship Between In Vitro, Dissolution Rates and Solubilities of Numerous Compounds Representative of Various Chemical Species", Mar. 31, 1965.
Kilometer. "The Complete Blog for the Preparation of Pharmaceutical Salts." http://www.usto8312.com/drugnews/messages/209_html. Mar. 2008.
Stedman's Medical Dictionary, 27th ed. Lippincott, Williams & Wilkins, Baltimore, 2000.

(Continued)

*Primary Examiner* — Ali Soroush
(74) *Attorney, Agent, or Firm* — Joseph T. Guy; Patent Filing Specialist, Inc.

(57) ABSTRACT

An abuse deterrent drug product is provided wherein the drug product comprises a matrix and a drug substance in the matrix wherein the drug substance is defined as a 1:1 salt of a pharmaceutically active compound and BNDO.

30 Claims, 118 Drawing Sheets

(56) References Cited

U.S. PATENT DOCUMENTS

2005/0266070 A1    12/2005    Mickle
2006/0051298 A1     3/2006    Groenewoud
2006/0104909 A1     5/2006    Vaghefi et al.

FOREIGN PATENT DOCUMENTS

FR        1461407        12/1966
GB         295656        11/1929
WO    WO -2005/012233 A1  *  2/2005

OTHER PUBLICATIONS

Berge SM, Bighley LD, and Monkhouse DC, "Pharmaceutical Salts", Journal of Pharmaceutical Sciences, Jan. 1977, 66(1), 1-19.
Morisette SL, Almarsson O Peterson ML, Remenar JF, Read MF, Lemmo AV, Ellis S. Cima MJ, Gardner CR, High-throughput crystalization: polymorphs, salts, co-crystals and solvates of pharmaceutical solids. Adv Drug Deliv Rev. Feb. 23, 2004; 56(3):275-300.
Grant & Hackh's; Chemical Dictionary; Fifth Edition, completely revised and edited by Rober Grant and Claire Grant; McGraw-Hill Book Company; pp. 258 and 145; copyright 1987 McGraw-Hill, Inc.
Declaration Under 37 CFR § 1.132 of Clifford Riley King, signed on Nov. 7, 2013 and filed in U.S. Appl. No. 13/331,298.

* cited by examiner

OPIOID AND ATTENTION DEFICIT HYPERACTIVITY DISORDER MEDICATIONS POSSESSING ABUSE DETERRENT AND ANTI-DOSE DUMPING SAFETY FEATURES

CROSS-REFERENCE TO RELATED APPLICATIONS

This application is a continuation in part of pending U.S. patent application Ser. No. 14/628,344 filed Feb. 23, 2015 which, in turn, is a continuation-in-part of each of: pending U.S. patent application Ser. No. 13/723,370 filed Dec. 21, 2012; U.S. patent application Ser. No. 13/334,842 filed Dec. 22, 2011 now U.S. Pat. No. 8,334,322 issued Dec. 18, 2012; pending U.S. patent application Ser. No. 13/313,870 filed Dec. 7, 2011; pending U.S. patent application Ser. No. 12/537,664 filed Aug. 7, 2009; U.S. patent application Ser. No. 12/080,513 filed Apr. 3, 2008 now U.S. Pat. No. 8,859,622 issued Oct. 14, 2014; abandoned U.S. application Ser. No. 12/080,531 filed Apr. 3, 2008; U.S. patent application Ser. No. 12/080,514 filed Apr. 3, 2008 now U.S. Pat. No. 8,575,151 issued Nov. 5, 2013 and abandoned U.S. patent application Ser. No. 11/805,225 filed May 22, 2007; and U.S. patent application Ser. No. 14/628,344 is a divisional appl. of each of: pending U.S. patent application Ser. No. 11/973,252 filed Oct. 5, 2007 and abandoned U.S. patent application Ser. No. 11/805,225 filed May 22, 2007 all of which are incorporated by reference. This application is also a continuation in part of pending U.S. patent application Ser. No. 13/444,191 filed Apr. 11, 2012 which is a divisional application of U.S. patent application Ser. No. 12/846,936 filed Jul. 30, 2010 now U.S. Pat. No. 8,653,106 issued Feb. 18, 2014 both of which are incorporated by reference. U.S. patent application Ser. No. 12/846,936 filed Jul. 30, 2010 now U.S. Pat. No. 8,653,106 issued Feb. 18, 2014 incorporates U.S. patent application Ser. No. 12/423,641 now U.S. Pat. No. 8,211,905 issued Jul. 3, 2012 therein.

BACKGROUND

The present invention is related to opioids and attention deficit hyperactivity disorder medications possessing abuse deterrent and anti-dose dumping safety features. More specifically, the present invention is related to bis-naphthyl bidentate organic salts having a carboxyl group and hydroxyl group in an ortho relationship to one another in each naphthyl ring and wherein only one of the substituted naphthyl rings is employed to form 1:1 salts of opioids and attention deficit hyperactivity disorder medications, their method of preparation of the salts, and enhanced drug products formulated therewith.

The ability to systematically impart abuse deterrent features to drug products via the drug substance component has been demonstrated within numerous U.S. Patents listed elsewhere herein. The unexpected findings associated with various organic acid salt forms of opiates, narcotics, stimulants and other amine-containing physiologically active and psychoactive drugs provides a universal approach to commercially revitalize a stable of useful medications while introducing additional features. Most pain and attention deficit hyperactivity disorder (ADHD) medications are subject to serious abuse which often leads to death of the abuser. No distinction is made herein between the recreational abuser and those that routinely abuse the medication. Whether as the free base, or in a salt form, the drug substance possesses the physiologically active portion of the drug product, and in the principal cases herein, constitutes a United States Drug Enforcement Administration "controlled substance". Historically, the controlled substances are provided in highly soluble salt forms, and particularly highly water soluble salt forms, wherein the basic amine within the active moiety is reacted with a mineral acid, such as hydrochloric acid, to form the hydrochloride salt. Of course, other salt forms, such as citrates, tartrates, and sulfates as exemplified by fentanyl citrate, hydrocodone bitartrate, and morphine sulfate are also used, but these too form highly water soluble salts in nearly every conceivable physiologically environment. Their high water solubility also allows for drug product tampering wherein the active moiety can be removed from the drug product matrix, optionally concentrated, and then abused. For the purposes of the instant application, tampering is defined as the in vitro manipulation and extraction of the active ingredient, but not necessarily of the specific drug substance used in the drug product. The tampering may result in the isolation of the active ingredient as the free base or in a different salt form from that originally used in the drug product.

The societal, governmental, economic and moral demands placed on drug manufacturers to reduce the abuse potential of a drug product has captured the attention of national and state legislatures particularly with the United States Food and Drug Administration's controversial market approval of Zohydro®, an extended release hydrocodone bitartrate drug product absent of abuse deterrent functionality. This drug product is available in several strengths, which if used in the intended route of administration, provides for the extended release of hydrocodone. Unfortunately, with up to 50 mg of hydrocodone available to a potential abuser desiring to get high, and the product susceptible to tampering, (such as by simple water extraction of hydrocodone bitartrate) an abuser may readily obtain a life-threatening amount of the extracted drug substance. It is arguable if the benefits arising from an extended release hydrocodone product outweigh the inherent dangers of tampering associated with such a product. Indeed, it appears that this scenario is a repeat of the hard-won lessons learned concerning the abuse of extended release oxycodone products wherein tampering allowed for the isolation of the highly water soluble oxycodone hydrochloride.

The paradox for pharmaceutical manufacturers is the provision of medications that work as intended when the route of administration and dosage strength regimens are followed, but are otherwise difficult to abuse. A top-level analysis of this paradox suggests the two conditions are mutually exclusive. The physical and chemical properties which make a drug difficult to abuse are likely to prevent its desired physiological activity. For instance, isolation of the active ingredient from a formulated matrix, or tampering, requires differential solubility between the active ingredient, drug substance, and the other constituents, or excipients, of the drug product. In addition, the differential solubility must be achieved in solvent property ranges of protic to aprotic, and polar to non-polar solvents. This introduces almost limitless possibilities. Secondly, should drug product tampering result in the isolation of the drug substance, that material needs to be abuse deterrent and not susceptible to insufflation, or snorting, as a mechanism of abuse, possess release characteristics unfavorable for administration to other mucosal membranes and preferably the drug product should be unsuitable for preparation for injection preferably by impeding its ability to be delivered by syringe. The contradictions in product features and requirements continue when considering that abuse deterrence must not be thwarted by the potential abuser grinding, milling, crushing or chewing the product to otherwise make the active ingredient more available for mucosal absorption or for injection abuse. Lastly, while the manufacturer introduces physical and chemical barriers to prevent abuse of the drug product, the same drug product must still satisfy a patient's legitimate medical need.

An absolute solution to the above paradox may only have a practical solution wherein a technology is introduced that derails most attempts at tampering or insufflation abuse, imposes great difficulties for injecting the drug product or some combination of remaining constituents after tampering with the drug product formulation, or prevents drug substance absorption at mucosal membranes.

The FDA's attempts to address prescription drug abuse have included their Risk Evaluation and Mitigation Strategies (REMS) initiative. This initiative, while not limited to just opioid based medications, was principally enacted to address opioid pain medications formulated into extended release dosage presentations. The extended release (ER) dosage presentation might easily include sufficient opioid to relieve patient pain for up to twenty-four hours, or commonly, a sufficient dosage for twelve hours. The opiate content of the ER products could represent multiple dosages of the comparable immediate release (IR) drug products. The availability of the ER products to potential drug abusers was cause for great alarm, and cause of many deaths, when the abuser could manipulate or dose dump an ER tablet and achieve a rapid "high" from an exceptionally high dose of opiate available all at once.

Pamoate salts, and derivatives thereof, have been demonstrated as a suitable platform for the formation of abuse and dose-dumping deterrent drug substances as exemplified in commonly assigned U.S. Pat. Nos. 8,211,905; 8,329,720; 8,338,444; 8,367,693; 8,476,291; 8,569,329; 8,569,330; 8,748,416; 8,846,766 and 8,921,386 each of which is incorporated herein by reference. These patents describe a large accumulation of work elucidating the features, advantages and benefits available from organic acid addition salts of amine containing pharmaceutically active species. More specifically, the organic acid family contains those salt forming compounds inclusive of bidentate pamoic acid derivatives. Also described throughout these patents is the ability to manipulate the amine content of pamoate derived salts in such a way that from 1:1 to 2:1 amine:pamoate salts are obtained. Similarly, mixed salts are obtained of the A-B-C variety wherein A is an amine-containing pharmaceutically active moiety, B is the pamoate derivative moiety and C can be selected from a variety of amine containing species selected from the group consisting of A, dissolution modifying species, hydrophilic or lipophilic adjustment species and the like. Further described therein is the ability to modify the amorphous or polymorphic characteristics of these compounds to achieve a desired dissolution profile or solubility parameter. The ability to predictably adjust pamoate salt stoichiometry and to ultimately achieve different morphologies introduces capability for engineering dissolution profiles of the drug substance of the pharmaceutically active amine as its pamoate derivative salt, and for inhibiting alternate routes of drug administration most often used for drug abuse. Though beneficial, the availability of 1:1 salts wherein the bidentate pamoate derivative has a free carboxyl group, thereby allowing for enhanced manipulation of the chemistry of the pamoate derivative salts, has been, heretofore, difficult to obtain.

The desire to predictably prepare 1:1 pamoate derivative salts of amine containing pharmaceutical active medications, despite the above setbacks, has been achieved and reported by Applicants in other disclosures. For instance, Applicants have demonstrated in commonly assigned U.S. Pat. No. 8,846,766 to King et al. the preparation of 1:1 methadone pamoate from methadone pamoate 2:1 salt by a solvent cracking technique wherein the 2:1 salt can be converted to the 1:1 salt by exposure to refluxing solvent. Alternatively, Applicants, in commonly assigned U.S. Pat. No. 8,653,065 to King et al., have produced both 1:1 imipramine pamoate and imipramine mono-triethylammonium pamoate 1:1:1 salt wherein the trimethylamine component has been used as a labile protecting group for the "open" carboxyl position while the other carboxyl of the pamoate is bound with an imipramine component. While these techniques are generally useful, particularly the ammonia or lower molecular weight amines as labile protecting groups, a more general route to 1:1 pamoate salts is still needed. This need arises from the interest in achieving different dissolution profiles for the 1:1 salts as may be dependent upon their morphology, or the ability to subsequently react the open position of the pamoate derivative with a dissolution modifying agent or other functional excipient to impede abuse, to improve drug substance compatibility with formulation components or techniques, and/or to improve drug substance stability.

In spite of extensive efforts, the art is still lacking salts of active pharmaceuticals, particularly 1:1 salts using bidentate pamoate derivatives wherein abuse deterrence is provided at the drug substance level and wherein the drug substances are less susceptible to dose dumping. A method for administering such salts, and drug products comprising the salts, are provided herein.

The bi-dentate characteristic of pamoate has also been observed by others and attempts are recorded throughout the literature to take advantage of this structural capacity. For instance, European Patent Application 0 137 600 [Stuart, et. al] filed Jul. 19, 1983, now abandoned, purports the preparation of morphine pamoate (1:1) salt by controlling the stoichiometry of reagents; ostensibly, two equivalents of morphine would yield the 2:1 salt with pamoic acid while only one equivalent of morphine would yield the 1:1 salt. Methodically replicating the experimental conditions described in the application failed to reproduce the analytical data reported by Stuart. Further, the analytical data included in the Stuart application supported the view that different compounds were prepared other than those proposed by Stuart. Nonetheless, morphine pamoate (1:1) salt was contemplated by Stuart, but the proposed stoichiometric relationship was not obtained.

The literature contains a more intensive foray into the preparation of 1:1 pamoate salts in U.S. Pat. No. 6,987,111 to Greco, et. al. Therein reported are experimental efforts directed toward the preparation of haloperidol pamoate 1:1, and aripiprazole pamoate 1:1. However, replication of the experimental conditions was performed in order to carefully assess the generality of preparing the 1:1 salts, but this effort was fruitless. Indeed, Greco's Example 1 was repeated, but instead of obtaining the expected haloperidol pamoate (1:1) salt, the haloperidol pamoate 2:1 salt was obtained. Within the experimental parameters left undefined by Greco, a further exploration was performed by Applicants to determine if the elusive 1:1 salt could be generated. Each perturbation still yielded the 2:1 salt. Upon further inspection, Greco reports yield data in Example 1 that is inconsistent with the stoichiometric possibility of obtaining the 1:1 salt. Additional characterization of the haloperidol pamoate 2:1 salt actually obtained by Applicants upon attempted replication of the Greco methodology can be found in the Experimental section herein.

Interestingly, and in contrast to the conflicting results above, Example 2 in Greco describes preparation of haloperidol pamoate 2:1 salt, and replicating this procedure multiple times yielded the following results: 1) a compound consistent with that found by Greco and, which when observed under magnification appeared to exist as geometrical plates, and 2) an amorphous 2:1 salt with slight crystallinity present. In fact, Claims 3 and 4 in Greco address haloperidol pamoates of either 1:1 or 2:1 stoichiometry as being "needles" or crystalline. In fact, Greco's FIG. 1 contains two SEM micrographs: one showing exclusively geometric plates, the other exclusively needles. No mention is made by Greco of obtaining an amorphous compound. Further, during repetitive trials and with reasonable experimental perturbations of Greco's method for preparing haloperidol pamoate 2:1 salt, no sample comprising any amount of needles was obtained. Finally, Applicants obtained a 1:1 haloperidol pamoate arising from modification of Greco's Example 2 which therein describes preparation of 2:1 haloperidol pamoate. The compound isolated by Applicants was consistent in structure assignment to 1:1 haloperidol pamoate through $^1$H-NMR; however microscopic assessment of its physical form (crystalline by PXRD) still did not match the forms disclosed by Greco's FIG. 1 micrographs. It is clear that Greco's methods—while contributing to the pathway for routine preparation of 1:1 pamoate salts—still did not provide a predictable synthetic route to these valuable compounds. Indeed, Applicants' attempted use of the Greco disclosure led to unexpected results, including but not limited to: a) an amorphous form of haloperidol pamoate 2:1 salt, and b) a more predictable route to preparing various 1:1 salts. Unfortunately, the scientific literature inclusive of references cited herein has purported to achieve an obvious result, but the analytical chemistry characterization of the isolated compounds from such endeavors indicates otherwise. Therefore, the invention disclosed herein resolves the issues associated with preparing the 1:1 pamoate salts and provides a more definitive utility for their use in modern pharmaceutical products.

SUMMARY OF THE INVENTION

It is an object of the invention to provide 1:1 salts of bis-naphthyl bidentate organic salts having a carboxyl group and a hydroxyl group in an ortho relationship to one another in each naphthyl ring wherein only one set of said carboxyl and hydroxyl on one said naphthyl rings is employed to form said 1:1 salt (hereinafter BNDO) with opioids or attention deficit hyperactivity disorder active pharmaceuticals; for the other naphthyl ring of the bis-naphthyl bidentate organic salts, the carboxyl group and hydroxyl group remain available. More specifically, the present invention is related to methods of administering the salts and drug products comprising the salts.

It is a feature of the present invention to selectively prepare amine salts of BNDO wherein the salt possesses a stoichiometric relationship therein of one mole of amine for each mole of BNDO.

It is a feature of the present invention to selectively prepare 1:1 amine salts of BNDO wherein BNDO is selected from Structures A and B detailed elsewhere herein.

Yet another feature of the present invention is the 1:1 salts of amines with BNDO wherein one salt forming site on the bis-naphthyl bidentate organic salts having a carboxyl group and a hydroxyl group in an ortho relationship to one another; the free carboxylic acid remains unreacted, and optionally, this carboxylic acid could, if desired, be converted to an ammonium, alkali or alkali metal cation salt.

Yet another feature of the present invention is the 1:1 salts of amine with BNDO having Structures A and B, wherein the salt may exist as the half-acid or its ammonium, alkali or alkali metal salt or mixture thereof and these all can exist in amorphous or polymorphic form.

A particular feature of the present invention is the ability to prepare 1:1 bis-naphthyl bidentate organic salts having a remaining carboxyl group and a hydroxyl group in an ortho relationship to one another. These encompass salts of haloperidol, hydrocodone, oxycodone, codeine, oxymorphone, naltrexone, morphine, methylphenidate, levothyroxine, imipramine, and methadone.

A particular feature of the present invention is the ability to provide a drug substance with a dissolution profiles of 1:1 salts prepared as the free-acid or essentially a mixture, such as a 50/50 mixture, of the free acid and mono-sodium salt having essentially identical dissolution profiles in corresponding dissolution environments such as 0.1N HCl, water, pH 4.5 and 6.8.

It is a particular feature, and unexpected finding of the present invention, that the dissolution profiles of the 1:1 salts examined essentially have identical dissolution profiles for their amorphous or polymorphic forms in the corresponding dissolution environments such as 0.1N HCl, water, pH 4.5 and 6.8.

It is a feature of the present invention to provide a drug product formulated with the 1:1 salts of a pharmaceutical active amine and BNDO of the present invention, having an inhibited dissolution profile compared with the analogous mineral acid, tartaric, citric acid salt, sulfate or bitartrate salt of the same physiologically active amine.

It is a feature of the present invention that the drug substances described herein exhibit resistance to dose dumping as compared to analogous drug substances presented as a mineral acid, or other highly water soluble salt.

It is a feature of the present invention that the drug substances described herein are suitable for formulation into drug products as immediate release, extended release and controlled release solid oral dose drug products.

These and other advantages, as will be realized, are provided in a drug substance selected from the group consisting of: amorphous hydrocodone pamoate 1:1 as a 1:1 mixture of mono-sodium salt and free carboxylic acid with a PXRD of FIG. 3; polymorphic hydrocodone pamoate 1:1 salt as the free carboxylic acid with a PXRD of FIG. 7; amorphous oxycodone pamoate 1:1 as a 1:1 mixture of mono-sodium salt and free carboxylic acid with a PXRD of FIG. 11; polymorphic haloperidol pamoate 1:1 with a PXRD of FIG. 15; polymorphic haloperidol pamoate 1:1 with a PXRD of FIG. 19; polymorphic haloperidol pamoate 1:1 as a 3:1 mixture of mono-sodium salt and free carboxylic acid with a PXRD of FIG. 23; amorphous morphine pamoate 1:1 as the 1:1 mixture of mono-sodium salt and free carboxylic acid with a PXRD of FIG. 27; amorphous oxymorphone pamoate 1:1 as the 1:1 mixture of mono-sodium salt and free carboxylic acid with a PXRD of FIG. 31; amorphous codeine pamoate 1:1 as a 1:1 mixture of mono-sodium salt and free carboxylic acid with a PXRD of FIG. 35; amorphous d-methylphenidate pamoate 1:1 as a 1:1 mixture of mono-sodium salt and free carboxylic acid with a PXRD of FIG. 39; polymorphic racemic methylphenidate pamoate 1:1 as a 1:1 ratio of sodium salt and free carboxyl with a PXRD of FIG. 43; amorphous naltrexone pamoate 1:1 salt as a 1:1 mixture of mono-sodium salt and free carboxylic acid with a PXRD of FIG. 47; polymorphic naltrexone pamoate 1:1 salt as the free carboxylic acid with a PXRD of FIG. 51; amorphous imipramine pamoate 1:1 as the 1:1 mixture of mono-sodium salt and free carboxylic acid with a PXRD of FIG. 55; amorphous methadone pamoate 1:1 as the 1:1 mixture of mono-sodium salt and free carboxylic acid with a PXRD of FIG. 59 and polymorphic L-thyroxine pamoate 1:1 as the mono-sodium carboxylate with a PXRD of FIG. 115.

Yet another embodiment is provided in a drug substance selected from the group consisting of hydrocodone pamoate 1:1; oxycodone pamoate 1:1; haloperidol pamoate 1:1; morphine pamoate 1:1; oxymorphone pamoate 1:1; codeine pamoate 1:1; d-methylphenidate pamoate 1:1; racemic methylphenidate pamoate 1:1; naltrexone pamoate 1:1; imipramine pamoate 1:1; methadone pamoate 1:1 and L-thyroxine pamoate 1:1.

Yet another embodiment is provided in a drug substance defined as a 1:1 salt of a pharmaceutically active compound and BNDO.

Yet another embodiment is provided in a product comprising a matrix and a drug substance in said matrix wherein said drug substance is defined as a 1:1 salt of a pharmaceutically active compound and BNDO.

Yet another embodiment is provided in a method of administering a pharmaceutically active compound comprising: forming a drug substance comprising the pharmaceutically active compound as a 1:1 salt BNDO; forming a drug product comprising the drug substance and a matrix; and introducing the drug product to a mucosal membrane wherein the drug substance is released from the drug product at a first kinetic rate and the pharmaceutically active compound is released from the drug product at a second kinetic rate.

Yet another embodiment is provided in a method of administering a pharmaceutically active compound comprising: forming a drug substance comprising the pharmaceutically active compound as a 1:1 salt with BNDO; forming an oral dose drug product comprising the drug substance and a matrix; and introducing the drug product to a mucosal membrane wherein the pharmaceutically active compound is bioavailable if the mucosal membrane is at stomach pH and the pharmaceutically active compound is not bioavailable if the mucosal membrane is not at stomach pH.

FIGURES

DESCRIPTION

Figure 1:
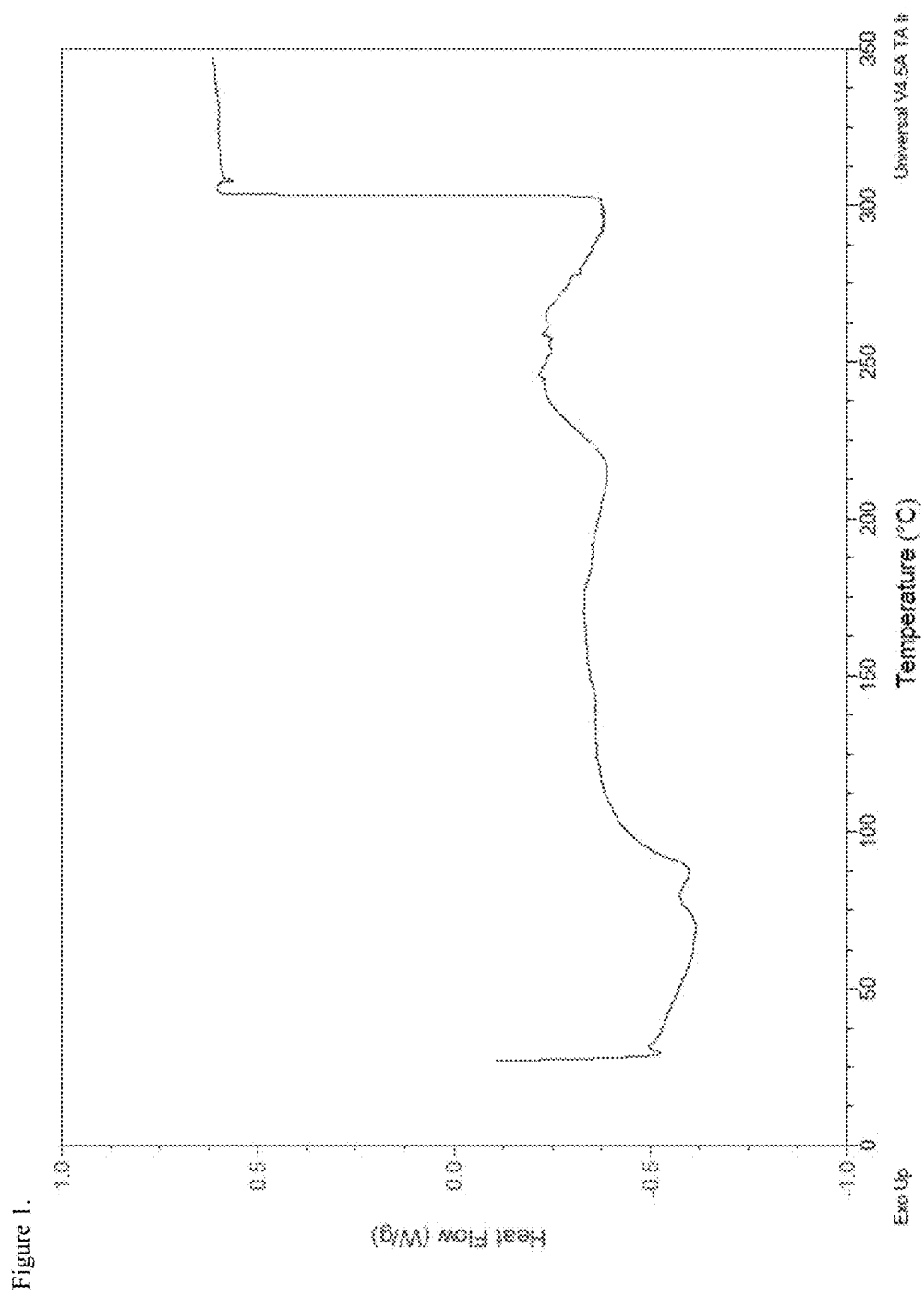
FIG. 1 is the differential scanning calorimetry (DSC) thermogram of amorphous hydrocodone pamoate 1:1 salt as 1:1 mixture of mono-sodium salt and free carboxylic acid.

The instant invention is specific to drug substances as 1:1 BNDO salts of opioids and attention deficit hyperactivity disorder medications possessing abuse deterrent and anti-dose dumping properties, methods for administering the drug substances and drug products comprising the drug substances.

BNDO salts of amine containing pharmaceutically active compounds have been shown to demonstrate abuse deterrent features. It has been observed that there is an overwhelming propensity when preparing BNDO that the 2:1 salt of an active amine and BNDO is preferred. A casual reflection upon this observation would suggest that proper adjustment of the reaction stoichiometry would be sufficient to selectively prepare either the 1:1 or the 2:1 salt. Unfortunately, this is not the case despite what often appears in the literatures as a hypothesis. Often when 1:1 equivalency of amine to BNDO is charged, meaning one mole of amine and one mole of BNDO, the anticipated 1:1 salt is not formed, but instead the 2:1 salt overwhelmingly prevails. Presumably, the equilibrium dynamics are controlling the stoichiometric outcome which favors the 2:1 salt. The equilibrium bias appears driven by the continual removal of the 2:1 salt from the reaction solution due to precipitation. However, on occasion, under the appropriate reaction and stoichiometric conditions, amine and BNDO react in such a manner to yield the intended 1:1 salt. This result most often occurs absent the precipitation event and the 1:1 salt is isolated upon removal of the reaction media by solvent removal at reduced pressure.

The BNDO moiety is unique in its salt forming ability when reacted with amine-containing compounds. No distinction is made herein between pamoic acid derivatives, a reactive salt form, such as disodium BNDO, or an esterified BNDO since each can serve as a synthon for forming BNDO salts with reactive amines. The cited compounds and others suitable for use as BNDO synthons are described elsewhere. One readily notes that the BNDO is bi-dentate and contains two carboxyl groups. The bi-dentate nature of the compounds allows for acid-base salt formation to occur with the carboxyl groups of the BNDO, yet chelation likely ensues wherein the salt is further anchored by the constituent hydroxyl groups on the BNDO. Given that the carboxyl and hydroxyl groups on the BNDO can contain acidic protons, salt formation and chelation provide for quite stable salt complexes with basic compounds. Indeed, this salt stability has been demonstrated in U.S. Pat. No. 7,858,663 [Bristol] issued Dec. 28, 2010, entitled, Physical and Chemical Properties of Thyroid Hormone Organic Acid Addition Salts, the disclosure of which is incorporated herein in its entirety.

Within the context of the present invention, organic acid addition salt is defined as 1:1 or 2:1 amine:acid salts, which relate to the families of di-basic, bi-dentate, di-acid organic acids described herein and as exemplified by pamoic acid derivatives. Similarly, such organic acids when used to produce the 1:1 or 2:1 salts may be employed in an alternative synthetic equivalent and not necessarily as a protonated (di)-carboxylic acid. Such synthetic equivalents of the organic acids herein may include but are not limited to their ammonium, alkali, alkali metal and low-boiling-amine salts and to lower molecular weight esters. Optionally the synthetic equivalent of the organic acid may include some combination of the preceding alternatives in addition to half-acid derivatives. By way of example, a useful synthetic equivalent for pamoic acid is optionally, disodium pamoate. When used in context, the term free acid means the non-salt form of one unreacted carboxylic acid residue of the pamoate moiety; contextually, this means it is the unreacted carboxyl function attached to the pamoate portion of a 1:1 salt formed between an amine containing compound and the pamoate moiety. Hence, such 1:1 pamoate salts may exist as the free acid, or the free acid functionality may be exemplified as another salt form, e.g. as a sodium salt, or the free acid may exist, for instance, as a mixture with the sodium salt. Important to the discovery disclosed herein are the actual structural determinations of the free acid form of the 1:1 salts—whether specifically as the free acid, as its sodium salt or some mixture thereof. Such definitive structural elucidation in the prior art has been un-determined, is indeterminate or mischaracterized principally since the 2:1 salts were actually obtained instead of the asserted 1:1 salt.

For the reasons set forth above some species are better represented as a mixture of salts. For example, amorphous oxycodone pamoate 1:1 salt is presented herein for the purposes of analysis as a 1:1 mixture of mono-sodium salt and free carboxylic acid indicating that the salt was measured as a 1:1 mixture of mono-sodium salt and free carboxylic acid. This language is not limited herein but is included for clarity and any instance of statements such as "as a 1:1 mixture of mono-sodium salt and free carboxylic acid" are intended to be interpreted, without limit thereto as "measured as a 1:1 mixture of mono-sodium salt and free carboxylic acid" to distinguish from the same measurement with a stoichiometric amount of sodium salt or a measurement with no sodium salt.

An "alkaloid" is an amine nitrogen containing natural product, synthetically modified or derivatized natural product, wholly synthesized analog of a natural product, or an amine containing compound that exhibits biological activity in animals or humans. The amine nitrogen can be present as a primary, secondary, tertiary or quaternary amine moiety and a given compound may contain more than one type of amine functionality. Examples of these materials are the US Drug Enforcement Agency's (DEA) Form 225 of Schedule I through V controlled substances, generally divided between narcotic and non-narcotic materials. There are also other compounds applicable to the present invention not found on the DEA list or which may be added to it in the future. Further, the compounds applicable to the present invention may arise from plant or animal origin, or may be totally obtained through human effort of design and synthesis. A reference to compound classes (i.e. pharmacophores) applicable to the invention are found within Strategies for Organic Drug Synthesis, by Daniel Lednicer, published by John Wiley and Sons, Inc. © 1998, Chapters 7 through 13 inclusive and individually, Chapter's 13 and 15. Classes of compounds subject to this invention include but are not limited to opiates, morphinoids, tropinoids, amphetamines, compounds containing a piperidine or substituted piperidine sub-structure within the molecule, benzodiazepines, benzazepines, and compounds containing a phenethyl amine or substituted phenethylamine sub-structure within the molecule. The common characteristic to each compound is the presence of an amine nitrogen whereby the amine nitrogen is either a primary, secondary or tertiary amine group and is capable of forming a salt with an inorganic or organic acid, or combinations thereof. Within the description of the invention, the term alkaloid or amine may be used interchangeably to identify a compound possessing, or suspected of possessing, biological activity in humans or animals, in its free base (non-salt) form or in a salt form. The differentiating factor defining the invention is the alkaloid's ability to form an organic acid salt that will retain the expected biological activity when used as intended for legitimate therapeutic purposes, but is not readily accessible for abuse by inhalation (smoking), mucosal application, nasal absorption (snorting) or by intravenous injection (shooting).

A "drug substance" is a molecular entity or compound, also known as an active pharmaceutical ingredient (API), or active pharmaceutical compound, that exhibits biological activity for the purpose of providing human or animal medication to treat disease, pain or any medically diagnosed condition. It is possible for a drug substance to be used in combination with one or more different drug substances to ultimately impart a biological response in humans or animals. A drug substance is typically formulated into a drug product with other, non-biologically active compounds to provide a means of predictable and quantitative dosage delivery, or optionally to impart acceptable stability features to the drug product. In some embodiments additional biologically active compounds may be incorporated into a drug product to provide synergistic, complimentary or additional treatments.

A drug product is a formulation, mixture or admixture of the drug substance with combinations of excipients, processing aids, buffers and optionally other inert ingredients that allow delivery of the drug substance by the selected delivery mechanism to the patient at a predictable dosage. Those elements of the drug product exclusive of the drug substance of interest are referred to as the carrier matrix without regard for the function of the components of the carrier matrix. Various delivery mechanisms include solid oral dosage, for example, pills, tablets, or capsules. Additional delivery systems can include solution or suspension injection dosage forms including depo drug products, transdermal patches, and nasal or inhalation devices. The dosage is the actual concentration delivered to the patient, and depending upon many factors and the actual delivery system selected preferably as a function of time, the dosage may be available for essentially immediate release, release over time, or manipulated by additional means for stimulated release such as for example, by irradiation.

For the purposes of the present invention a therapeutic dosage presentation is characterized by the following definitions. 1) Immediate-release tablets and capsules release the active ingredient within a small period of time, typically less than 30 minutes. 2) Extended-release tablets and capsules release the active ingredient at a sustained and controlled release rate over a period of time. Typically extended-release tablets and capsules release their ingredient with time periods of 8 hours, 12 hours, 16 hours, and 24 hours. 3) Delayed-release tablets and capsules release the pharmaceutical dosage after a set time. The delayed-release tablets and capsules are frequently enteric-coated in order to prevent release in the stomach and, thus, release the dosage in the intestinal tract.

The term "drug system" refers to a dosage wherein at least two doses are provided. The two doses can be concurrent, sequential, or overlapping and each of the two doses may be the same or different.

Throughout the specification the term organic acid is used generically to refer to the acid form or the salt form of a compound.

Pharmaceutically active compounds which can be incorporated with the present invention as a 1:1 salt with a BNDO include those selected from the group consisting of caffeine, acetorphine, acetylmethadol, allylprodine, alphacetylmethadol, bufotenine, dextromoramide, diethyltryptamine, etorphine, heroin, ibogaine, ketobemidone, lysergic acid diethylamide, mescaline, methaqualone, 3,4-methylenedioxyamphetamine, 3,4-methylenedioxymethamphetamine, N-ethyl-1-phenylcyclohexylamine, peyote, 1-(1-phenylcyclohexyl)pyrrolidine, psilocybin, psilocin, 1-{1-(2-thienyl)-cyclohexyl}-piperidine, alphaprodine, anileridine, cocaine, dextropropoxyphene, diphenoxylate, ethylmorphine, glutethimide, hydrocodone, hydromorphone, levorphanol, meperidine, morphine, opium, oxycodone, oxymorphone, poppy straw, thebaine, amphetamine, methamphetamine, methylphenidate, phencyclidine, codeine, benzphetamine, ketamine, alprazolam, chlorodiazepoxide, clorazepate, diethylpropion, fenfluramine, flurazepam, halazepam, lorazepam, mazindol, mebutamate, midazolam, oxazepam, pemoline, pentazocine, phentermine, prazepam, quazepam, temazepam, triazolam, zolpidem, buprenorphine, apomorphine, dihydrocodeine, codeinone, thebaine, morphothebaine, thebenine, metathebainone, phenyldihydrothebaine, thebainhydroquinone, flavothebanone, alpha-codeimethine, 14-hydroxycodeinone, sinomenine, dihydrosinomenine, hasubanonine, nalbuphine, nalmefene, naloxone, naltrexone, noscapine, oripavine, haloperidol, methadone, L-thyroxine and imipramine.

Particularly preferred pharmaceutically active compounds are selected from the group consisting of haloperidol, hydrocodone, oxycodone, codeine, oxymorphone, naltrexone, morphine, methylphenidate, imipramine, amphetamine, L-thyroxine and methadone. Even more particularly preferred pharmaceutically active compounds are selected from the group consisting of d-methylphenidate, racemic methylphenidate and dextro-amphetamine.

Particularly preferred drug substances are selected from the group consisting of hydrocodone 1:1; oxycodone pamoate 1:1; haloperidol pamoate 1:1; morphine pamoate 1:1; oxymorphone pamoate 1:1; codeine pamoate 1:1; d-methylphenidate pamoate 1:1; racemic methylphenidate pamoate 1:1; naltrexone pamoate 1:1; imipramine pamoate 1:1, methadone pamoate 1:1 and L-thyroxine pamoate 1:1.

Even more preferred drug substances are selected from the group consisting of amorphous hydrocodone pamoate 1:1; polymorphic hydrocodone pamoate 1:1; amorphous oxycodone pamoate 1:1; polymorphic haloperidol pamoate 1:1; amorphous morphine pamoate 1:1; amorphous oxymorphone pamoate; amorphous codeine pamoate 1:1; amorphous d-methylphenidate pamoate 1:1; polymorphic racemic methylphenidate pamoate 1:1; amorphous naltrexone pamoate 1:1; polymorphic naltrexone pamoate 1:1; amorphous imipramine pamoate 1:1; amorphous methadone pamoate 1:1 and polymorphic L-thyroxine pamoate 1:1.

Particularly preferred embodiments of bis-naphthyl bidentate organic salts have a carboxyl group and a hydroxyl group in an ortho relationship to one another in each naphthyl ring, BNDO herein, are represented in Structure A and Structure B wherein Structure A is referred to in the art as pamoate and throughout the specification the term "pamoate derivative" refers to a compound represented by Structure A or Structure B unless otherwise stated.

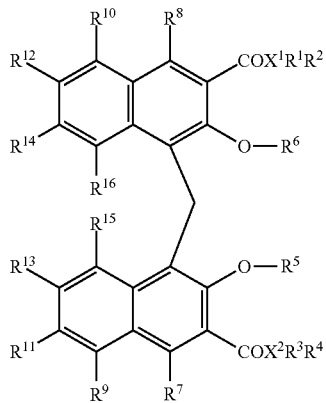

Structure A

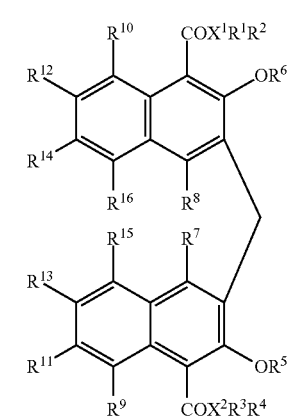

Structure B wherein:

$X^1$ and $X^2$ are independently selected from nitrogen, oxygen and sulfur and most preferably $X^1$ and $X^2$ are oxygen;

$R^1$-$R^4$ are independently selected from H, an alkali metal, alkyl or substituted alkyl of 1-6 carbons, aryl or substituted aryl of 6-12 carbons, alkylacyl, substituted alkylacyl, arylacyl or substituted arylacyl analogues sufficient to satisfy the valence of X, such as to provide a mixed anhydride or carbamate with the proviso that in the drug substance one of $R^1$-$R^4$ will be a pharmaceutically active compound;

$R^5$ and $R^6$ independently represent H, alkyl or substituted alkyl or 1-6 carbons, alkylacyl or substituted alkylacyl, arylacyl or substituted arylacyl and most preferably $R^5$ and $R^6$ are hydrogen;

$R^7$-$R^{16}$ are independently selected from H, alkyl or substituted alkyl of 1-6 carbons, adjacent groups may be taken together to form a cyclic alkyl or cyclic aryl moiety, either of which may be substituted; and when $X^1$ or $X^2$ is O, one of $R^1$ or $R^2$ or one of $R^3$ or $R^4$ is not present and the other may represent H, an alkali metal cation or ammonium.

A synthetic equivalent to pamoic acid, pamoic acid analogs or its regio-isomer derivatives are materials that provide the structural moiety independent of its particular salt, ester, or amide form and that upon pH adjustment yields the associated alpha-hydroxy-carboxylate functionality suitable for reaction, preferably with one equivalent of an amine-containing active pharmaceutical ingredient to form the salt. Examples of synthetic equivalents of the BNDO capable of manipulation to produce BNDO salts include but are not limited to, disodium pamoate, mono-alkali metal pamoate, di-ammonium pamoate, di-potassium, lower molecular weight di-alkyl and/or di-aryl amine pamoate, lower molecular weight di-alkyl and/or di-aryl esters of pamoic acid, and lower molecular weight di-alkylacyl and/or di-arylacyl O-esters of pamoic acid, i.e. those alkylacyl and arylacyl esters formed using the hydroxyl moiety of pamoic acid and not the carboxylic acid functional group. The descriptor phrase "lower molecular weight" used above means the indicated moiety has a molecular mass contribution within the BNDO of less than about 200 amu. Of course, this concept can be extended to other substituted BNDOs and regio-isomer compounds.

For clarity, the use of lower molecular weight di-alkyl or di-aryl amine pamoate allows for the exchange of higher molecular weight amines, or drug free bases, to be exchanged for the lower molecular weight amine component during the salt formation reaction. Similarly, the use of lower molecular weight di-alkylacyl and/or di-arylacyl pamoates allow for their conversion through ester hydrolysis to the pamoic/pamoate moiety followed by reaction with the desired drug free base.

Throughout the instant disclosure the terms alkyl, or a specific alkyl such as methyl, ethyl, propyl, etc.; refers to substituted or unsubstituted alkyls. Similarly, the term aryl, or a specific aryl such as phenyl or naphthyl, refers to substituted or unsubstituted aryls.

A useful and unexpected observation was made while preparing the selected organic acid addition salts of these compounds. Bristol et al. (cited above) describes processes for preparing the pamoate, xinafoate and salicylate families of amine-containing controlled substances. Further, and in particular during preparation of the pamoate salts, the salt precipitated from the reaction mixture and exhibited poor solubility characteristics in the primarily aqueous reaction medium. As the pamoate salts of various controlled substances were isolated, they were subjected to a host of manipulations to obtain different polymorphic forms of the salt. In King et al., also cited above, these different pamoate polymorphic forms of the same active ingredient were demonstrated to behave significantly differently than expectation. In general, the findings reported herein for the opioid active ingredients do not follow the observed processing trends or dissolution features found for other organic acid addition salt compounds. The amorphous and polymorphic forms were shown to have essentially identical dissolution profiles. There appears to be a unique feature to the salt formed between the opiate moiety and the organic acid components of the present invention. Formation of the salt within an aqueous medium affords a precipitate, however, with unforeseen characteristics.

It is reasoned that the careful isolation conditions are required to defeat the hydrophilic character of the opioids, even as their pamoate salts, and to remove excess amounts of water from the compounds. As amorphous and polymorphic opiate salts were isolated, analytical characterization confirmed the presence of water from about 0 to 8 percent. Despite this water content, the taffy, or gummy-like nature of the original isolates was not observed.

For the purposes of the present invention an API of a drug product is not directly isolable if it cannot be isolated by solubilizing the drug product to form a solubilized drug substance and filtering the solubilized drug substance without further chemical processing.

API salts and their polymorphs often exhibit different dissolution characteristics. For instance, the rate of dissolution is pH dependent, and therefore yields a different pharmacokinetic profile and/or therapeutic efficacy depending upon route of administration. Sometimes, a given drug product formulation technique or methodology can accommodate any biological effects the API salt and/or morphic form present. Conversely, drug product formulation and the resulting mechanical properties of a tablet, capsule or bead can be dominated by the physical behavior of the API salt and/or its particular crystal structure. It is not unusual that difficult trade-offs must be made between the ease of manufacture of the drug product and the pharmacokinetics desired.

Drug product formulation can impact the pharmacokinetics of an API salt candidate, and potential morphic form, by a host of technologies, including but not limited to, preparing formulated beads, different sized beads, coated beads, combinations of various bead technologies, formulated matrix systems, addition of hydrophobic layers to tablets, capsules or beads for example, as a control mechanism to limit the dissolution rate of hydrophilic gelatin capsules, coated tablets and capsules, capsules filled with beads, and different mixtures of beads with different coatings. These formulation and processing techniques make available a wide range of drug product properties including, but not limited to, immediate, extended, or delayed release drug pharmacokinetics. These activities are dependent upon the API salt selected, and any potential polymorph issues, because of the salt's dissolution profile at the pH where drug release of the drug substance from the drug product is to occur. In fact, different API salts and formulation techniques can be selected based on where the desired release is to occur in the gastrointestinal tract and the formulator can use the API salt's pKa, solubility, melting point, shape and particle size as primary factors to utilize, moderate or overcome localized insolubility through the use of formulation techniques.

In a preferred embodiment of the invention, at least one equivalent of the amine containing drug substance is reacted per mole of disodium pamoate to yield the drug substance pamoic acid salt in a 1:1 ratio. Typically, an aqueous acidic solution of the amine containing drug substance is combined with a basic solution of pamoic acid or disodium pamoate. The acid/base reaction ensues and the insoluble organic acid salt precipitates from the aqueous solution or can be isolated by removal of the water. Optionally, the salt can be purified, dried and milled to obtain a drug substance ready for formulation into the desired delivery format. The drug product formulated with the drug substances then possesses the targeted delivery characteristics of the drug substance and the potential for abuse of either the drug substance and/or drug product is eliminated or greatly reduced when abuse is attempted via the mucosal surfaces or by injection.

It is a well-known chemical principle that an acid and a base will react to form a salt. It is sometimes possible to predict the physical and chemical properties of these compounds in generalized concepts such as which way a melting point, or phase transition temperature will change compared to the un-reacted acid or base. Dissolution and dissociation rates of drug salts and their associated achievable solution concentrations are substantially less predictable when attempting to correlate this experimental data to some anticipated bio-availability of the drug. For instance, at a given pH, an observed dissolution rate and the associated solution concentration of the drug may be dissociation controlled, i.e. ionization, rather than governed strictly by solubility parameters. Indeed, different salts of the same amine-containing active ingredient are likely to display diverging mechanisms of bio-availability as a function of pH. As such, an evaluation of amine-containing active ingredients and their different salts would help elucidate their bio-availability mechanisms. This approach could be incorporated into a broader design feature to address drug abuse.

This phenomenon of selectively producing the 1:1 salts of amine and BNDO was further explored by a series of control experiments. In the first experiment, a 2:1 pamoate salt was subjected to the reaction and isolation/work-up conditions found to yield the 1:1 salts. If, under these conditions, the 2:1 salt would disproportionate to the 1:1 salt and an equivalent of solubilized amine, then a methodology would be established for reversing the formation of the, presumably, more thermodynamically favored 2:1 salt and the kinetically favored 1:1 salt could be isolated.

In a similar control experiment, a 2:1 pamoate salt was subjected to the reaction condition for preparing the 1:1 pamoate salts. In this case, an additional equivalent of disodium pamoate was added to the reaction mixture with the intention of forming an additional mole of 1:1 amine: pamoate salt should the 2:1 salt disproportionate. Unlike the first control experiment described above, the liberated amine equivalent would now be captured as another molar equivalent of 1:1 amine: pamoate. Upon reaction work-up, isolation of 2 moles of 1:1 amine: pamoate would result from the 2:1 salt and an equivalent of pamoate synthon, the pamoate moiety delivered to the reaction mixture as a pamoic acid equivalent.

The general (in)solubility features of the cited salts are one aspect of imparting abuse deterrent features to opioid drug substances. The active ingredient, as the free base or a mineral acid salt is often extracted from the dosage presentation by employing a readily available organic solvent such as iso-propanol (IPA), acetone, toluene, xylenes or a petroleum fuel. The poor solubility of the organic acid addition salts in these media exacerbates the attempts to isolate the active from the dosage form for purposes of abuse.

It is often preferred by the traditional pharmaceutical formulation scientist to formulate with an API which exhibits pH independent release such as that observed for the mineral acid, tartrate and similar salts. However, an API dissolution profile exhibiting pH independent release affords little opportunity to use physiological pH ranges as a means to control drug abuse. Initially, the opioid pamoate dissolution profiles were interpreted to have the "undesirable" pH dependence yet this characteristic confers an additional inventive contribution to the present invention. For instance, the dissolution profiles are substantially attenuated for the higher pH conditions and less so for the pH 1 (0.1N HCl) and pH 4.5 conditions. This circumstance is not a hindrance to the commercial development of formulated product offering but represents a desired feature. The dissolution at the pH 1 condition is easily manipulated in a proposed dosage by enterically coating the tablet or capsule. The coating allows for the tablet to pass from the low pH stomach to the higher pH intestines where the API is generally released slowly after the enteric coating is dissolved. Further, the dissolution profile for the pH 4.5 condition represents that intermediate range between the low pH of the stomach and the progressively higher pH range encountered in the intestines. In all cases, the pamoate exhibits an extended release profile when compared to the traditional salts and the minor pH dependencies are actually advantageous to producing abuse deterrent opioid products. For instance, at pH near 4.5, the pamoates would not be soluble in the body's mucosal membranes.

The US FDA has issued a draft, available at the FDA website, concerning oxymorphone hydrochloride and has requested specific dissolution tests be performed to demonstrate alcohol, specifically ethanol, does not promote dose dumping. An Oct. 26, 2005 overview presentation by the deputy director OPS/CDER of the FDA and entitled "Preventing Alcohol Induced Dose Dumping is a Desired Product Design Feature" describes the dose-dumping phenomenon. Dose dumping can be employed by those with the deliberate intention of abusing the drug, but may also occur during the normal/moderate consumption of alcohol while taking a prescribed medication. Simply, dose dumping is that condition "in which the complete dose may be more rapidly released from the dosage form than intended, creating a potential safety risk". Clearly, with the opioid narcotics, dose dumping for the intention of experiencing the "high" or rush, may have severe, even deadly consequences. The presentation further categorizes the results from dose dumping testing as either vulnerable, rugged or uncertain. If the dissolution profile in the presence of alcohol accelerates the release of the active ingredient, the product is classified as vulnerable and would likely not receive FDA market approval. In contrast, a rugged product design is achieved when the dissolution profile of the drug substance, again in the presence of alcohol, is identical to or is available to a lesser extent as compared to the control. The testing regimen recommended within the FDA's draft guidance includes determining the dissolution profile in 0.1N HCl solutions wherein the sample is tested in the medium and at increasing levels of ethanol, specifically at 5, 20 and 40% alcohol. The current invention demonstrates the ability to formulate anti-dose-dumping pharmaceutical products specifically for those compounds often the subject of abuse, e.g. oxycodone, hydrocodone, and the like. When any dosage formulated drug product which is susceptible to dose dumping, whether by intended abuse or by unintentional action, severe consequences, including patient death, can arise. Ideally, drug products would not be susceptible to dose dumping, and an ideal test result, at the various ethanol concentrations, and in the presence of acid, would be that alcohol does not promote the release of the drug product any faster than that observed in a 0.1N HCl condition in the absence of ethanol. The invention herein demonstrates the BNDO salts are useful in attenuating the release of the pharmaceutical active ingredient from BNDO under the prescribed dose dumping test regimen. Herein however, a non-dose dumping drug substance will be defined from a practical perspective considering that an abuser generally seeks the "high" within thirty minutes of abusing the drug. Hence, a BNDO based drug substance exhibiting less than or equal to fifty percent release ($\leq 50\%$) of the active ingredient under 0.1N HCl conditions containing 5, 20 and 40% ethanol is not susceptible to dose dumping. All of the BNDO exemplars herein except polymorphic naltrexone pamoate (see FIG. 102) do not exhibit a propensity to dose dump. Even this would not present a problem, however as an abuser would not likely desire naltrexone to dose dump since this would compete with the active ingredient creating the intended "high" and diminish the experience. Thus, attempts to extract the naltrexone from the drug product and isolate the desired active ingredient would still be impeded.

The hygroscopic nature of the opioids is well known, and as their mineral acid or small organic acid salts, these materials often exhibit high solubility in water or organic solvents, especially ethanol. This very high solubility hinders formulated dose manufacturing since processes employed to impart abuse deterrent features such as wet granulation or particle coating may lead to the opioid salt dissolving instead of agglomerating or being receptive to coating. Consequently, the purpose of the formulation to impart abuse-deterrent properties, by inhibiting extraction of the active dosage form, requires difficult manufacturing procedures using materials essentially incompatible with the manufacturing process required. Of the many consequences to this mismatch of purpose and manufacturing capability is the likelihood of dose uniformity failure, i.e. too much tablet-to-tablet, or capsule-to-capsule dose variation.

In contrast, the opioid salts of the present invention and their formulations disclosed herein improve the capability of commercially existing opioid formulations and provide more manufacturing options for formulation techniques. By way of example, the higher molecular weights of the salts disclosed herein allow for more accurate weighing, dispensing and formulation of the opioid active as compared with the mineral acid salts. Oxycodone hydrochloride has a molecular weight of about 352 grams/mole whereas the corresponding 1:1 pamoate salt has a molecular weight about two times larger. To obtain dose uniformity on highly active compounds, such as the opioids, it is much easier to weigh the larger mass required for equal dosing when using the pamoate salt than it is for the hydrochloride salt, or similar low molecular weight salts. As the physiological activity of the opioid increases, this benefit attributable to the molecular weight difference increases dramatically. To a patient who obtains an incorrect dosage administration, the medical consequences can be severe. If the dosage is too low and a therapeutic dosage is not obtained, but too high a dose and death may occur. In addition to the molecular weight differences, pre-formulation of the opioid organic acid addition salt with additional organic acid component using different pharmaceutically active compounds on either side of the BNDO allows for greater dosage control in the fully formulated drug product. Indeed, this pre-formulated material is suitable for use as the formulated product—in a tablet by direct compression or in a capsule.

In contrast, it is relevant to the present invention to note the importance of pH in controlling the release of a drug substance from its product formulation to achieve absorption and consequently, the medicinal effect. The pH of the gastrointestinal tract essentially remains highly acidic with the exception of the lower colon which reaches pH 8; vaginal pH is typically around 5.8 and the nasal cavity is approximately pH 4.5. More generally, each of the mucosal surfaces, particularly ocular, nasal, pulmonary, buccal, sublingual, gingival, rectal and vaginal are receptive to drug absorption if release can occur. A dominating feature of the present invention is the severely retarded release of the controlled substance, particularly exemplified by the invention described herein of amine-containing controlled substance BNDO derivative in the pH range of about 4 to 9 which encompasses the physiological pH of the mucosa. These release properties were an unexpected finding recognized and observed after performing dissolution tests over a wide pH range on several unrelated compounds. The release property profiles of controlled substance BNDO salts and the like are a means to evaluate the abuse deterrent feature of said salts if a (multiple)-dosage is applied to the mucosa. With the inventive disclosure herein, the non-release of the active pharmaceutical compound from the drug substance in the 4 to 9 pH range negates absorption and prevents the physical act of abuse. For the amine-containing hydrochloride salts, an abuse mechanism remains operative since these salts do not exhibit the discriminating "on/off" switch of the present invention and are soluble, and therefore bioavailable, at essentially all pH values.

Also disclosed herein are processes for the preparation of drug substances and DEA controlled drug substances (APIs) using organic acid addition salts of the active pharmaceutical ingredient (API) which are optionally formulated with other non-therapeutic materials to aid in delivery, stability, efficacy, targeted release and to engineer a pharmacokinetic profile of the organic acid addition salts as compared to other salt forms, including inorganic (mineral) acid salt forms. The present invention provides for release of the API for its intended purpose and prevents availability of the drug substance for typical routes of abuse. The present invention describes a method for evaluating, and formulations for, the organic acid addition salts of appropriate APIs to provide an efficacious and therapeutic dosage to animals and humans.

A drug formulation which is selected for the prevention of drug abuse is specifically a drug which is bio-unavailable or not isolable if efforts to alter the intended or established route of administration are undertaken. In a preferred embodiment the drug formulation is not released under aqueous conditions at a pH of about 4 to about 9 and generates a solid of an organic acid at pH below about 4. At pH above about 9, the organic acid, as its inorganic salt, and the amine containing active pharmaceutical ingredient, as its free base, are sufficiently soluble as to prevent separation of the components and thus inhibiting direct isolation of the API, as its free base, without additional processing.

In the present invention a drug product can be prescribed and administered in a manner wherein proper administration provides a therapeutic effect and the function of the API is realized. With a different manner of administration, in other words, a non-therapeutic administration of the said API does not enter the bloodstream in an amount sufficient to satisfy the abuser seeking a "high".

A particularly preferred embodiment and method of administering the amine-containing pharmaceutically active compound is by oral dose. The oral dose is prepared by first preparing a drug substance as an BNDO salt of the active compound. The drug substance is then formulated into a carrier matrix to provide an oral dose drug product. The carrier matrix is composed of ingredients (excipients) optionally selected from the group, but not limited to binders, fillers, flow enhancers, surfactants, disintegrants, buffers, and the like, typically employed in the art and found in the "Handbook of Pharmaceutical Excipients", Rowe, Sheskey and Owen (Editors), Fifth Edition, 2006, Pharmaceutical Press (publishers). When the oral dose is ingested the organic salt dissociates under physiological conditions. The organic acid portion of the amine-containing organic acid addition salt, or drug substance, forms the insoluble organic acid while the active compound is liberated and becomes bio-available. Efforts to directly isolate the active compound from the oral dose would be thwarted as described herein.

The present invention is applicable to a variety of drug delivery presentations including solid oral dose, parenteral dosage forms (depo-type products) and by devices and formulations suitable for transdermal delivery and nasal/inhalation administration. It is responsibly acknowledged that many factors may influence the overall pharmacokinetic profile of a drug product. For instance, the particle size distribution of the drug substance may markedly influence drug substance bioavailability. Hence, the optimum practice of this invention, when employed for a specific drug product, must account for the multitude of additional factors. The benefit of the current invention is a means to provide a dominating or controlling factor to prevent abuse while achieving efficacious and therapeutic patient dosages to which refinements, adjustments or modifications can be asserted to yield an optimal response.

In regard to either the 2:1 or 1:1 salts of BNDO, there are two kinetic steps that must occur for the pharmaceutically active ingredient to achieve bio-availability. The drug substance, herein as a BNDO salt, must first be released from the drug product as the drug substance. The drug product may arrive from a variety of dosage preparation techniques, but focusing on a solid oral dose product, the drug substance is formulated with excipients, functional or otherwise, into a dosage formulation matrix. During dissolution testing, or administration of the drug product to a patient, the drug substance must first be released from the drug product matrix. Upon release from the matrix, availability of the active ingredient is dependent upon the dissolution rate of the drug substance from its salt form. For both the drug product, and the drug substance, the kinetic steps of dissolution are media dependent. As a simple example, the enteric coating added to a solid oral dose drug product allows for the passage of the tablet through the acidic conditions of the stomach so as to allow dissolution of the tablet in the small intestine. Upon dissolution of the tablet, the second kinetic step is initiated wherein the drug substance dissolution profile for that environment begins. Interestingly, the development practice has been to provide drug substance salts that are essentially absent any dissolution differentiation to the extent that the drug substance salt is highly soluble over a broad pH range. For such salts, principally mineral acid salts of the amine containing active ingredient, the rate determining step for bioavailability of the active ingredient has been the release of the drug substance from the drug product matrix. In contrast, with the 1:1 BNDO salts a further rate determining step for bioavailability is the dissolution profile of the drug substance. For the BNDO salts, like the mineral acid salts, the drug product formulation matrix can be manipulated to control the kinetic step associated with release of the drug substance from the drug product. With BNDO salts, the kinetics can be manipulated beyond what is available to the mineral acid salts with the advantage of controlling the availability of the active ingredient via the environment of release, and at a slower rate. This feature of drug substance BNDO salts provides a chemical and physical mechanism driven approach to providing abuse deterrent drug substances and drug products.

As a contrasting example, a drug product comprising a mineral acid salt of an opioid wherein the drug substance salt is in a melt extruded oleophilic composition, the rate determining release rate for bioavailability of the active ingredient is first, the diffusion controlled release of hydrophilic drug substance from the hydrophobic formulation matrix. After release from the matrix, the salt is essentially instantaneously soluble—particularly in an aqueous environment. In contrast, a BNDO based drug substance, while compatible with the postulated oleophilic composition, upon release of the drug substance from the drug product, a second dissolution profile may dominate release of the active ingredient prior to the active being bioavailable.

In context of the present discussion, the drug substance BNDO can be further modified to control release rates. The emphasis herein has been the selective preparation of 1:1 amine containing active ingredient: BNDO moiety. However, beyond stoichiometric considerations, the morphological characteristics of these salts also impact release rates. Whereas a 1:1 salt, either as the free carboxylic acid grouping remaining on the BNDO, or present as the carboxylate (i.e. as the alkali carboxylate), may influence drug substance solubility vs. its analogous 2:1 salt, the dissolution profiles of the 1:1 vs. 2:1 salt analogues, (common amine containing active as the BNDO salt just differing in stoichiometric composition), can also vary substantially. Intrinsic dissolution study comparisons allow for a rapid assessment of these differences; thereby the selection of morphology and stoichiometry to fit a pre-determined dissolution profile is available. These selection choices serve as tuning knobs for BNDO drug substance salts which are otherwise unavailable to the comparable mineral acid salts or the simple, highly water soluble organic acid salts such as citrates or (bi)-tartrates.

The BNDO salts of pharmaceutically active compounds, as a 1:1 salt, can be prepared with 0 to 1 mole of a non-hydrogen counterion. At 0 moles of counterions the 1:1 salt is referred to herein as a free carboxyl salt with intermediate ranges referred to as combination of a mixture. A particularly preferred counterion is an alkali metal and preferably sodium. For the purposes of the present invention the counterion may be reported as a ratio, such as 1:1 indicating half a mole of counterion per mole of 1:1 salt of BNDO and pharmaceutically active compound as the concentration of the drug substance with a counterion and the concentration of the drug substance which has a free carboxyl are approximately equal. The amount of counterion, as a molar ratio, is preferably at least 0.1 or the ratio is 9:1 of free carboxyl to counterion, sodium for example. By way of example, a 3:1 mixture of sodium salt would therefore represent 0.75 moles of sodium salt, and 0.25 moles of free carboxyl per mole of drug substance.

For comparative purposes between the prior art and the invention disclosed herein, the haloperidol series of 2:1 and 1:1 pamoates provide a good framework for scope and analysis. Example 1 of U.S. Pat. No. 6,987,111 to Greco et al. was executed according to the procedure described therein. Greco's Example 1 purports to deliver 1:1 haloperidol pamoate salt; however Applicants carefully executed this procedure and explored the reaction sensitivity to various parameters and found that the disclosed process yielded only the 2:1 haloperidol pamoate salt. Unfortunately, Greco provides no analytical characterization for the salt isolated, and thus, no conclusion can be drawn as to the actual compound isolated by Greco other than Greco's procedure did not yield the 1:1 salt. Further, Applicants executed Greco's Example 2 reported for the preparation of 2:1 haloperidol pamoate with the expectation of identifying a possible administrative error where, perhaps, Greco's examples had been mislabeled/reversed for obtaining the 1:1 and 2:1 haloperidol pamoate salts. However, Greco's Example 2 does yield 2:1 haloperidol pamoate salt, but in either an amorphous form, with overnight stirring, or a different polymorphic form, with no stirring and sitting about three days, than that described by Greco, and in any case, the preparation of the 1:1 salt was not resolved. The Greco procedure as written does not provide haloperidol pamoate 1:1. However, applicants definitively obtained specific haloperidol pamoate 1:1 salt(s) with analytical characterization for both an amorphous and polymorphic form according to the procedures described further herein. Besides the preparation and complete characterization of new compounds, the Applicants also evaluated the dissolution properties of each compound to further analytically characterize and differentiate the host of compounds prepared herein.

Figure 83:
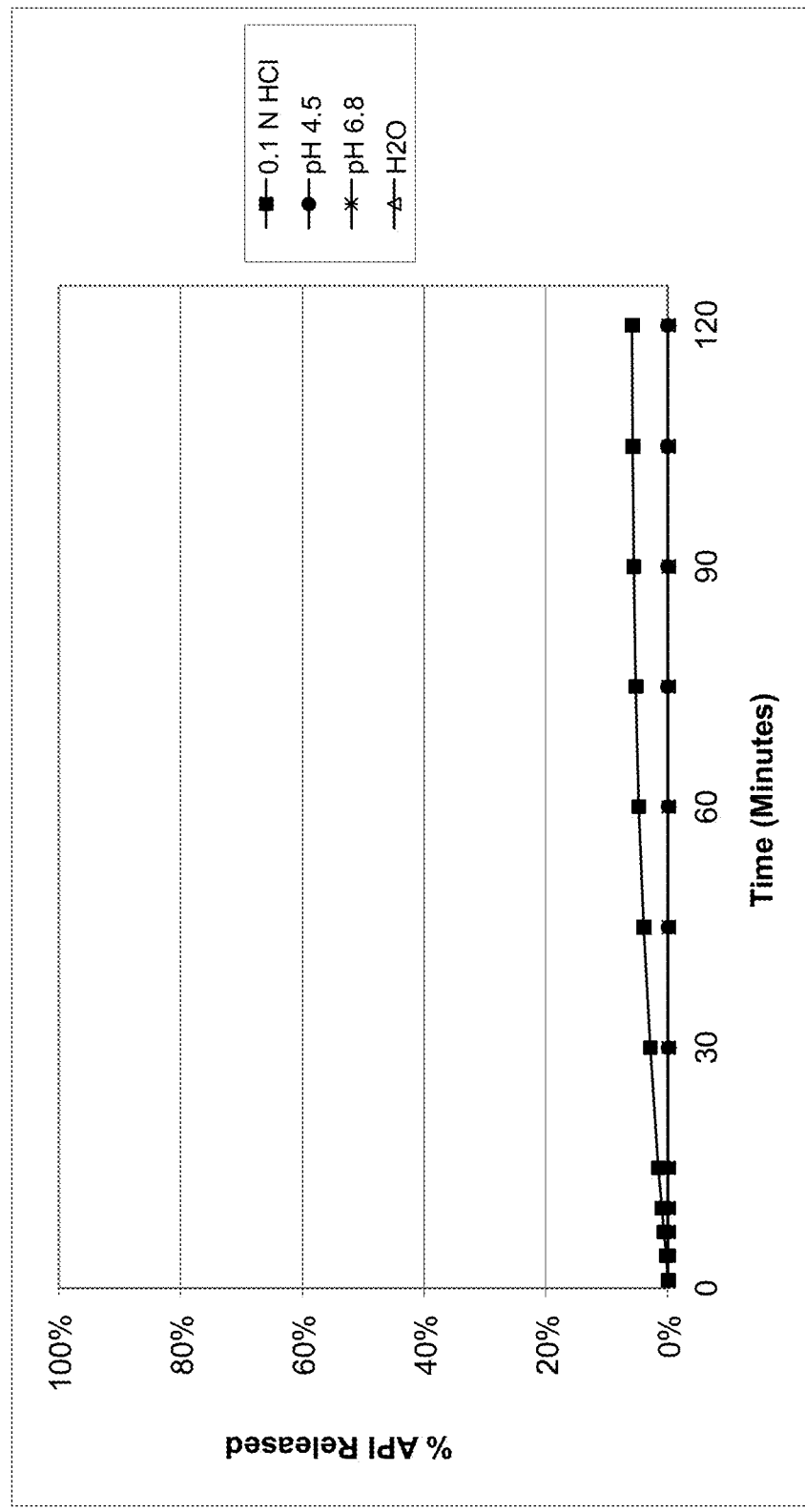
FIG. 83 is the graphical representation of the dissolution profiles for polymorphic haloperidol pamoate 1:1 salt as the free carboxylic acid, first polymorph, as a function of pH.
Figure 84:
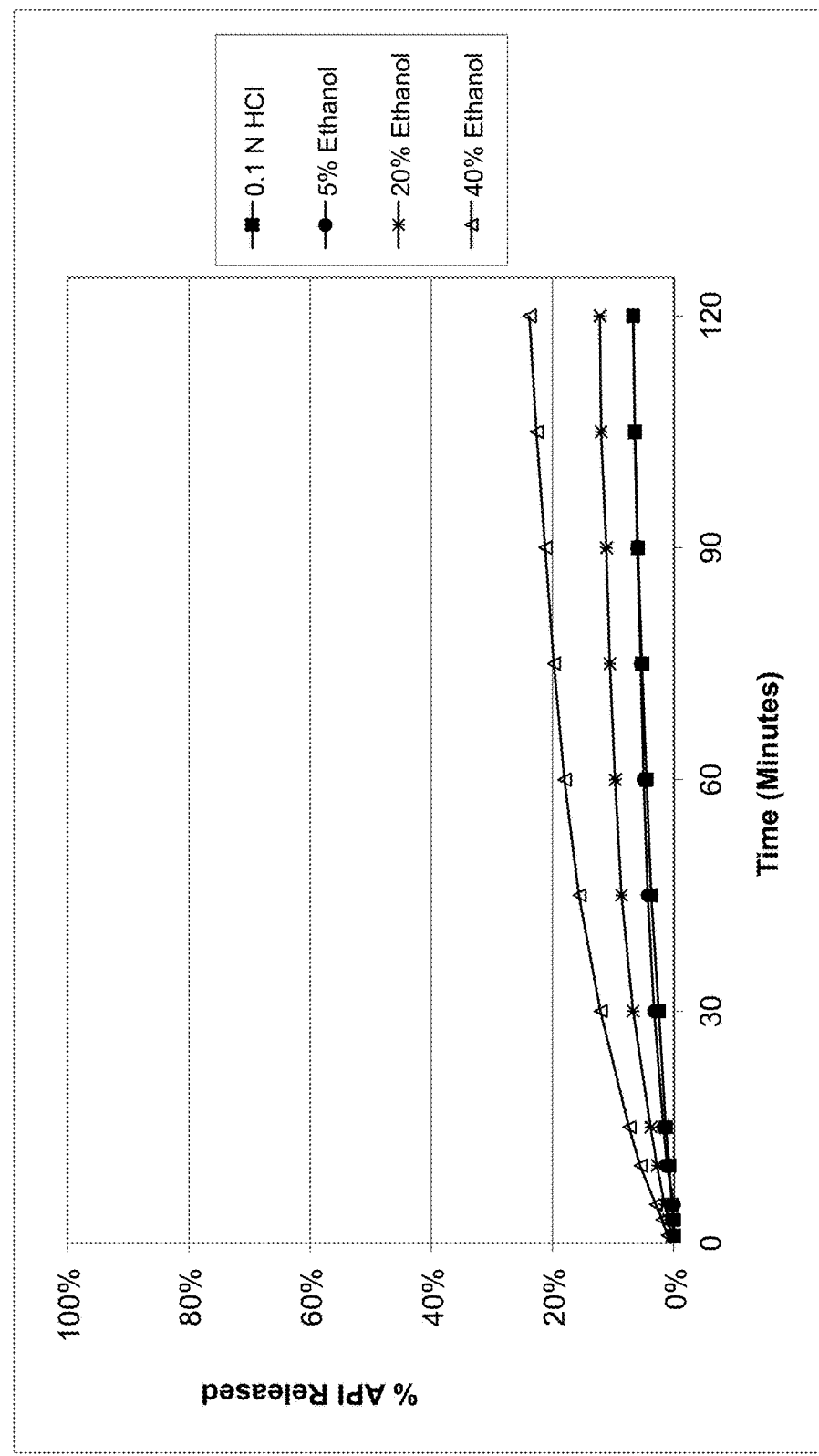
FIG. 84 is the graphical representation of the dissolution profiles for polymorphic haloperidol pamoate 1:1 salt as the free carboxylic acid, first polymorph, as a function of ethanol concentration.
Figure 85:
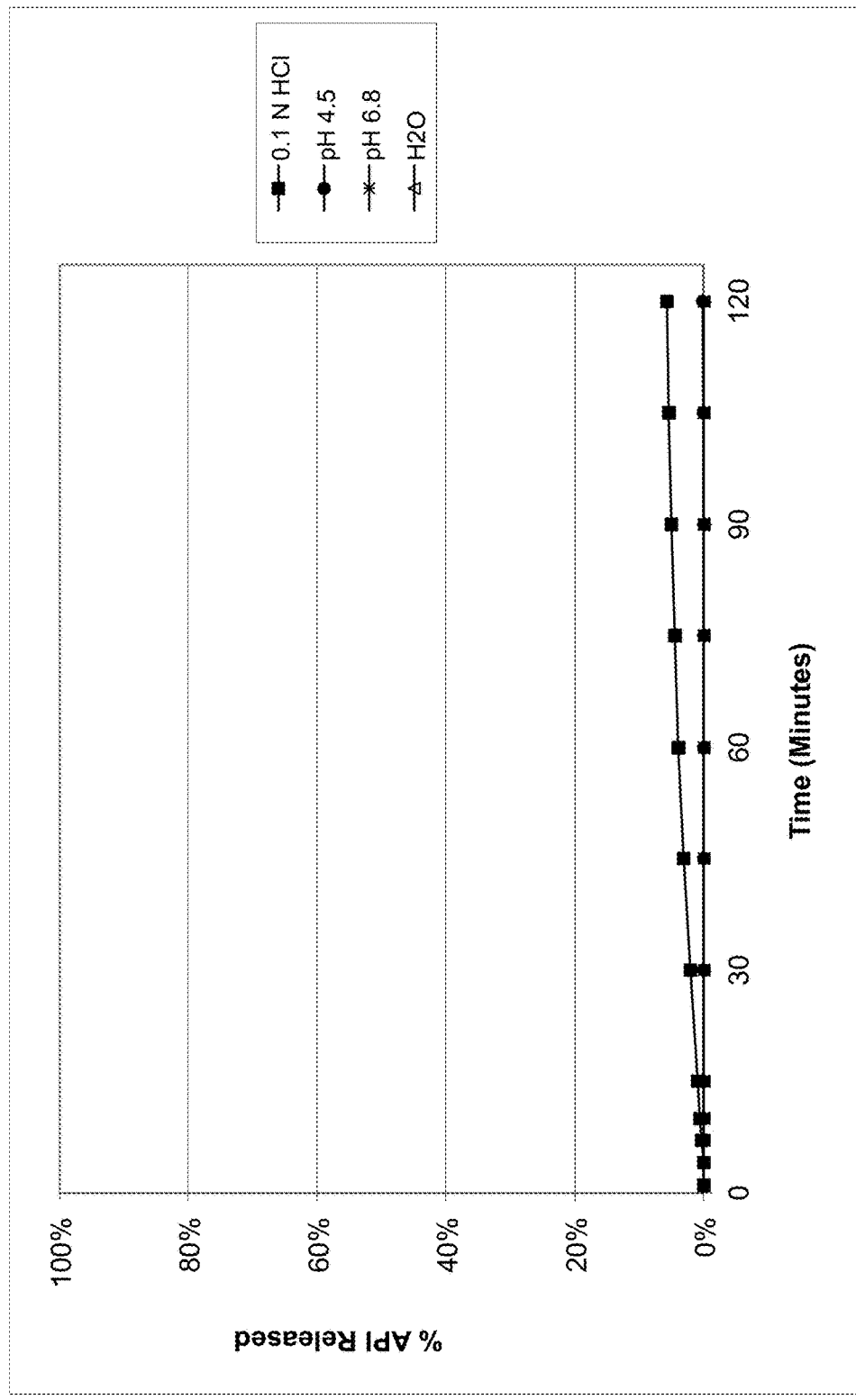
FIG. 85 is the graphical representation of the dissolution profiles for polymorphic haloperidol pamoate 1:1 salt as the free carboxylic acid, second polymorph, as a function of pH.
Figure 86:
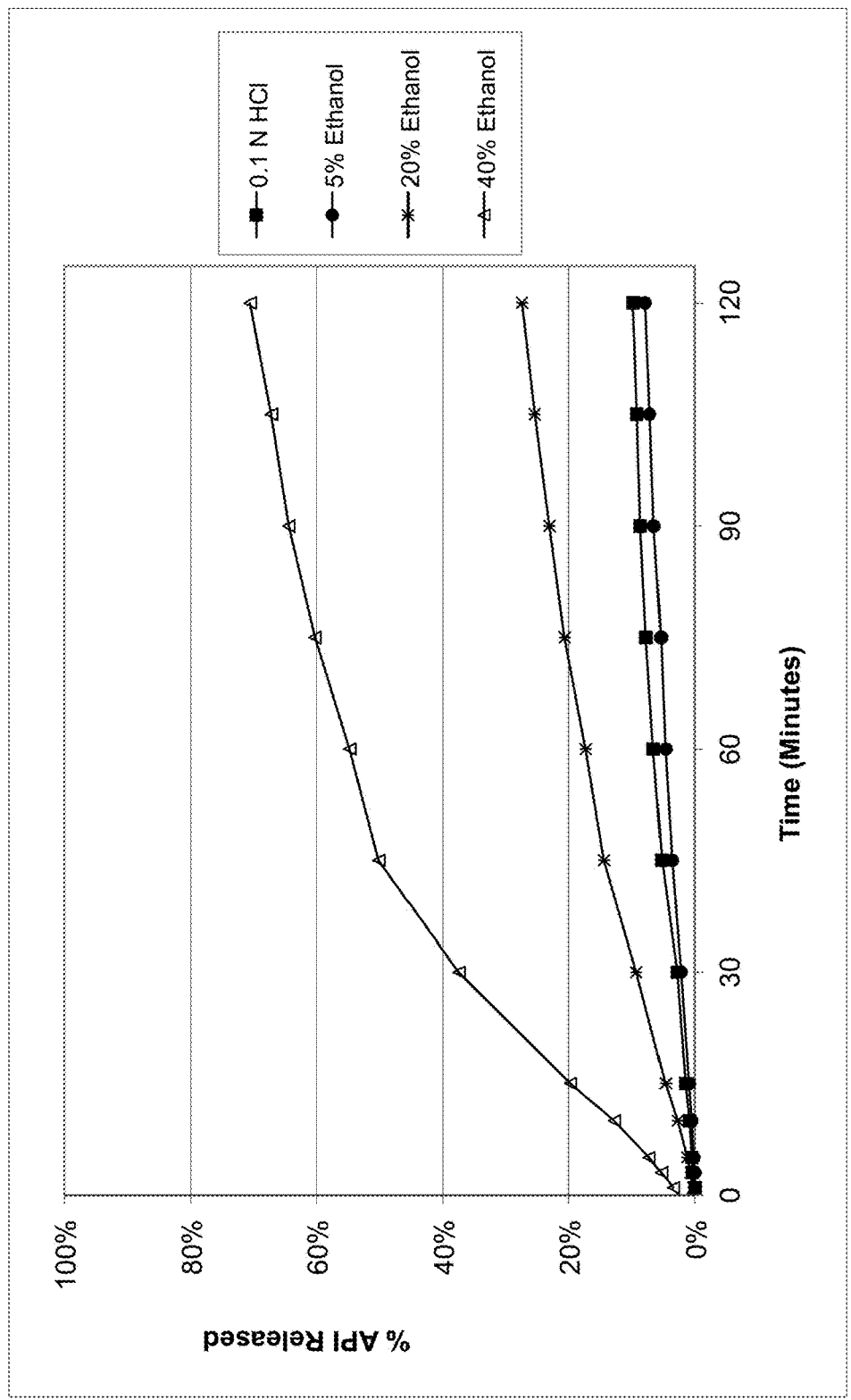
FIG. 86 is the graphical representation of the dissolution profiles for polymorphic haloperidol pamoate 1:1 salt as the free carboxylic acid, second polymorph, as a function of ethanol concentration.
Figure 87:
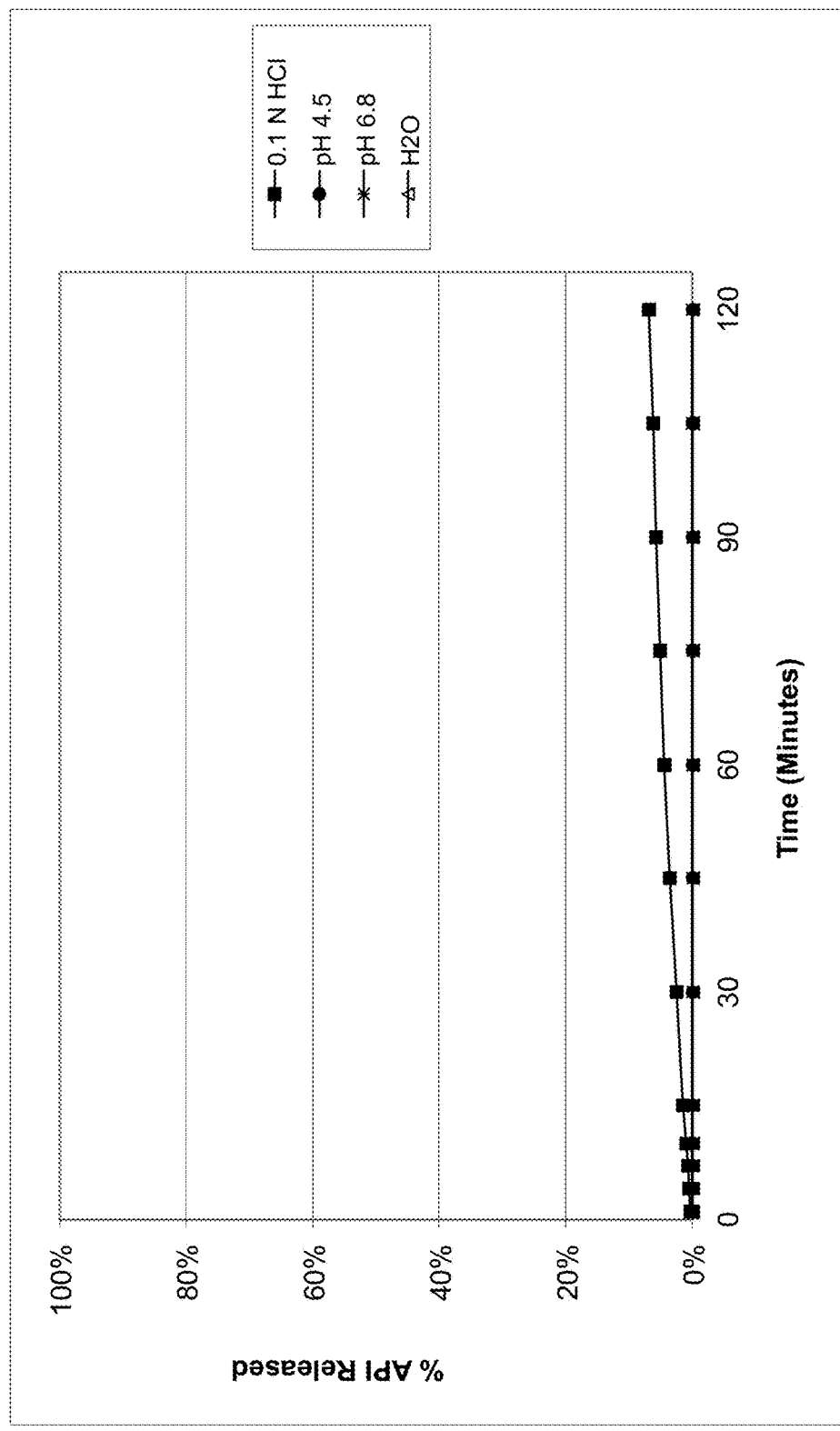
FIG. 87 is the graphical representation of the dissolution profiles for amorphous haloperidol pamoate 1:1 salt as a 3:1 mixture of mono-sodium salt and free carboxylic acid as a function of pH.
Figure 88:
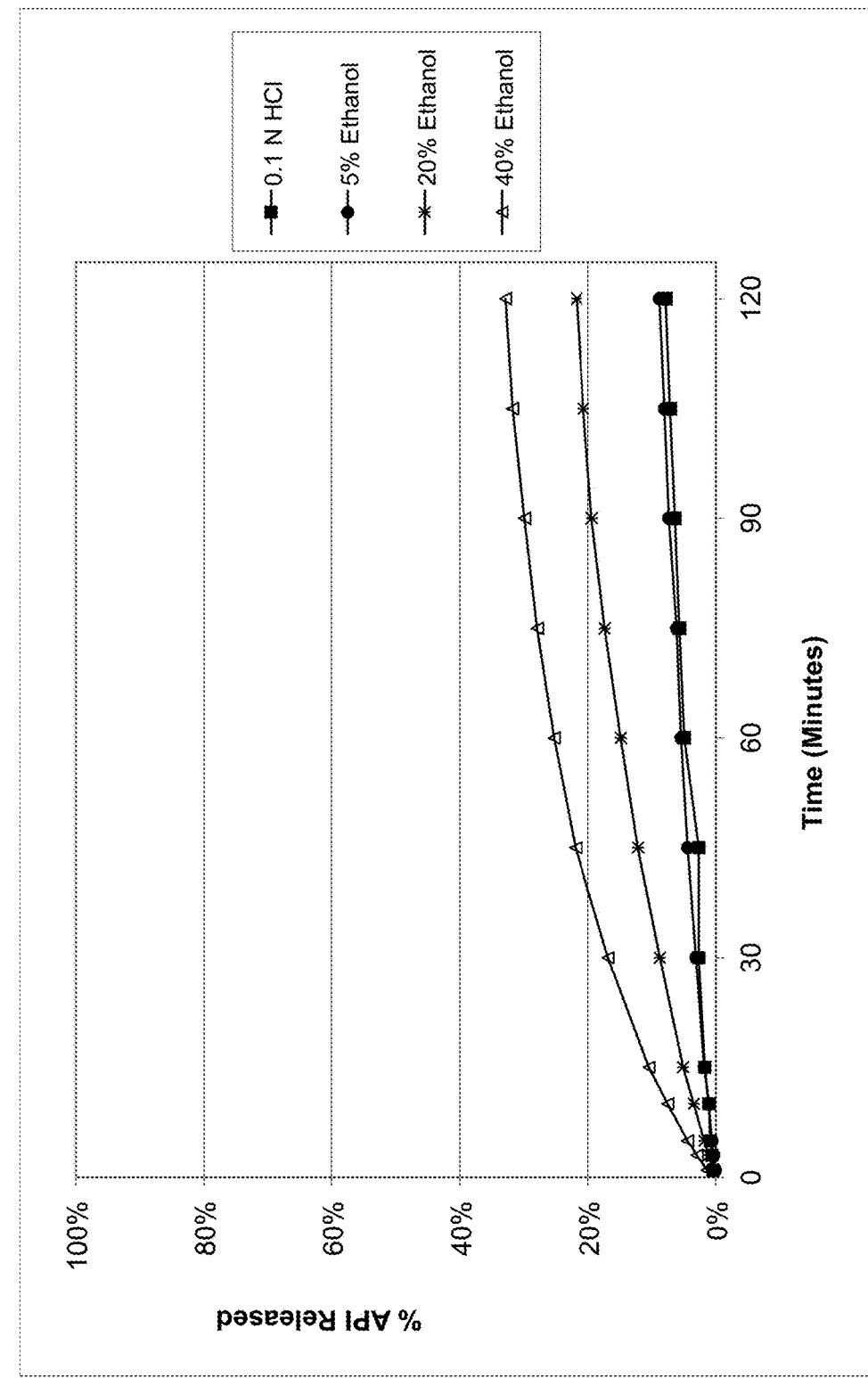
FIG. 88 is the graphical representation of the dissolution profiles for amorphous haloperidol pamoate 1:1 salt as a 3:1 mixture of mono-sodium salt and free carboxylic acid as a function of ethanol concentration.
Figure 107:
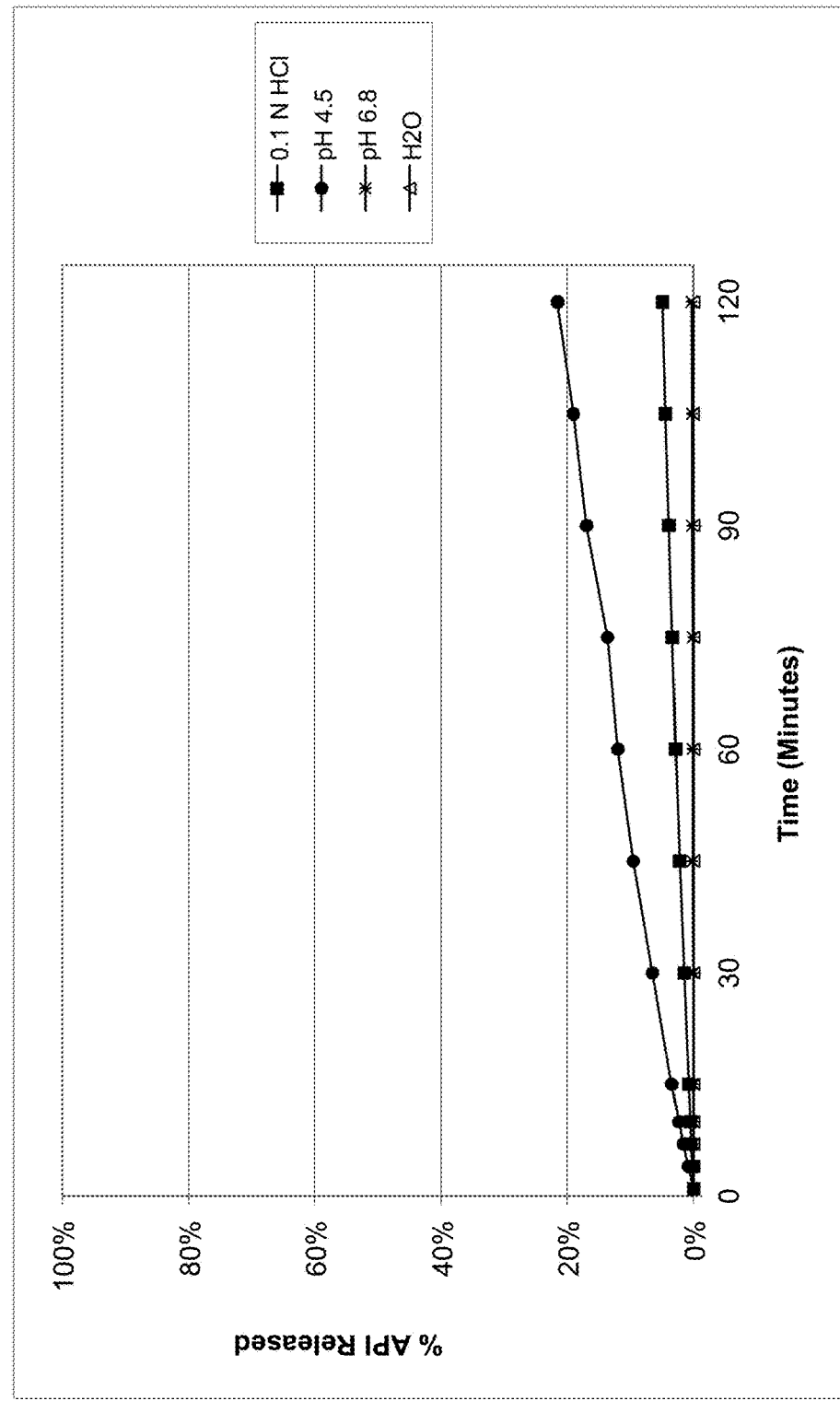
FIG. 107 is the graphical representation of the dissolution profiles for haloperidol base as a function of pH.
Figure 108:
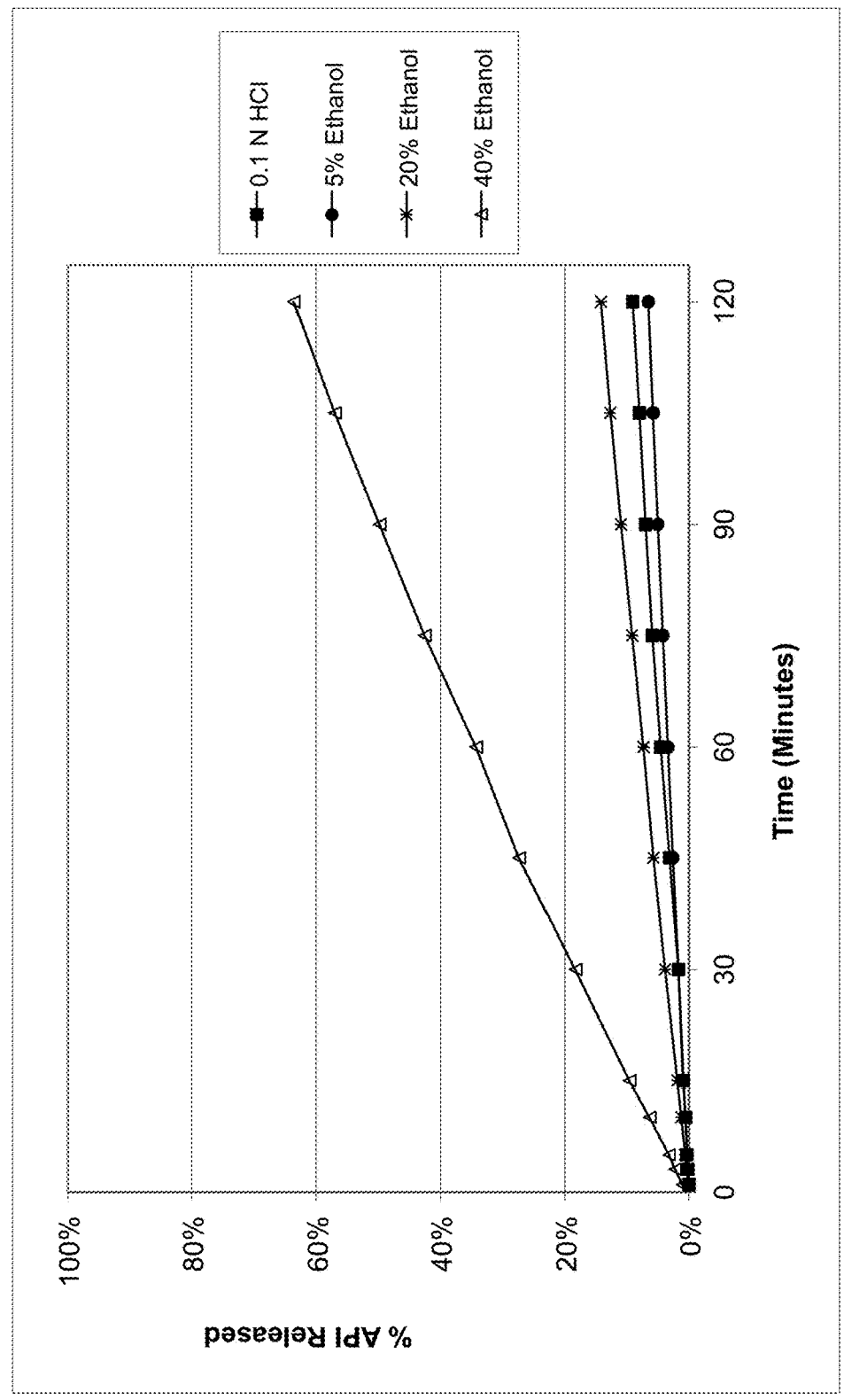
FIG. 108 is the graphical representation of the dissolution profiles for haloperidol base as a function of ethanol concentration.
Figure 109:
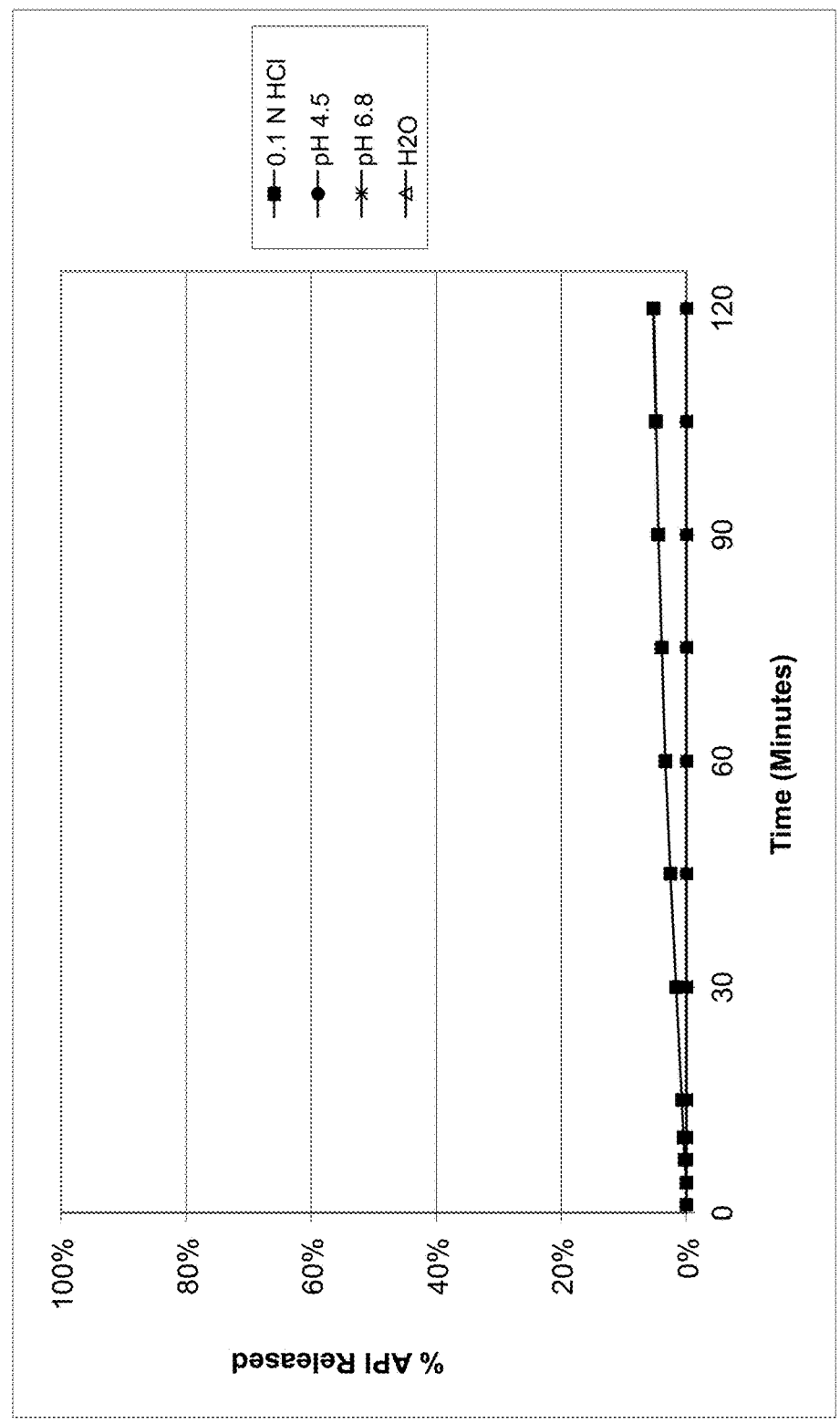
FIG. 109 is the graphical representation of the dissolution profiles for polymorphic haloperidol pamoate 2:1 for attempting to reproduce Greco Patent Example 1 no stirring and sitting about three days as a function of pH.
Figure 110:
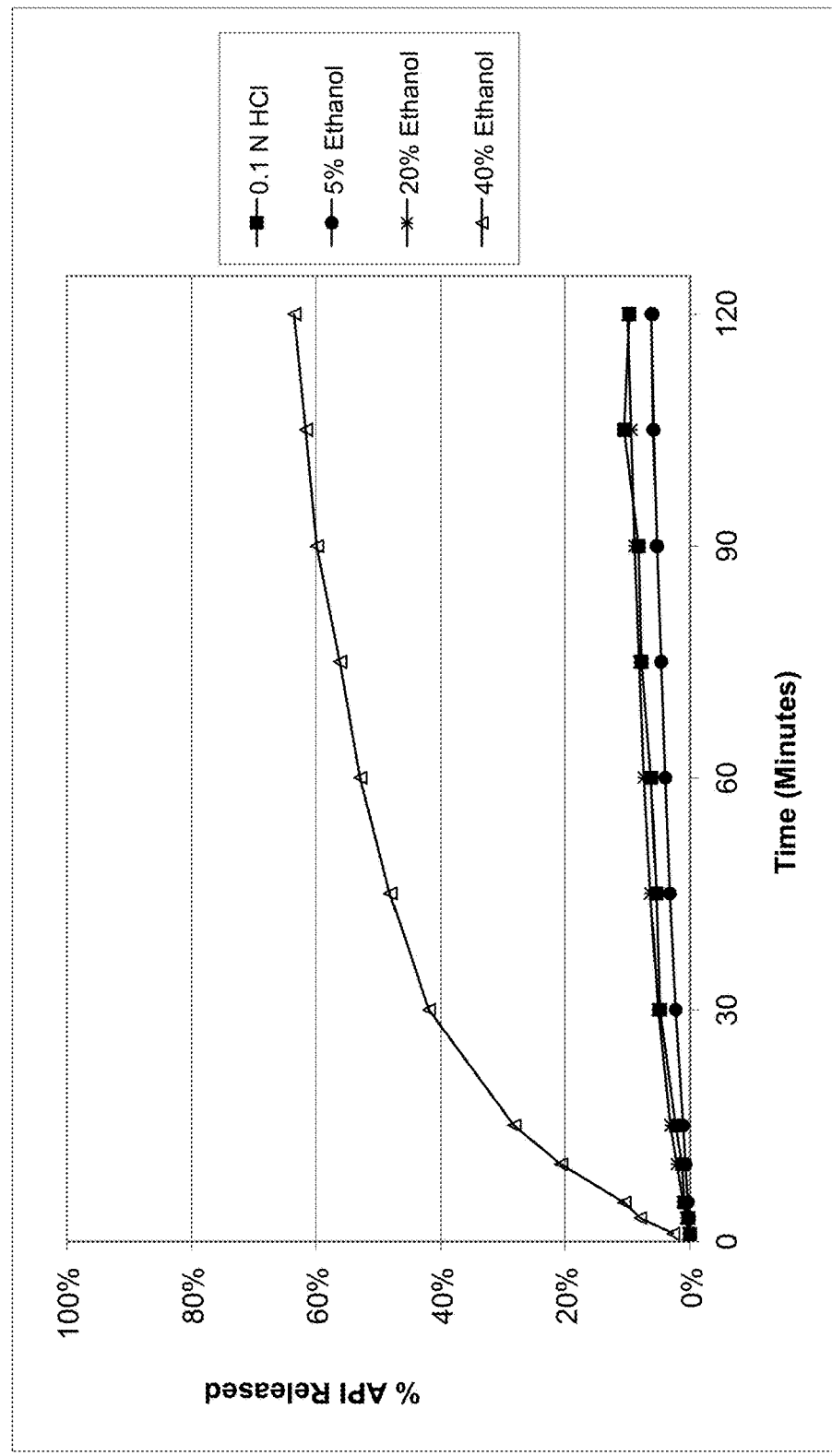
FIG. 110 is the graphical representation of the dissolution profiles for polymorphic haloperidol pamoate 2:1 for attempting to reproduce Greco Patent Example 1 no stirring and sitting about three days as a function of ethanol concentration.
Figure 111:
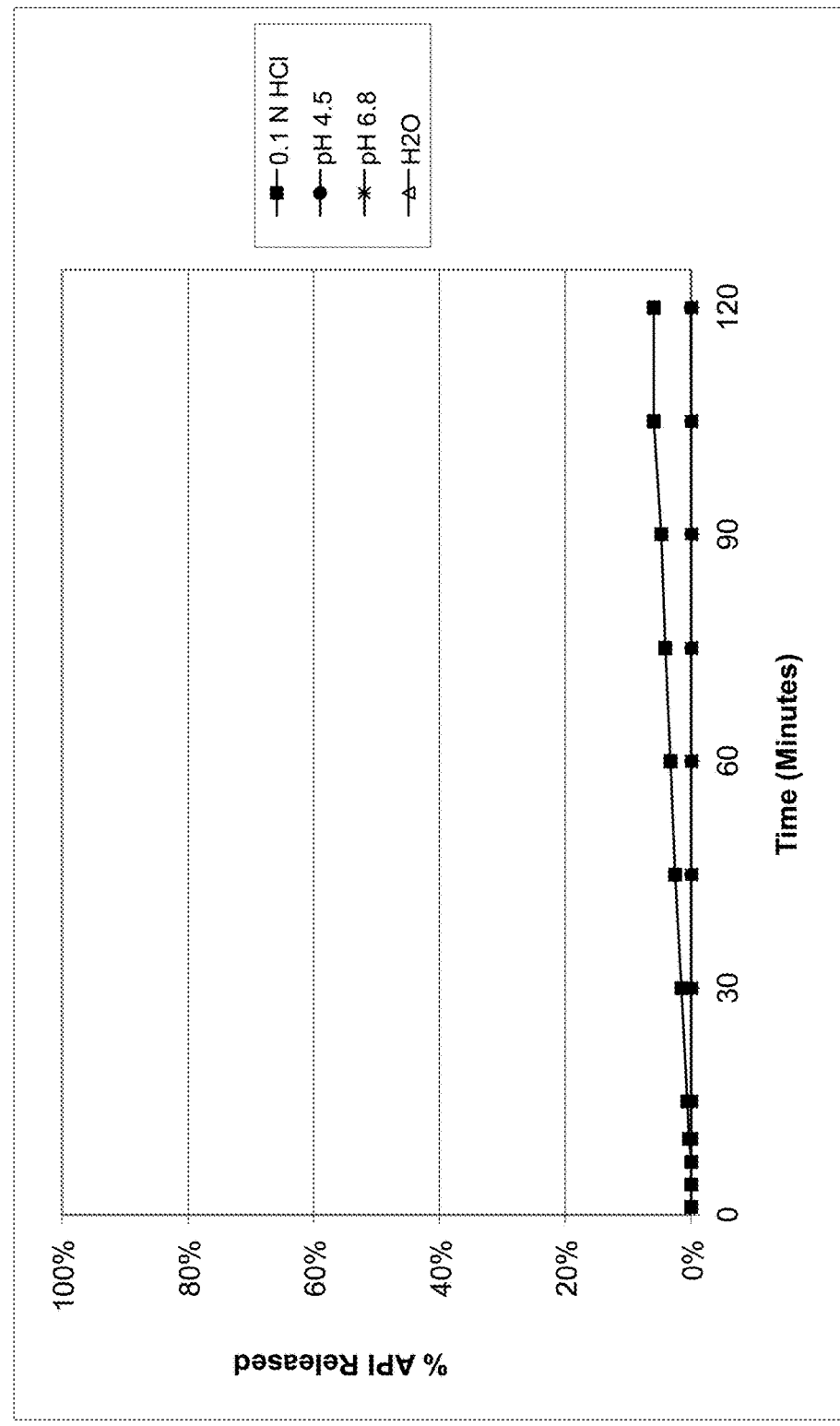
FIG. 111 is the graphical representation of the dissolution profiles for polymorphic haloperidol pamoate 2:1 for attempting to reproduce Greco Patent Example 2 no stirring and sitting about three days as a function of pH.
Figure 112:
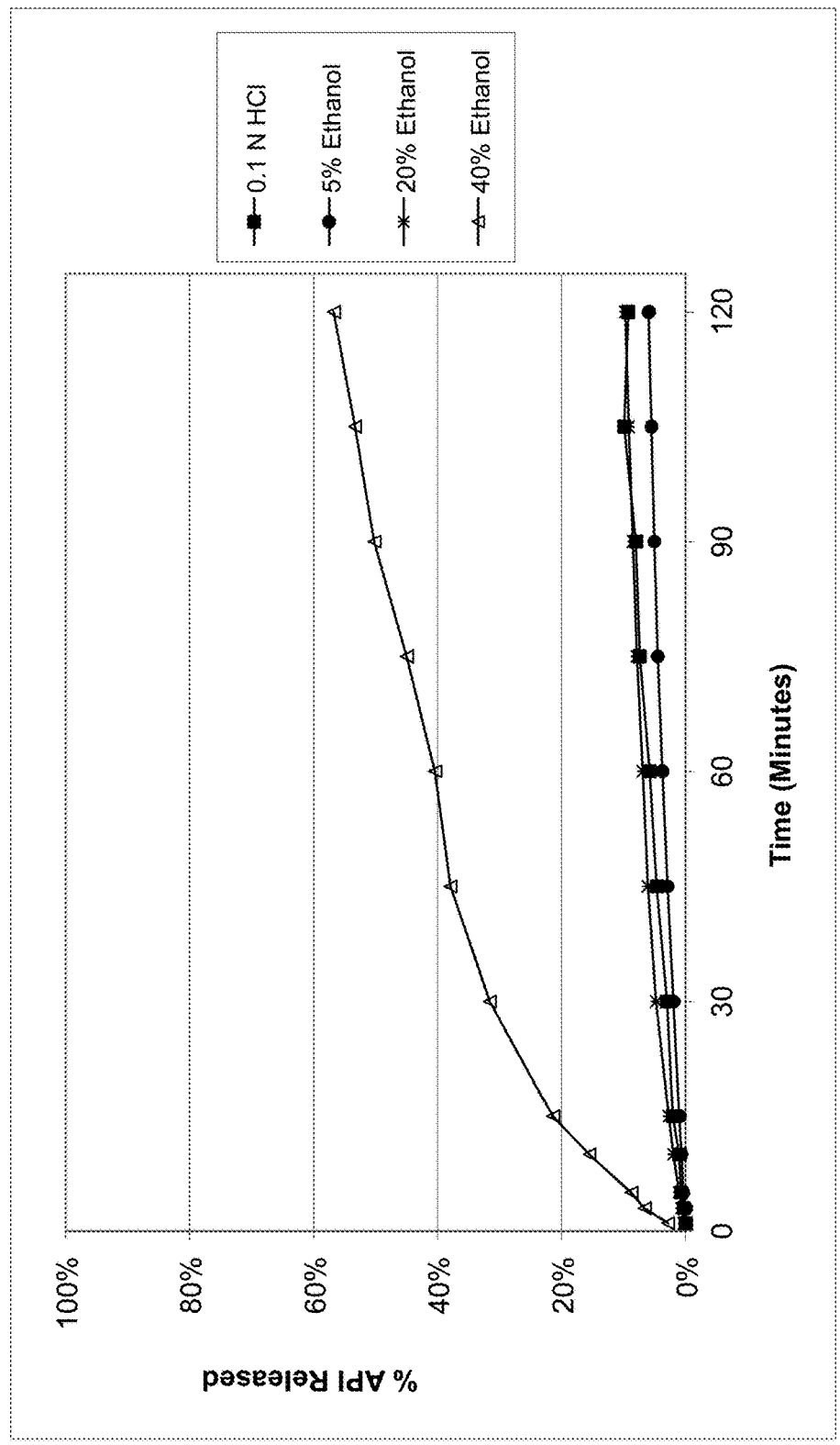
FIG. 112 is the graphical representation of the dissolution profiles for polymorphic haloperidol pamoate 2:1 for attempting to reproduce Greco Patent Example 2 no stirring and sitting about three days as a function of ethanol concentration.

Two types of analytical characterization were performed to evaluate the dissolution properties of the new drug substances for comparison to other salt forms including different salts such as hydrochloride, bitartrate, sulfate, or free base and/or different morphologies such as amorphous vs. polymorphic. Continuing with the haloperidol pamoate series mentioned in the previous paragraph, FIGS. 83 and 84 are the graphical responses of haloperidol pamoate 1:1 salt in its free acid form for pH and dose dumping dissolution studies. These studies indicate that this particular polymorphic haloperidol pamoate first polymorph has little response over the pH range and is not susceptible to dose dumping. Similarly, FIGS. 85 and 86 are the graphical responses to pH and dose dumping studies of the second polymorph of haloperidol pamoate 1:1 salt in its free acid form prepared by an alternate procedure. Here too, this compound has an essentially identical set of dissolution profiles as the first polymorph except that the compound may be slightly more susceptible to dose dumping at the 40% ethanol concentration, but generally not to the extent it would likely be abused by imbibing alcohol. FIGS. 87 and 88 are the pH and dose dumping dissolution profiles for amorphous haloperidol pamoate 1:1 prepared as the approximately 3:1 mixture of mono-sodium salt and free carboxylic acid. Only a modest differentiation is obtained between these polymorphic and amorphous forms of haloperidol 1:1 salt and only in the dose dumping dissolution profiles. Further, it would appear that whether the salt is in a free acid form or its mono-sodium salt analogue, the overall dissolution profile is not appreciably impacted. Comparison of the previously described figures to FIGS. 107 and 108 wherein the pH and dose dumping dissolution profiles of haloperidol base are illustrated, respectively, helps to explain the unexpected observations of previous FIGS. 83-88. Clearly, haloperidol base has only slight solubility, even in 0.1N HCl, and dissolution only improves in the presence of 40% ethanol. Such insolubility overwhelms any differentiation which may have been obtained through haloperidol pamoate in any form of salt. This conclusion is further exemplified by evaluation of FIGS. 109 and 110. The drug substance obtained by Applicants' execution of the Greco Example 1 yielded polymorphic haloperidol pamoate as a 2:1 salt. The pH and dose dumping dissolution profiles of this salt are graphically presented in FIGS. 109 and 110, respectively. Only the 40% acidic ethanol condition led to any significant dissolution. For completeness, Applicants' execution of Greco Example 2, with no stirring and sitting about three days, also yielded polymorphic haloperidol pamoate 2:1 salt and its pH and dissolution profiles were, not surprisingly, comparable to the results obtained for the other polymorphic haloperidol pamoate 2:1 salt as illustrated in FIGS. 111 and 112, respectively. Given that haloperidol base exhibits a very high degree of insolubility under a broad range of pH and solvent conditions, dissolution performance differentiation through the use of a pamoate salt, stoichiometric manipulation, physical form selection, or some variation of free acid, sodium salt or some mixture thereof, had little impact on modifying dissolution results. While the preceding results provide little satisfaction, the effort resolved the gap in the prior art and confirmed Applicants have identified a route to prepare 1:1 pamoate salts which has otherwise been elusive.

Figure 77:
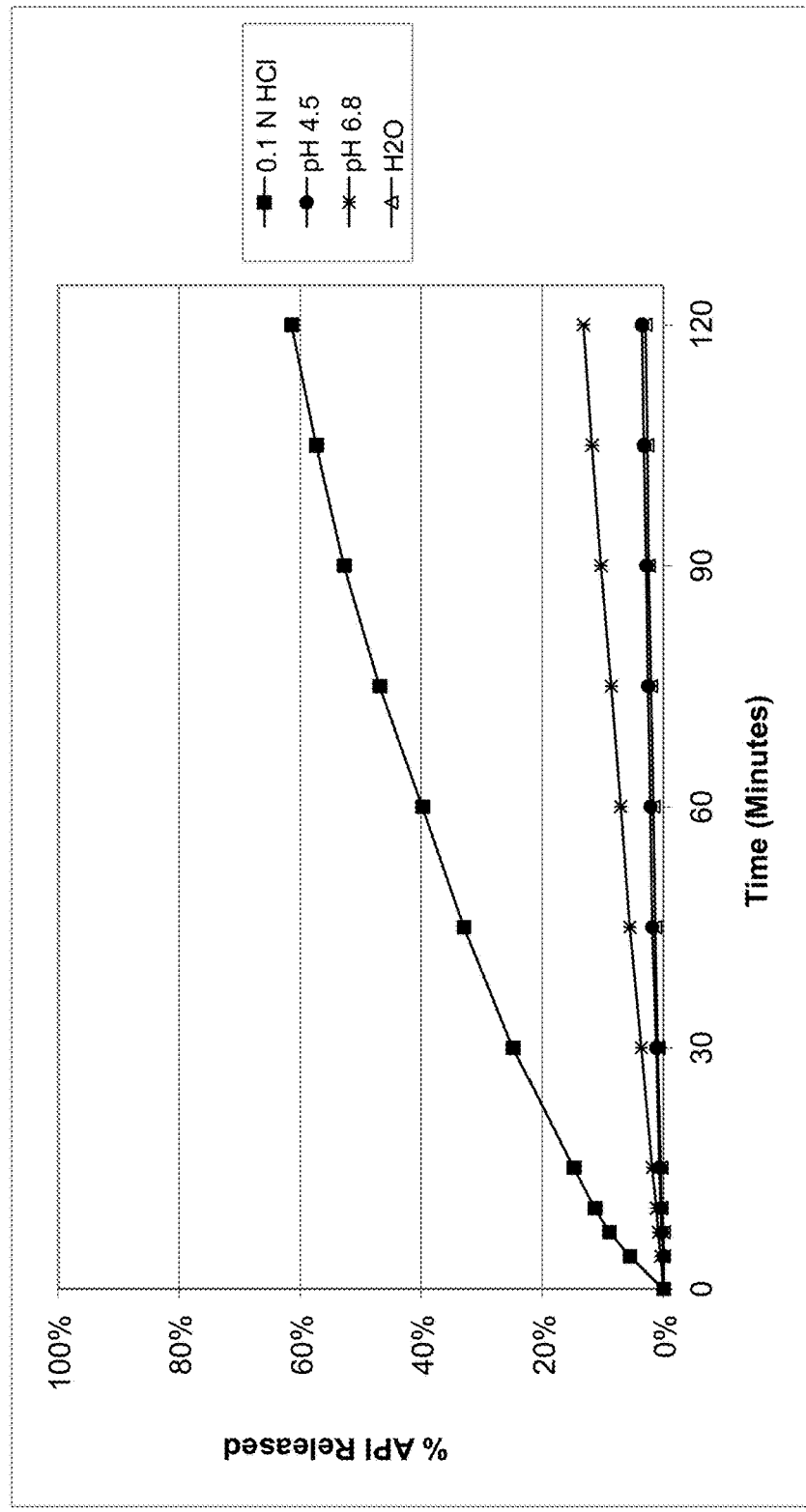
FIG. 77 is the graphical representation of the dissolution profiles for amorphous hydrocodone pamoate 1:1 salt as a 1:1 mixture of mono-sodium salt and free carboxylic acid as a function of pH.
Figure 78:
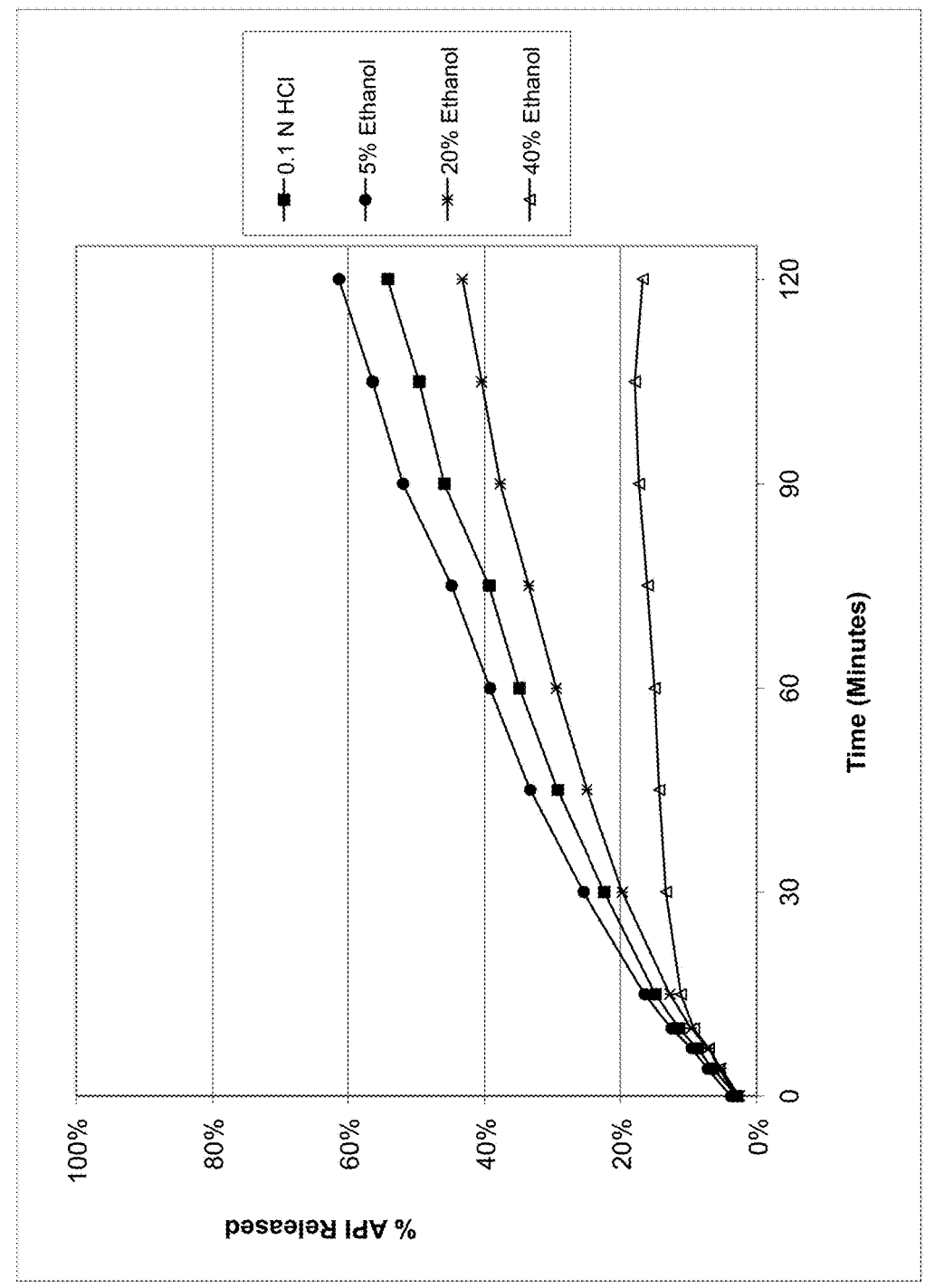
FIG. 78 is the graphical representation of the dissolution profiles for amorphous hydrocodone pamoate 1:1 salt as a 1:1 mixture of mono-sodium salt and free carboxylic acid as a function of ethanol concentration.
Figure 79:
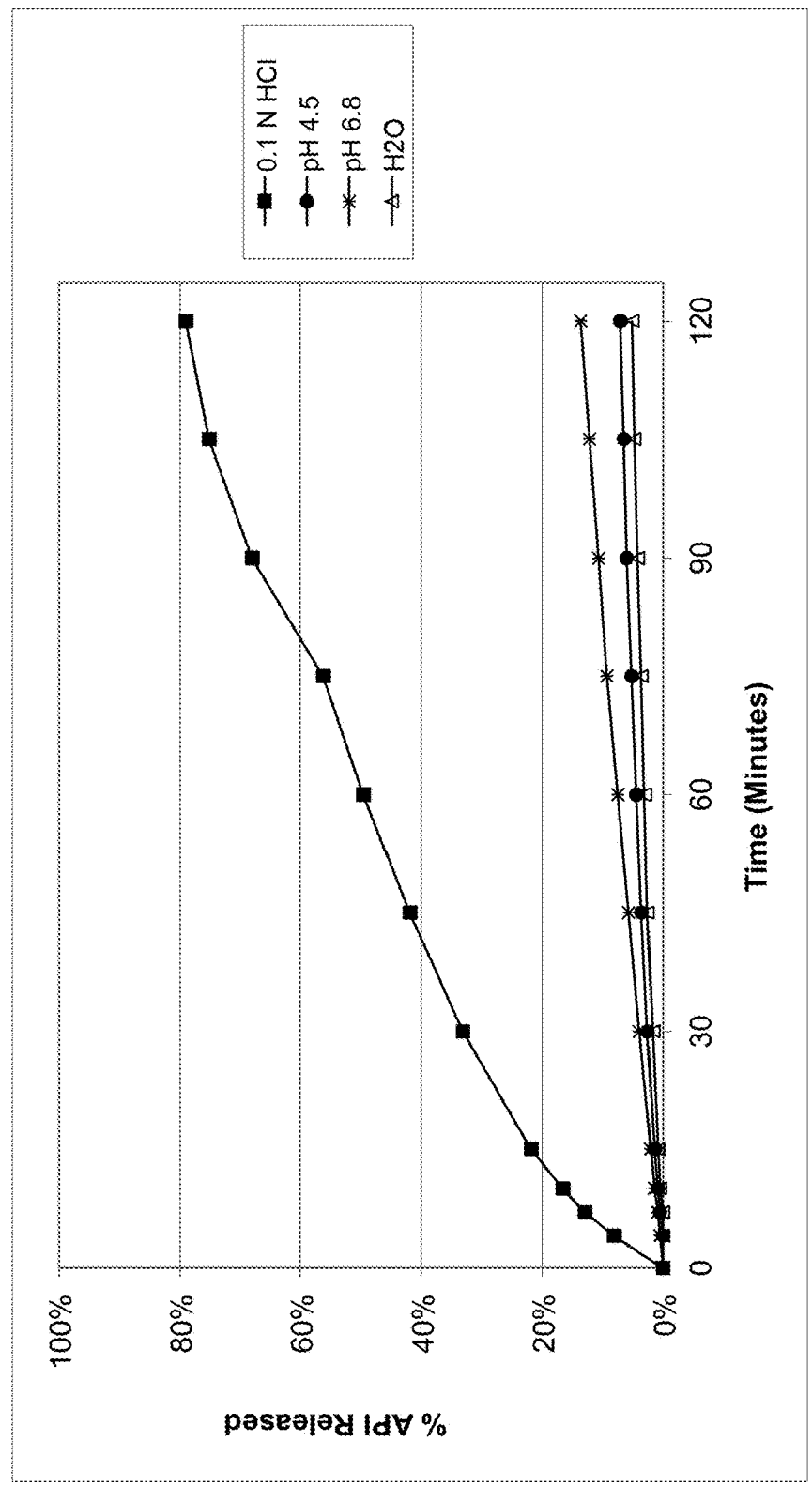
FIG. 79 is the graphical representation of the dissolution profiles for polymorphic hydrocodone pamoate 1:1 salt as the free carboxylic acid as a function of pH.
Figure 80:
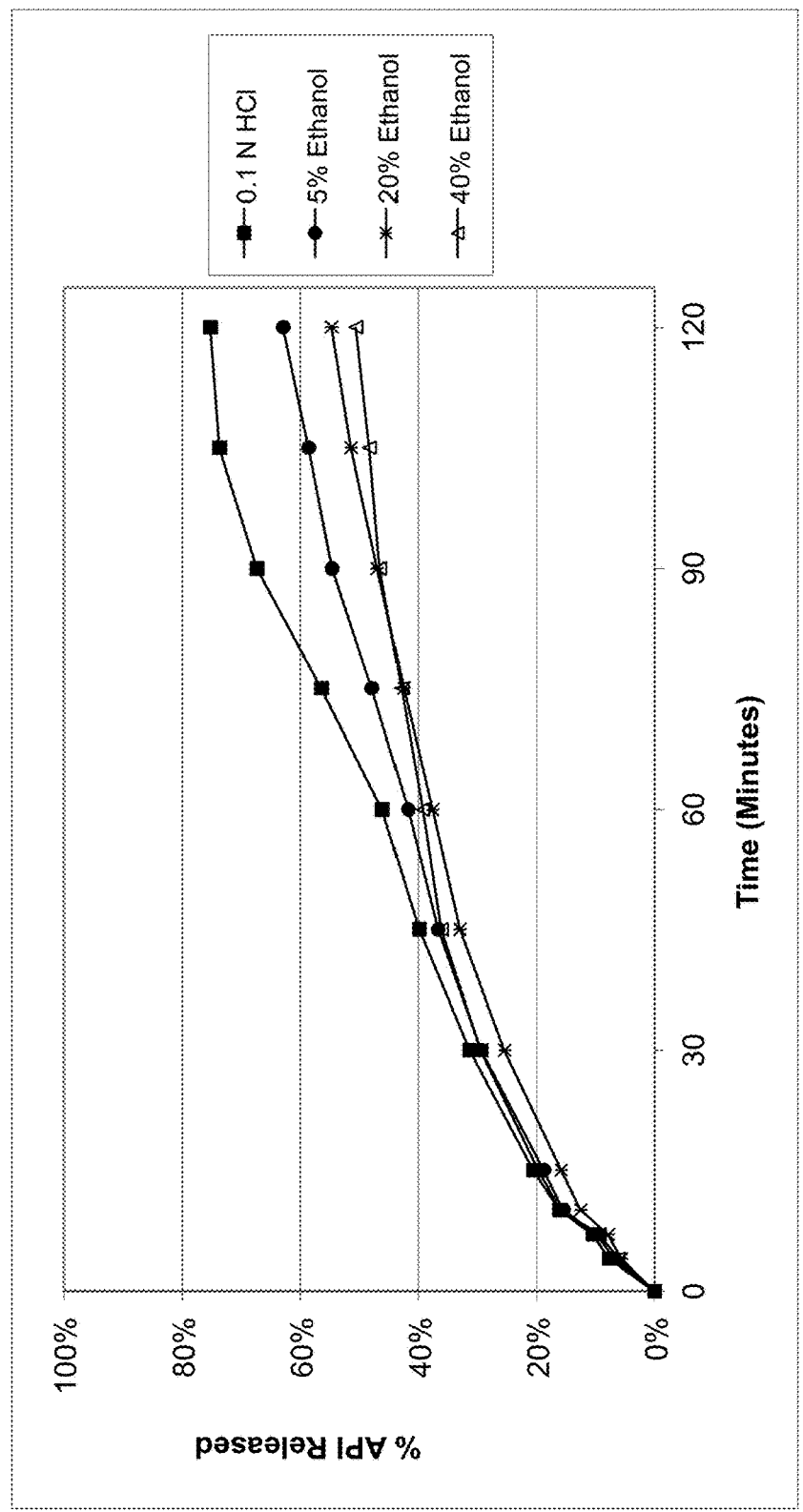
FIG. 80 is the graphical representation of the dissolution profiles for polymorphic hydrocodone pamoate 1:1 salt as the free carboxylic acid as a function of ethanol concentration.

Hydrocodone pamoate 1:1 salt was prepared in its amorphous and polymorphic forms. For demonstration purposes, the amorphous hydrocodone pamoate 1:1 salt was prepared as the 1:1 mixture of free acid and sodium salt. FIGS. 77 and 78 represent the pH and dose dumping dissolution profiles, respectively, of this compound. Both dissolution profiles are quite encouraging in that even the 0.1N HCl dissolution profile indicates a steady, slow release of hydrocodone. Such a release profile would be quite useful for an extended release (ER) drug product formulation without significant reliance on formulation techniques to achieve the attenuated release. By comparison, hydrocodone bitartrate drug products rely exclusively on formulation techniques to achieve such release profiles since hydrocodone bitartrate essentially releases instantaneously under a broad range of pH conditions. Additionally, the 1:1 pamoate salt does not exhibit a tendency to release under neutral and basic conditions. Furthermore, increasing levels of ethanol under acidic conditions generally only decrease the dissolution rate of amorphous hydrocodone pamoate 1:1 salt. These release profiles make this compound an ideal candidate for an extended release or sustained release tamper resistant and abuse deterrent drug product. Similarly, polymorphic hydrocodone pamoate 1:1 salt as the free acid exhibits analogous qualities. FIGS. 79 and 80 are the graphical representation of the pH and dose dumping dissolution profiles, respectively, of the cited pamoate salt. The polymorphic form, contrary to expectation, has a slightly faster rate of dissolution for the 0.1N HCl dissolution condition than the amorphous form which would be expected to have a lower lattice energy to overcome for dissolution. The practical differences between these observed profiles are likely not significant and either drug substance could be used in product formulation. Also, whether the open carboxyl group of the pamoate exists as the free acid or is present as the sodium carboxylate does not appear to be a strong factor in the observed dissolution profiles.

Figure 81:
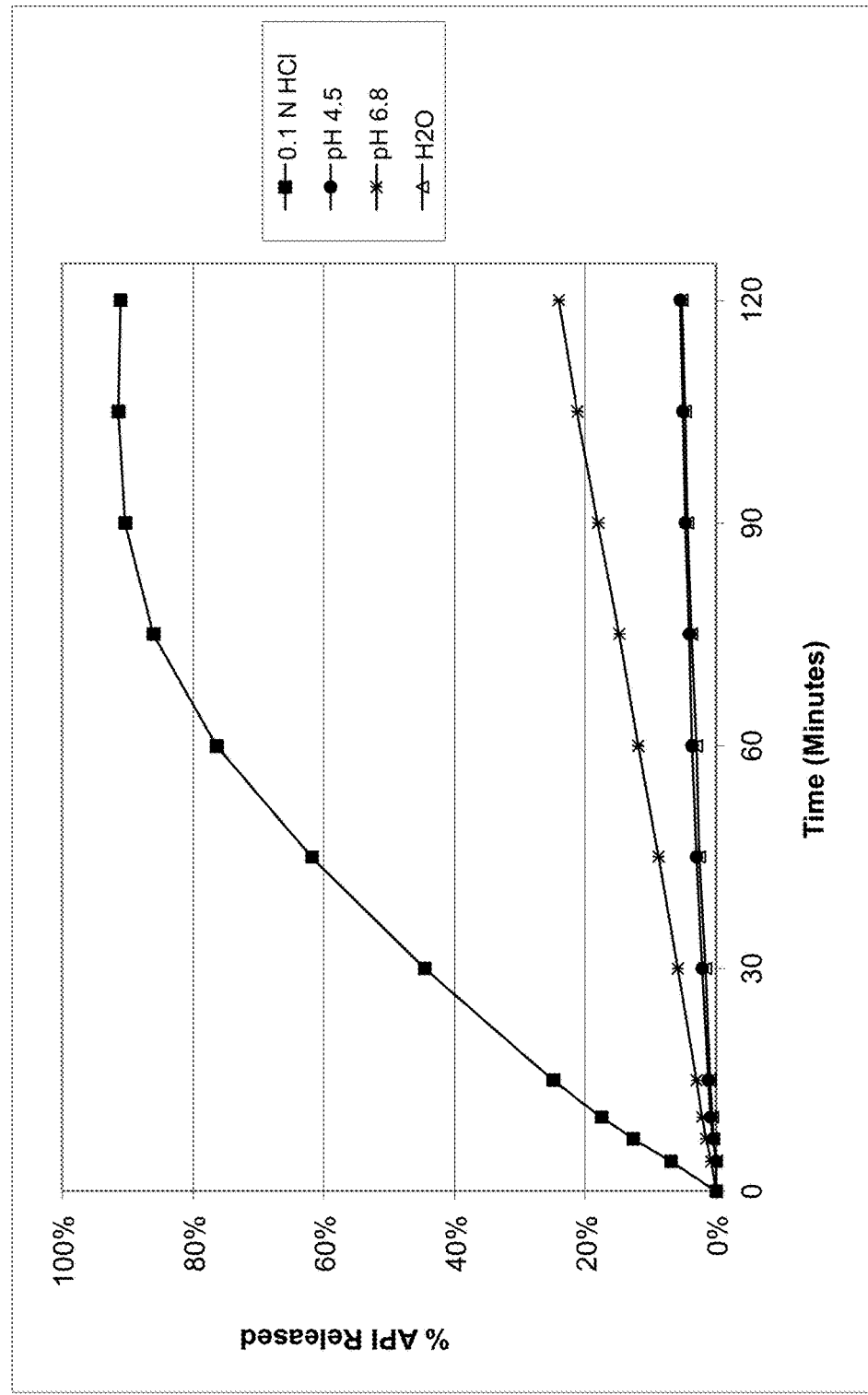
FIG. 81 is the graphical representation of the dissolution profiles for amorphous oxycodone pamoate 1:1 salt as a 1:1 mixture of mono-sodium salt and free carboxylic acid as a function of pH.
Figure 82:
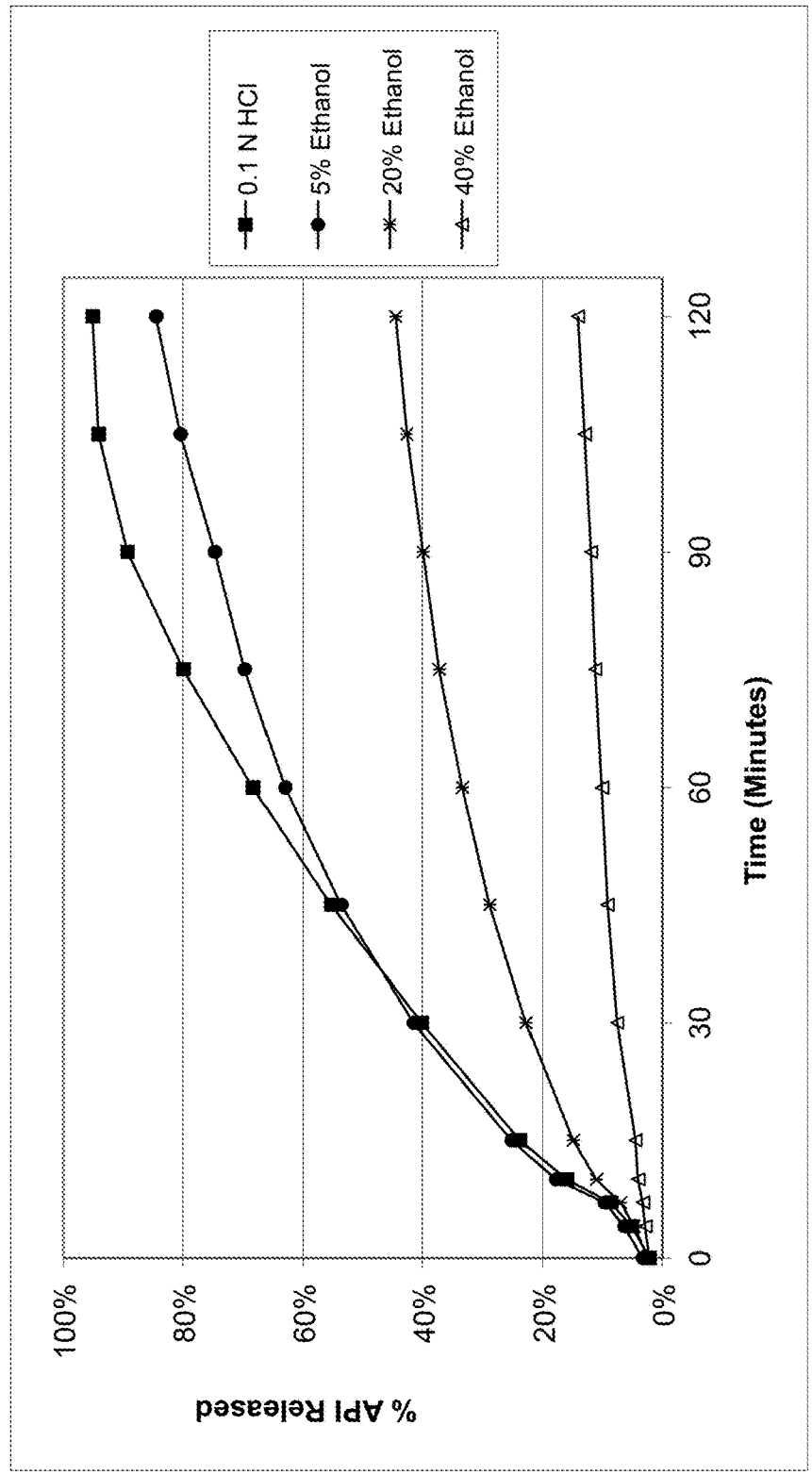
FIG. 82 is the graphical representation of the dissolution profiles for amorphous oxycodone pamoate 1:1 salt as a 1:1 mixture of mono-sodium salt and free carboxylic acid as a function of ethanol concentration.

Amorphous oxycodone pamoate 1:1 salt was prepared as the approximately 1:1 mixture of its free acid and mono-sodium salt. The pH and dose dumping dissolution profiles of this compound are graphically presented in FIGS. 81 and 82, respectively. This salt form of oxycodone pamoate indicates its viability for an extended release tablet formulation since the 0.1N HCl condition indicates no appreciable immediate release propensity, and at high pH levels, only a very slow release is observed. In addition, the salt shows no dose dumping response to increased ethanol concentrations in acidic media.

Figure 89:
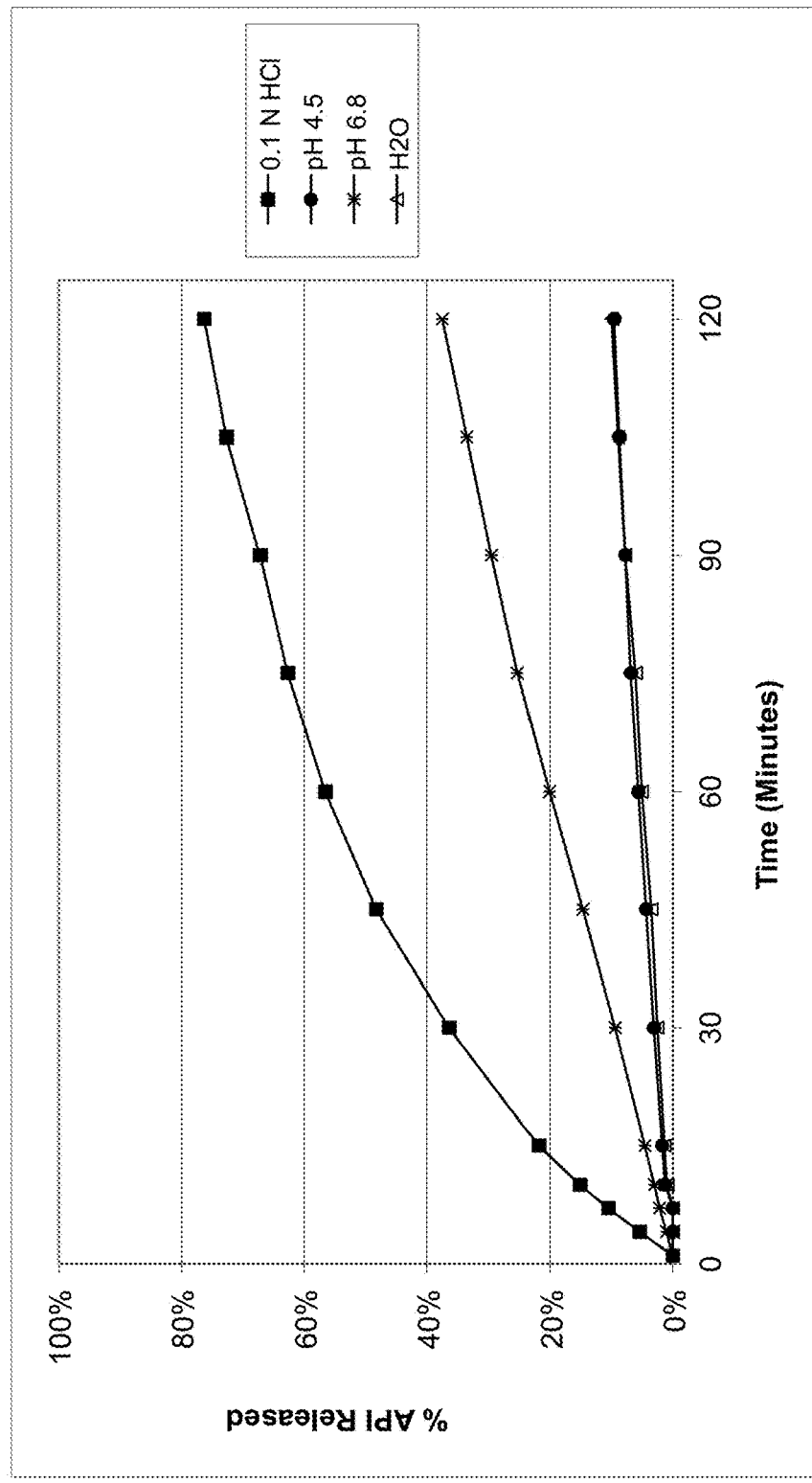
FIG. 89 is the graphical representation of the dissolution profiles for amorphous morphine pamoate 1:1 salt as the 1:1 mixture of mono-sodium salt and free carboxylic acid as a function of pH.
Figure 90:
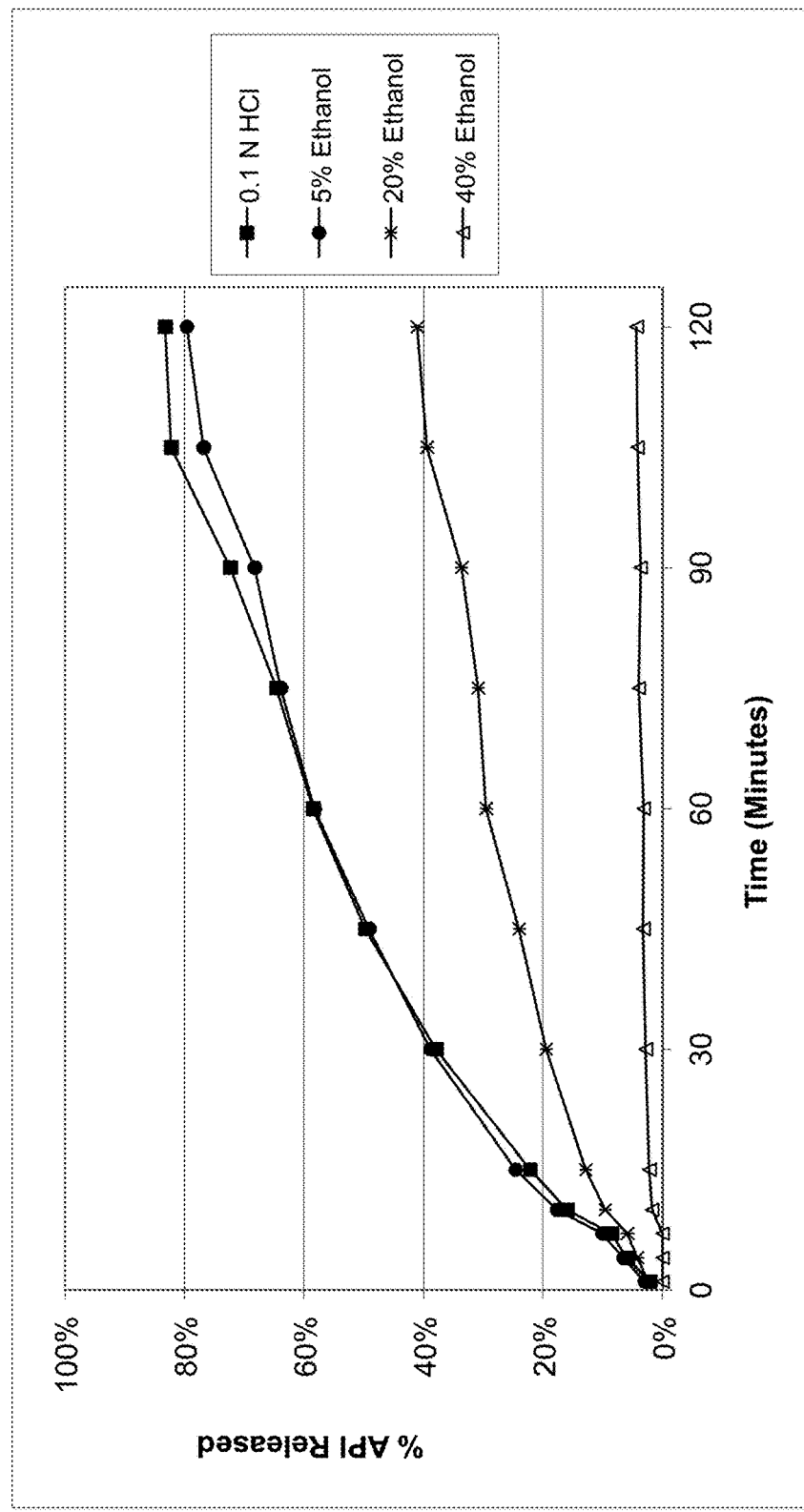
FIG. 90 is the graphical representation of the dissolution profiles for amorphous morphine pamoate 1:1 salt as the 1:1 mixture of mono-sodium salt and free carboxylic acid as a function of ethanol concentration.

Amorphous morphine pamoate 1:1 salt was prepared as the approximately 1:1 mixture of its free acid and mono-sodium salt. The pH and dose dumping dissolution profiles of this morphine organic acid addition salt showed great promise in extended release drug product formulations based on its intrinsic dissolution profile. The pH dissolution response for the amorphous morphine derivative is graphically presented in FIG. 89. Under acidic conditions, the morphine component gradually releases from its salt form, while at higher pH, the release of the active is quite slow. Similarly, the dose dumping dissolution profile for the morphine adduct is presented graphically in FIG. 90. Amorphous morphine pamoate 1:1 does not exhibit dose dumping and increasing concentrations of ethanol under acidic conditions does not promote the release of morphine from the salt form. For this salt, or for any other BNDO salt herein disclosed, there is inhibition of dose dumping as analytically evaluated, and one could consequently expect oral administration of a formulated product would enter the acidic environment of the stomach and the presence of alcohol would not accelerate the dissolution of the active from its salt form.

Figure 91:
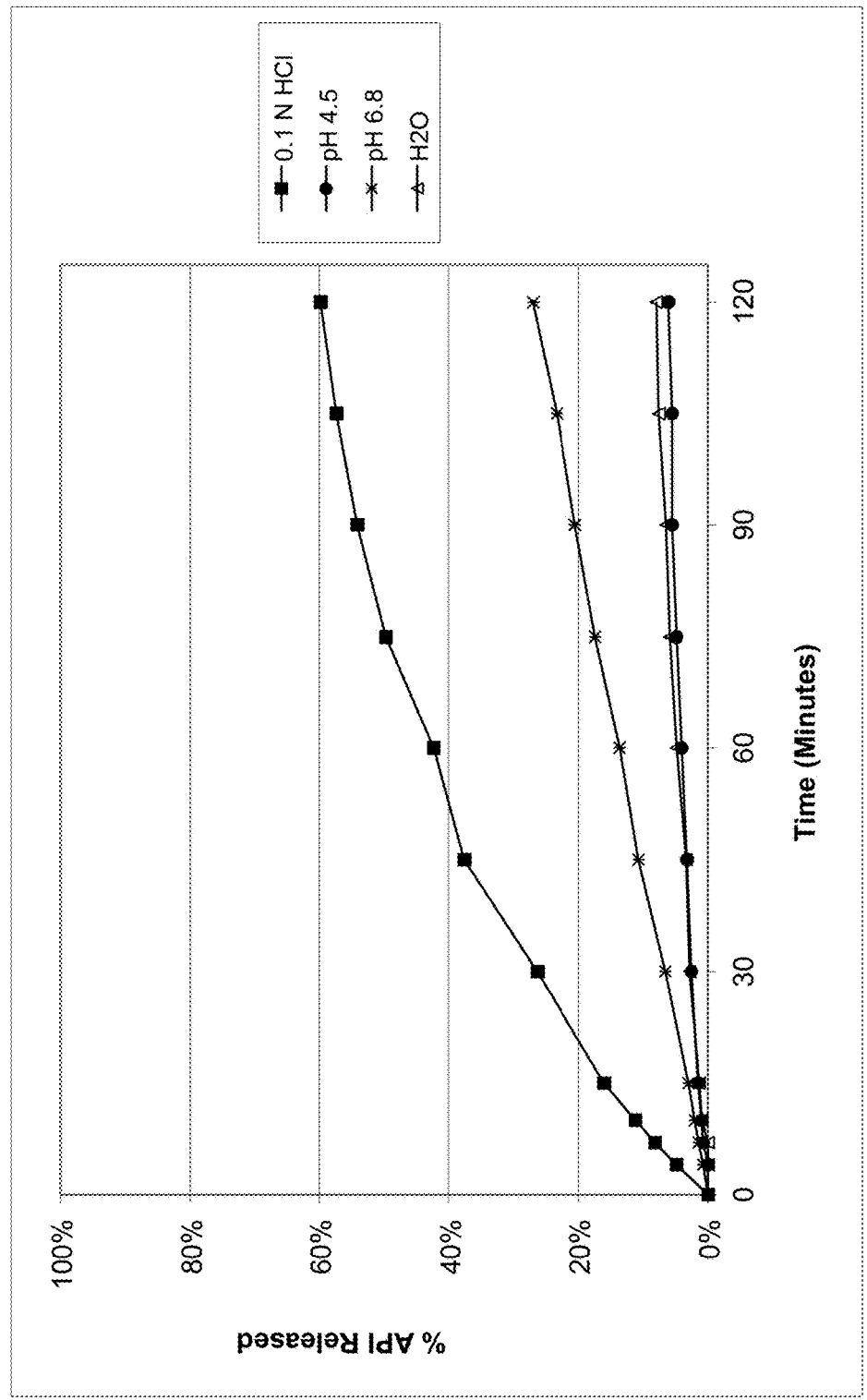
FIG. 91 is the graphical representation of the dissolution profiles for amorphous oxymorphone pamoate 1:1 salt as a 1:1 mixture of mono-sodium salt and free carboxylic acid as a function of pH.
Figure 92:
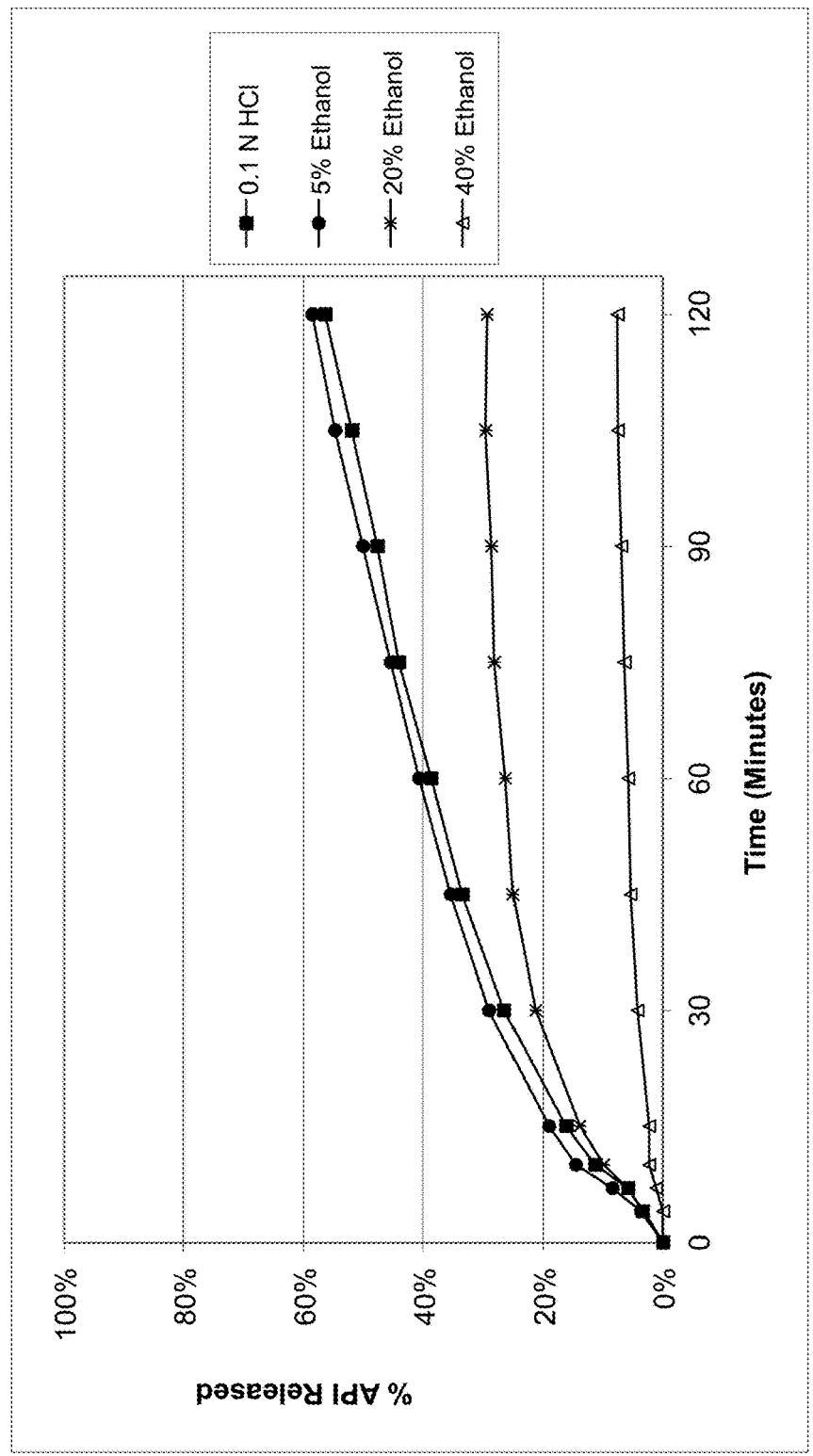
FIG. 92 is the graphical representation of the dissolution profiles for amorphous oxymorphone pamoate 1:1 salt as a 1:1 mixture of mono-sodium salt and free carboxylic acid as a function of ethanol concentration.

FIG. 91 represents the graphical presentation of the pH dissolution profile of amorphous oxymorphone pamoate 1:1 salt as an approximately 1:1 mixture of its free acid and mono-sodium salt. FIG. 92 summarizes the dose dumping dissolution profile of this oxymorphone derivative. It is clear from the experimental data that a dissolution trend can be established for the 1:1 pamoate salts of opiates. For the oxymorphone salt, acidic conditions provide for a slow, sustained release of oxymorphone from its salt form, and the compound exhibits no propensity for dose dumping.

Figure 93:
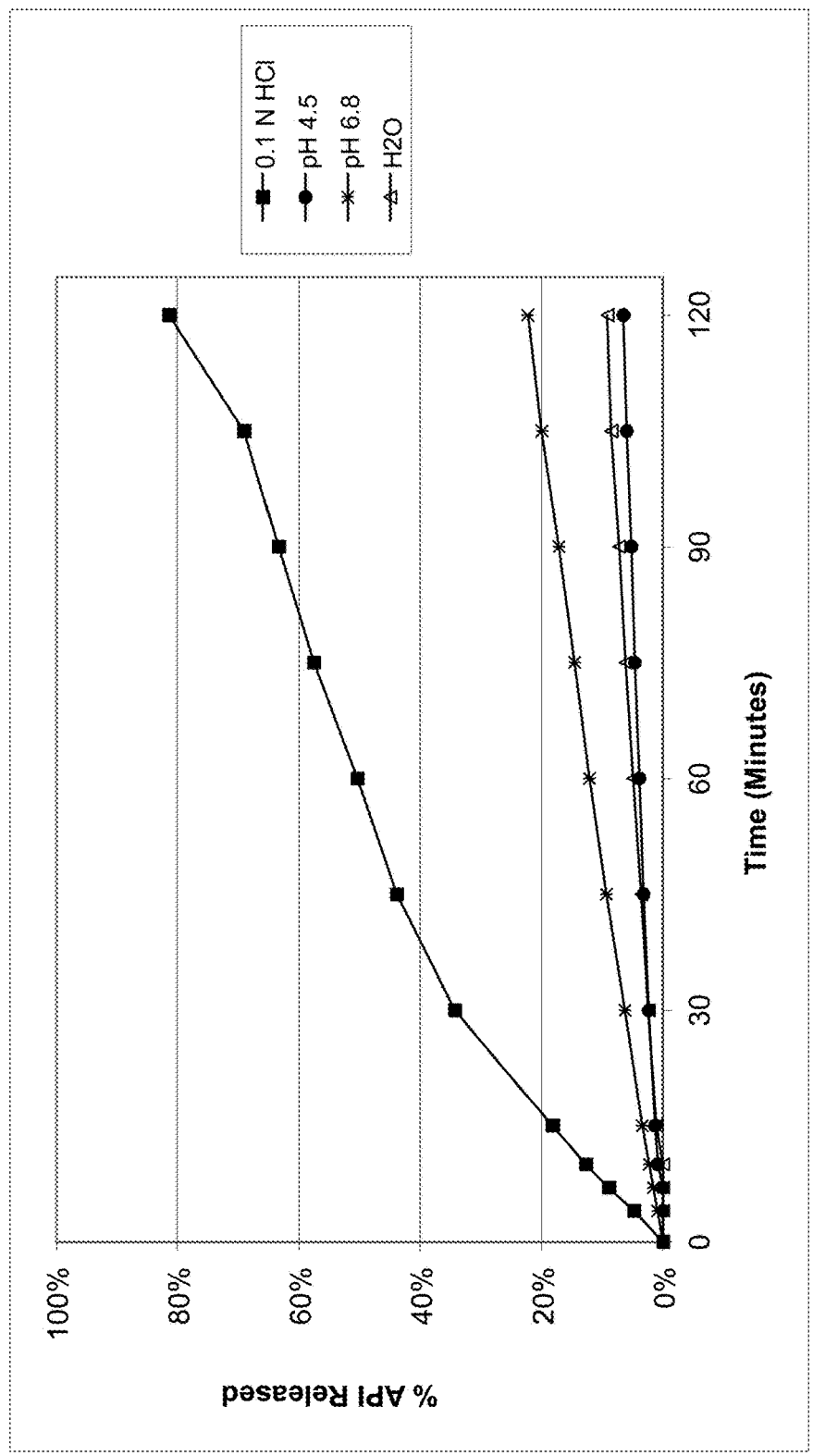
FIG. 93 is the graphical representation of the dissolution profiles for amorphous codeine pamoate 1:1 salt as a 1:1 mixture of mono-sodium salt and free carboxylic acid as a function of pH.
Figure 94:
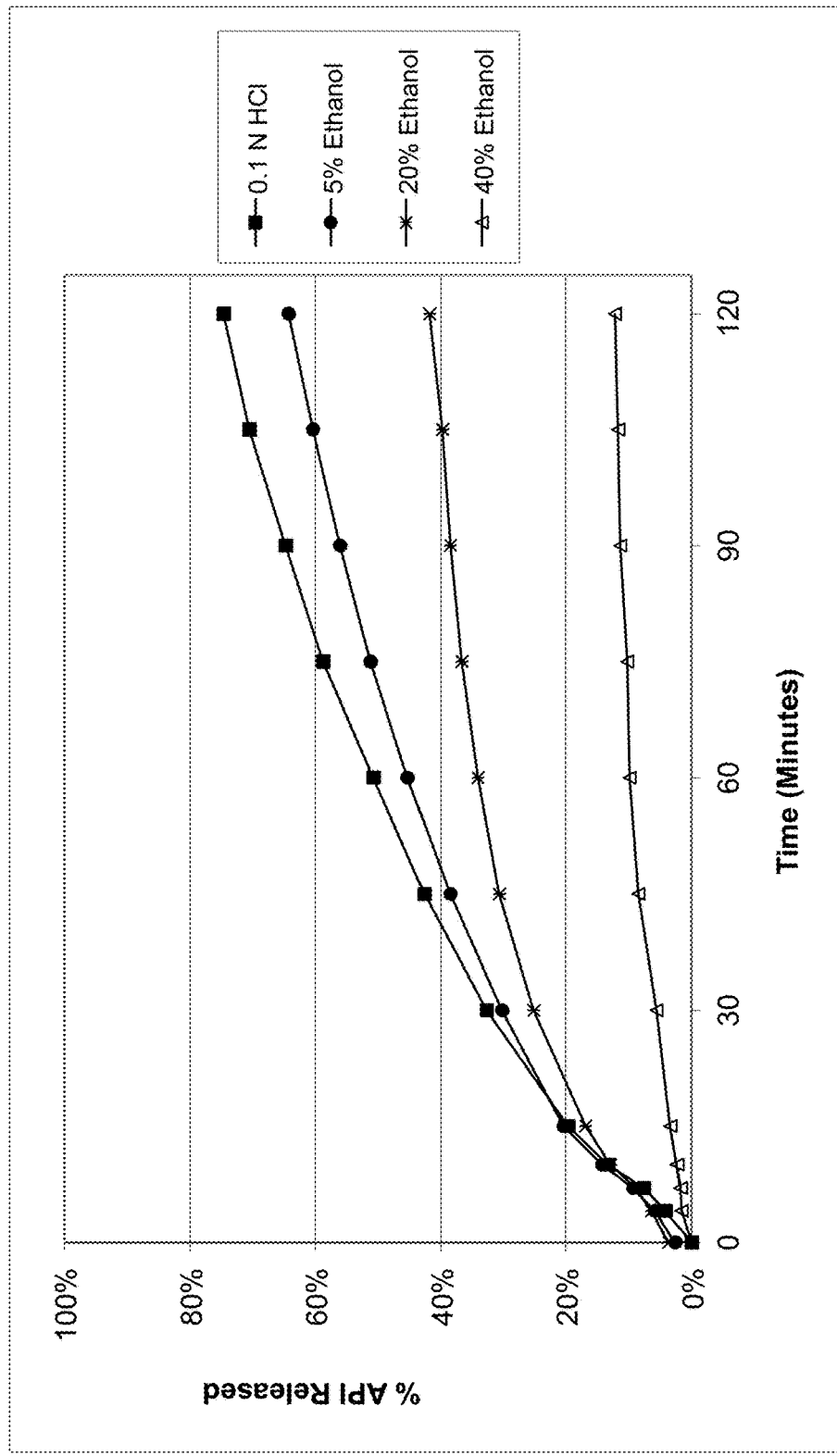
FIG. 94 is the graphical representation of the dissolution profiles for amorphous codeine pamoate 1:1 salt as a 1:1 mixture of mono-sodium salt and free carboxylic acid as a function of ethanol concentration.

Further establishing the noted trend, FIG. 93 summarizes the pH dissolution profile of amorphous codeine pamoate 1:1 salt as an approximately 1:1 mixture of its free acid and mono-sodium salt. FIG. 94 summarizes the dose dumping dissolution profile of the codeine derivative. Again, extended release behavior is noted under acidic conditions. At higher pH levels only a slow release is observed and increased concentrations of ethanol in acidic media does not accelerate dose dumping of codeine form its salt form.

Figure 95:
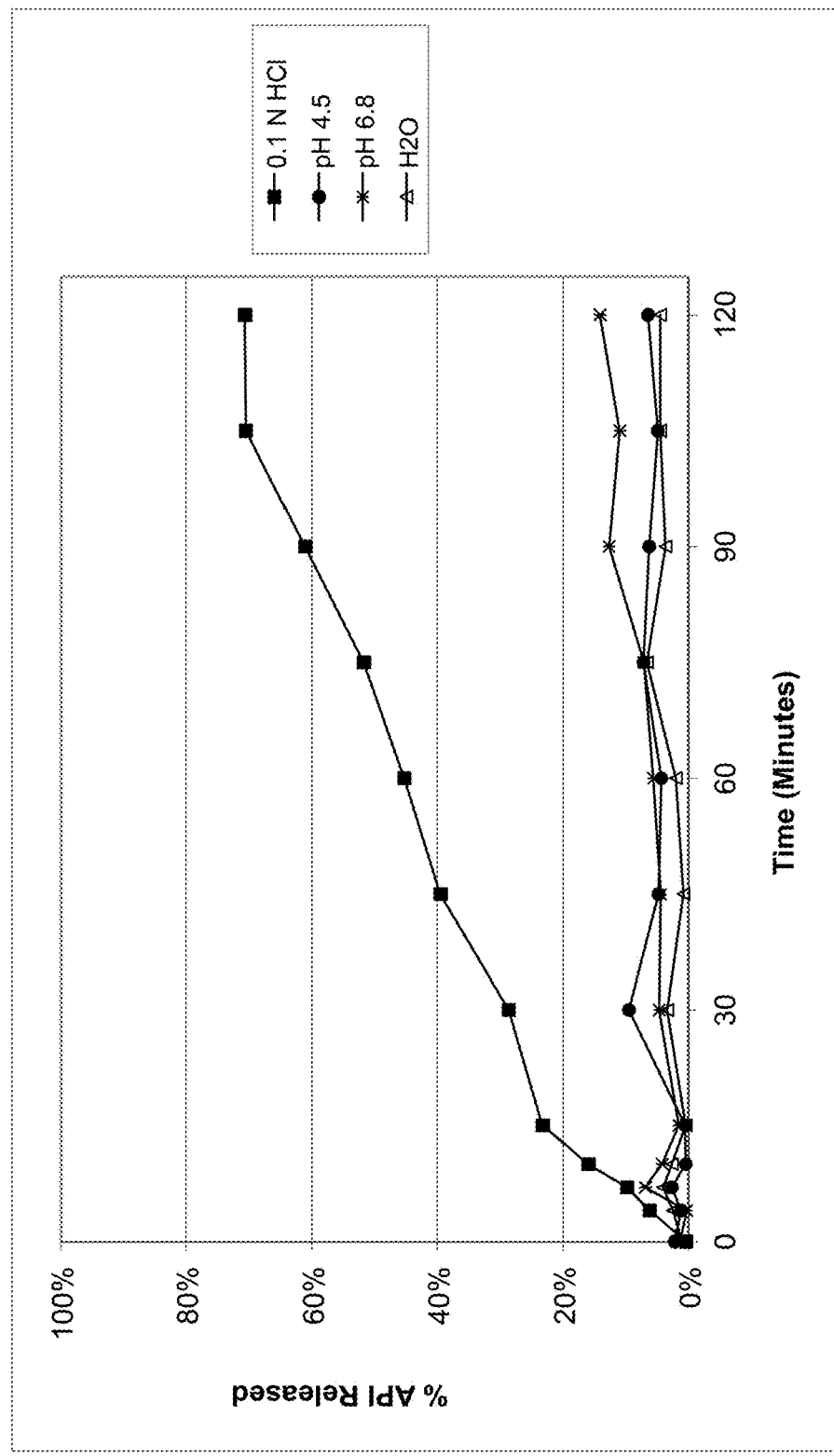
FIG. 95 is the graphical representation of the dissolution profiles for amorphous d-methylphenidate pamoate 1:1 salt as a 1:1 mixture of mono-sodium salt and free carboxylic acid as a function of pH.
Figure 96:
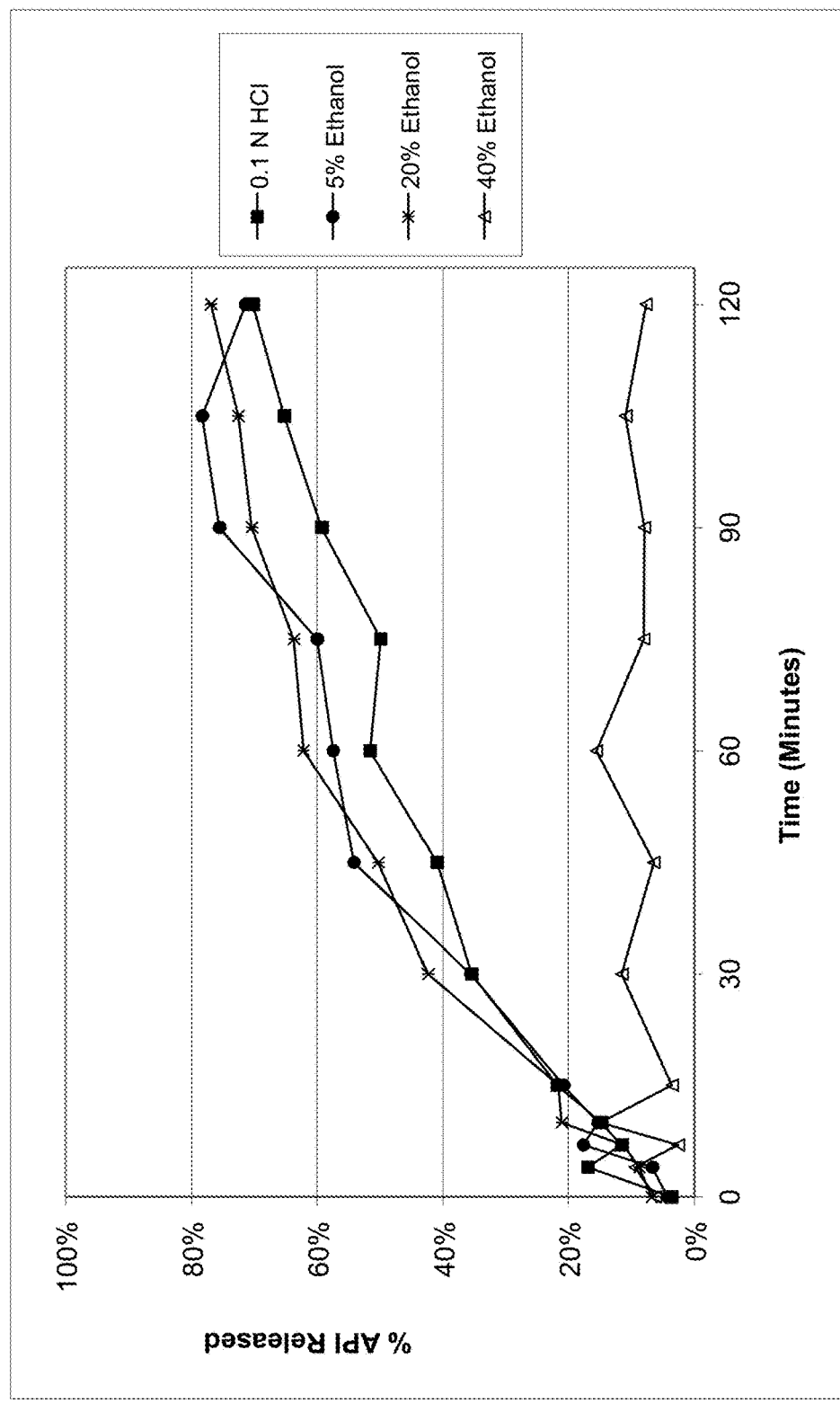
FIG. 96 is the graphical representation of the dissolution profiles for amorphous d-methylphenidate pamoate 1:1 salt as a 1:1 mixture of mono-sodium salt and free carboxylic acid as a function of ethanol concentration.

Both single isomer and racemic methylphenidate pamoate 1:1 salts were prepared and evaluated for their pH and dose dumping dissolution responses. FIG. 95 summarizes the pH dissolution response of amorphous d-methylphenidate pamoate 1:1 salt as an approximately 1:1 mixture of its free acid and mono-sodium salt. FIG. 96 is the dose dumping profile of this salt. This single isomer salt exhibits a slow extended release of the active from its salt form under acidic conditions with only a highly attenuated release under higher pH conditions. Somewhat surprisingly, the salt did respond to acidic ethanol conditions with little differentiation between the 0.1N HCl condition and the acidic media containing either 5% or 20% ethanol. However, the release with, or without ethanol at these levels, was essentially the same. In the presence of 40% ethanol there was very little release of the active from its salt form and with this result serving as a good indication that extraction of the active from its salt form or in a formulated product would prove difficult.

Figure 97:
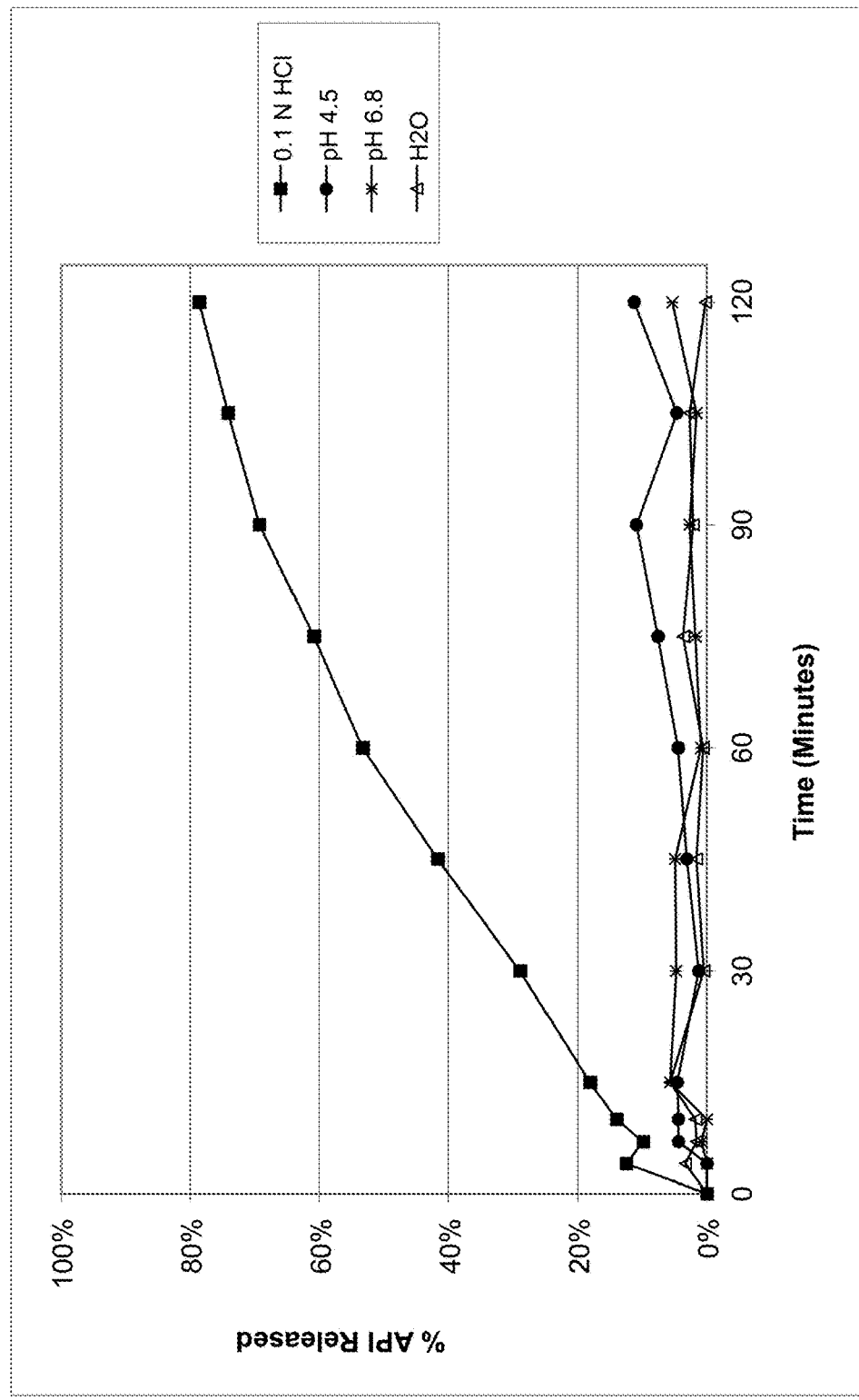
FIG. 97 is the graphical representation of the dissolution profiles for polymorphic racemic-methylphenidate pamoate 1:1 salt as a 1:1 mixture of mono-sodium salt and free carboxylic acid as a function of pH.
Figure 98:
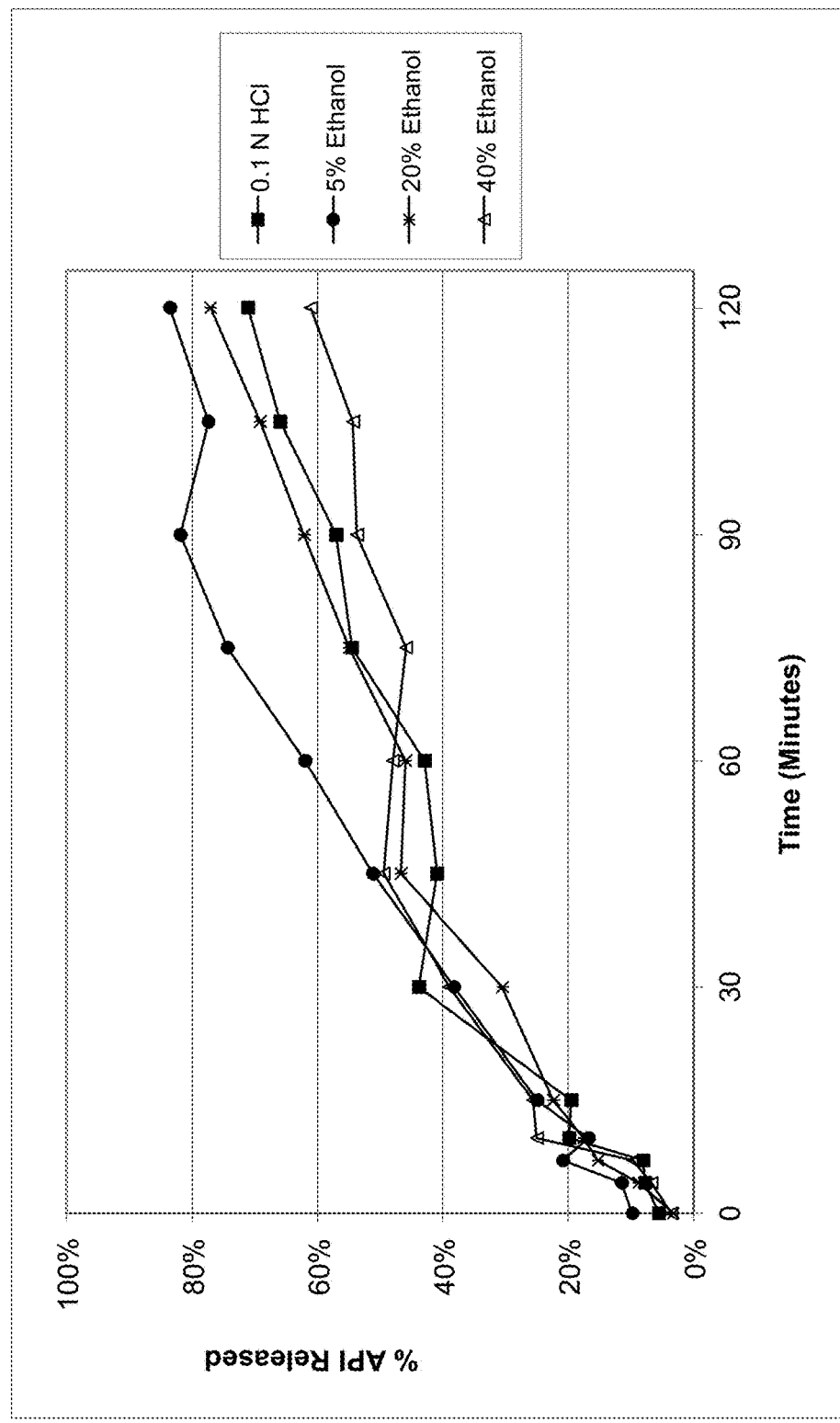
FIG. 98 is the graphical representation of the dissolution profiles for polymorphic racemic-methylphenidate pamoate 1:1 salt as a 1:1 mixture of mono-sodium salt and free carboxylic acid as a function of ethanol concentration.

During the evaluation of racemic methylphenidate pamoate 1:1 salts, an interesting observation was obtained. FIG. 97 summarizes the pH dissolution profile of polymorphic racemic methylphenidate pamoate 1:1 salt prepared as an approximately 1:1 mixture of its free acid and mono-sodium salt. As a first assessment, one would not expect a difference in physical behaviors between the single isomer and racemic versions of comparable methylphenidate pamoate 1:1 salts. Indeed, their pH dissolution profiles are quite similar and the polymorphic form exhibits a slow and steady release rate of the active from its salt form under the 0.1N HCl condition. However, the dose dumping dissolution comparison is somewhat different. The polymorphic racemate salt appears to be more sensitive to alcohol concentration than does its amorphous single isomer form at the 40% ethanol condition. Overall however, the methylphenidate pamoate salt series does not dose dump.

Figure 99:
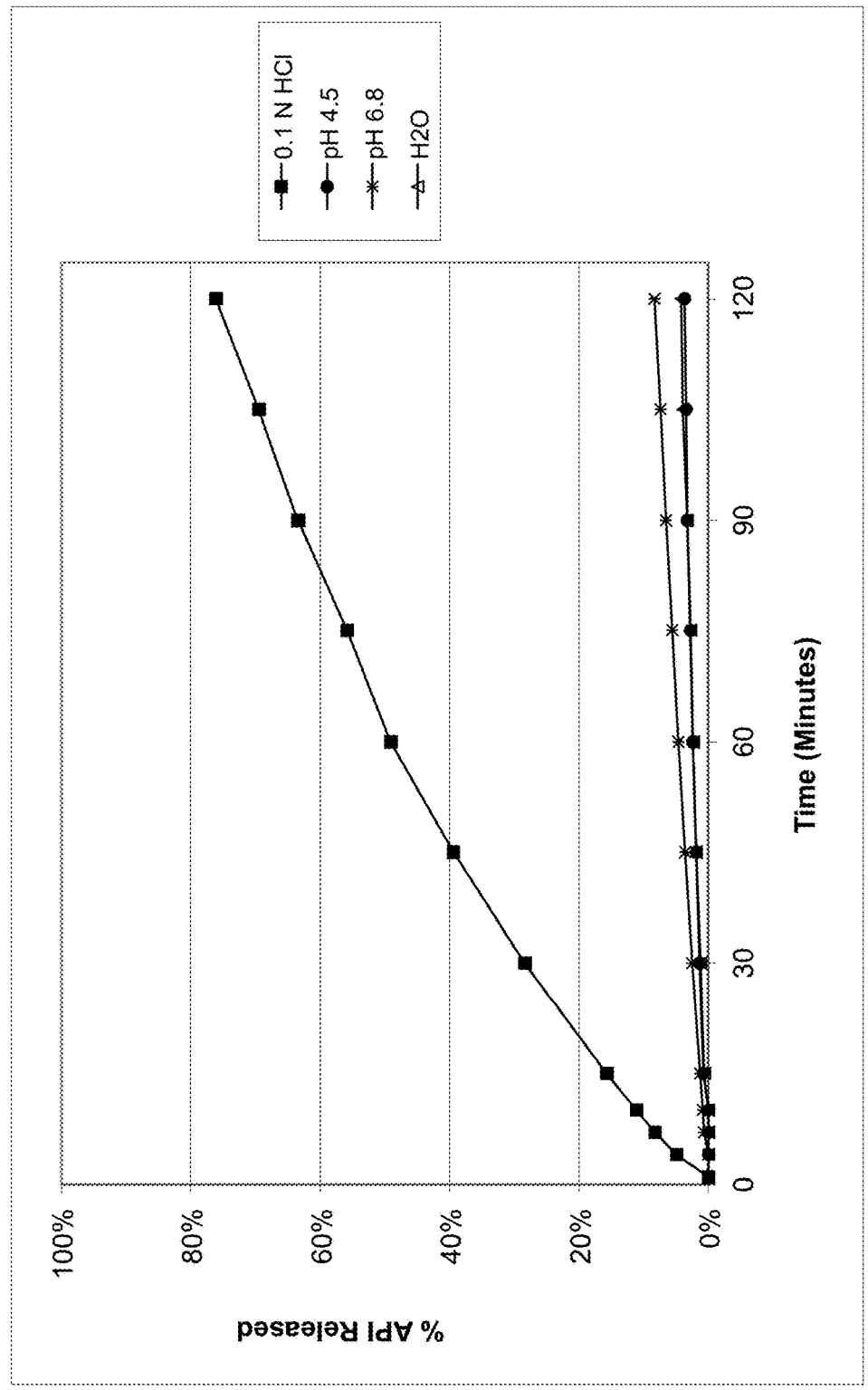
FIG. 99 is the graphical representation of the dissolution profiles for amorphous naltrexone pamoate 1:1 salt as a 1:1 mixture of mono-sodium salt and free carboxylic acid as a function of pH.
Figure 100:
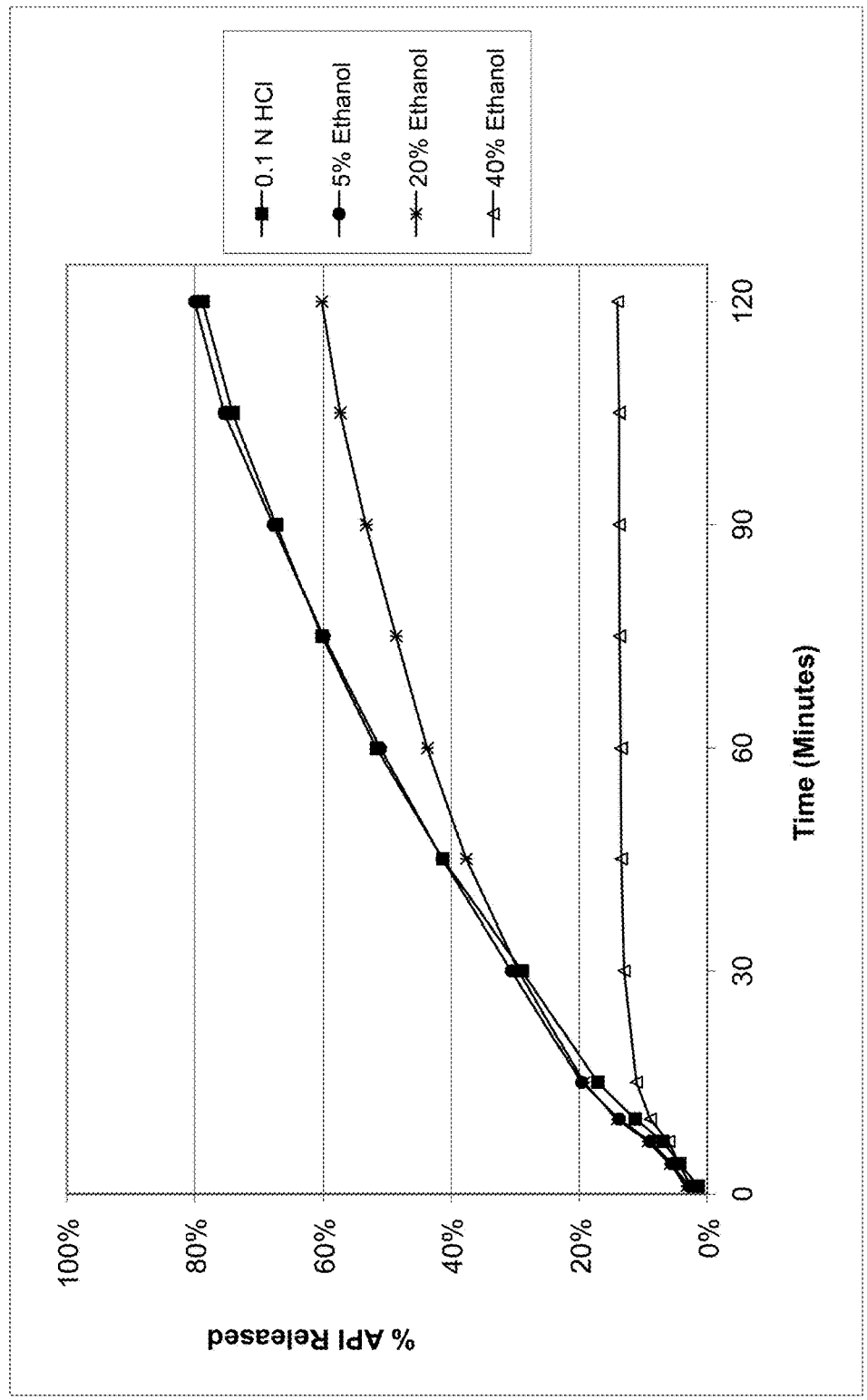
FIG. 100 is the graphical representation of the dissolution profiles for amorphous naltrexone pamoate 1:1 salt as a 1:1 mixture of mono-sodium salt and free carboxylic acid as a function of ethanol concentration.

Amorphous naltrexone pamoate 1:1 salt was prepared as its approximately 1:1 mixture of the free acid and mono-sodium salt. FIG. 99 summarizes the pH dissolution profile of this salt; FIG. 100 presents the results of the salt's dose dumping dissolution response. In keeping with the trend, this opiate derivative has a slow, steady release under 0.1N HCl conditions, but its release is greatly attenuated under higher pH conditions. The salt does not exhibit a propensity to dose dump under acidic ethanolic conditions.

Figure 101:
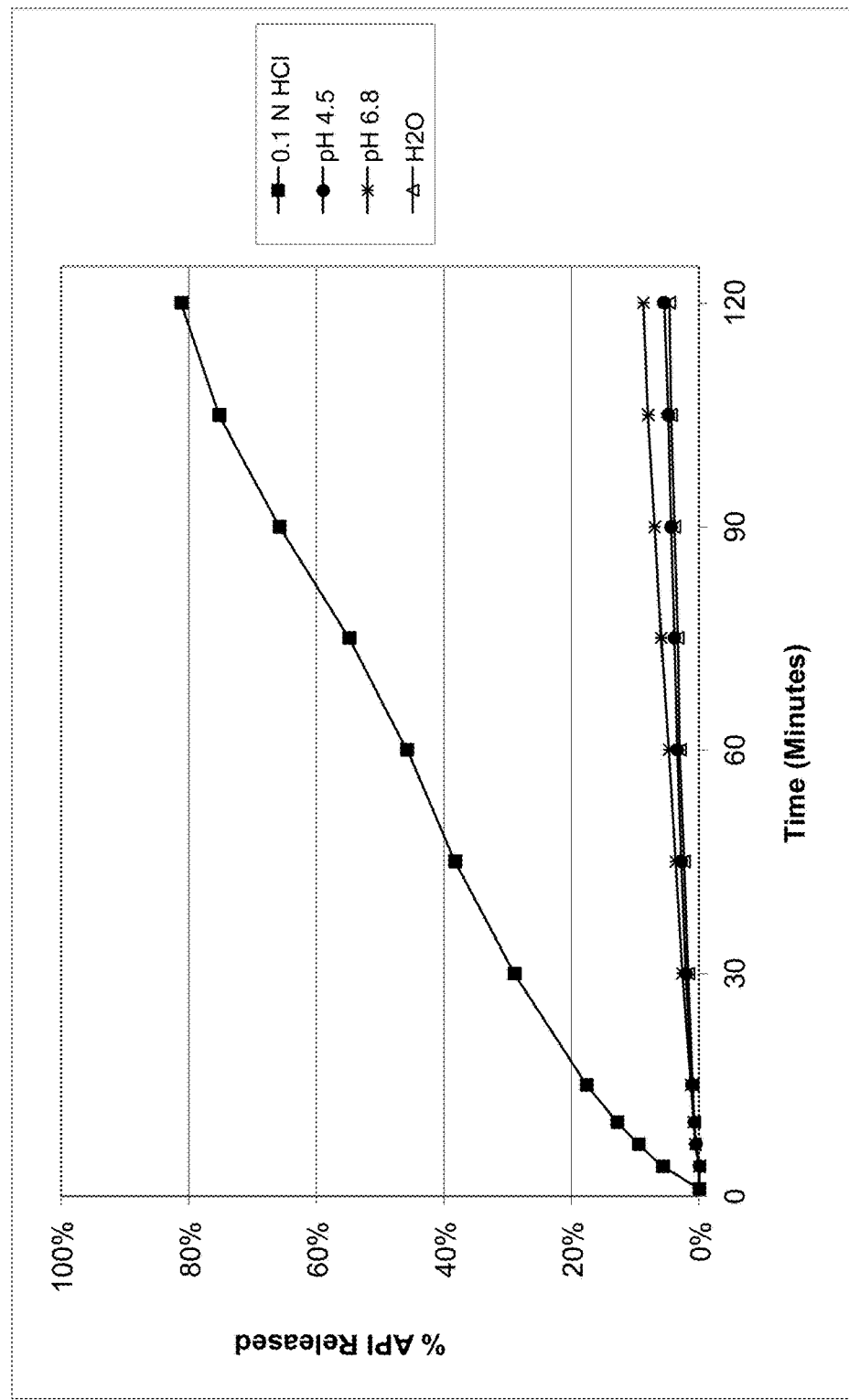
FIG. 101 is the graphical representation of the dissolution profiles for polymorphic naltrexone pamoate 1:1 salt as the free carboxylic acid as a function of pH.
Figure 102:
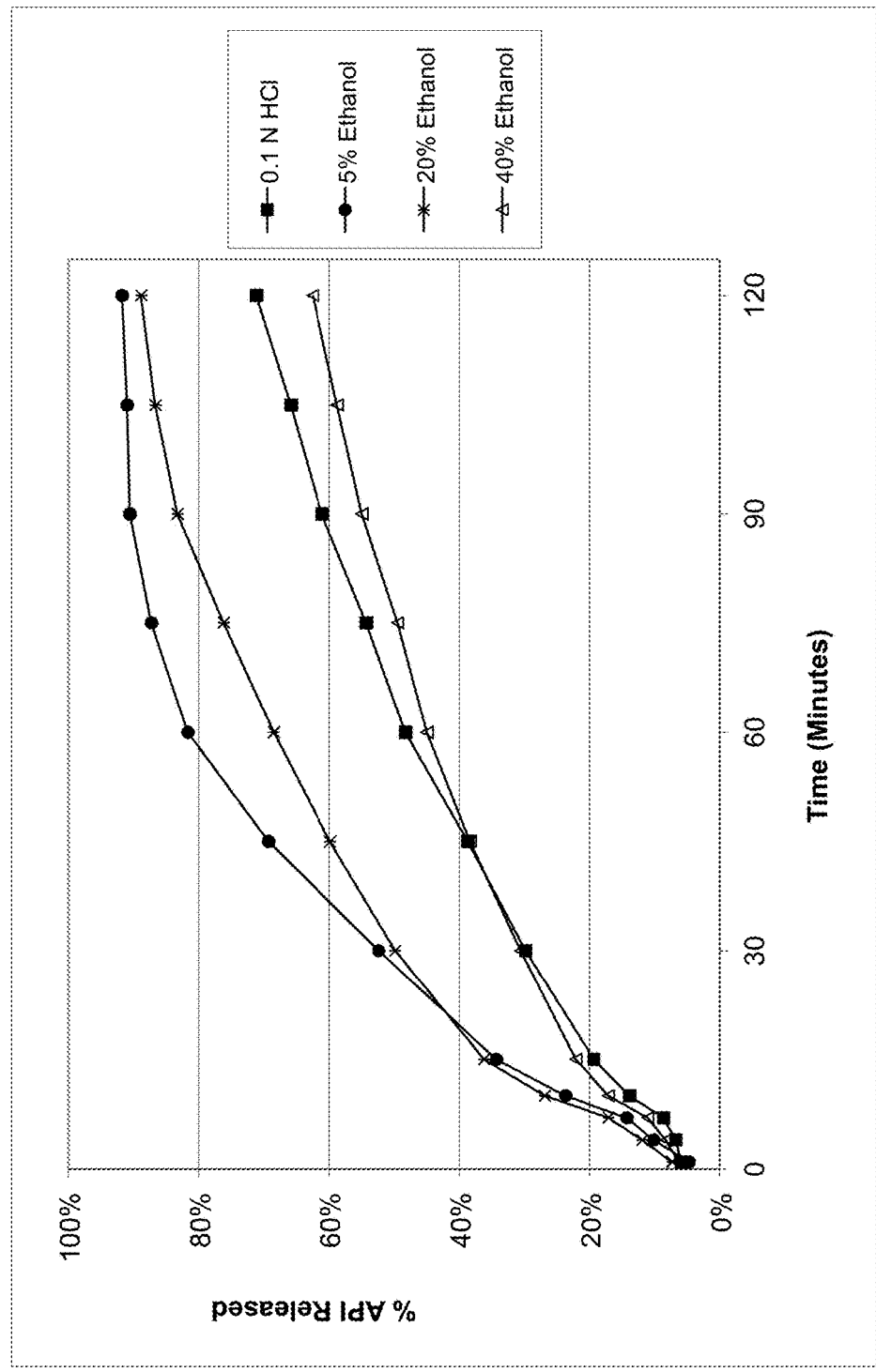
FIG. 102 is the graphical representation of the dissolution profiles for polymorphic naltrexone pamoate 1:1 salt as the free carboxylic acid as a function of ethanol concentration.

Similarly, polymorphic naltrexone pamoate 1:1 salt was prepared in its free acid form. The polymorphic salt's pH dissolution profile is summarized in FIG. 101 which indicates the salt's release performance is virtually identical to its amorphous analogue. Like the findings discussed above for the methylphenidate pamoate series, one would expect a different dissolution rate between the amorphous and polymorphic forms of a compound due to differences in lattice energies. Traditional pharmaceutical teachings encourage the use of amorphous compounds in an effort to hasten dissolution. The finding for naltrexone and methylphenidate pamoate salts would suggest there is a more dominating factor for dissolution rate than just the physical, amorphous or crystalline, form of the compounds. FIG. 102 summarizes the dose dumping dissolution performance of polymorphic naltrexone pamoate 1:1 salt in its free acid form. Interestingly, the compound shows a faster dissolution response to the acidic 5% and 20% conditions than the 0.1N HCl condition which is essentially equivalent to the 40% ethanol condition. Strangely, like the methylphenidate pamoate series, the polymorphic form appears more susceptible to ethanol promoting dissolution and in general, represents a contrary teaching away from the literature.

Figure 103:
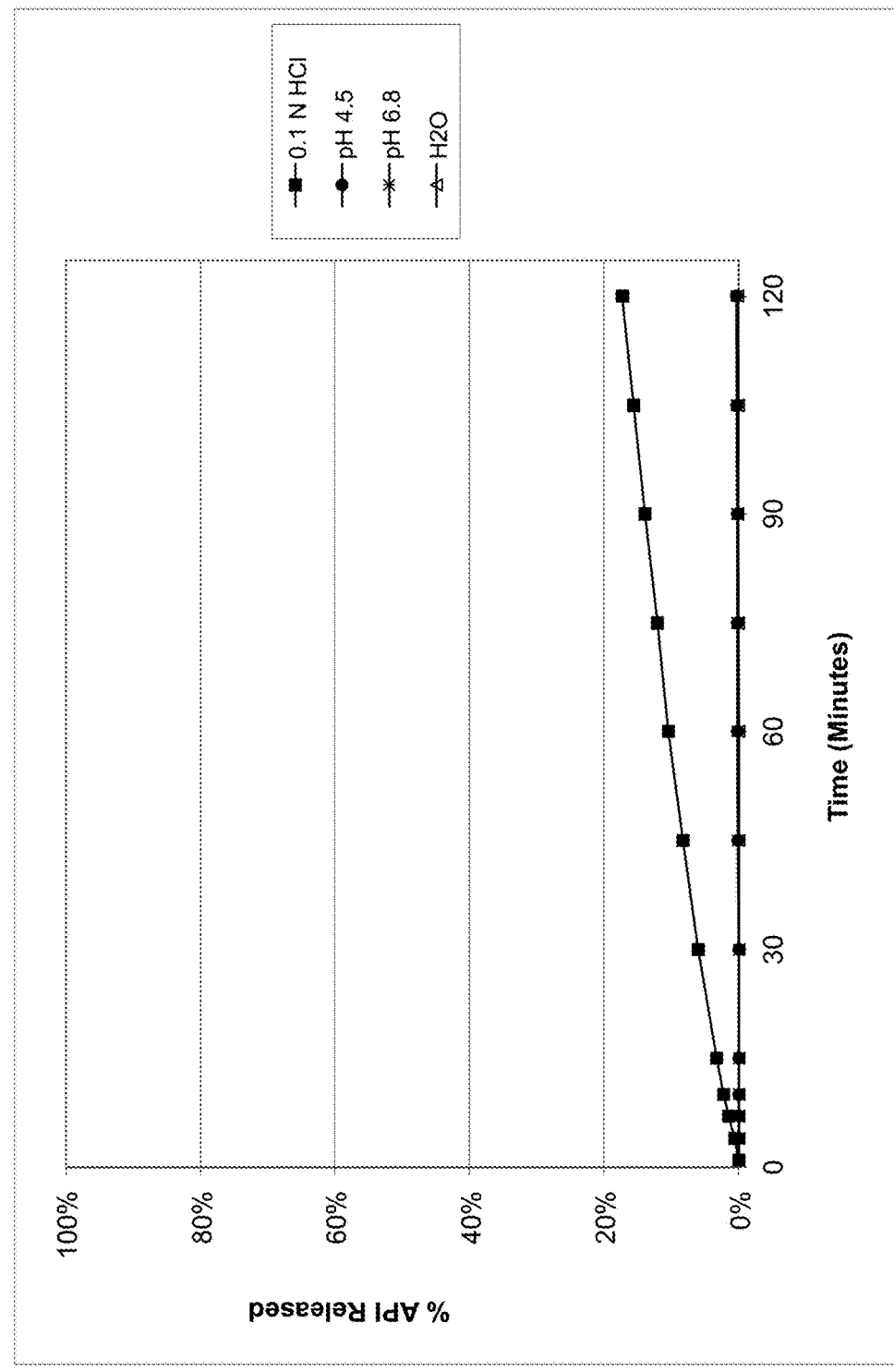
FIG. 103 is the graphical representation of the dissolution profiles for amorphous imipramine pamoate 1:1 salt as a 1:1 mixture of mono-sodium salt and free carboxylic acid as a function of pH.
Figure 104:
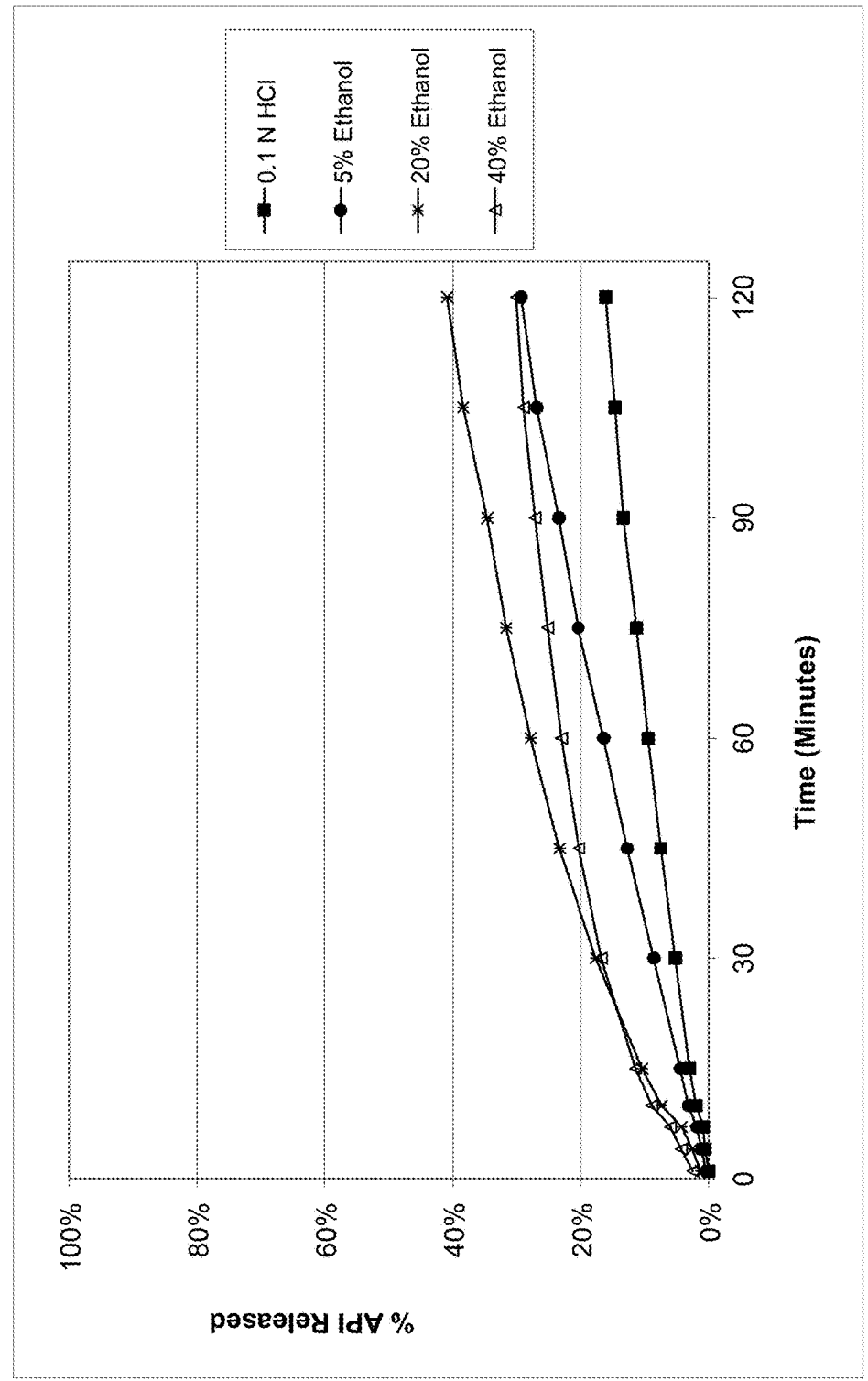
FIG. 104 is the graphical representation of the dissolution profiles for amorphous imipramine pamoate 1:1 salt as a 1:1 mixture of mono-sodium salt and free carboxylic acid as a function of ethanol concentration.

FIG. 103 summarizes the pH dissolution profile of amorphous imipramine pamoate 1:1 salt prepared as an approximately 1:1 mixture of its free acid and mono-sodium salt. FIG. 104 summarizes the dose dumping dissolution profile of this same pamoate salt. The selection of this compound within the context of opiate-related, attention deficit hyperactivity disorder (ADHD) drugs, such as methylphenidate and abuse deterrent drugs, such as naltrexone and perhaps imipramine, was designed to show an intersection with previously reported results concerning imipramine pamoate. The literature is replete with incorrect conclusions regarding the pamoate salts and their supposed singular use for providing sustained release drug substance properties. Applicants have shown that indeed the pamoate salts can, and do afford immediate release dissolution profile opiates under the proper selection of the organic acid salt forming family, salt stoichiometry, and salt morphology while still offering characteristics useful for abuse deterrence. Therefore the more direct methodology for obtaining 1:1 pamoate salts, as described herein can be compared with the more laborious routes reported previously. In U.S. Pat. No. 8,653,065 to King et al. entitled, "Abuse Deterrent and Anti-Dose Dumping Pharmaceutical Salts Useful for the Treatment of Attention Deficit/Hyperactivity Disorder", incorporated herein by reference in its entirety, was prepared both amorphous and polymorphic forms of imipramine pamoate 1:1 salts. Each form was analytically characterized for structure confirmation and dissolution properties. In regard to the comparison between the amorphous form disclosed herein and that of the '065 patent, the pH dissolution properties are essentially identical. This result is worthy of comment in that the composition of the amorphous form disclosed herein contains about an equal portion of the compound as the sodium salt and the issue arises as to how the mixture of the free acid and the sodium salt responds to the dissolution conditions versus just the free acid component. This nuance can now be set aside as not being a factor in the overall dissolution response of the mixture for the following reasons: 1) the dissolution medium for the 0.1N HCl condition has a considerable excess of acid to protonate the comparably minimal amount of carboxylate present as the sodium salt; and 2) the dissolution medium for the higher pH conditions is beyond the pKa of pamoic acid. Therefore the acid functionality is ionized and behaves like the sodium salt. Consequently, whether amorphous imipramine pamoate 1:1 salt as the 1:1 mixture of free acid and mono-sodium salt or imipramine pamoate 1:1 salt prepared as its free acid via hydrolysis of a labile amine protecting group, as in the '065 Patent, the dissolution response is the same.

For completeness and pharmaceutical elegance, a comparison to polymorphic imipramine pamoate 1:1 salt prepared as its free acid is included. This compound was prepared by an indirect synthetic procedure as described in the '065 patent. The pH and dose dumping profiles were also reported therein and are comparable to the amorphous mixture dissolution results reported above; both forms indicated the higher levels of ethanol used in the dose dumping regimen led to higher levels of imipramine released from its salt form compared to the 0.1N HCl condition. Still, the absolute amounts of imipramine release would not inhibit use of this compound as a medication.

Figure 105:
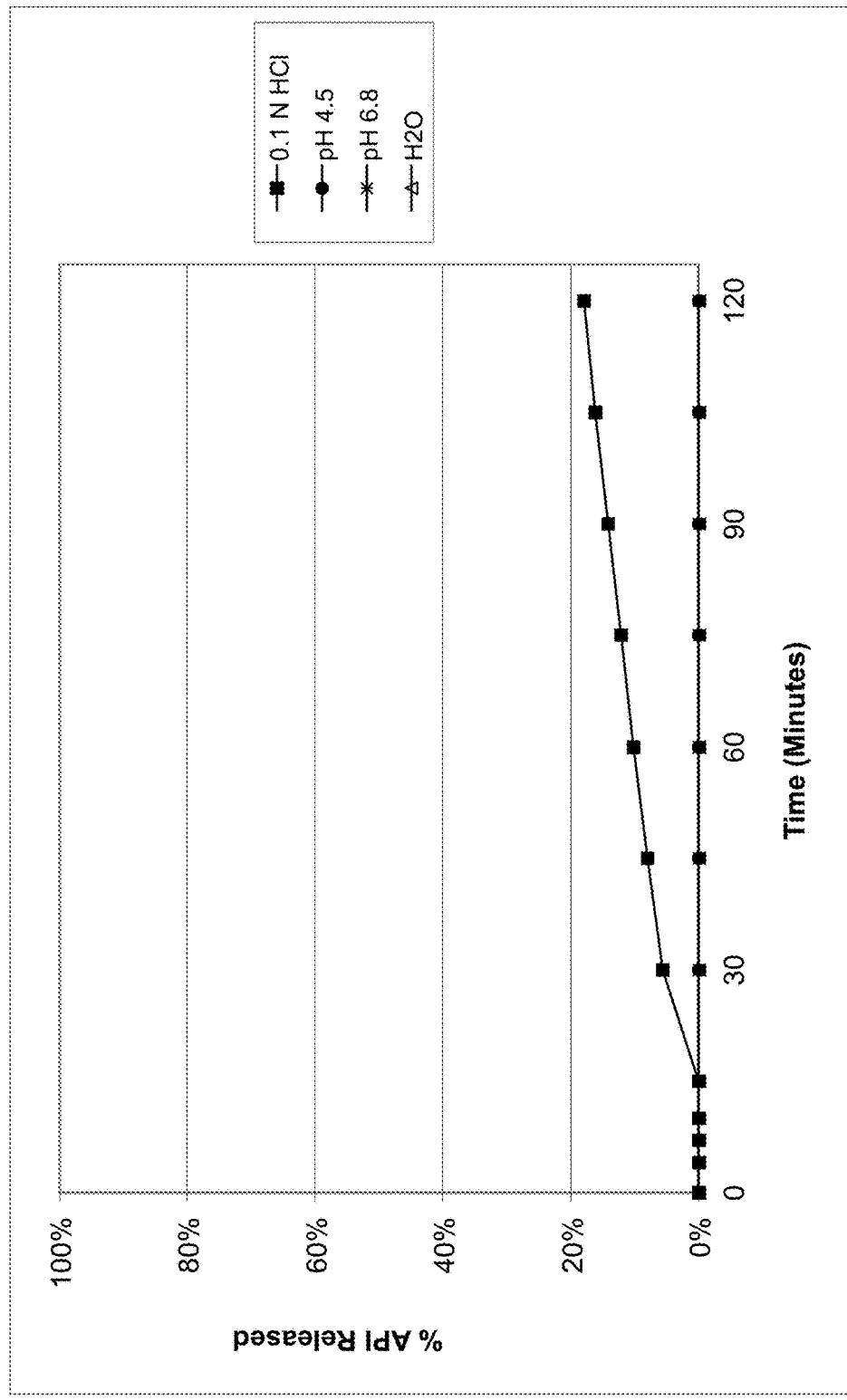
FIG. 105 is the graphical representation of the dissolution profiles for amorphous methadone pamoate 1:1 salt as a 1:1 mixture of mono-sodium salt and free carboxylic acid as a function of pH.
Figure 106:
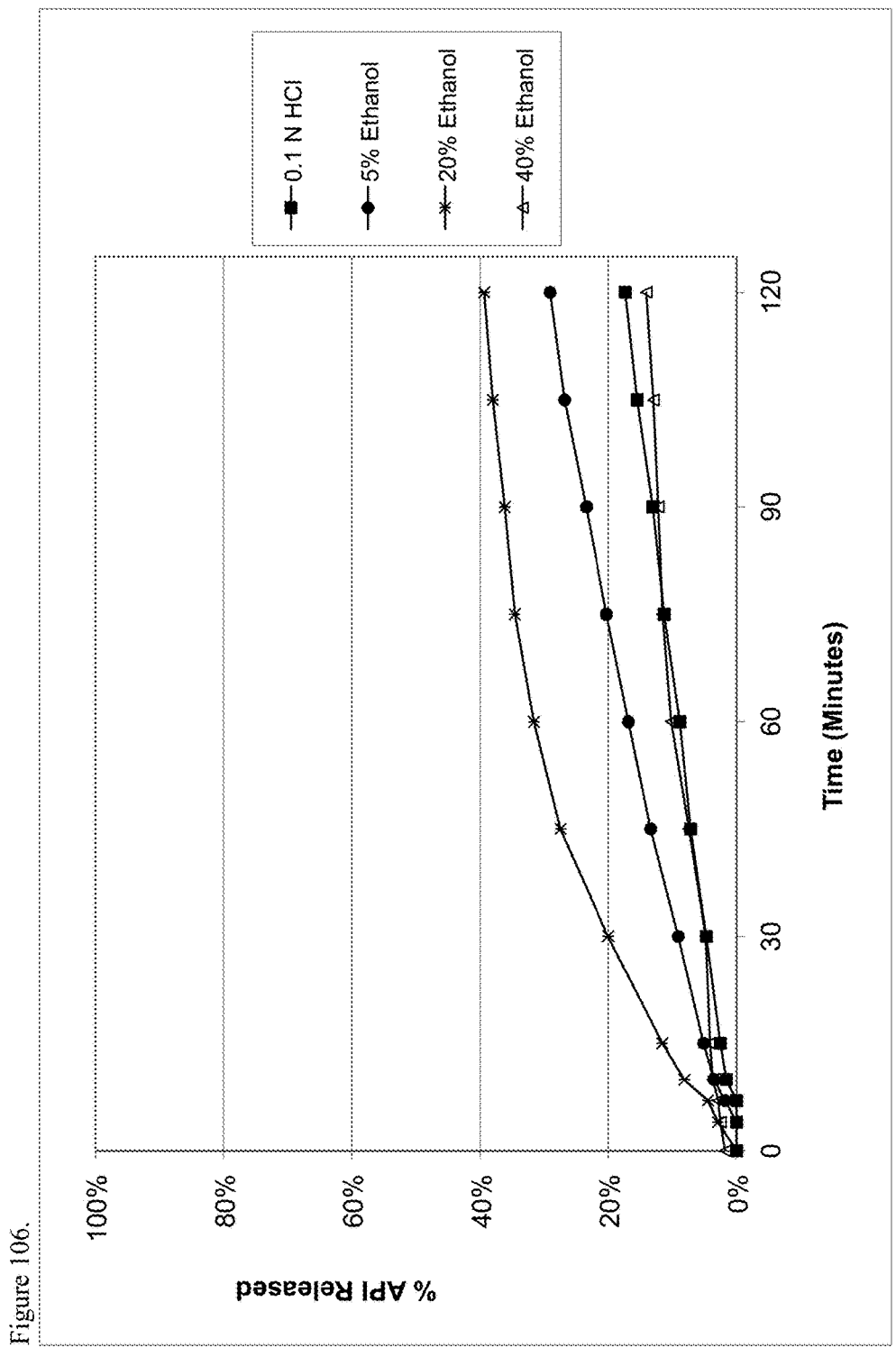
FIG. 106 is the graphical representation of the dissolution profiles for amorphous methadone pamoate 1:1 salt as a 1:1 mixture of mono-sodium salt and free carboxylic acid as a function of ethanol concentration.

Amorphous methadone pamoate 1:1 salt was prepared as an approximately 1:1 mixture of its free acid and monosodium salt. FIG. 105 summarizes the pH dissolution profile of this compound; FIG. 106 summarizes its dose dumping profile. Methadone, as a free base, precipitates from solutions having pH>6 as set forth in the Merck Index $14^{th}$ Edition. However, methadone hydrochloride is very soluble in water. Hence, the BNDO salts offer an intermediate dissolution profile and are therefore useful as abuse deterrent forms of methadone. The pamoate salt exhibits a very slow release in 0.1N HCl and essentially no substantive release rate at the higher pH levels. The dose dumping characteristics of the pamoate salt are equally attenuated. Perhaps by definition, methadone pamoate would dose dump in the presence of acidic 5% and 20% ethanol, but acidic 40% ethanol yields a dissolution rate overlapping with the rate found in 0.1N HCl. Even though the somewhat accelerated dissolution rates resulting from the presence of alcohol are measureable, these levels are not sufficient to disqualify methadone pamoate as useful in abuse deterrent products since the release is still low and additional alcohol does not continue to aid release. It should be noted that methadone is commonly used to treat drug abuse, but it is also an analgesic, is routinely abused by patients, and its overdose often leads to death.

Figure 117:
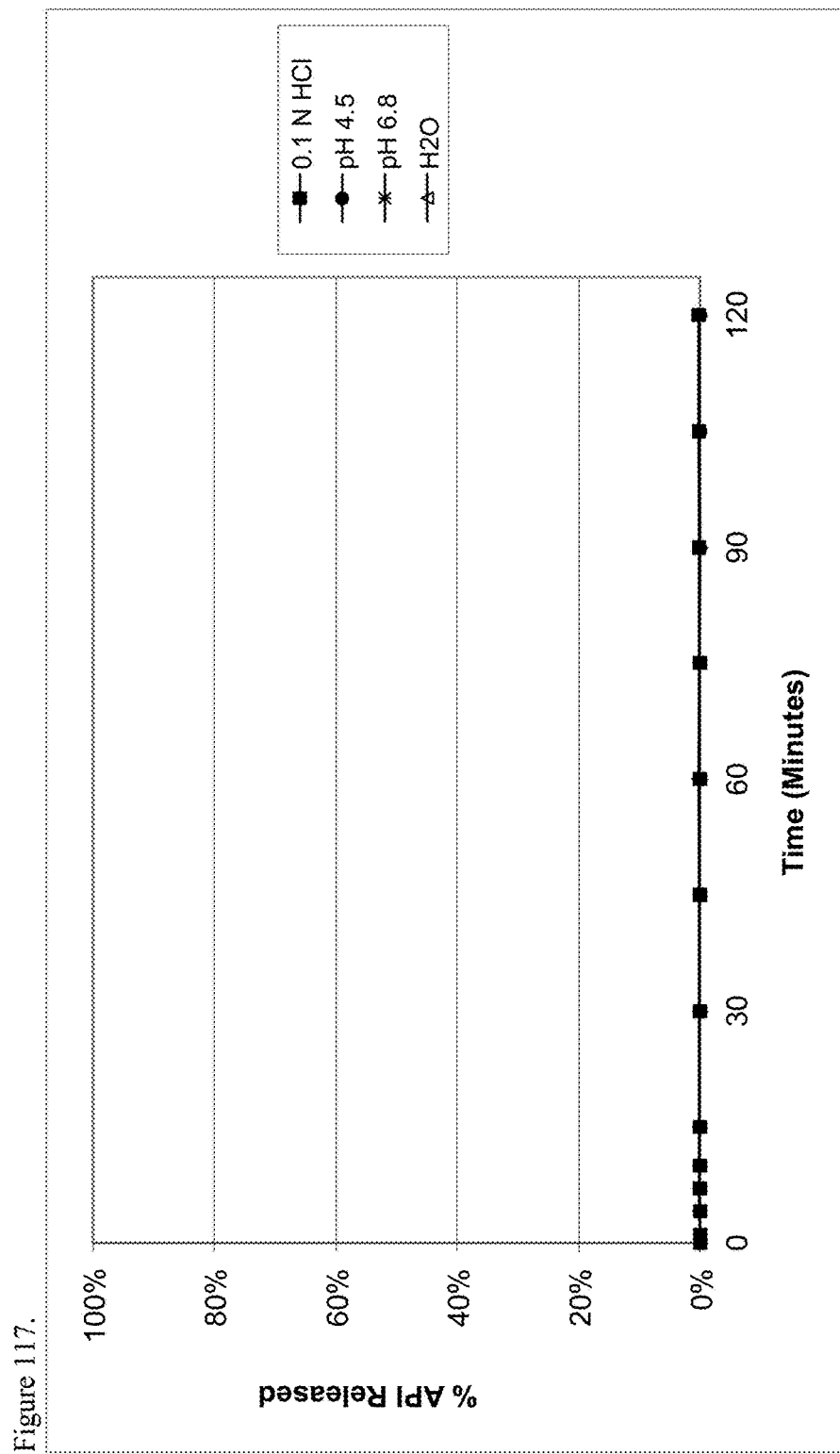
FIG. 117 is the graphical representation of the dissolution profiles for polymorphic L-thyroxine pamoate 1:1 salt as the mono-sodium carboxylate as a function of pH.
Figure 118:
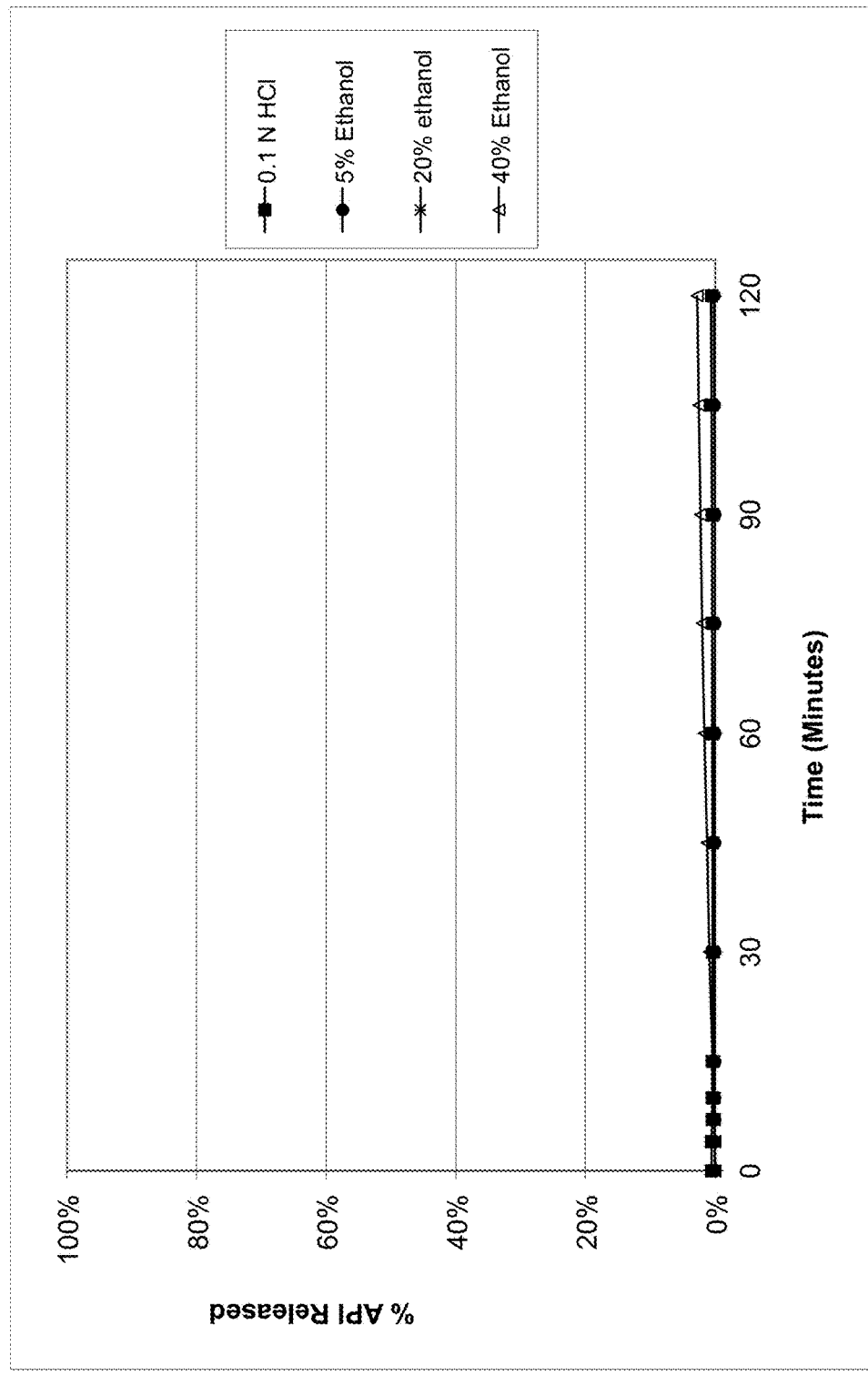
FIG. 118 is the graphical representation of the dissolution profiles for polymorphic L-thyroxine pamoate 1:1 salt as the mono-sodium carboxylate as a function of ethanol concentration.

In addition to preparing imipramine pamoate, 1:1 salt, the generality of preparing 1:1 pamoate salts was explored using the thyroid hormone, L-thyroxine (also known as levothyroxine). The carboxylic acid form of L-thyroxine was generated in situ as the active reactant for salt formation. This approach avoids the regiochemical ambiguity within the formed salt for the location of the sodium ion. Based on the comparative pKa values of the L-thyroxine carboxyl moiety and the more acidic carboxyl functionality of the BNDO moiety, it was reasonable to conclude the sodium ion resides on the BNDO moiety as the sodium carboxylate. In this case, this assignment is somewhat irrelevant since the pH and dose dumping dissolution profiles of L-thyroxine pamoate 1:1 salt (FIGS. 117 and 118, respectively) were significantly retarded and observed to be essentially insoluble under each of the dissolution conditions. This observance would further indicate the sodium ion was incorporated as the pamoate carboxylate since under the neutral to basic conditions, L-thyroxine sodium salt (potentially generated after dissolution from the pamoate salt) would be expected to have a greater solubility than its free acid analogue. The Merck Index, Fourteenth Edition reports that DL-thyroxine is insoluble in water, but in the presence of mineral acids or alkalis, it dissolves in alcohol. In contrast sodium L-thyroxine is soluble in water (15 mg/100 mL; 25° C.), and more soluble in alcohol. With respect to the dissolution profiles obtained with the pamoate salt, carboxylate protonation under acidic conditions would be expected to be faster than dissolution rates, but other factors may dominate and the observed dissolution profiles are obtained. Such low rates of dissolution would suggest L-thyroxine pamoate, 1:1 salt is a candidate for an extended release dosage form.

A comparison of extended release and immediate release challenges pertaining to the formulation of abuse deterrent products warrants comment. Extended release (ER) products, particularly opiate-based products, are attractive to those intent on abusing the drug since the ER product contains a substantially higher amount of active ingredient than the comparable immediate release (IR) product. Hence the formulator is confronted with a difficult and complex task to provide an ER formulation that delivers controlled dosage release over an extended period, yet the active ingredient is otherwise unavailable for abuse. To be unavailable is a qualitative term, but essentially means the active ingredient is not susceptible to extraction from the formulated dosage, and grinding, chewing or other mechanical means will not provide a pathway to freeing the active ingredient from the formulated matrix. So, the formulator has a paradox to overcome: the ER product must release properly when used as intended, but product tampering cannot accommodate abuse routes which would yield a large amount of active ingredient possessing an immediate release profile. Citations incorporated by reference herein provide dissolution profiles of the traditional mineral acid and low molecular weight organic acid salts of a variety of opiates. Each and every one of these salts has an immediate release profile as the drug substance. The formulator utilizes various excipients and processing techniques to provide an ER formulation using an IR drug substance, and the formulation must work as intended yet in all circumstances still defeat tampering efforts for abuse. To date, commercial efforts to accomplish this task have been futile. In contrast, the BNDO salts provide a viable route to accomplishing both design features: ER products which possess abuse deterrence and are highly resistant to tampering.

Besides the reliance on formulation, other investigators are addressing abuse deterrence at the API level. KemPharm, Signature Therapeutics, Collegium, and Shire each has their version of a modified active ingredient as the basis to achieving abuse deterrence, and to date, only Shire's product, Vyvanse® has received market approval. Shire, KemPharm and Signature each use a pro-drug approach (covalently bound active and modifying group); Collegium appears to be preparing ionic bound salts of myristic acid. KemPharm's enol benzoate hydrocodone likely exhibits hydrolysis ease in mild acid or base and would then be susceptible to extraction. Shire and Signature have essentially attached a peptide oligomer to the active moiety; however a quick Google search instructs would-be abusers to cleave these protecting groups with trypsin to yield the active. Collegium's myristic acid salt is used to increase the lipophilicity of the active for formulation as waxy beads. Here too, defeating the abuse-deterrent characteristic by extraction is highly probable. It should be emphasized that myristic acid salts are not equivalent to pamoate salts. Myristic acid is a C-14 linear acid with a single pKa. The pamoate moiety in contrast has two pKa values, two regiochemical sites for binding up to two equivalents of amine-containing active, and the binding is by a chelation mechanism in addition to an acid-base salt formation. The large pamoate moiety (C-23) substantially decreases the opioid's solubility in water and organic solvents. Fortunately too, attempts to free-base the opioid from the pamoate are hindered by pamoate's emulsifying tendencies. These features make the pamoate the salt of choice over other commercial offerings.

IR products typically have a specification wherein at least 85% of the active is released within 30 minutes in 0.1N HCl and given that the traditional mineral acid salts of actives meet this criteria prior to dosage formulation, the formulator must provide a release-neutral formulation with excipients that are compatible with the drug substance. The comparable BNDO salts can also be used in IR products; however, the formulator generally must use dissolution modifying agents and surfactants to assist in the two-step kinetic process of a) release of the drug substance from the formulated matrix, and b) release of the active ingredient from the drug substance salt form.

ER products, where higher amounts of drug substance are within the dosage presentation (pill, capsule, tablet), require substantial expertise by the formulator to convert the traditional, highly soluble mineral acid active ingredient salts to formulated products with a time-dependent controlled release. The BNDO salts, by use of stoichiometry, morphology, and acid salt-forming family selection can be designed to yield drug substances more easily formulated into ER products and wherein anti-tampering/abuse deterrent features are also available. BNDO salts suitable for extended release products are those which in 0.1N HCl have a release of not more than 60% at 30 minutes. Indeed, as an oral dosage passes through the gastrointestinal system, the dissolution time dependence of that transit also is an important factor. For the active ingredient BNDO salts disclosed herein, each fulfills the specification of not more than 60% release at 30 minutes. Hence, within a formulated dosage, the drug's transit continuum in the body changes from a highly acidic condition to ultimately a basic environment of the bowel. And from the dissolution profiles disclosed herein, the neutral and basic conditions evaluated indicate the BNDO salts have a highly attenuated release under these conditions. Consequently, the BNDO salts disclosed herein are valuable components to ER products possessing both the controlled time-dependent release of sufficient active ingredient necessary for 8-24 hour dosing within a desired therapeutic range, but also provides for anti-tampering and abuse deterrent properties.

Abuse deterrent drug products are in high commercial and regulatory demand; the BNDO salts offer a direct and unequivocal means of introducing abuse-deterrent and tamper resistant properties into highly abused drug products. In addition, non-selective opioid receptor antagonists such as naltrexone pamoate can be employed as a formulation compatible, second line of defense within abuse deterrent products. These and other valuable contributions are available from the invention described herein and the examples in no way should limit the scope or application of the embodiments disclosed.

EXPERIMENTAL

Experimental Methods
Differential Scanning Calorimetry

Samples were evaluated using a Differential Scanning calorimeter from TA Instruments (DSC 2010). Prior to analysis of samples, a single-point calibration of the TA Instruments DSC 2010 Differential Scanning calorimeter (DSC 2010) with the element indium as calibration standard (156.6±0.25° C.) was completed.

Infrared Spectroscopy

IR Spectra were obtained in a KBr disc using a Perkin Elmer Spectrum BX Fourier Transform Infrared Spectrophotometer.

Powder X-Ray Diffraction (PXRD)

Powder X-Ray diffraction patterns were acquired on a Scintag XDS2000 powder diffractometer using a copper source and a germanium detector. A powder is defined herein as amorphous if the counts per second of the underlying broad (>2° 2θ at half height) absorption exceeds the counts per second of narrow (<5° 2θ at half height) peaks rising there above. A powder is defined herein as crystalline if the counts per second of the underlying broad (>20° 2θ at half height) absorption is less than the counts per second of narrow (<5° 2θ at half height) peaks rising there above. Crystalline and polycrystalline are not distinguished herein. Crystalline materials are defined as having a morphology even if the actual morphology is not elucidated. Polycrystalline materials are defined as being polymorphic.

High Pressure Liquid Chromatography (HPLC)

HPLC analyses were performed on a Waters 2695 HPLC system equipped with a Waters 2996 photo diode array detector.

$^1$H NMR Spectroscopy $^1$H NMR spectra were obtained on a 400 MHz Varian Inova 400 spectrometer. Spectra were referenced to solvent (DMSO-$d_6$).

Dissolution

Dissolution testing was performed using a Distek Dissolution System 2100 consisting of six 1000 mL dissolution vessels with covers containing sampling ports, six stainless steel paddles and spindles, RPM control unit, and a Distek TCS0200C Water Bath, Temperature Controller Unit.

Example 1. Preparation of Amorphous Hydrocodone Pamoate 1:1 Salt

Figure 2:
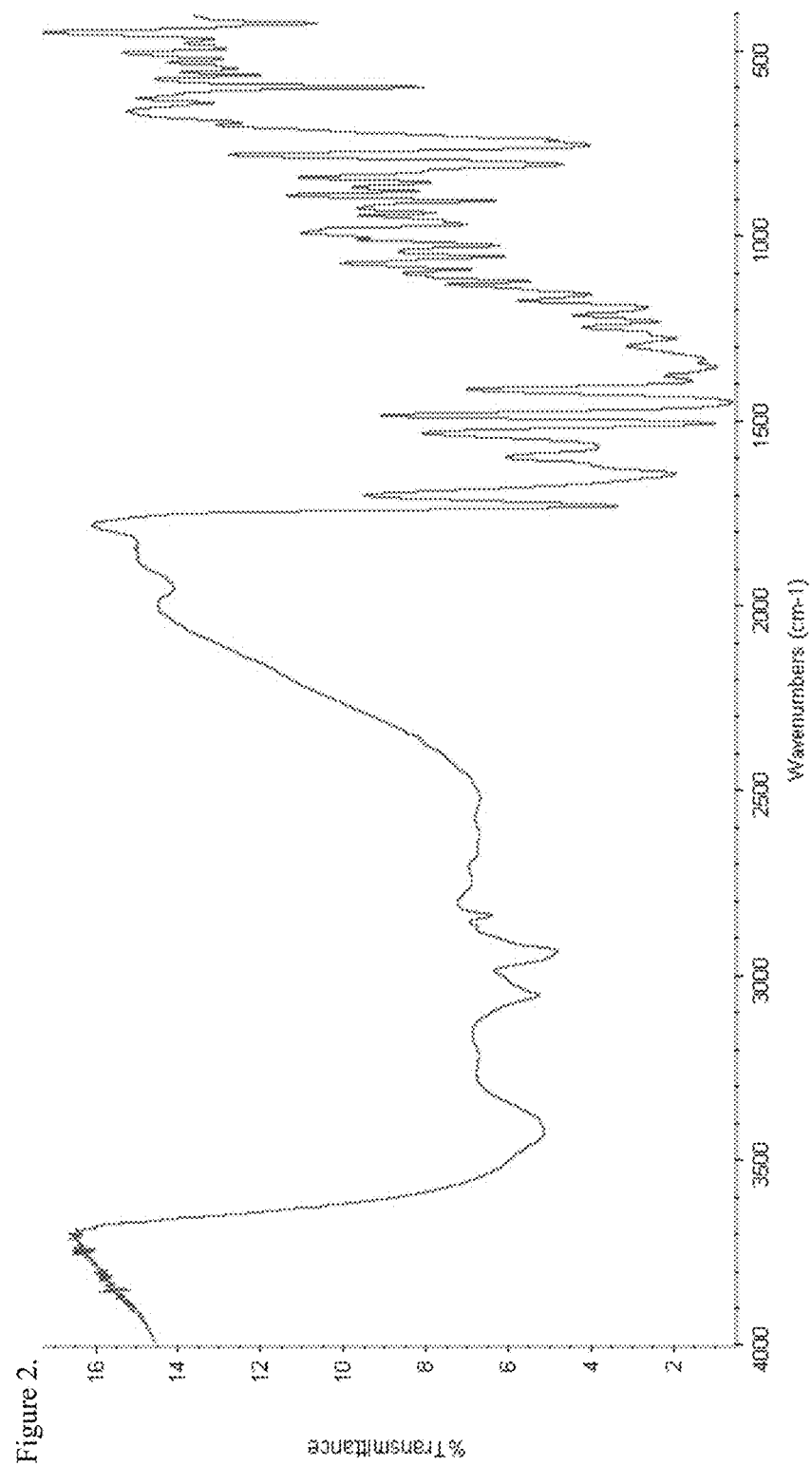
FIG. 2 is the Fourier transform infrared (FTIR) spectrum of amorphous hydrocodone pamoate 1:1 salt as 1:1 mixture of mono-sodium salt and free carboxylic acid.
Figure 3:
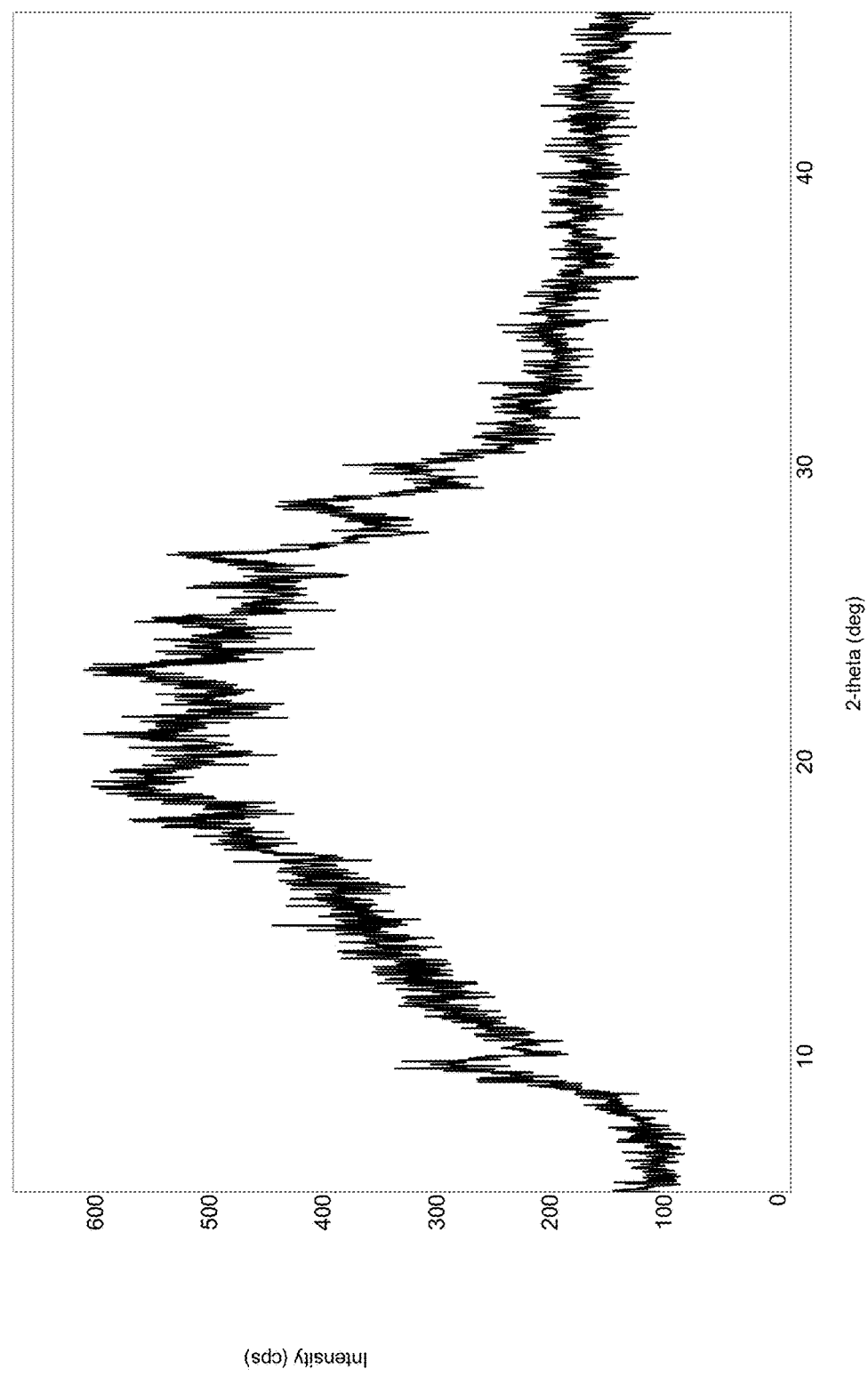
FIG. 3 is the powder X-ray diffraction (PXRD) diffractogram of amorphous hydrocodone pamoate 1:1 salt as 1:1 mixture of mono-sodium salt and free carboxylic acid.
Figure 4:
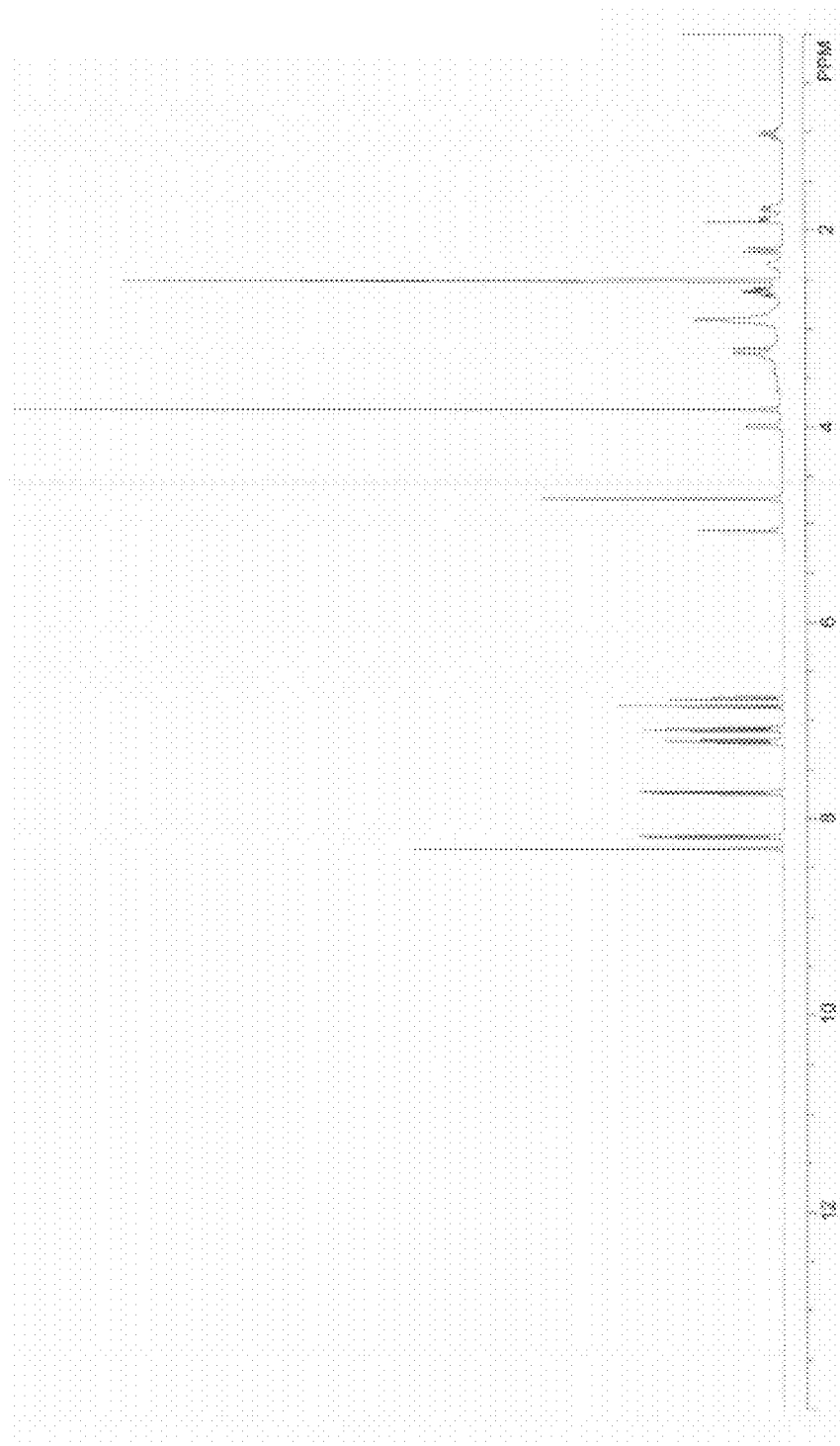
FIG. 4 is the proton nuclear magnetic resonance ($^1$H NMR) spectrum of amorphous hydrocodone pamoate 1:1 salt as 1:1 mixture of mono-sodium salt and free carboxylic acid.

To a 250 mL three-neck round-bottom flask equipped with a magnetic stir bar, thermowell, nitrogen inlet and addition funnel was charged disodium pamoate (1.50 g, 3.34 mmol) and 67 mL 75:25 ethanol/water, and the contents stirred at ambient temperature under a nitrogen atmosphere. A hydrocodone acetic acid salt solution was prepared in a separate vessel according to the following procedure. To a 50 mL round-bottom flask equipped with a magnetic stir bar was charged hydrocodone base (1.0 g, 3.34 mmol) and 13.4 mL 5% acetic acid/ethanol solution and the mixture stirred at ambient temperature under a nitrogen atmosphere. The hydrocodone acetic acid solution was added over a period of about one minute to the disodium pamoate solution via an addition funnel, the pH of the combined solutions was recorded as about 6.2 and the mixture was stirred overnight under a nitrogen atmosphere at ambient temperature. The solution was concentrated under reduced pressure (28.7 inches Hg and 22° C. water bath temperature) to provide the hydrocodone pamoate (1:1) salt. The sample was triturated in water (about 34 g), the solids isolated by filtration through a medium frit filter with the solids then washed with a small portion of water and dried under vacuum to provide 2.18 g (95% yield) of a light yellow powder. The product was characterized by DSC (FIG. 1), FTIR (FIG. 2), PXRD (FIG. 3), $^1$H-NMR (FIG. 4), HPLC and by sodium analysis. Both the HPLC analysis and the $^1$H-NMR spectrum confirmed the relative stoichiometry of the formed salt to be 1:1. The PXRD diffractogram indicated the sample contained predominantly amorphous content. Sodium analysis indicated the remaining carboxyl portion of the pamoate moiety within the 1:1 hydrocodone pamoate salt was approximately a 50-50 mixture of sodium salt carboxylate and free carboxylic acid. Karl Fischer titration analysis indicated the salt contained 5.88% water.

Example 2. Preparation of Polymorphic Hydrocodone Pamoate, (1:1) Salt

Figure 5:
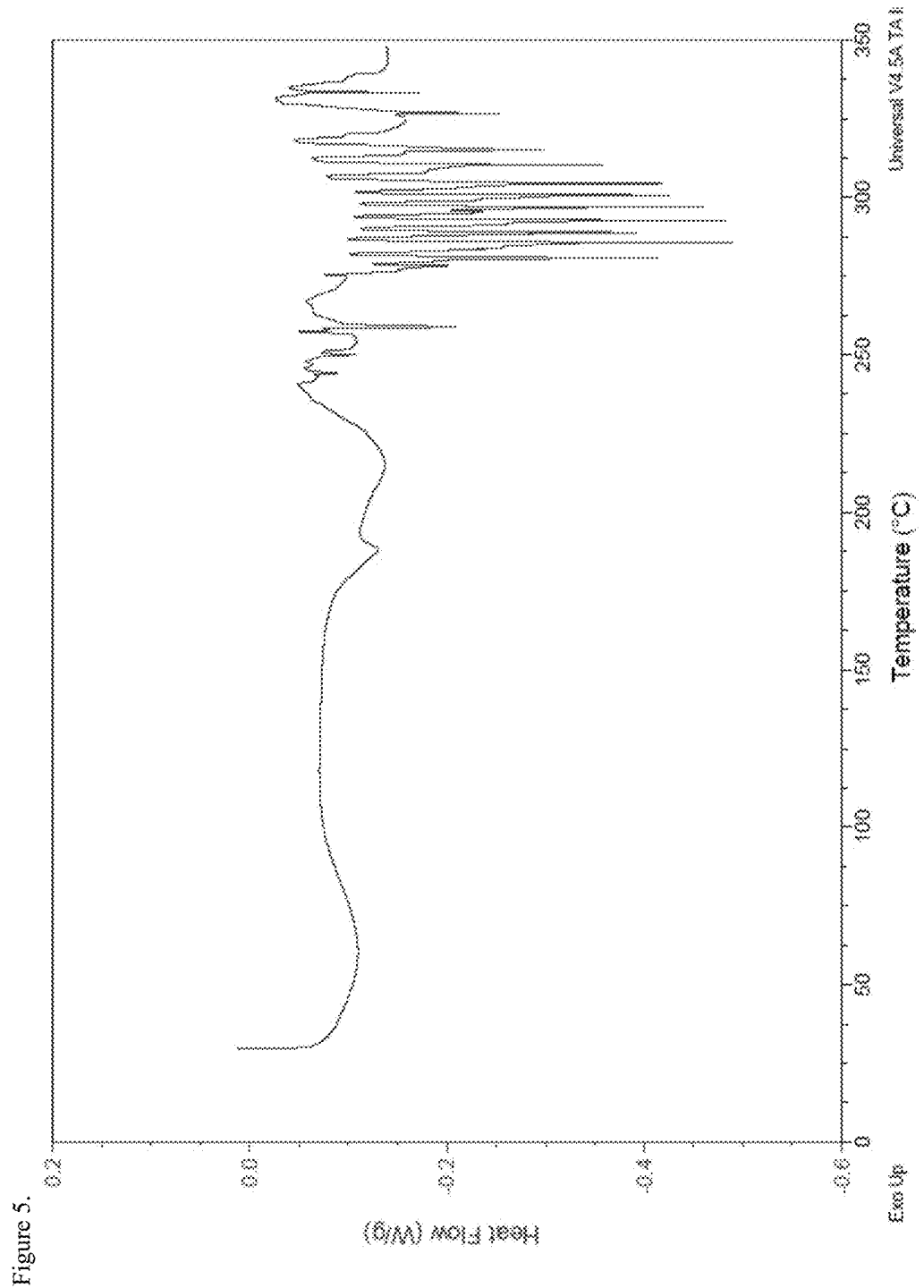
FIG. 5 is the differential scanning calorimetry (DSC) thermogram of polymorphic hydrocodone pamoate 1:1 salt as the free carboxylic acid.
Figure 6:
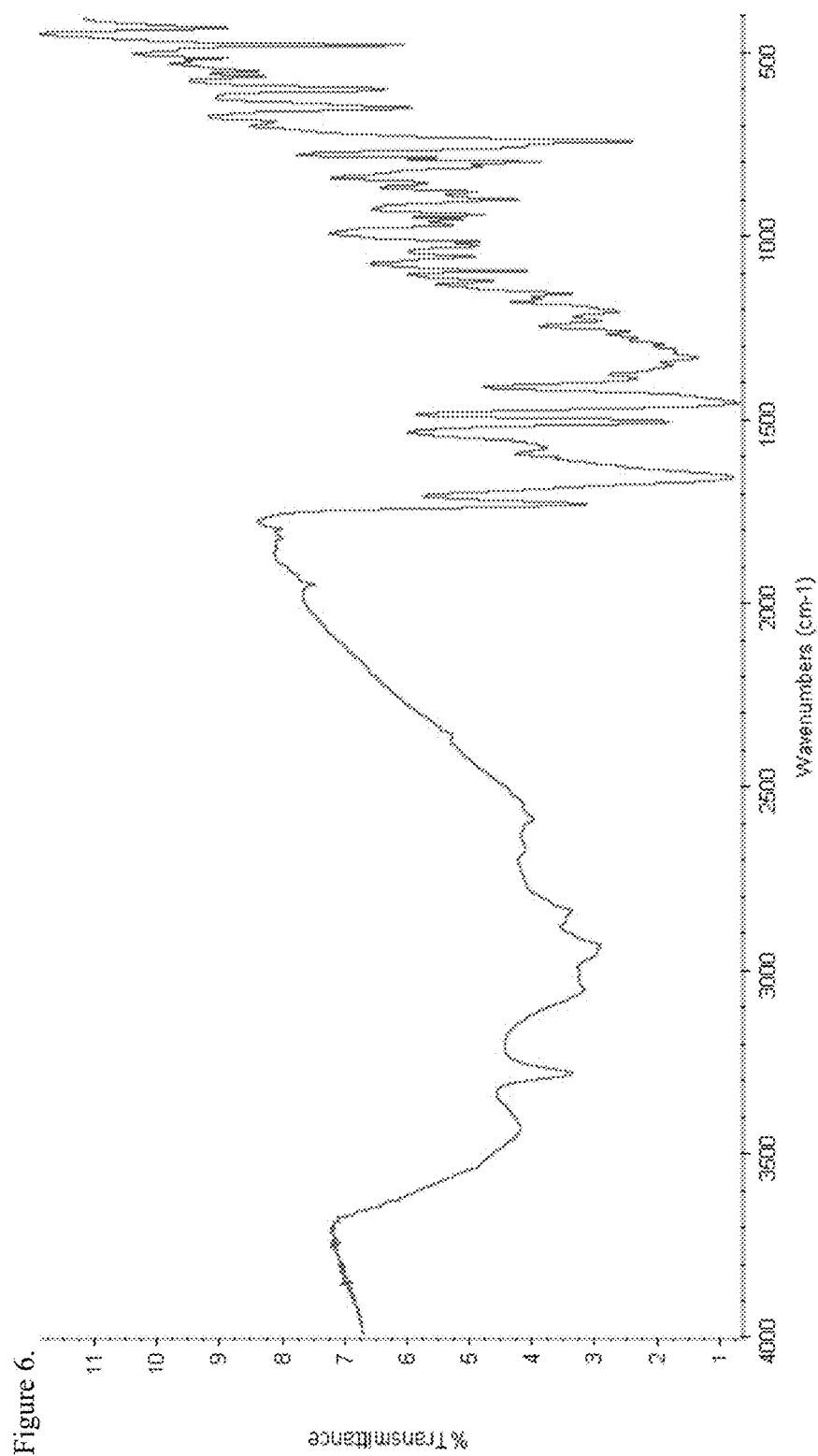
FIG. 6 is the Fourier transform infrared (FTIR) spectrum of polymorphic hydrocodone pamoate 1:1 salt as the free carboxylic acid.
Figure 7:
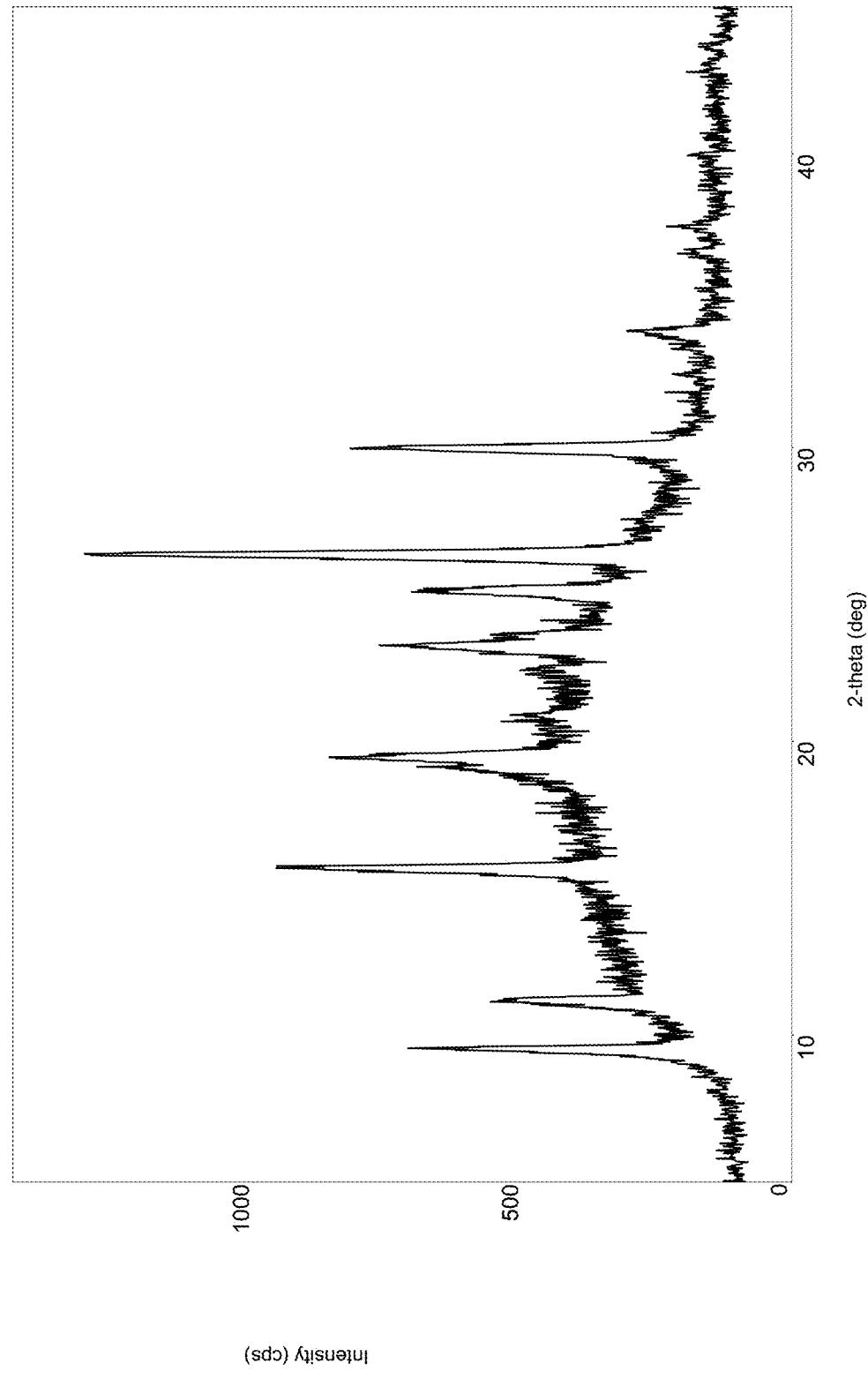
FIG. 7 is the powder X-ray diffraction (PXRD) diffractogram of polymorphic hydrocodone pamoate 1:1 salt as the free carboxylic acid.
Figure 8:
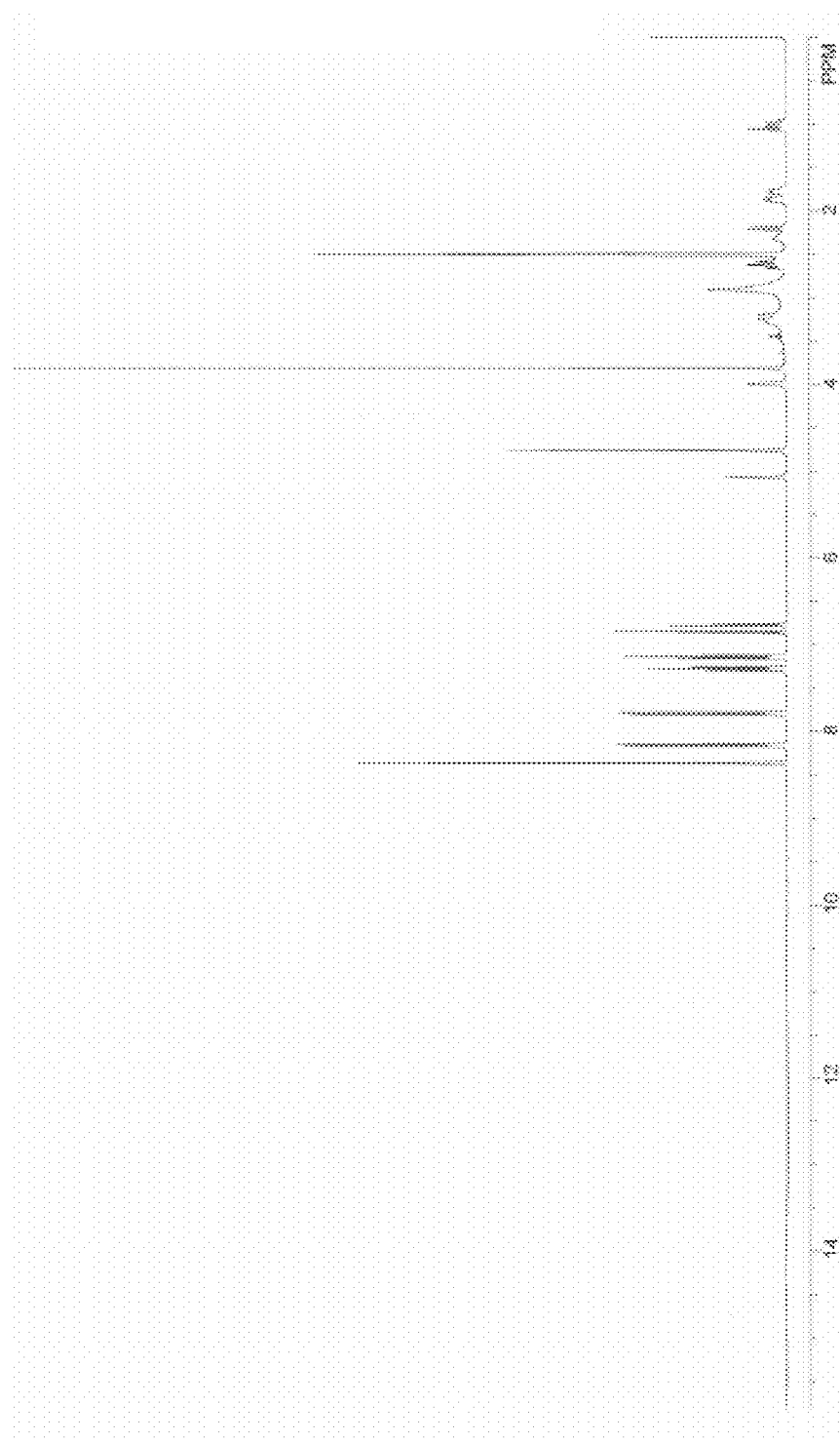
FIG. 8 is the proton nuclear magnetic resonance ($^1$H NMR) spectrum of polymorphic hydrocodone pamoate 1:1 salt as the free carboxylic acid.

To a 250 mL three-neck round-bottom flask equipped with a magnetic stir bar, thermowell, nitrogen inlet and addition funnel was charged disodium pamoate (1.06 g, 2.34 mmol)

and 48 mL 75:25 ethanol/water, and the contents stirred at ambient temperature under a nitrogen atmosphere. A hydrocodone formic acid salt solution was prepared in a separate vessel according to the following procedure. To a 50 mL round-bottom flask equipped with a magnetic stir bar was charged hydrocodone base (701.7 mg, 2.34 mmol), 7 mL ethanol and 7 mL 5% formic acid (88%)/ethanol solution and the contents stirred at ambient temperature under a nitrogen atmosphere. The hydrocodone formic acid solution was added to the disodium pamoate solution over a period of about one minute via an addition funnel, and the mixture stirred overnight under nitrogen at ambient temperature. The pH of the resultant solution was recorded as about 5.2. The solution was concentrated under reduced pressure (28.7 inches Hg and 22° C. water bath temperature) to provide hydrocodone pamoate, (1:1) salt. The product was stirred for about one minute in a solution consisting of 320 mg citric acid in 66 g water, the solids were quickly isolated by filtration through a medium frit filter and subsequently, the isolated solids washed with 50 g water. The sample was re-slurried in water (about 58 g) and stirred for about ten minutes, the solids again isolated by filtration through a medium frit filter and then the solids dried under vacuum to provide 1.41 g (88% yield) of a light yellow powder. The salt was characterized by DSC (FIG. 5), FTIR (FIG. 6), PXRD (FIG. 7), $^1$H-NMR (FIG. 8) and by sodium analysis. The $^1$H-NMR spectrum, in conjunction with sodium analysis, indicated the formed salt's 1:1 stoichiometry of hydrocodone and pamoate moieties with at least 98% of the remaining carboxylic acid functionality of the salt's pamoate moiety present as the free acid. The PXRD diffractogram confirmed the formed salt was predominantly crystalline with Karl Fischer titration analysis indicating the presence of 1.89% water.

Example 3. Preparation of Amorphous Oxycodone Pamoate 1:1 Salt

Figure 9:
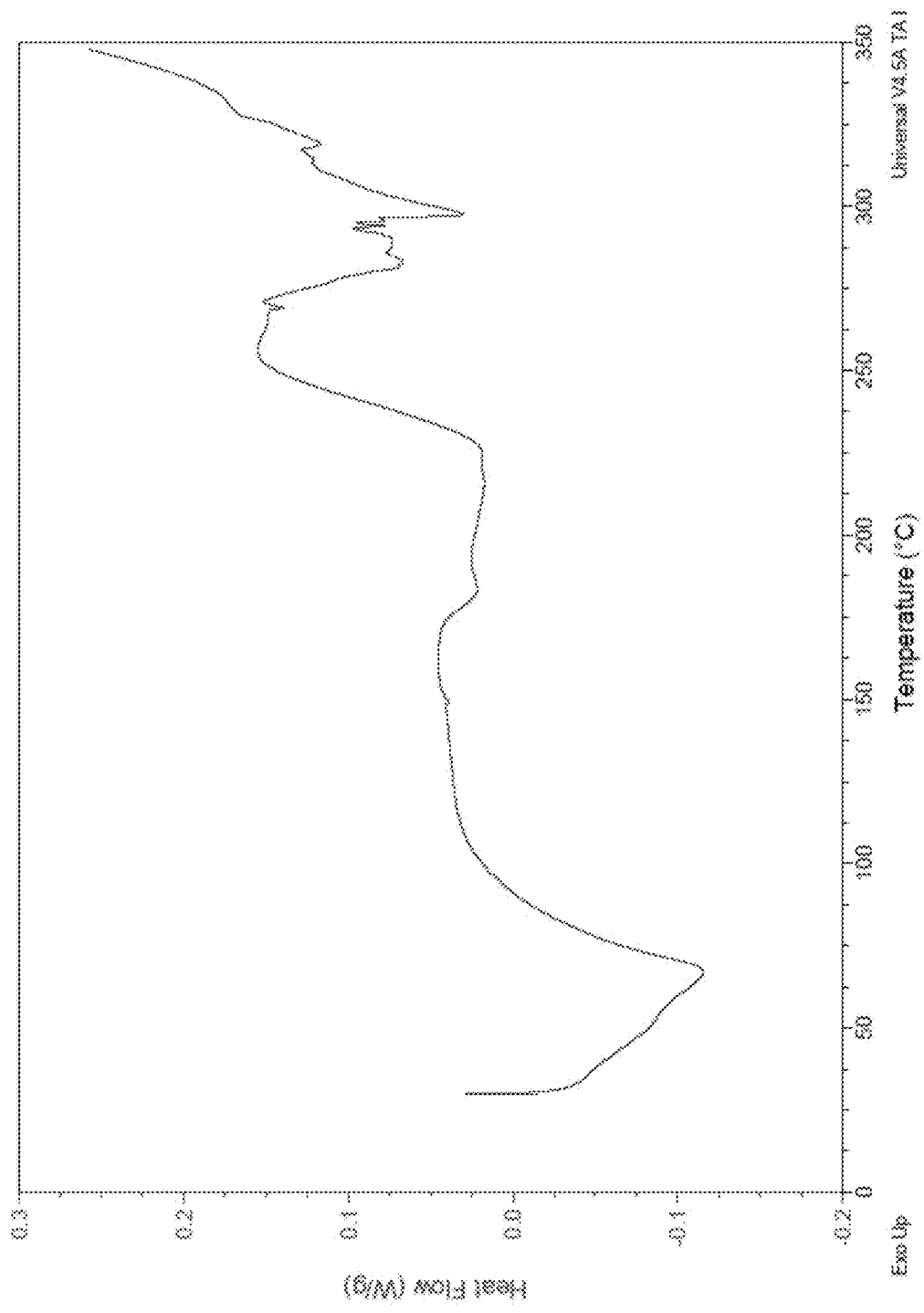
FIG. 9 is the differential scanning calorimetry (DSC) thermogram of amorphous oxycodone pamoate 1:1 salt as a 1:1 mixture of mono-sodium salt and free carboxylic acid.
Figure 10:
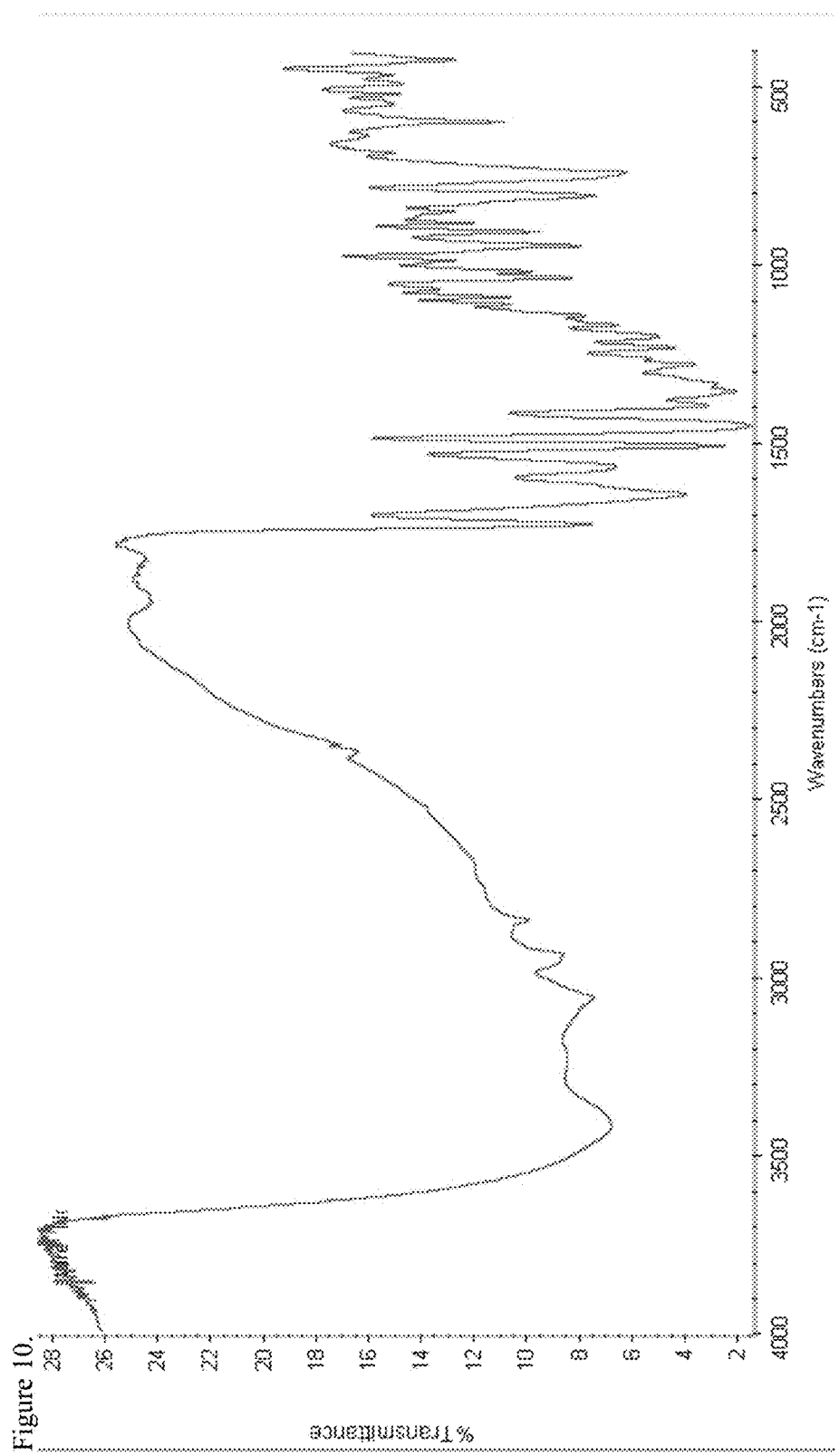
FIG. 10 is the Fourier transform infrared (FTIR) spectrum of amorphous oxycodone pamoate 1:1 salt as a 1:1 mixture of mono-sodium salt and free carboxylic acid.
Figure 11:
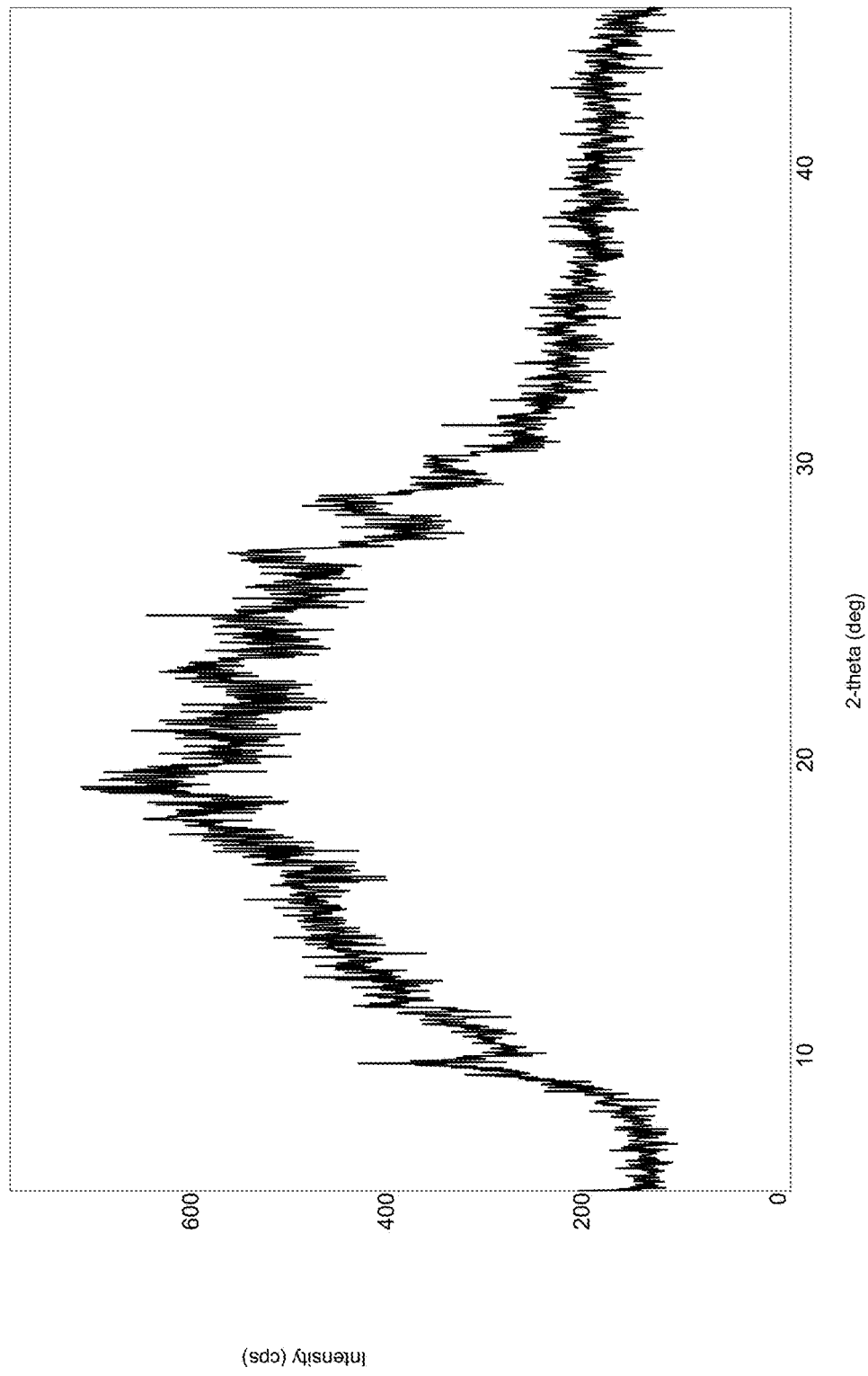
FIG. 11 is the powder X-ray diffraction (PXRD) diffractogram of amorphous oxycodone pamoate 1:1 salt as a 1:1 mixture of mono-sodium salt and free carboxylic acid.
Figure 12:
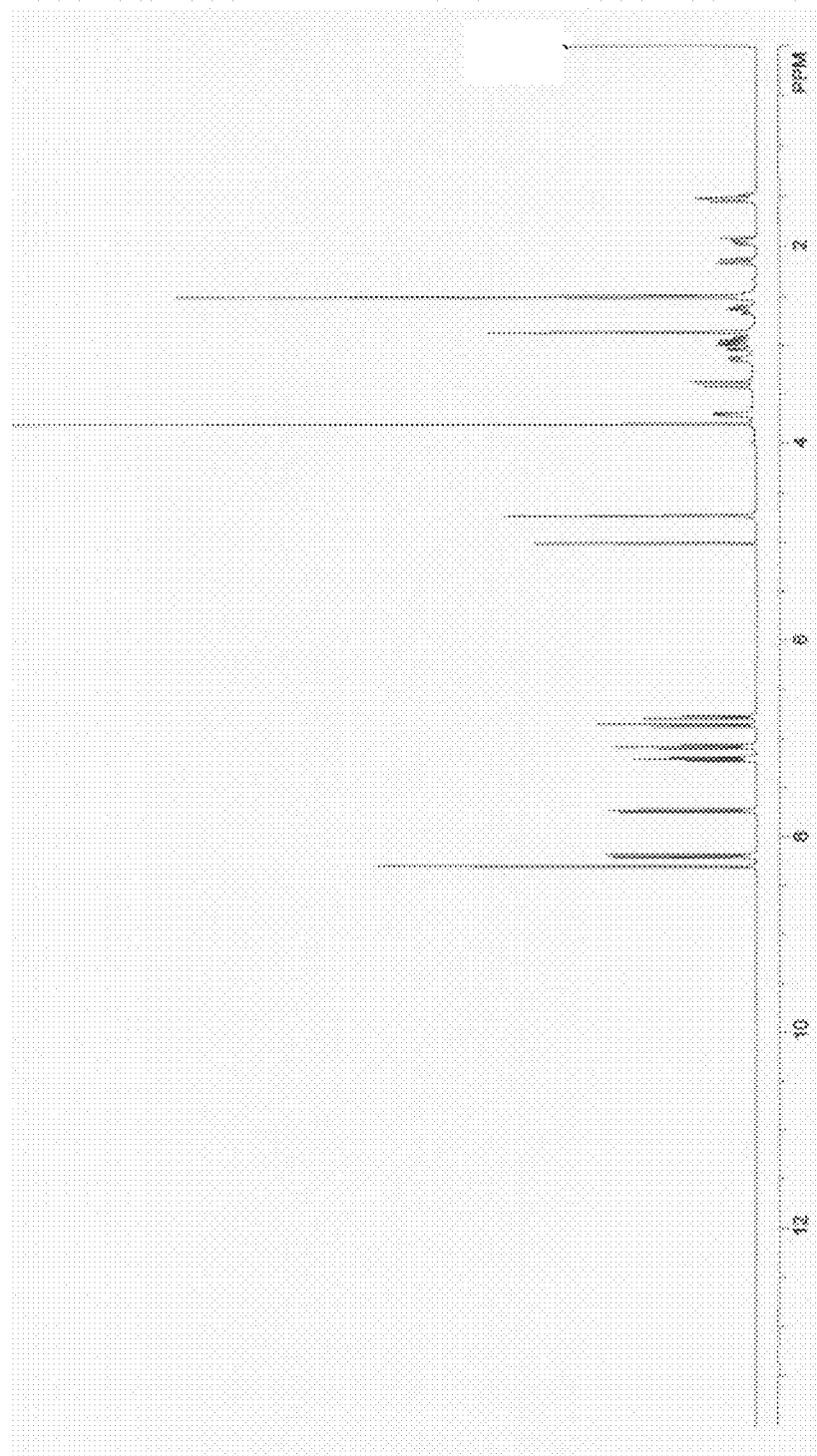
FIG. 12 is the proton nuclear magnetic resonance ($^1$H NMR) spectrum of amorphous oxycodone pamoate 1:1 salt as a 1:1 mixture of mono-sodium salt and free carboxylic acid.

To a 250 mL three-neck round-bottom flask equipped with a magnetic stir bar, thermowell, nitrogen inlet and addition funnel was charged disodium pamoate (1.50 g, 3.34 mmol) and 67 mL 75:25 ethanol/water and the contents stirred at ambient temperature under a nitrogen atmosphere. An oxycodone acetic acid salt solution was prepared in a separate vessel according to the following procedure. To a 50 mL round-bottom flask equipped with a magnetic stir bar was charged oxycodone base (1.05 g, 3.34 mmol) and 13.4 mL 5% acetic acid/ethanol solution and the mixture stirred at ambient temperature under a nitrogen atmosphere. The oxycodone acetic acid solution was added to the disodium pamoate solution over a period of about one minute via an addition funnel and the pH of the combined solutions was recorded as about 6.1; the mixture was stirred overnight under nitrogen at ambient temperature. The solution was concentrated under reduced pressure (28.7 inches Hg and 22° C. water bath temperature) to provide the oxycodone pamoate, (1:1) salt. The sample was triturated in water (about 34 g), the solids isolated by filtration through a medium frit filter washed with a small portion of water and subsequently dried under vacuum to provide 2.20 g (94% yield) of a light yellow powder. The product was characterized by DSC (FIG. 9), FTIR (FIG. 10), PXRD (FIG. 11), and $^1$H-NMR (FIG. 12). The $^1$H-NMR spectrum indicated the isolated oxycodone pamoate salt was essentially a 1:1 ratio of the two components with the PXRD diffractogram indicating the isolated salt was principally amorphous.

Figure 13:
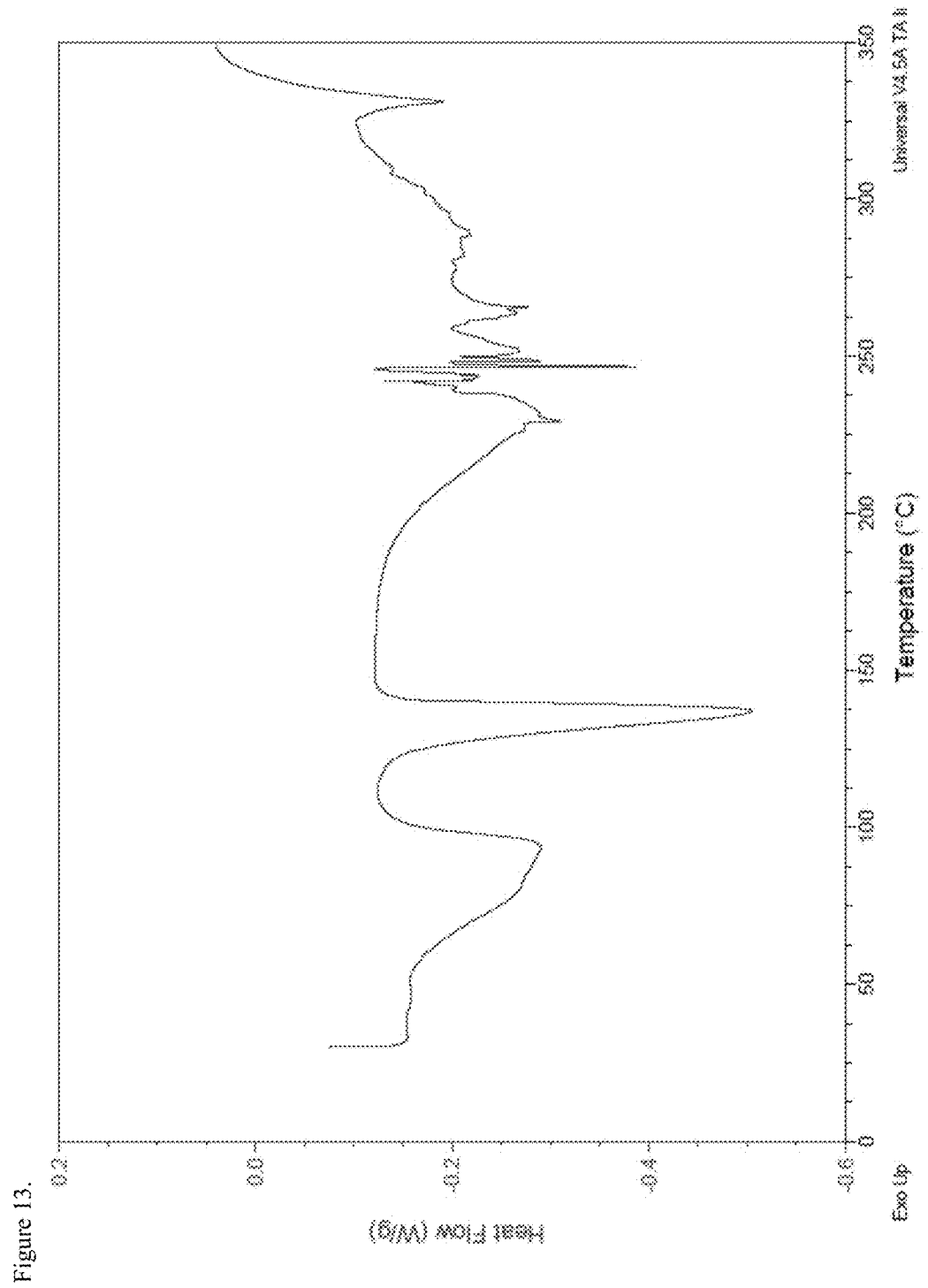
FIG. 13 is the differential scanning calorimetry (DSC) thermogram of polymorphic haloperidol pamoate 1:1 salt as the free carboxylic acid, first polymorph.
Figure 14:
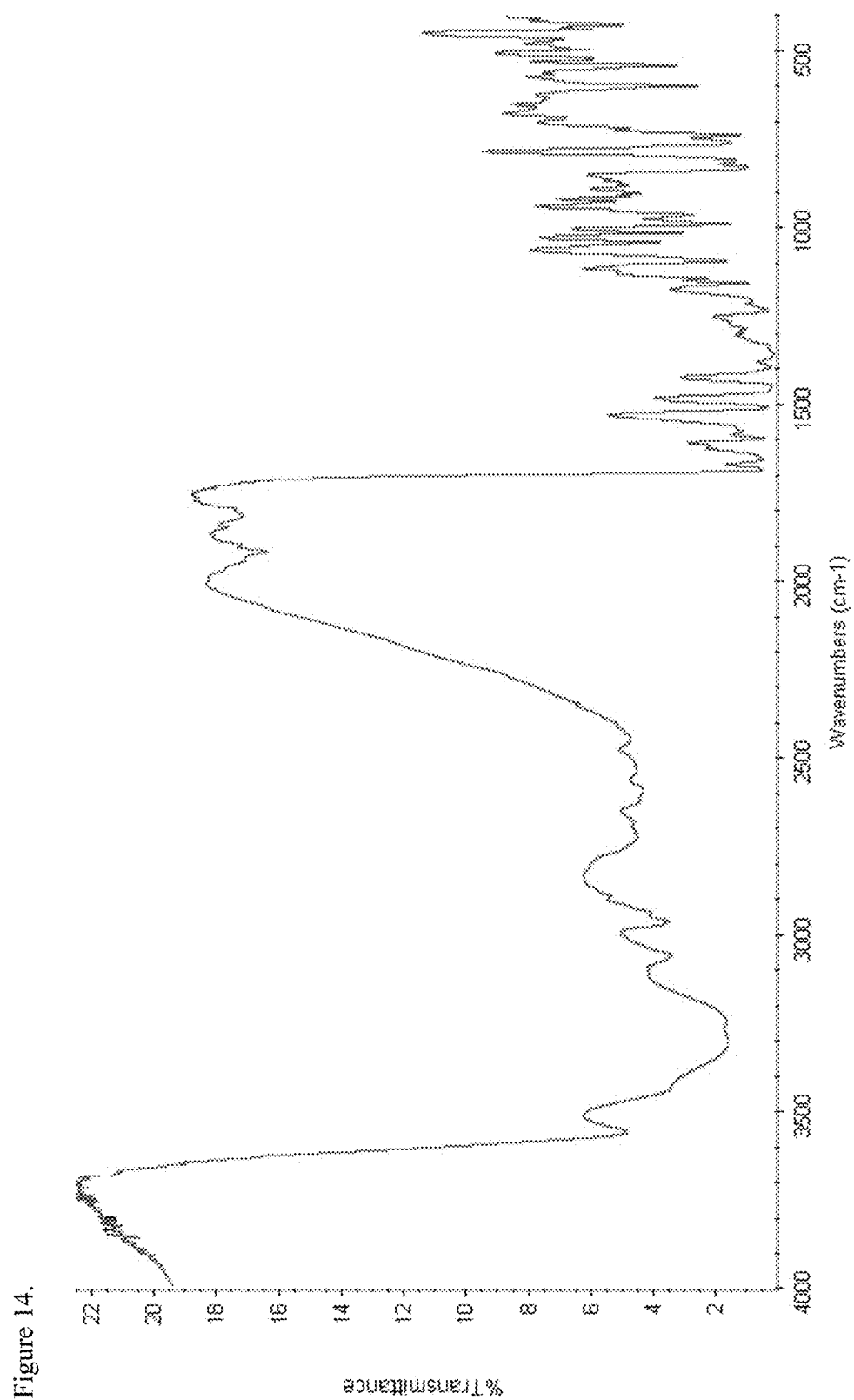
FIG. 14 is the Fourier transform infrared (FTIR) spectrum of polymorphic haloperidol pamoate 1:1 salt as the free carboxylic acid, first polymorph.
Figure 15:
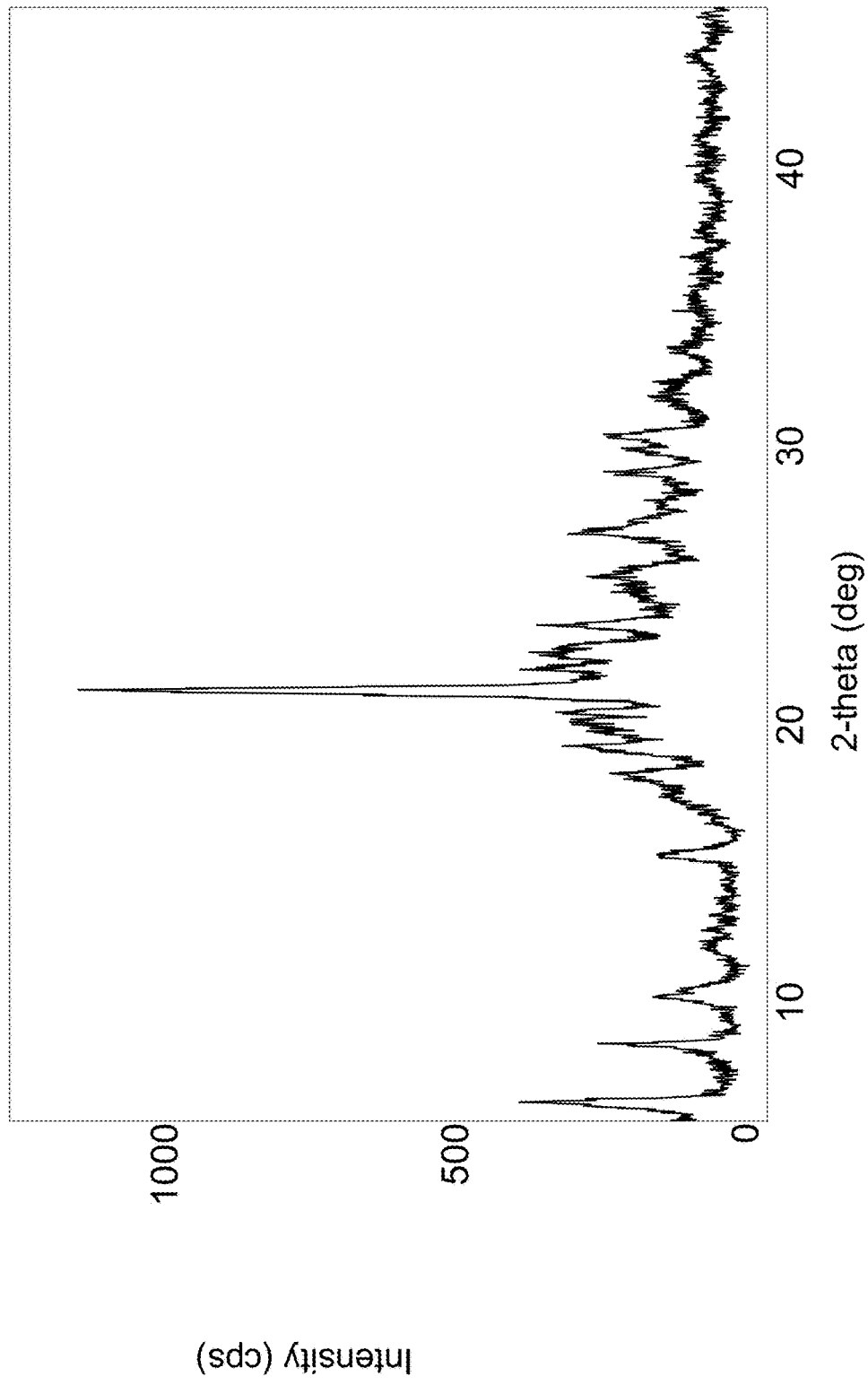
FIG. 15 is the powder X-ray diffraction (PXRD) diffractogram of polymorphic haloperidol pamoate 1:1 salt as the free carboxylic acid, first polymorph.
Figure 16:
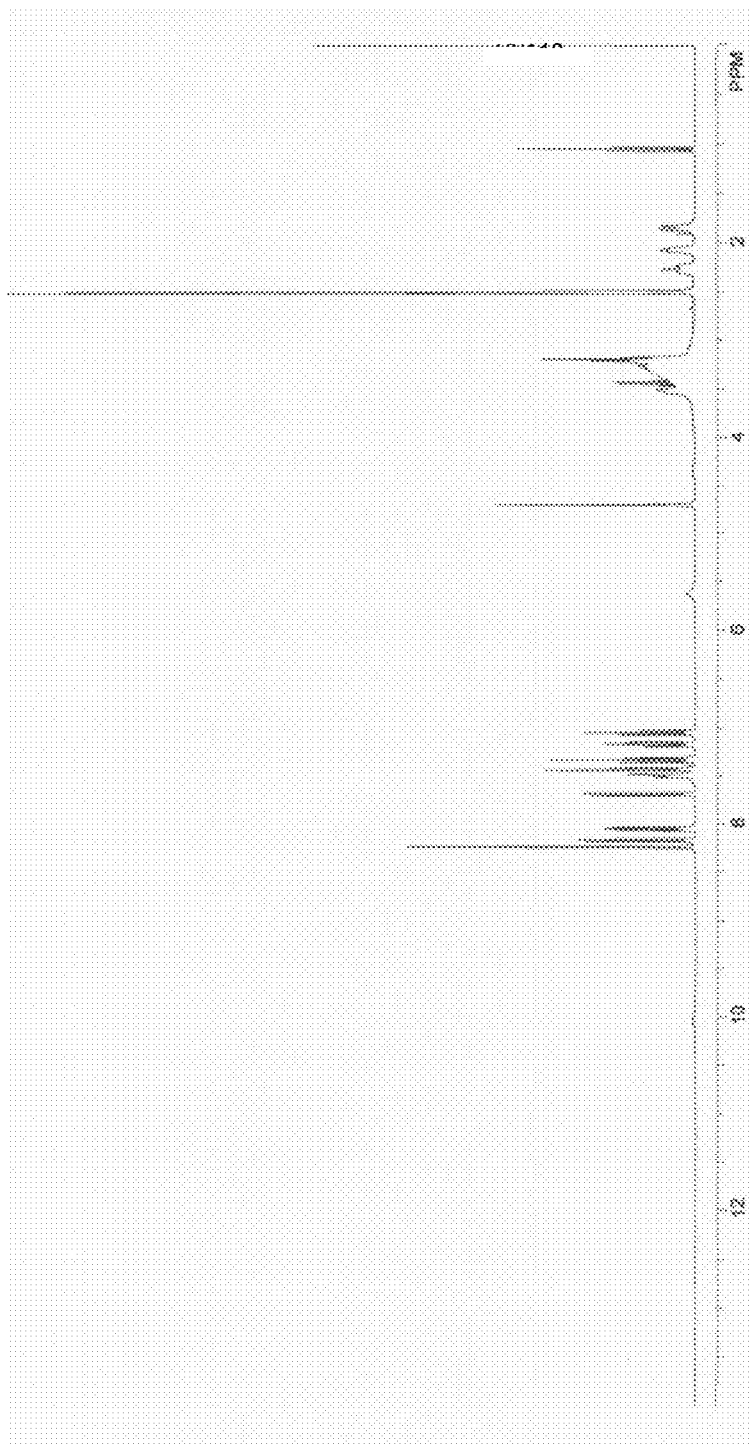
FIG. 16 is the proton nuclear magnetic resonance ($^1$H NMR) spectrum of polymorphic haloperidol pamoate 1:1 salt as the free carboxylic acid, first polymorph.

Example 4. Preparation of Polymorphic Haloperidol Pamoate 1:1 Salt, First Polymorph To a 1 L three-neck round-bottom flask equipped with a magnetic stir bar, thermowell, nitrogen inlet and addition funnel was charged disodium pamoate (1.50 g, 3.34 mmol) and 200 mL 75:25 ethanol/water and the contents stirred at ambient temperature under a nitrogen atmosphere. To a 50 mL round-bottom flask equipped with a magnetic stir bar was charged haloperidol (1.26 g, 3.34 mmol) and 13.4 mL 5% acetic acid/ethanol solution, and the mixture stirred at ambient temperature under a nitrogen atmosphere. The haloperidol acetic acid solution was added to the disodium pamoate solution over a period of about one minute via an addition funnel and after about five minutes the solution became cloudy whereupon the solution was diluted with 300 mL ethanol. The mixture was stirred for about one hour at ambient temperature under a nitrogen atmosphere. The solution was then concentrated under reduce pressure (28.7 inches Hg and 22° C. water bath temperature) to provide the haloperidol pamoate, (1:1) salt. The sample was triturated in water (about 40 g), the solids isolated by filtration through a medium frit filter and subsequently dried under vacuum to provide 2.46 g (96% yield) of an off-white powder. The salt was characterized by DSC (FIG. 13), FTIR (FIG. 14), PXRD (FIG. 15) and $^1$H-NMR (FIG. 16), and sodium analysis. The $^1$H-NMR spectrum was consistent with a 1:1 ratio of haloperidol and pamoate moieties. The PXRD diffractogram indicated the product was predominantly crystalline. Sodium analysis indicated the remaining carboxylic acid functionality of the pamoate moiety of 1:1 haloperidol pamoate salt was present as the free carboxylic acid with only trace amounts of the sodium carboxylate present. Karl Fischer titration analysis indicated the presence of 3.48% water.

Figure 17:
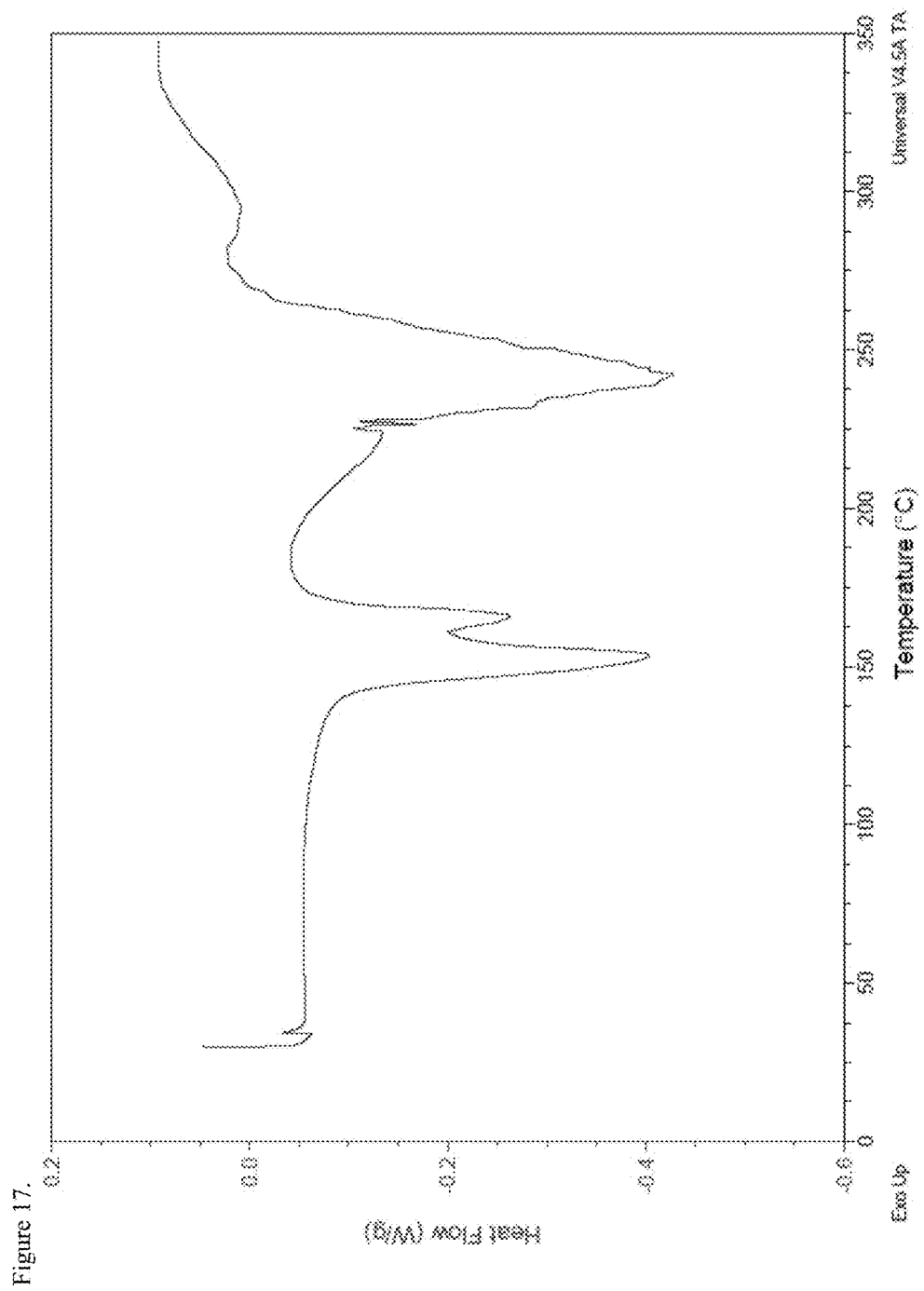
FIG. 17 is the differential scanning calorimetry (DSC) thermogram of polymorphic haloperidol pamoate 1:1 salt as the free carboxylic acid, second polymorph.
Figure 18:
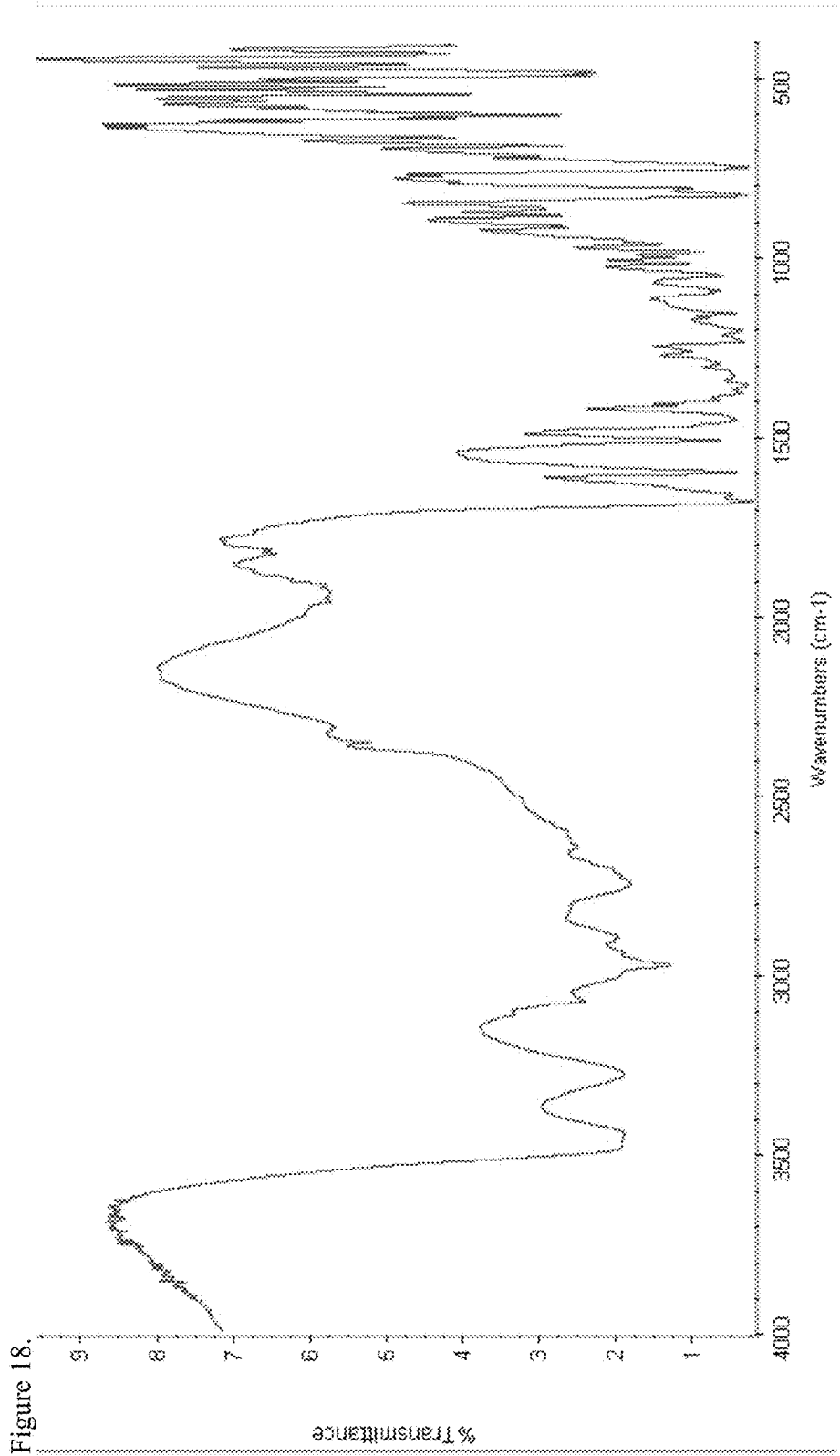
FIG. 18 is the Fourier transform infrared (FTIR) spectrum of polymorphic haloperidol pamoate 1:1 salt as the free carboxylic acid, second polymorph.
Figure 19:
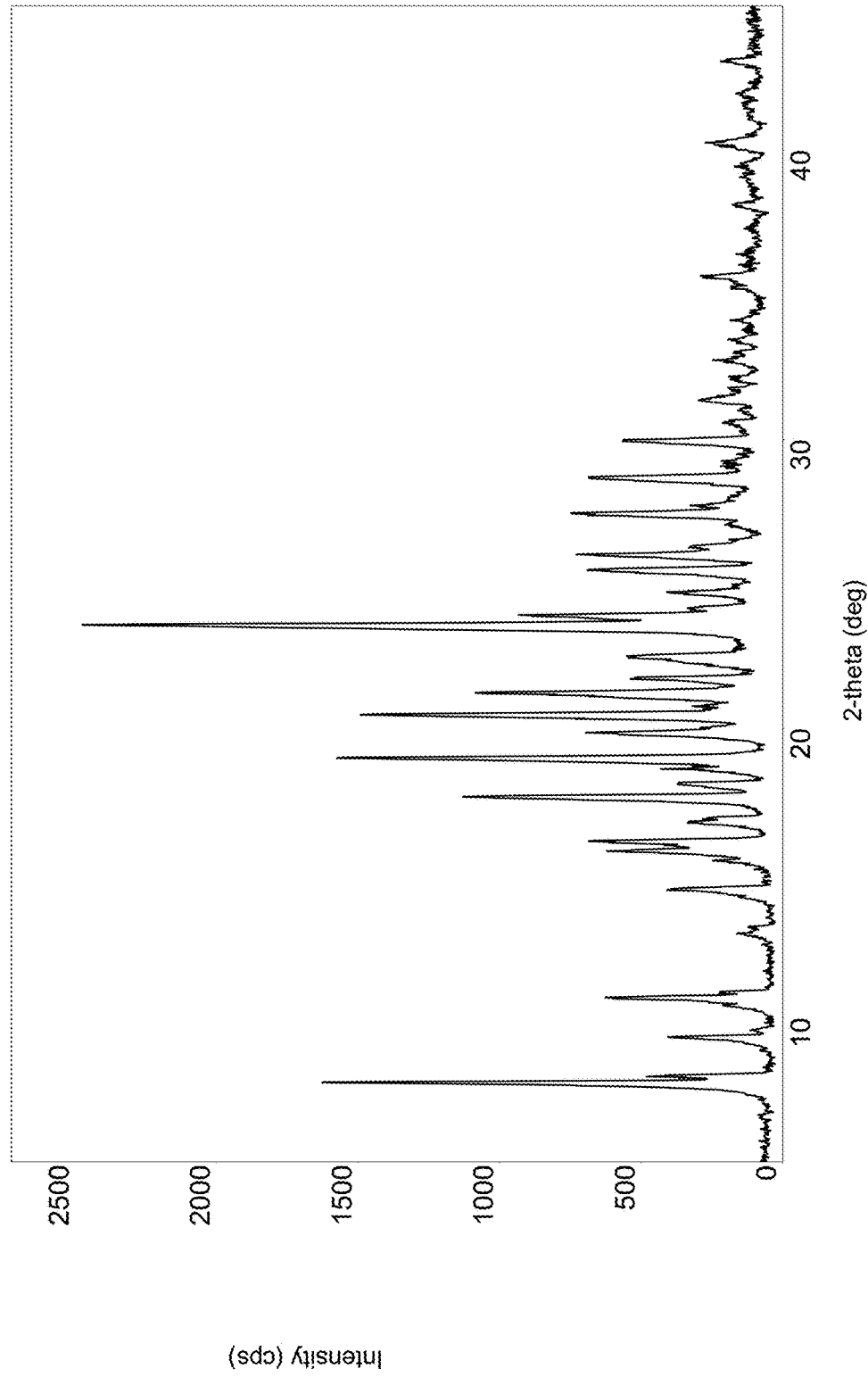
FIG. 19 is the powder X-ray diffraction (PXRD) diffractogram of polymorphic haloperidol pamoate 1:1 salt as the free carboxylic acid, second polymorph.
Figure 20:
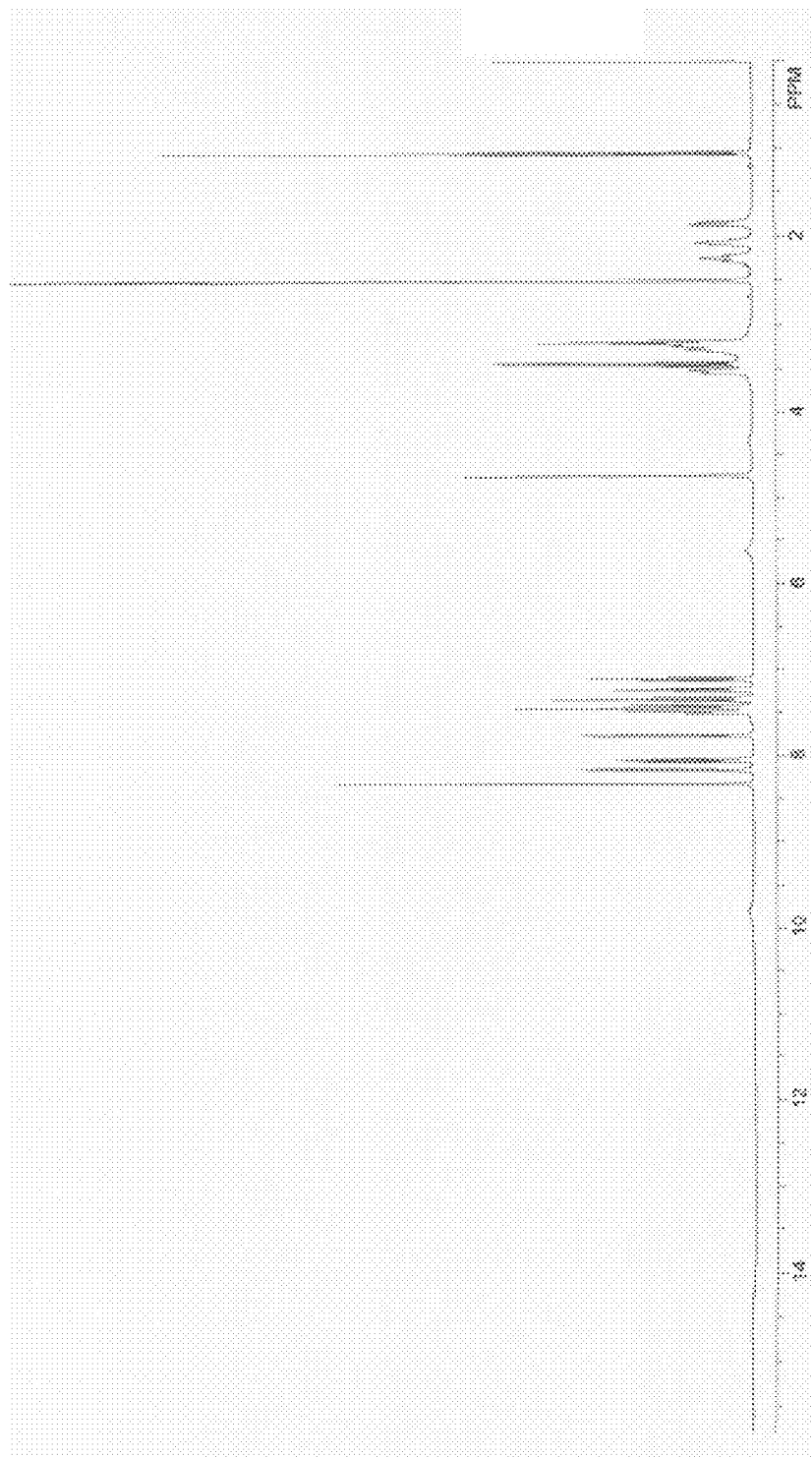
FIG. 20 is the proton nuclear magnetic resonance ($^1$H NMR) spectrum of polymorphic haloperidol pamoate 1:1 salt as the free carboxylic acid, second polymorph.

Example 5. Preparation of Polymorphic Haloperidol Pamoate 1:1 Salt, Second Polymorph To a 250 mL three-neck round-bottom flask equipped with a magnetic stir bar, thermowell, nitrogen inlet and addition funnel was charged disodium pamoate (0.75 g, 1.67 mmol) and 34 mL 75:25 ethanol/water and the contents stirred at ambient temperature under a nitrogen atmosphere. To a 50 mL round-bottom flask equipped with a magnetic stir bar was charged haloperidol (0.63 g, 3.34 mmol) and 6.7 mL 5% formic acid (88%)/ethanol, and the mixture stirred at ambient temperature under a nitrogen atmosphere. The haloperidol formic acid solution was added to the disodium pamoate solution over a period of about one minute via an addition funnel and after about two minutes the solution became cloudy. The pH of the solution was measured as about 4.8. The mixture was stirred overnight at ambient temperature under a nitrogen atmosphere. The solution was then concentrated under reduced pressure (28.7 inches Hg and 22° C. water bath temperature) to provide the haloperidol pamoate, (1:1) salt. The sample was triturated in water (about 40 g), the solids isolated by filtration through a medium frit filter and then subsequently dried under vacuum to provide 1.24 g (97% yield) of an off-white to pale yellow powder. The salt was characterized by DSC (FIG. 17), FTIR (FIG. 18), PXRD (FIG. 19) and $^1$H-NMR (FIG. 20). The $^1$H-NMR spectrum was consistent with a 1:1 ratio of haloperidol to pamoate stoichiometry of salt formation. The PXRD diffractogram indicated the product was crystalline. Sodium analysis indicated the remaining carboxylic acid functionality of the pamoate component of 1:1 haloperidol pamoate salt was present at about 95% free carboxylic acid. Karl Fischer titration analysis indicated the presence of 1.07% water.

Figure 21:
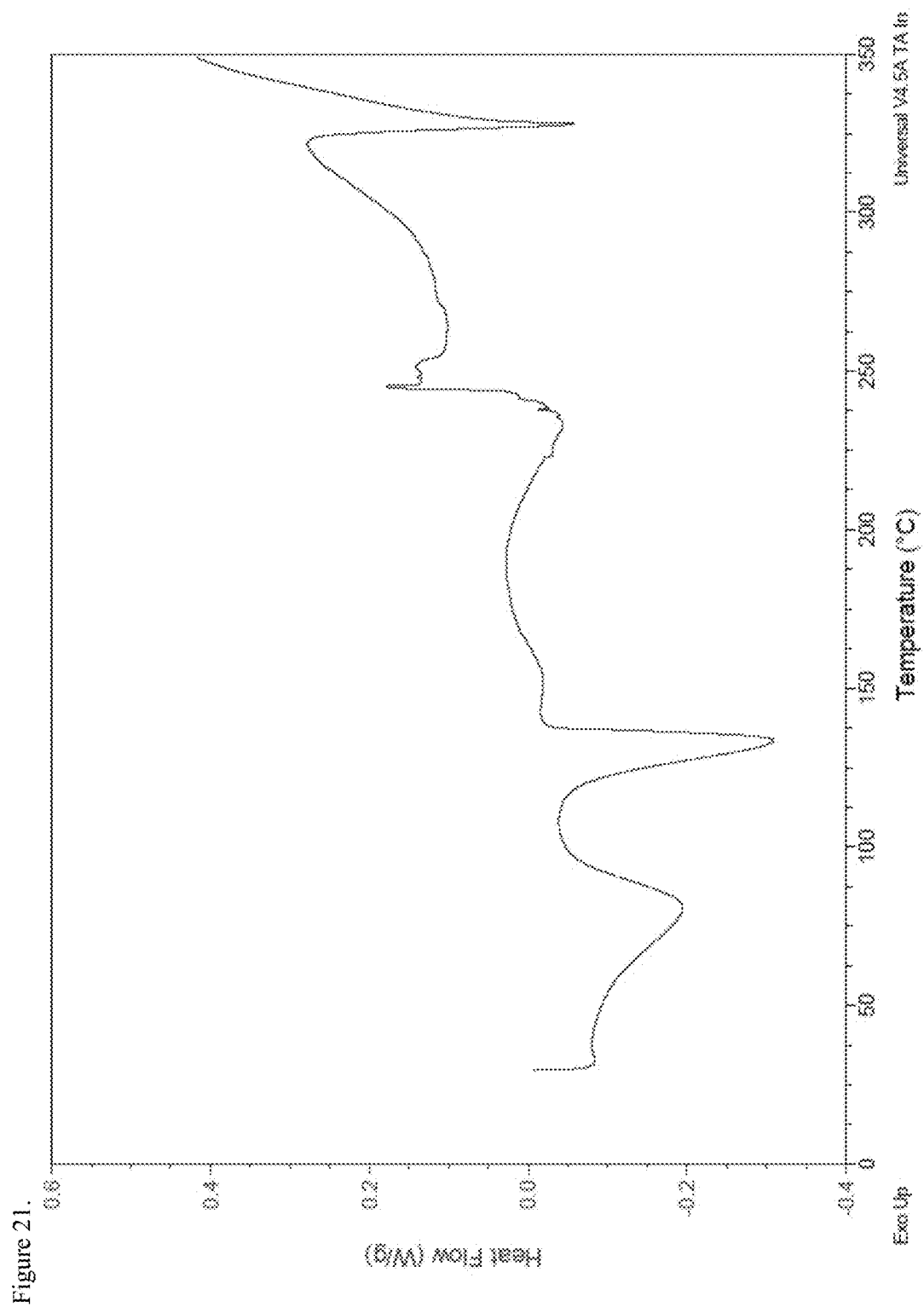
FIG. 21 is the differential scanning calorimetry (DSC) thermogram of polymorphic haloperidol pamoate 1:1 salt as a 3:1 mixture of mono-sodium salt and free carboxylic acid.
Figure 22:
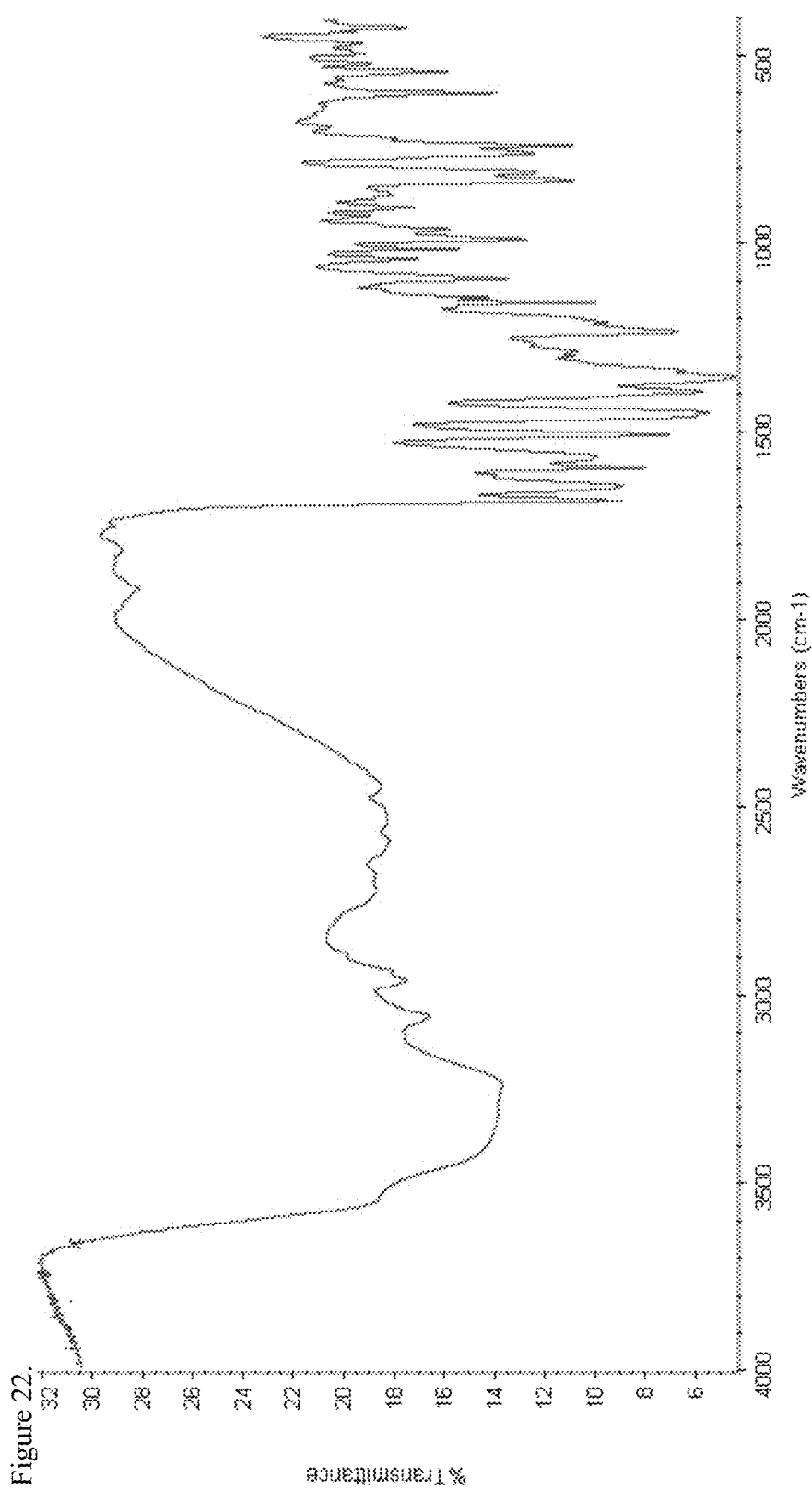
FIG. 22 is the Fourier transform infrared (FTIR) spectrum of polymorphic haloperidol pamoate 1:1 salt as a 3:1 mixture of mono-sodium salt and free carboxylic acid.
Figure 23:
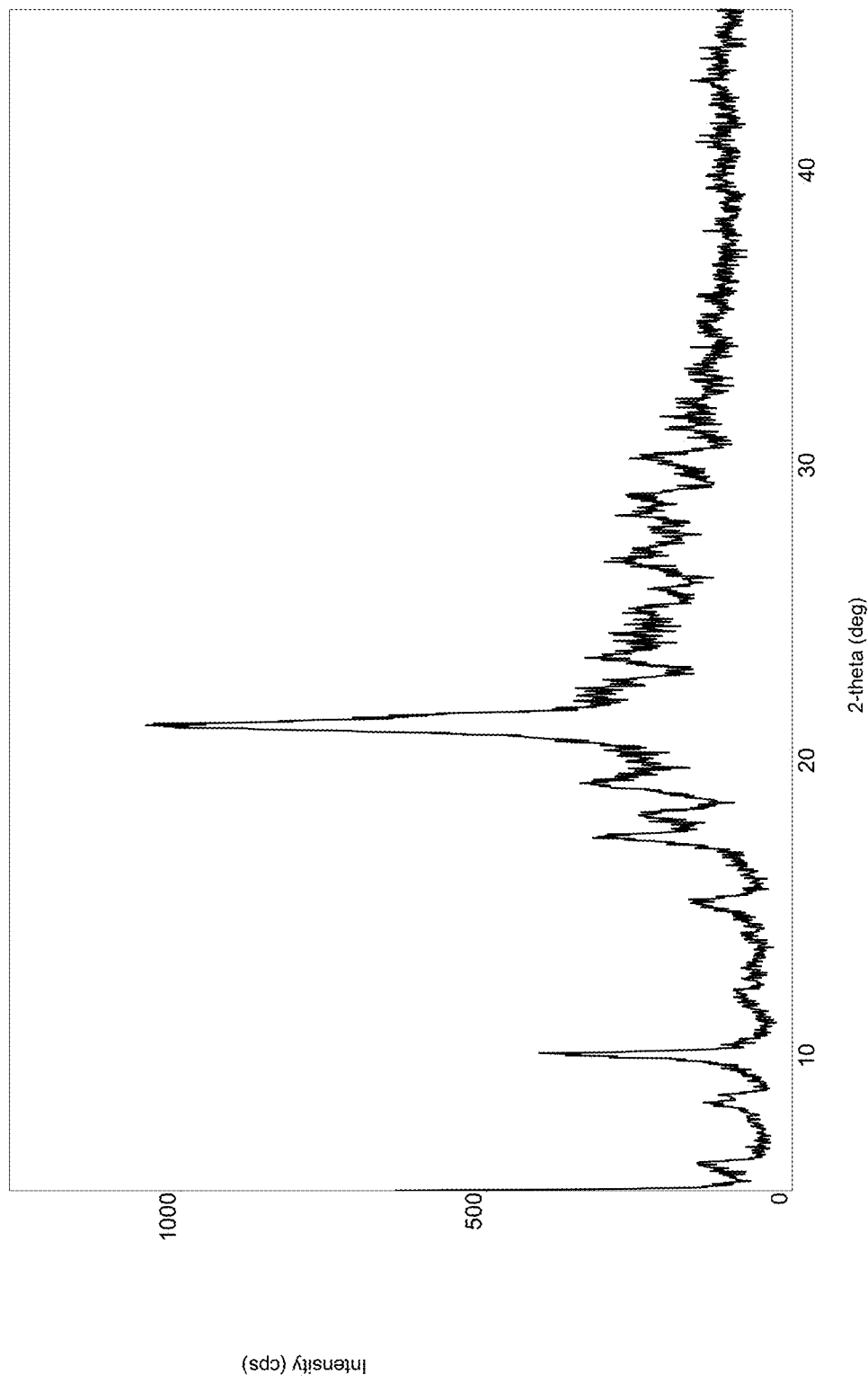
FIG. 23 is the powder X-ray diffraction (PXRD) diffractogram of polymorphic haloperidol pamoate 1:1 salt as a 3:1 mixture of mono-sodium salt and free carboxylic acid.
Figure 24:
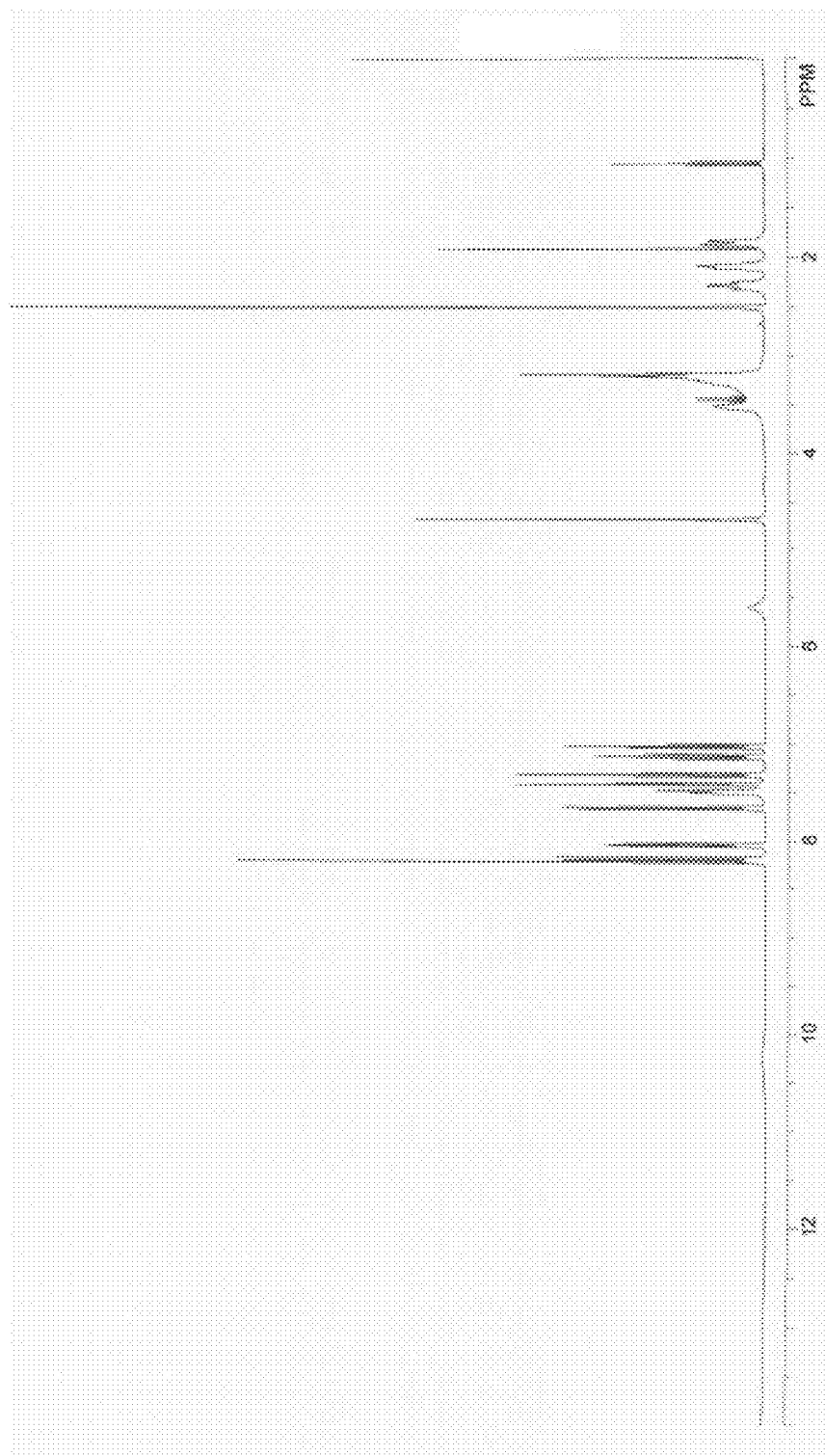
FIG. 24 is the proton nuclear magnetic resonance ($^1$H NMR) spectrum of polymorphic haloperidol pamoate 1:1 salt as a 3:1 mixture of mono-sodium salt and free carboxylic acid.

Example 6. Preparation of Polymorphic Haloperidol Pamoate 1:1 Salt as the Mixture of Sodium Salt and Free Carboxylic Acid To a 100 mL one-neck round-bottom flask equipped with a magnetic stir bar, thermowell, nitrogen inlet and addition funnel was charged disodium pamoate (0.75 g, 1.67 mmol) and 34 mL 75:25 ethanol/water, and the contents stirred at ambient temperature under a nitrogen atmosphere. To a 50 mL round-bottom flask equipped with a magnetic stir bar was charged haloperidol (0.63 g, 1.67 mmol) and 10 mL 10% acetic acid/ethanol solution and the mixture stirred at ambient temperature under a nitrogen atmosphere. The haloperidol acetic acid solution was added over a period of about one minute to the disodium pamoate solution via an addition funnel; this addition was immediately followed by the addition of a solution prepared from 1 g sodium bicarbonate in 12 mL water. After about two minutes the solution became cloudy and the pH was measured as about 6.4. The mixture was stirred overnight at ambient temperature. The solution was then concentrated under reduced pressure (28.7 inches Hg and 22° C. water bath temperature) to provide the haloperidol pamoate, (1:1) salt. The sample was triturated in water (about 34 g), the solids isolated by filtration through a medium frit filter and the solids subsequently dried under vacuum to provide 1.26 g (96% yield) of an off-white powder. The product was characterized by DSC (FIG. 21), FTIR (FIG. 22), PXRD (FIG. 23) and $^1$H-NMR (FIG. 24), and sodium analysis. The $^1$H-NMR spectrum was consistent with a 1:1 stoichiometric ratio of haloperidol to pamoate moieties of the formed salt. The PXRD diffractogram was consistent with a polymorphic material. Sodium analysis indicated the remaining carboxylic acid functionality of the salt's pamoate moiety was approximately a 75:25 mixture of sodium carboxylate and free carboxylic acid, respectively.

Example 7. Preparation of Amorphous Morphine Pamoate, (1:1) Salt

Figure 25:
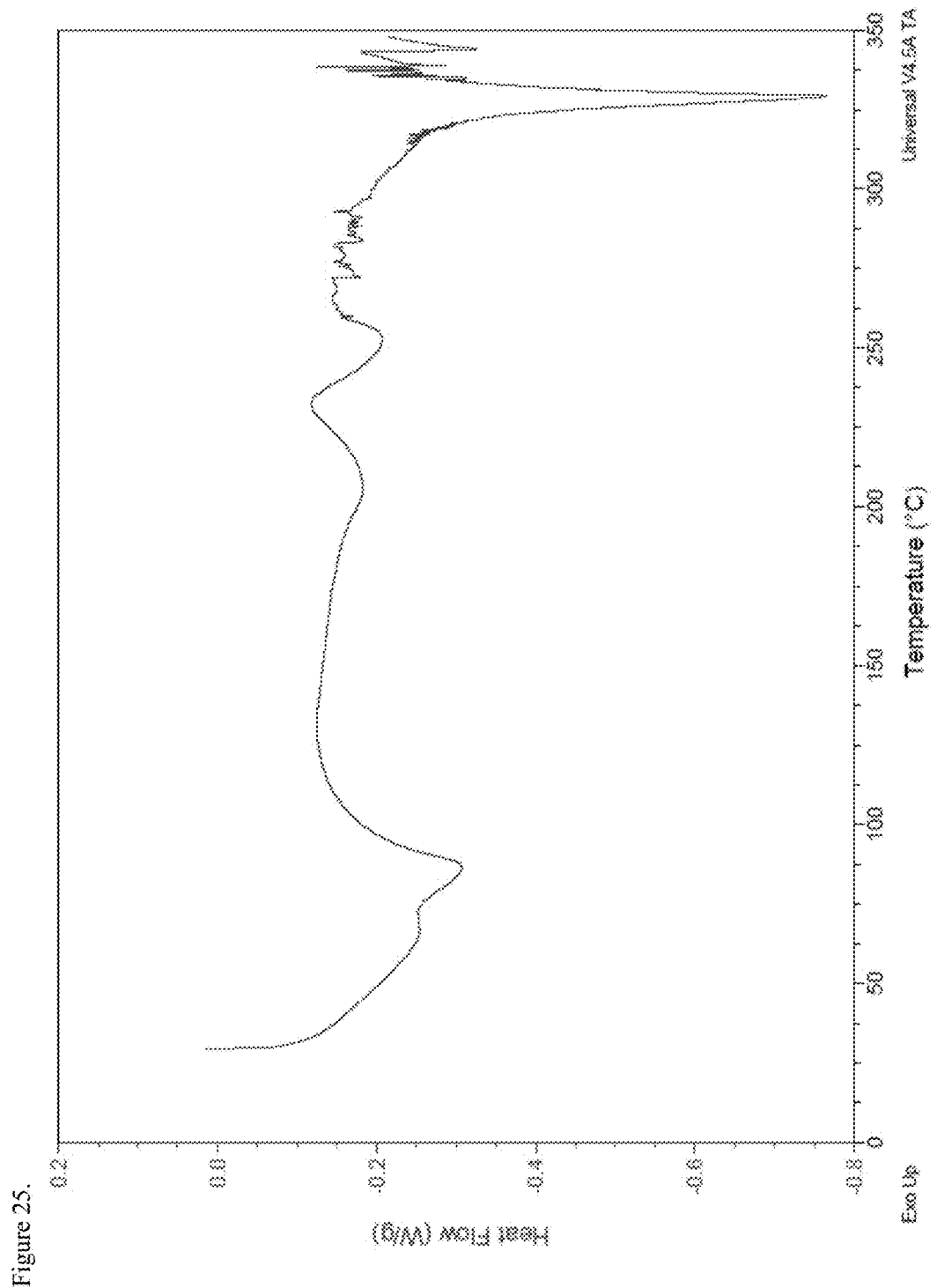
FIG. 25 is the differential scanning calorimetry (DSC) thermogram of amorphous morphine pamoate 1:1 salt as the 1:1 mixture of mono-sodium salt and free carboxylic acid.
Figure 26:
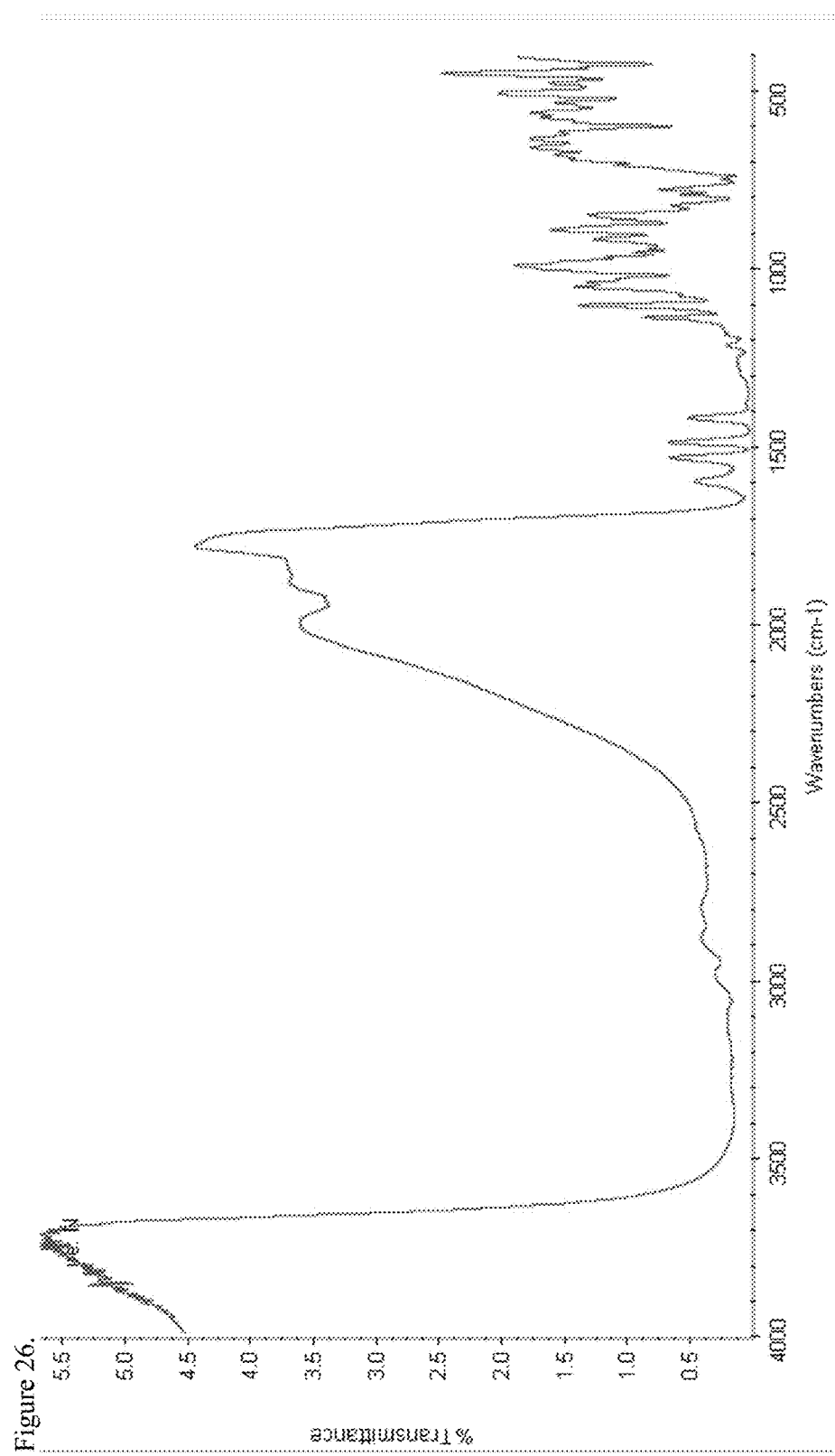
FIG. 26 is the Fourier transform infrared (FTIR) spectrum of amorphous morphine pamoate 1:1 salt as the 1:1 mixture of mono-sodium salt and free carboxylic acid.
Figure 27:
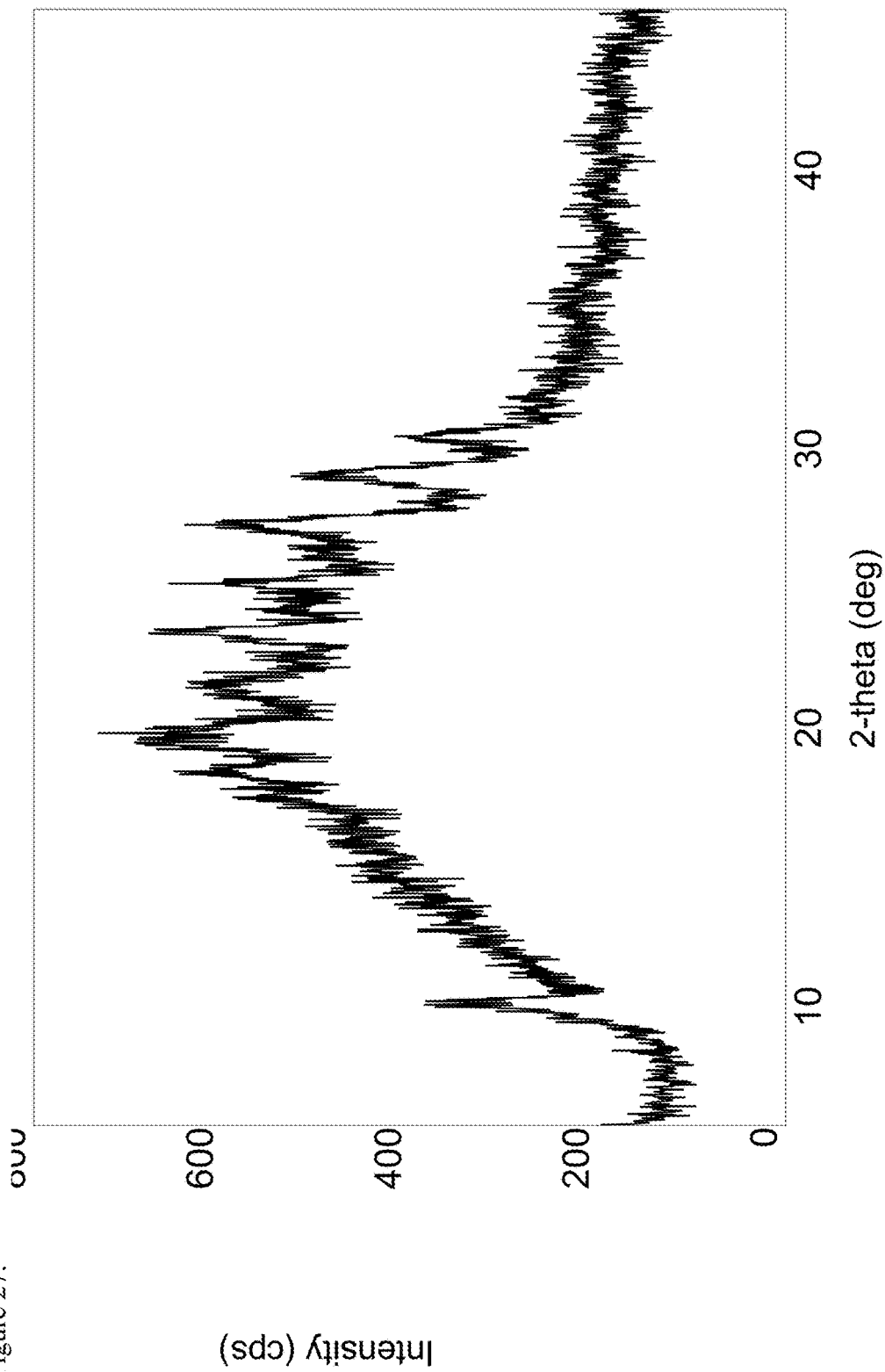
FIG. 27 is the powder X-ray diffraction (PXRD) diffractogram of amorphous morphine pamoate 1:1 salt as the 1:1 mixture of mono-sodium salt and free carboxylic acid.
Figure 28:
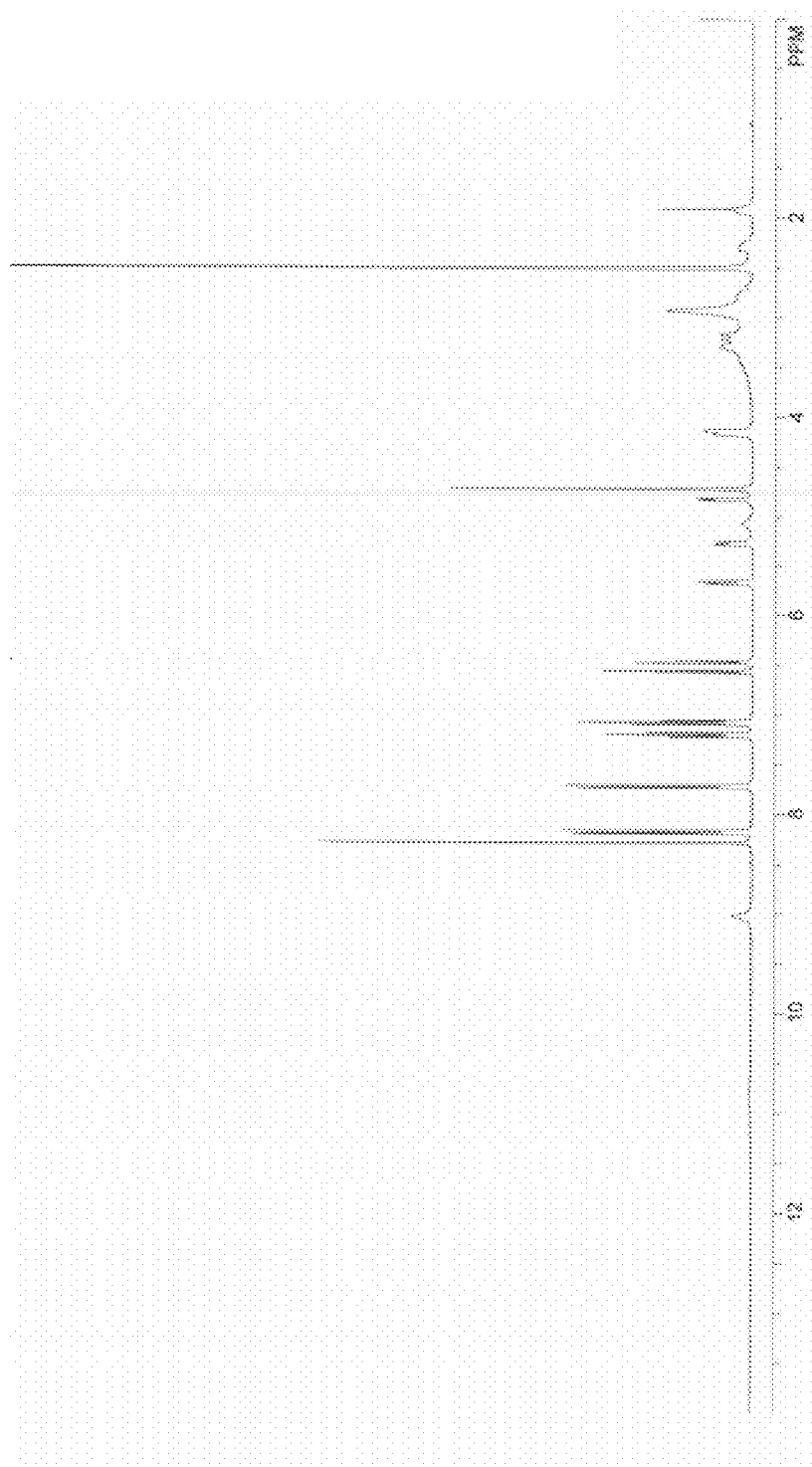
FIG. 28 is the proton nuclear magnetic resonance (¹H NMR) spectrum of amorphous morphine pamoate 1:1 salt as the 1:1 mixture of mono-sodium salt and free carboxylic acid.

To a 250 mL three-neck round-bottom flask equipped with a magnetic stir bar, thermowell, nitrogen inlet and addition funnel was charged disodium pamoate (1.50 g, 3.34 mmol) and 67 mL 75:25 ethanol/water, and the contents stirred at ambient temperature under a nitrogen atmosphere. A morphine acetic acid salt solution was prepared in a separate vessel according to the following procedure. To a 50 mL round-bottom flask equipped with a magnetic stir bar was charged morphine monohydrate (1.01 g, 3.34 mmol) and 13.4 mL 5% acetic acid/ethanol solution, and the mixture stirred at ambient temperature under a nitrogen atmosphere. The morphine acetic acid solution was added to the disodium pamoate solution over a period of about one minute via an addition funnel with the pH of the combined solutions at about 6.0. The mixture was stirred for about an additional hour under nitrogen at ambient temperature. The solution was then concentrated under reduced pressure (28.7 inches Hg and 22° C. water bath temperature) to provide the morphine pamoate, (1:1) salt. The sample was triturated in water (about 34 g), the solids isolated by filtration through a medium frit filter, washed with a small portion of water and subsequently dried under vacuum to provide 2.04 g (91% yield) of a light yellow powder. The product was characterized by DSC (FIG. 25), FTIR (FIG. 26), PXRD (FIG. 27) and $^1$H-NMR (FIG. 28). The $^1$H-NMR spectrum was consistent with a 1:1 ratio of morphine to pamoate moieties in the formed salt. The PXRD diffractogram indicated the product was predominantly amorphous.

Example 8. Preparation of Amorphous Oxymorphone Pamoate, (1:1) Salt

Figure 29:
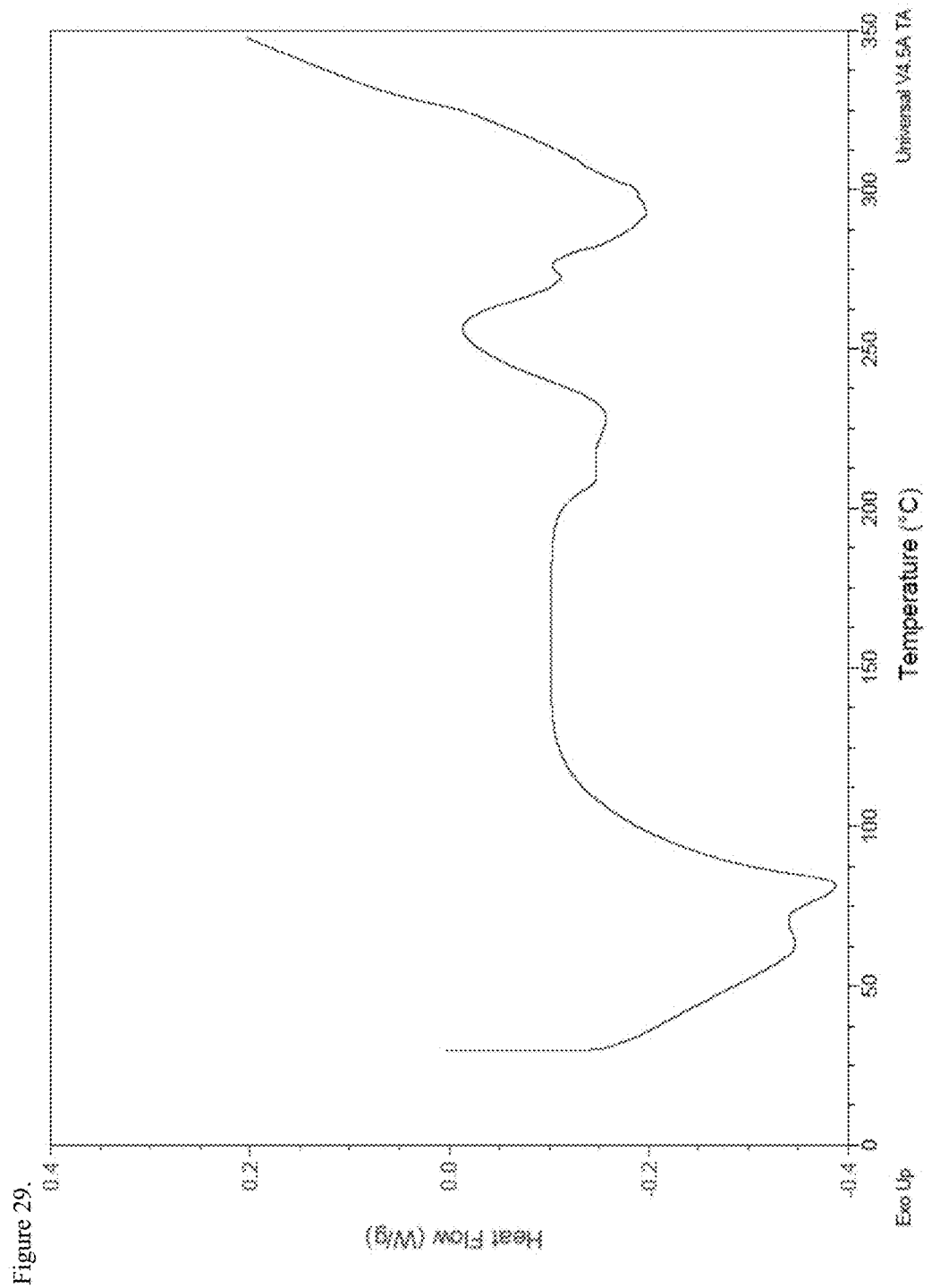
FIG. 29 is the differential scanning calorimetry (DSC) thermogram of amorphous oxymorphone pamoate 1:1 salt as a 1:1 mixture of mono-sodium salt and free carboxylic acid.
Figure 30:
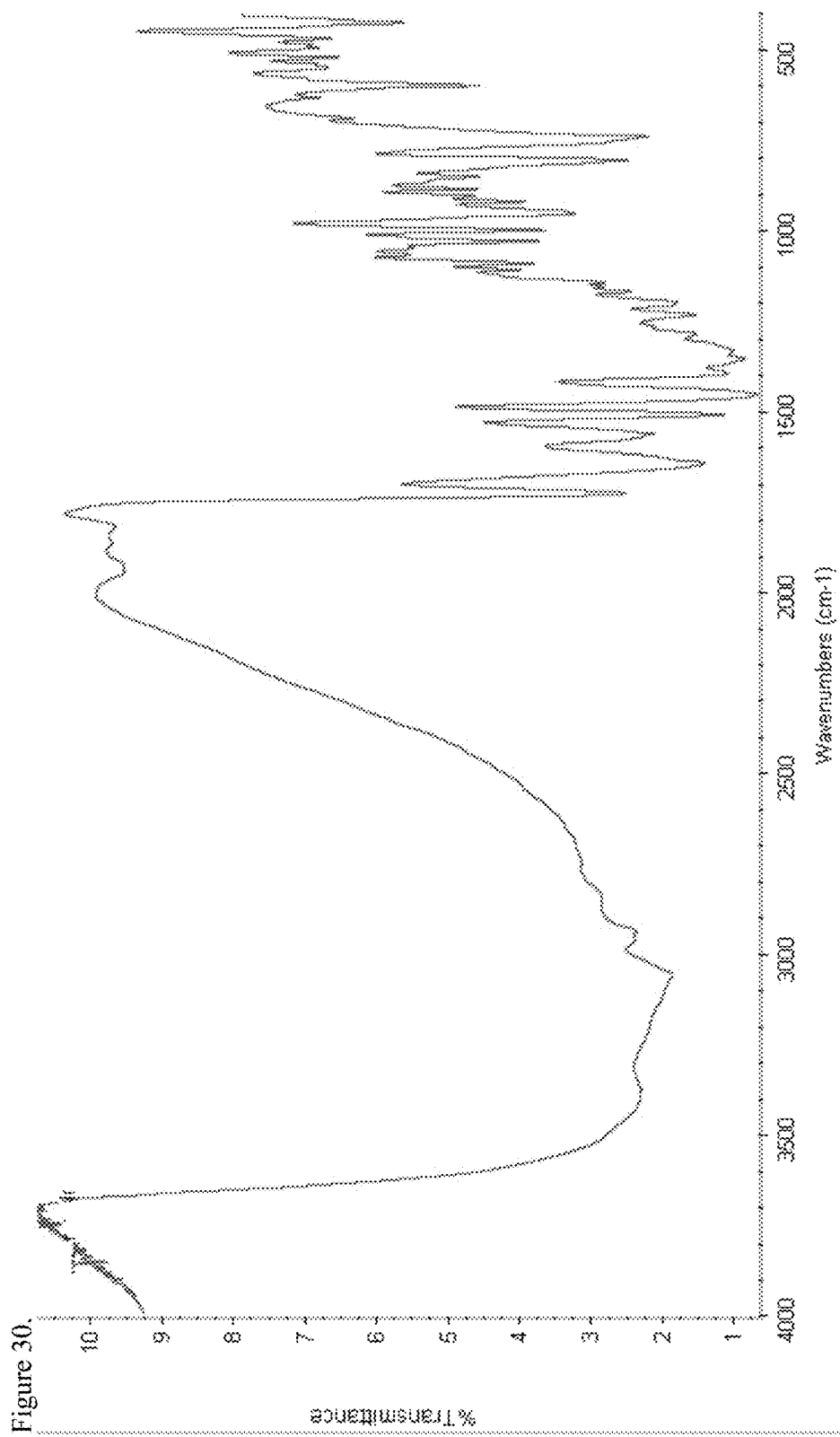
FIG. 30 is the Fourier transform infrared (FTIR) spectrum of amorphous oxymorphone pamoate 1:1 salt as a 1:1 mixture of mono-sodium salt and free carboxylic acid.
Figure 31:
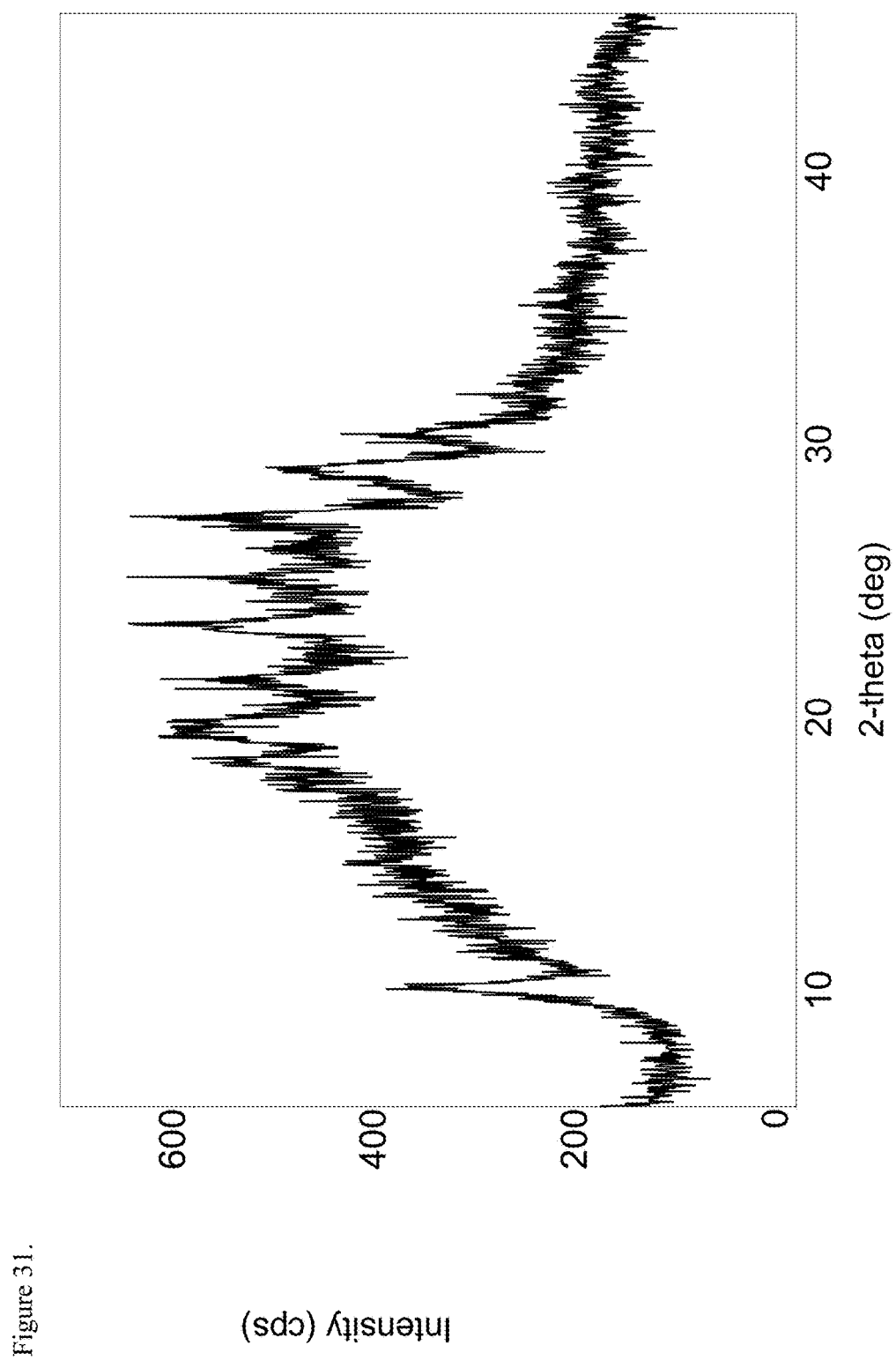
FIG. 31 is the powder X-ray diffraction (PXRD) diffractogram of amorphous oxymorphone pamoate 1:1 salt as a 1:1 mixture of mono-sodium salt and free carboxylic acid.
Figure 32:
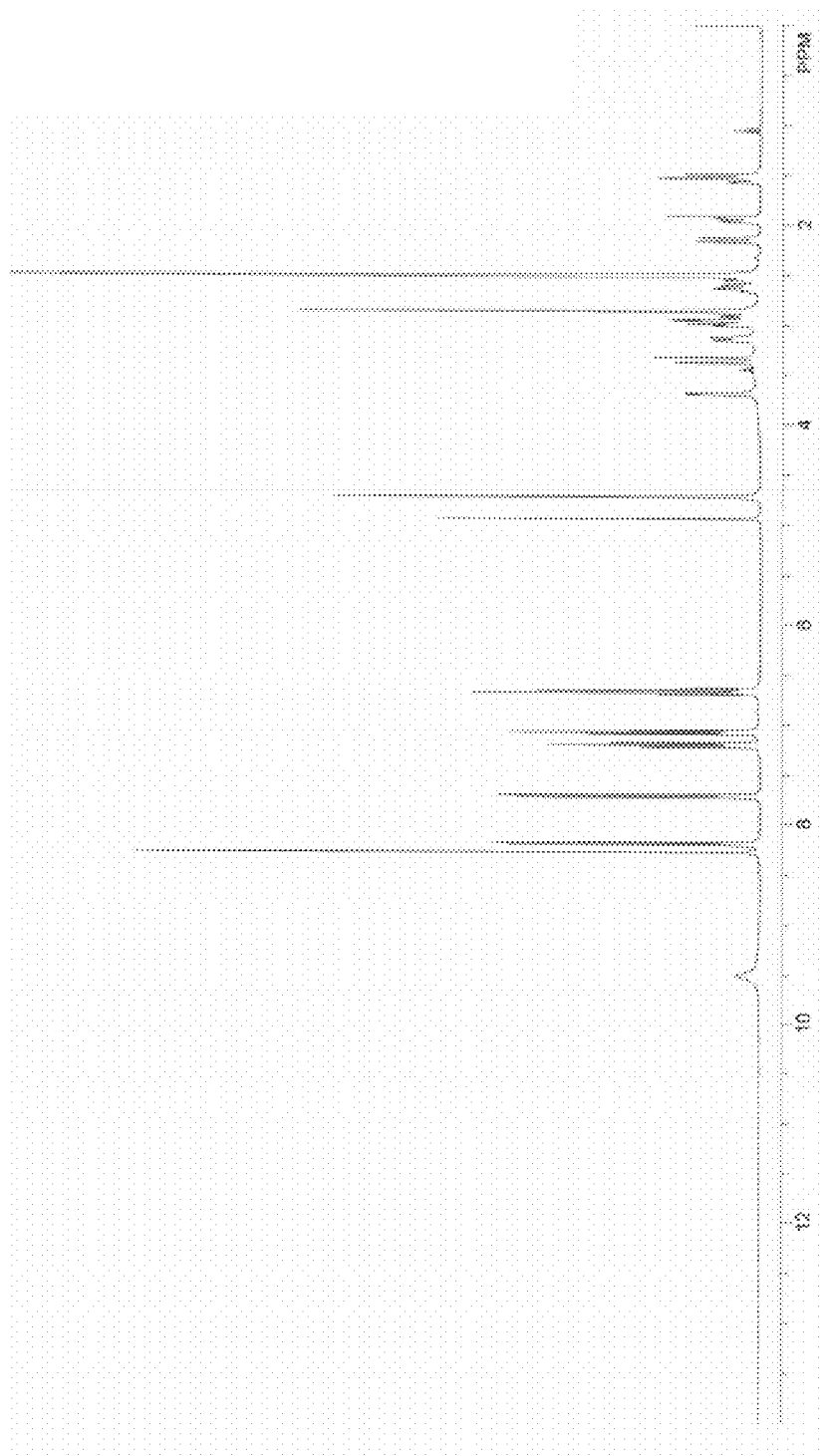
FIG. 32 is the proton nuclear magnetic resonance (¹H NMR) spectrum of amorphous oxymorphone pamoate 1:1 salt as a 1:1 mixture of mono-sodium salt and free carboxylic acid.

To a 250 mL three-neck round-bottom flask equipped with a magnetic stir bar, thermowell, nitrogen inlet and addition funnel was charged disodium pamoate (1.50 g, 3.34 mmol) and 82 mL 75:25 ethanol/water and the contents stirred at ambient temperature under a nitrogen atmosphere. An oxymorphone acetic acid salt solution was prepared according to the following procedure. To a 50 mL round-bottom flask equipped with a magnetic stir bar was charged oxymorphone base (1.01 g, 3.34 mmol) and 13.4 mL 5% acetic acid/ethanol solution, and the contents stirred at ambient temperature under a nitrogen atmosphere. The oxymorphone acetic acid solution was added to the disodium pamoate solution over a period of about one minute via an addition funnel with the pH of the combined solutions recorded as about 6.1. The mixture was stirred for an additional about one hour at ambient temperature under a nitrogen atmosphere. The solution was concentrated under reduced pressure (28.7 inches Hg and 22° C. water bath temperature) to provide oxymorphone pamoate, (1:1) salt. The sample was triturated in water (about 34 g), the solids isolated by filtration through a medium frit filter, washed with a small portion of water and dried under vacuum to provide 2.1 g (91% yield) of a light yellow powder. The product was characterized by DSC (FIG. 29), FTIR (FIG. 30), PXRD (FIG. 31) and $^1$H-NMR (FIG. 32). The $^1$H-NMR spectrum was consistent with a 1:1 ratio of oxymorphone to pamoate moieties in the formed salt. The PXRD diffractogram confirmed the salt was predominantly amorphous.

Example 9. Preparation of Amorphous Codeine Pamoate, (1:1) Salt

Figure 33:
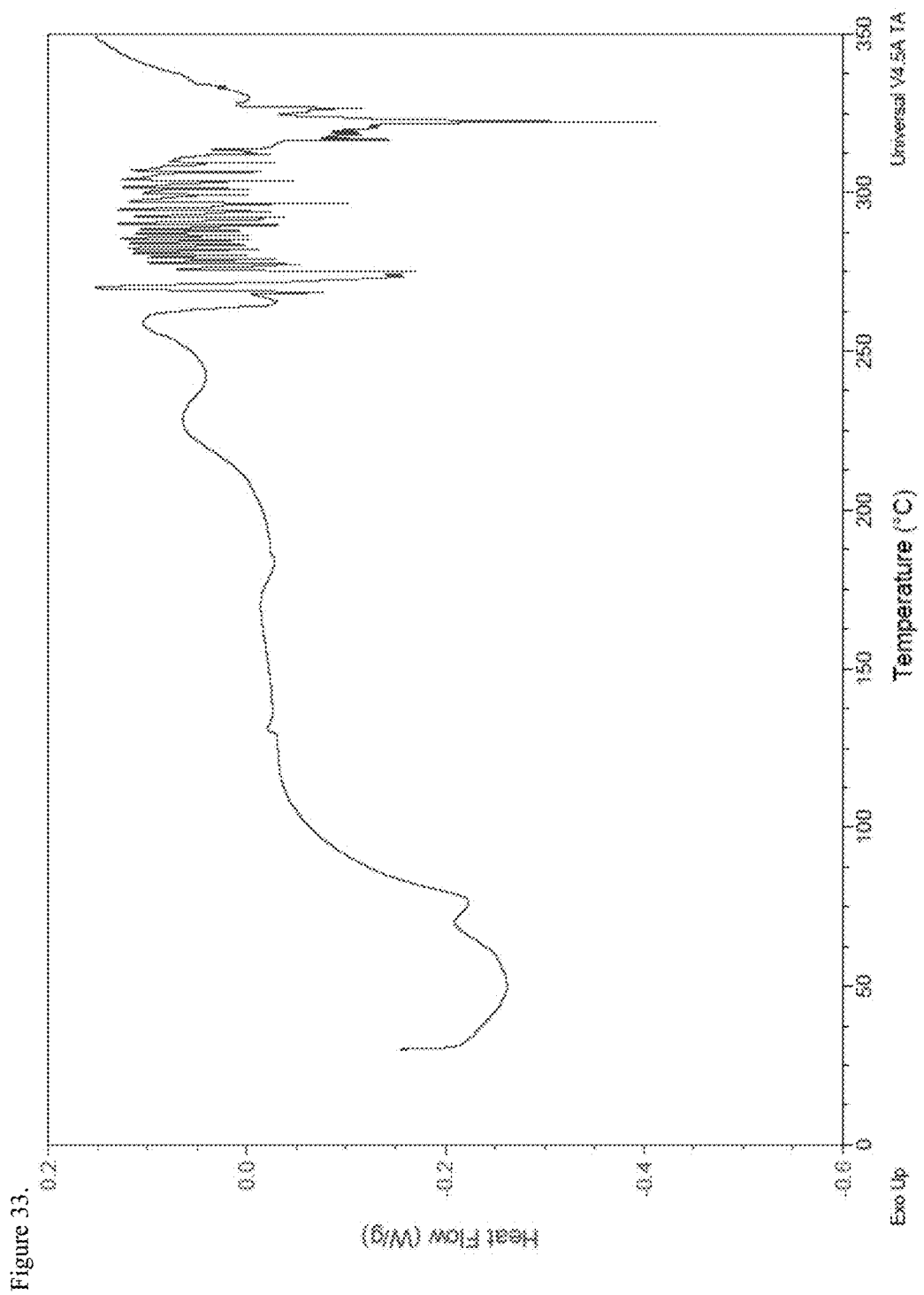
FIG. 33 is the differential scanning calorimetry (DSC) thermogram of amorphous codeine pamoate 1:1 salt as a 1:1 mixture of mono-sodium salt and free carboxylic acid.
Figure 34:
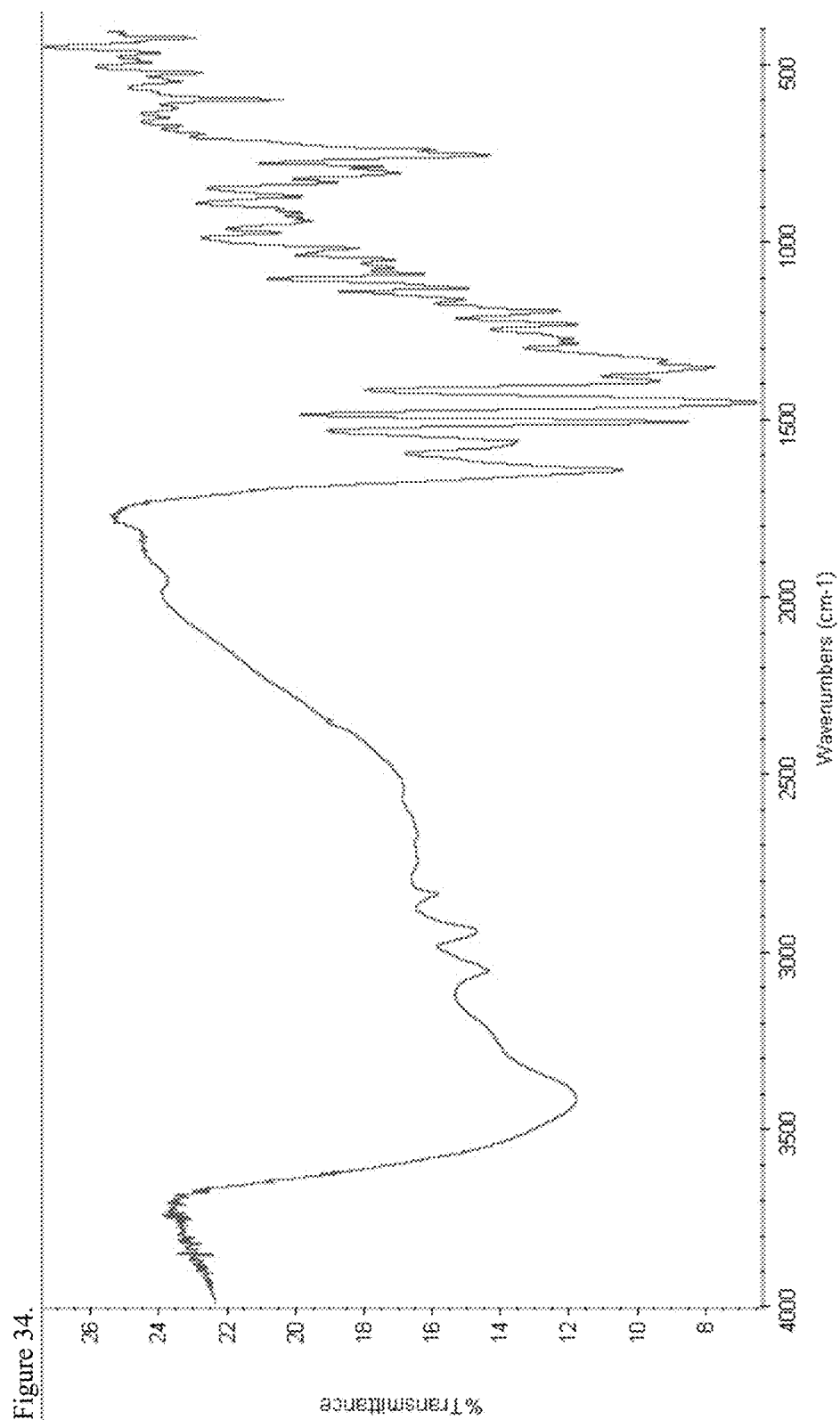
FIG. 34 is the Fourier transform infrared (FTIR) spectrum of amorphous codeine pamoate 1:1 salt as a 1:1 mixture of mono-sodium salt and free carboxylic acid.
Figure 35:
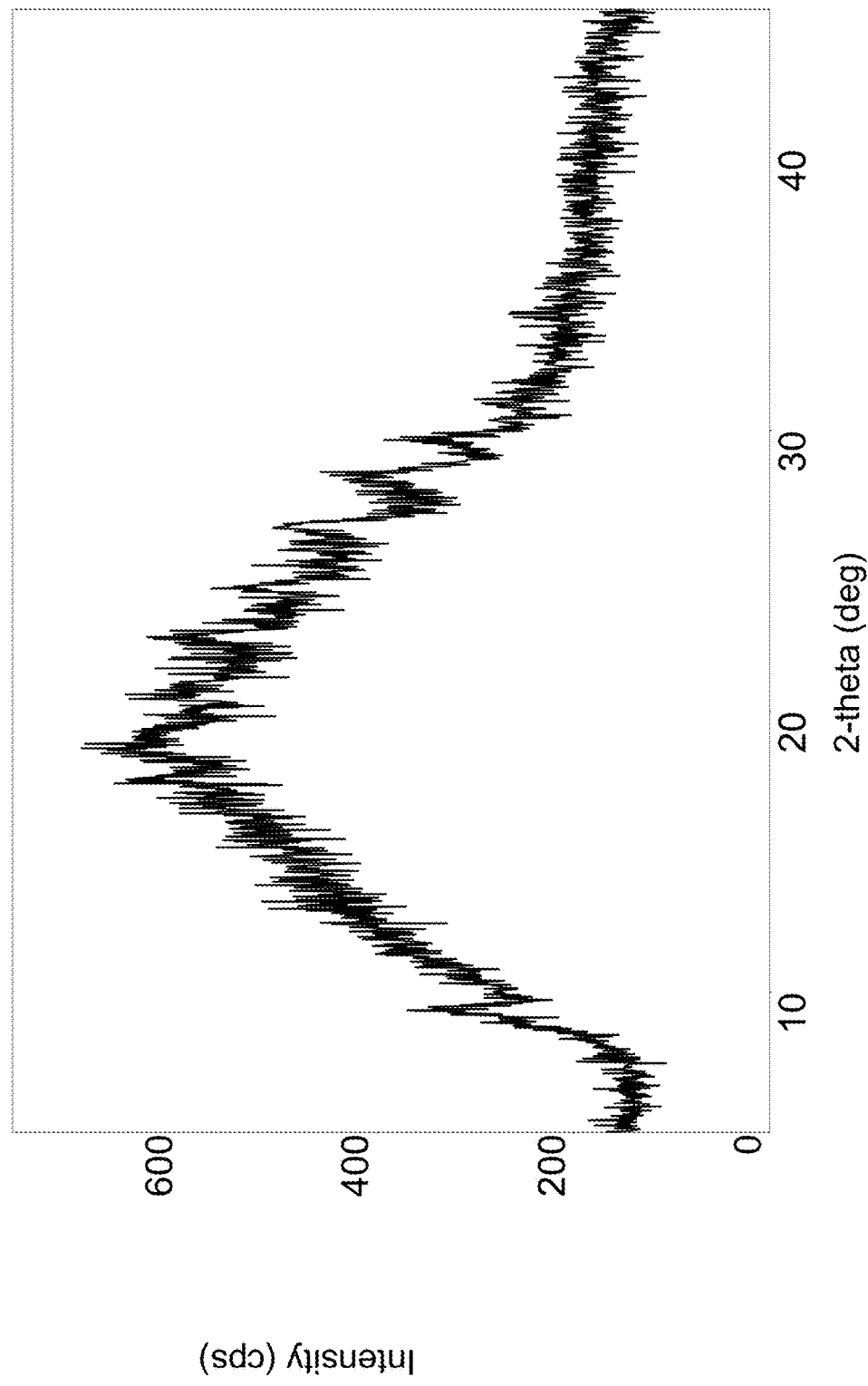
FIG. 35 is the powder X-ray diffraction (PXRD) diffractogram of amorphous codeine pamoate 1:1 salt as a 1:1 mixture of mono-sodium salt and free carboxylic acid.
Figure 36:
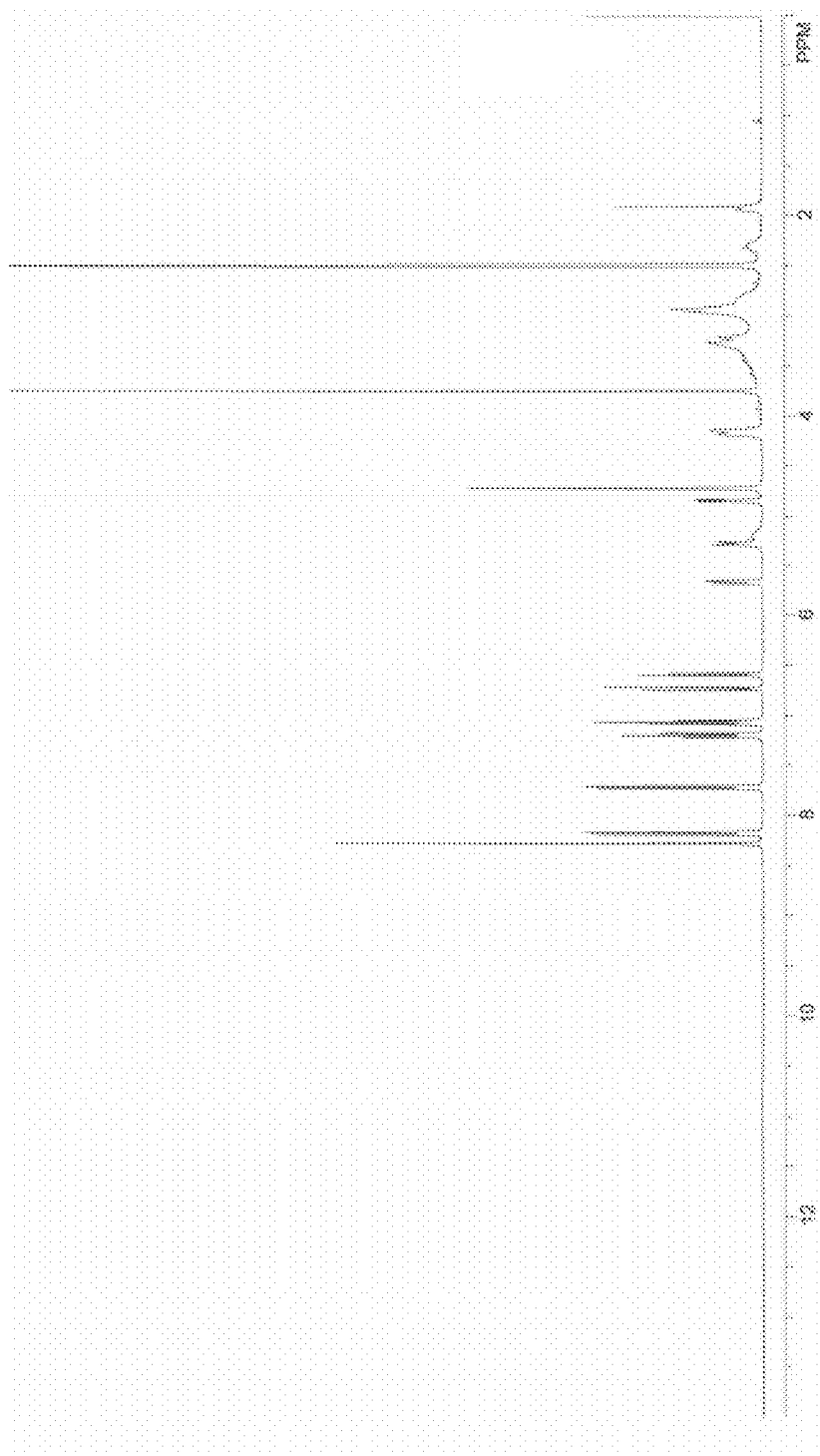
FIG. 36 is the proton nuclear magnetic resonance (¹H NMR) spectrum of amorphous codeine pamoate 1:1 salt as a 1:1 mixture of mono-sodium salt and free carboxylic acid.

To a 250 mL three-neck round-bottom flask equipped with a magnetic stir bar, thermowell, nitrogen inlet and addition funnel was charged disodium pamoate (1.50 g, 3.34 mmol) and 77 mL 75:25 ethanol/water, and the contents stirred at ambient temperature under a nitrogen atmosphere. A codeine acetic acid salt solution was prepared according to the following procedure. To a 50 mL round-bottom flask equipped with a magnetic stir bar and placed under nitrogen was charged codeine monohydrate base (1.06 g, 3.34 mmol) and 13.4 mL 5% acetic acid/ethanol solution was added. An additional portion of ethanol (17 g) was added to completely dissolve the solids and the solution was stirred at ambient temperature under a nitrogen atmosphere. The codeine acetic acid solution was added to the disodium pamoate solution over a period of about one minute via addition funnel, the pH of the combined solutions was about 6.3 and the mixture stirred for about an additional one hour at ambient temperature under a nitrogen atmosphere whereupon the solution was concentrated under reduced pressure (28.7 inches Hg and 22° C. water bath temperature) to provide the codeine pamoate (1:1) salt. The sample was triturated in water (about 34 g), the solids isolated by filtration through a medium frit filter, washed with a small portion of water and subsequently dried under vacuum to provide 2.17 g (94% yield) of a light yellow powder. The product was characterized by DSC (FIG. 33), FTIR (FIG. 34), PXRD (FIG. 35) and $^1$H-NMR (FIG. 36). The $^1$H-NMR spectrum was consistent with a 1:1 ratio of codeine to pamoate moieties in the formed salt. The PXRD diffractogram indicated the salt was predominantly amorphous.

Example 10. Preparation of Amorphous d-Methylphenidate Pamoate, (1:1) Salt

Figure 37:
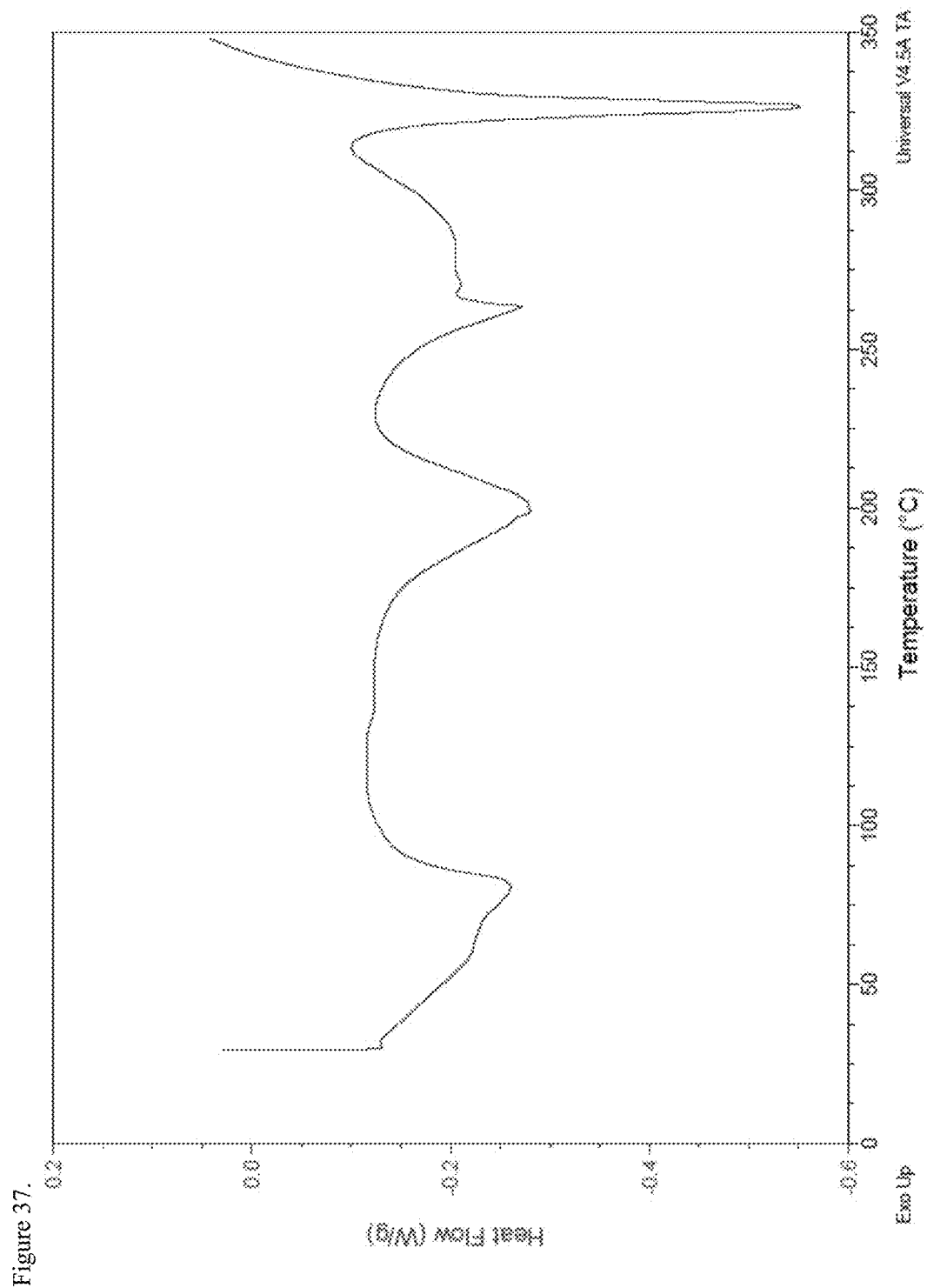
FIG. 37 is the differential scanning calorimetry (DSC) thermogram of amorphous d-methylphenidate pamoate 1:1 salt as a 1:1 mixture of mono-sodium salt and free carboxylic acid.
Figure 38:
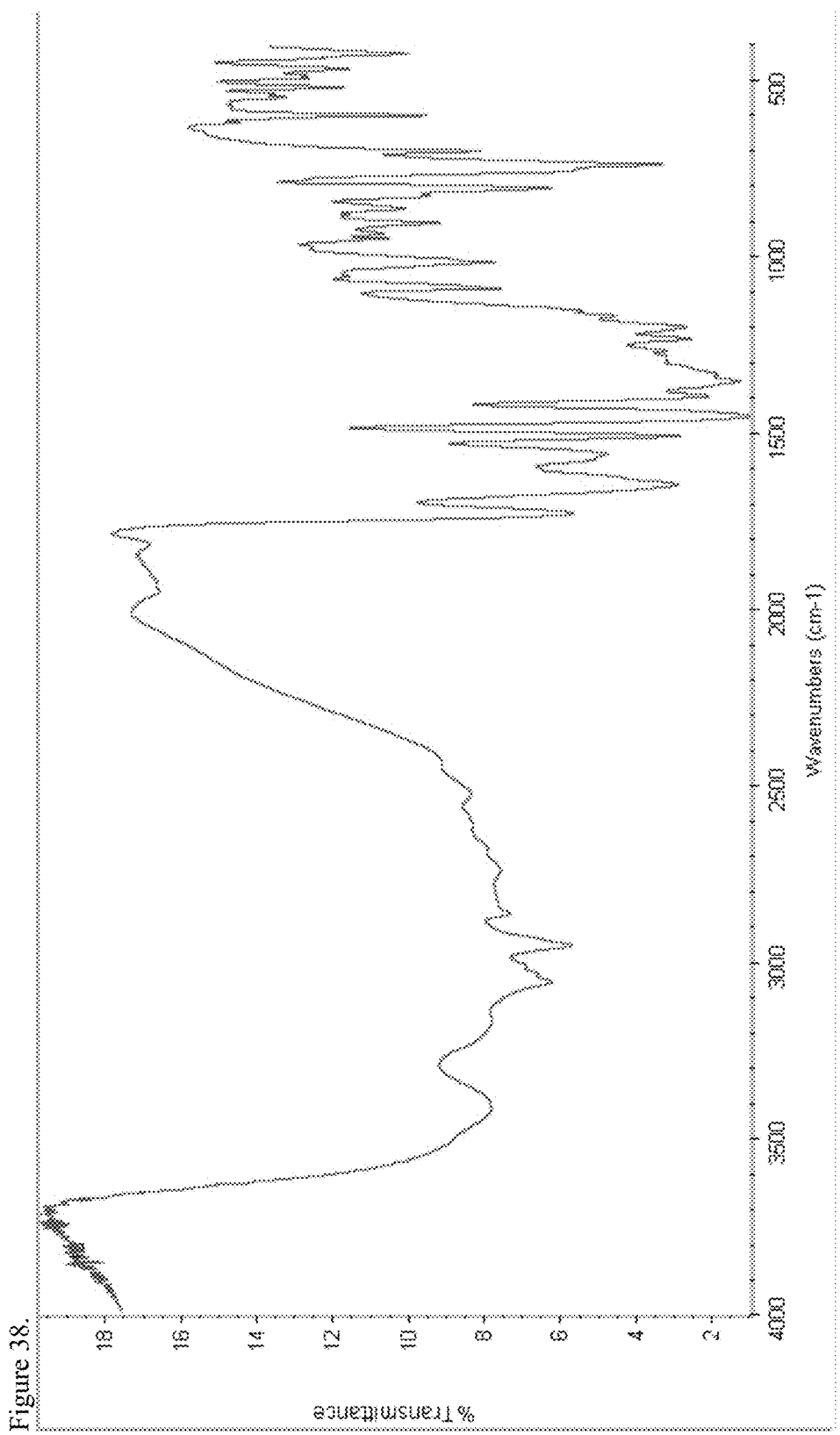
FIG. 38 is the Fourier transform infrared (FTIR) spectrum of amorphous d-methylphenidate pamoate 1:1 salt as a 1:1 mixture of mono-sodium salt and free carboxylic acid.
Figure 39:
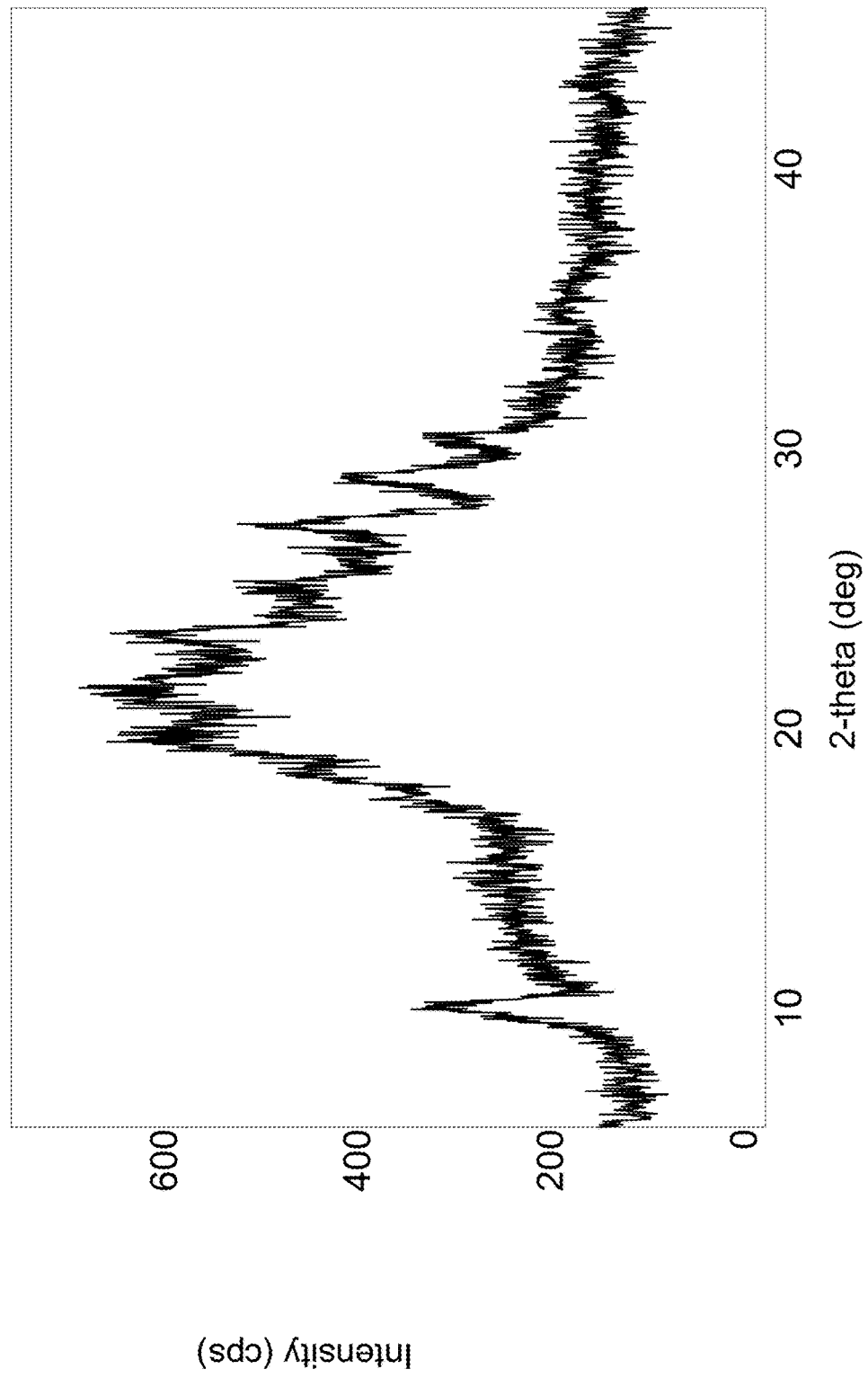
FIG. 39 is the powder X-ray diffraction (PXRD) diffractogram of amorphous d-methylphenidate pamoate 1:1 salt as a 1:1 mixture of mono-sodium salt and free carboxylic acid.
Figure 40:
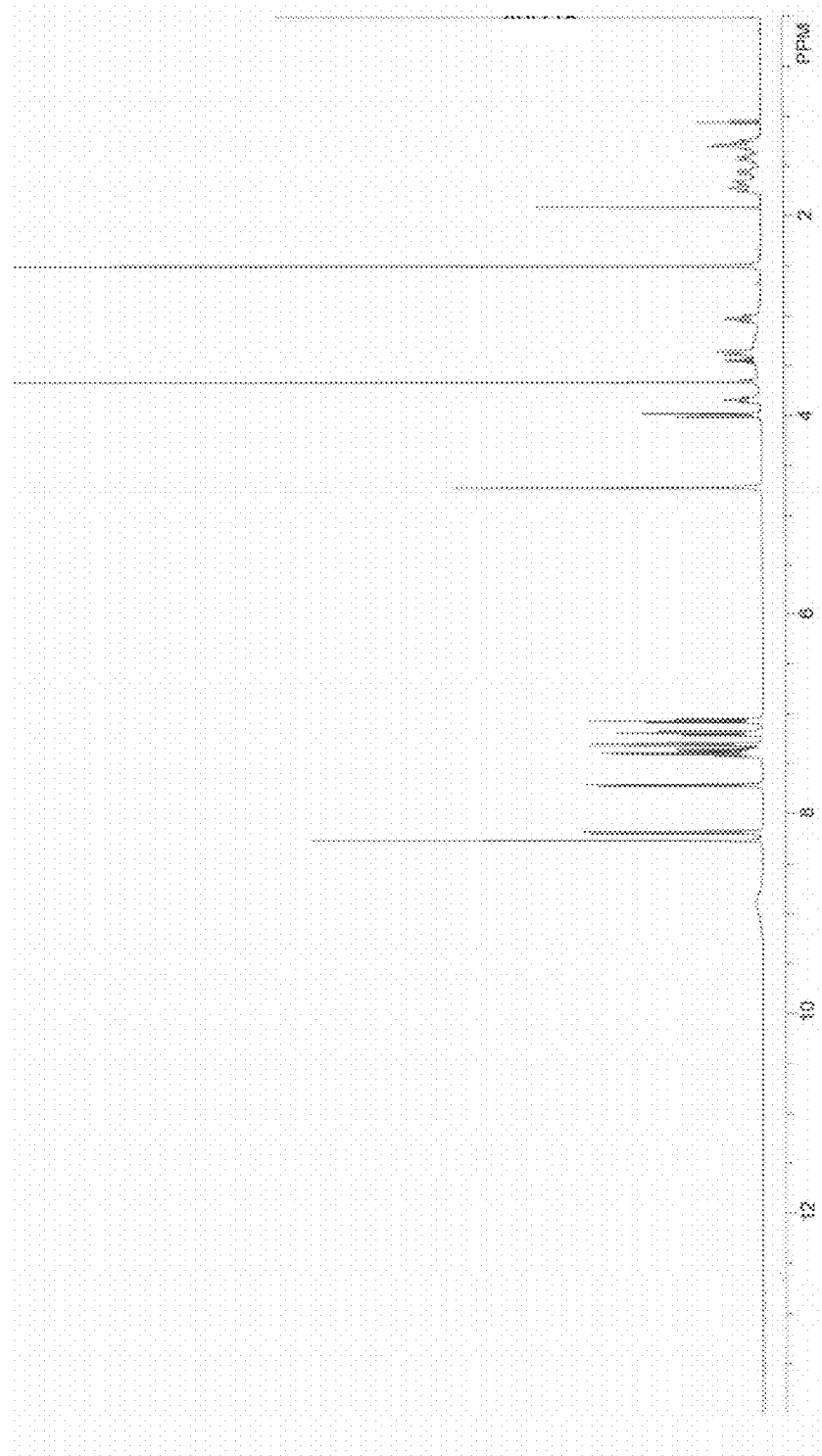
FIG. 40 is the proton nuclear magnetic resonance (¹H NMR) spectrum of amorphous d-methylphenidate pamoate 1:1 salt as a 1:1 mixture of mono-sodium salt and free carboxylic acid.

To a 250 mL three-neck round-bottom flask equipped with a magnetic stir bar, thermowell, nitrogen inlet and addition funnel was charged disodium pamoate (1.50 g, 3.34 mmol) and 67 mL 75-25 ethanol/water, and the contents stirred under a nitrogen atmosphere. A d-methylphenidate acetic acid salt solution was prepared according to the following procedure. To a 50 mL round-bottom flask equipped with a magnetic stir bar and was charged d-methylphenidate base (787.0 mg, 3.37 mmol) and 13.4 mL 5% acetic acid/ethanol solution and the solution stirred at ambient temperature under a nitrogen atmosphere. The d-methylphenidate acetic acid solution was added to the disodium pamoate solution over a period of about one minute via an addition funnel with the pH of the combined solutions observed as about 6.1. The mixture was stirred for about an additional one hour at ambient temperature and under a nitrogen atmosphere. The solution was concentrated under reduced pressure (28.7 inches Hg and 22° C. water bath temperature) to provide the d-methylphenidate pamoate, (1:1) salt. The sample was triturated in water (about 34 g), the solids isolated by filtration through a medium frit filter, washed with a small portion of water and dried under vacuum to provide 1.99 g (96% yield) of a light yellow powder. The product was characterized by DSC (FIG. 37), FTIR (FIG. 38), PXRD (FIG. 39) and $^1$H-NMR (FIG. 40). The $^1$H-NMR spectrum was consistent with a 1:1 ratio of d-methylphenidate to pamoate moieties of the salt. The PXRD diffractogram indicated the sample was predominantly amorphous.

Figure 41:
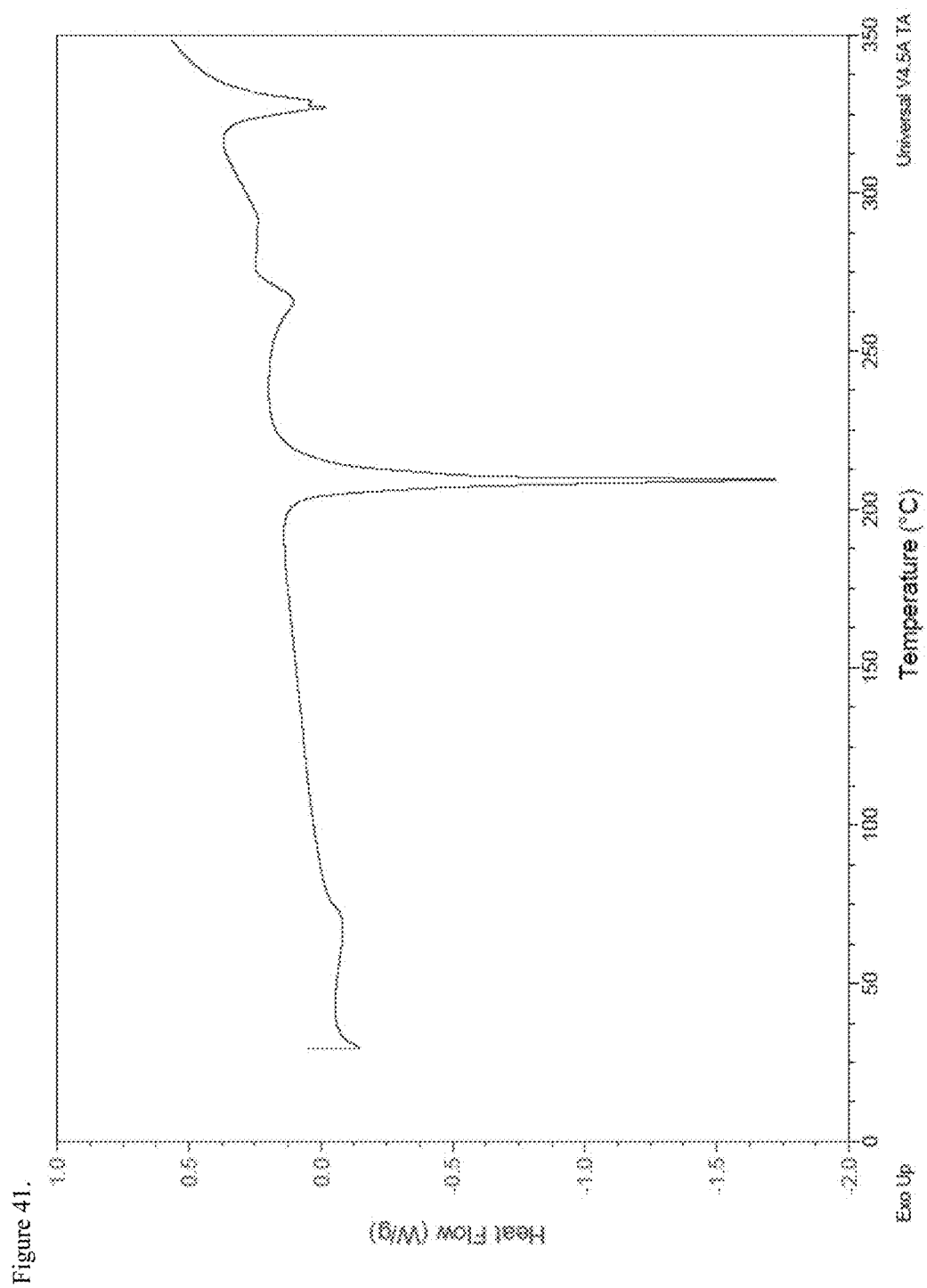
FIG. 41 is the differential scanning calorimetry (DSC) thermogram of polymorphic racemic methylphenidate pamoate 1:1 salt as a 1:1 mixture of mono-sodium salt and free carboxylic acid.
Figure 42:
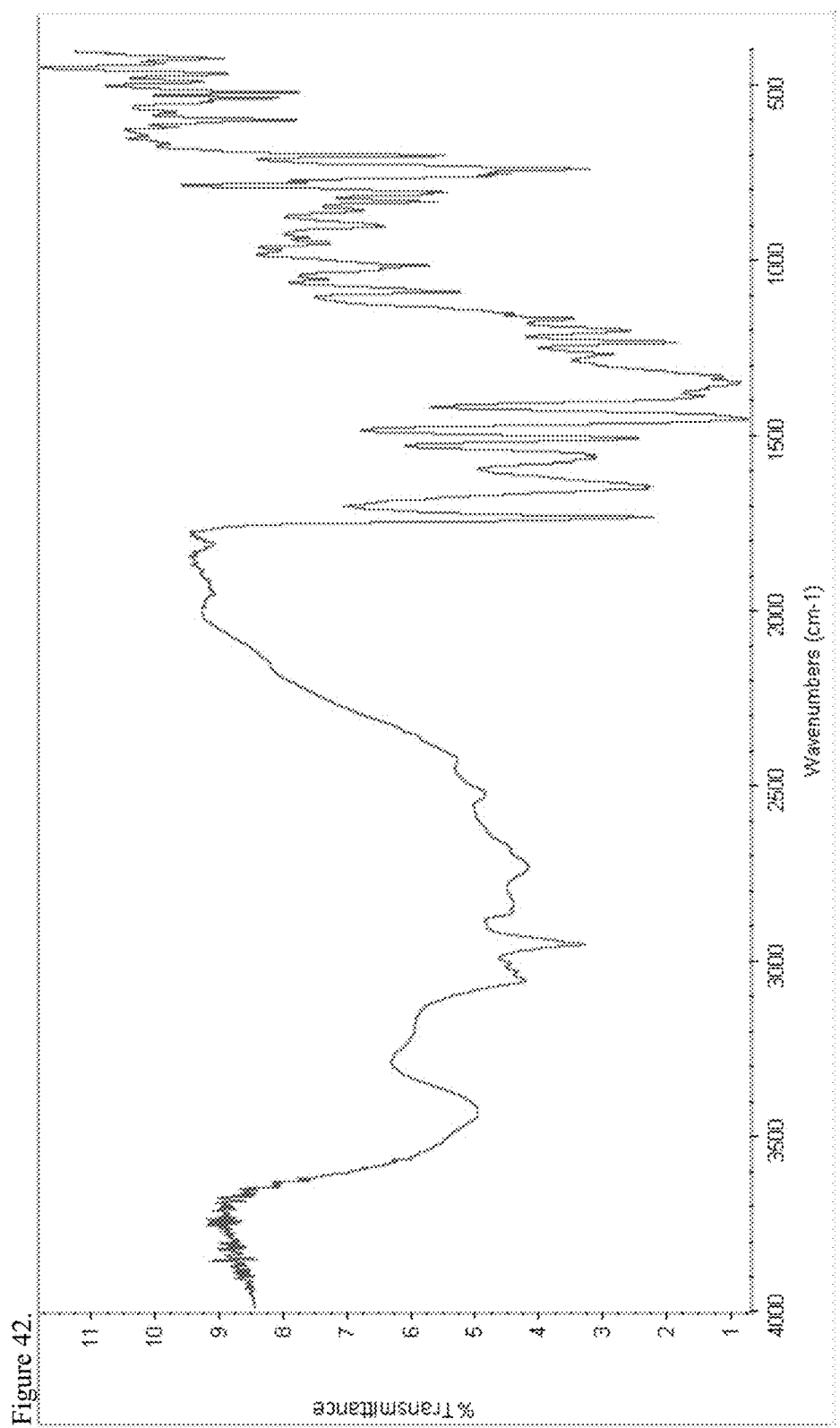
FIG. 42 is the Fourier transform infrared (FTIR) spectrum of polymorphic racemic methylphenidate pamoate 1:1 salt as a 1:1 mixture of mono-sodium salt and free carboxylic acid.
Figure 43:
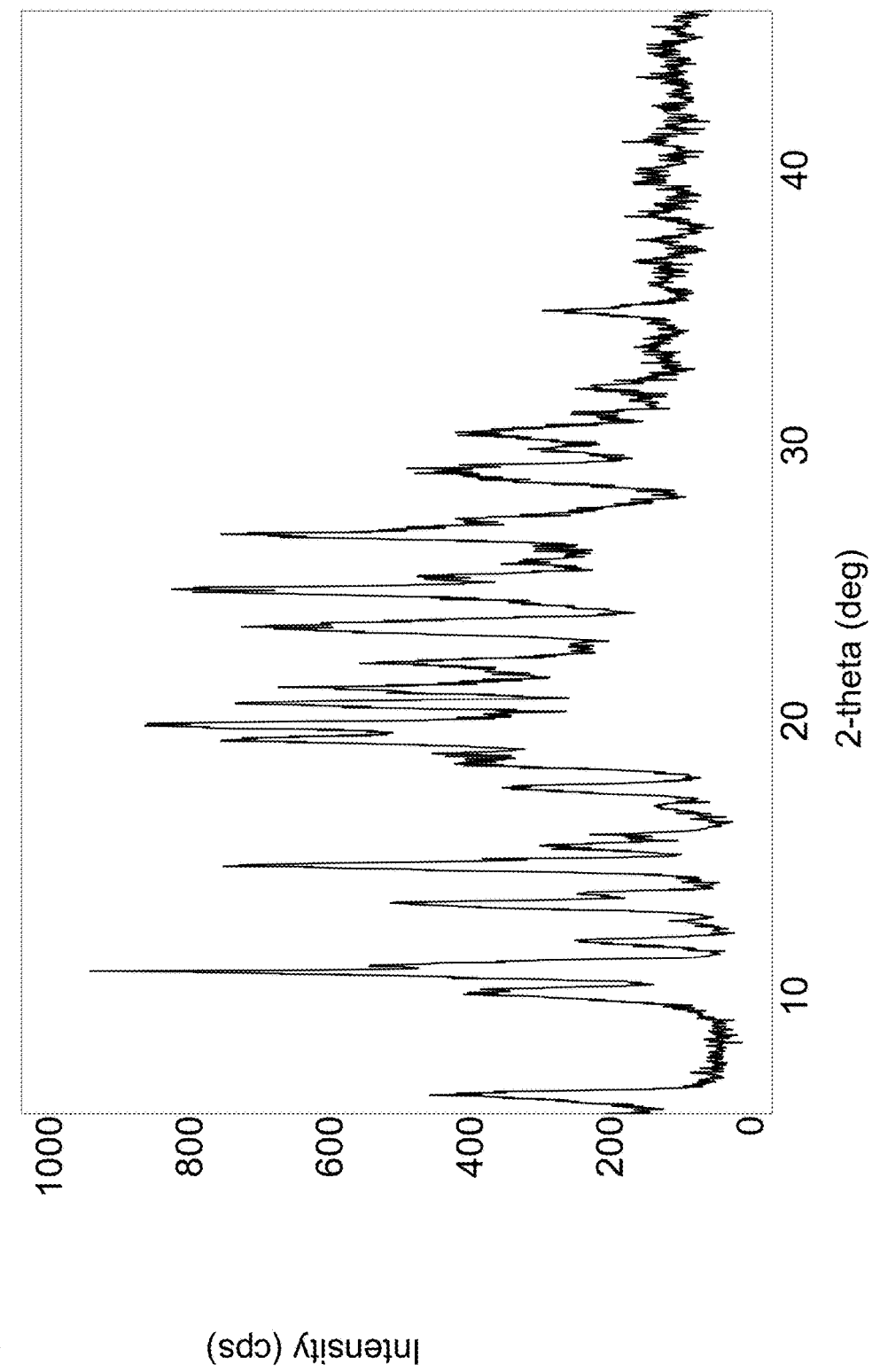
FIG. 43 is the powder X-ray diffraction (PXRD) diffractogram of polymorphic racemic methylphenidate pamoate 1:1 salt as a 1:1 mixture of mono-sodium salt and free carboxylic acid.
Figure 44:
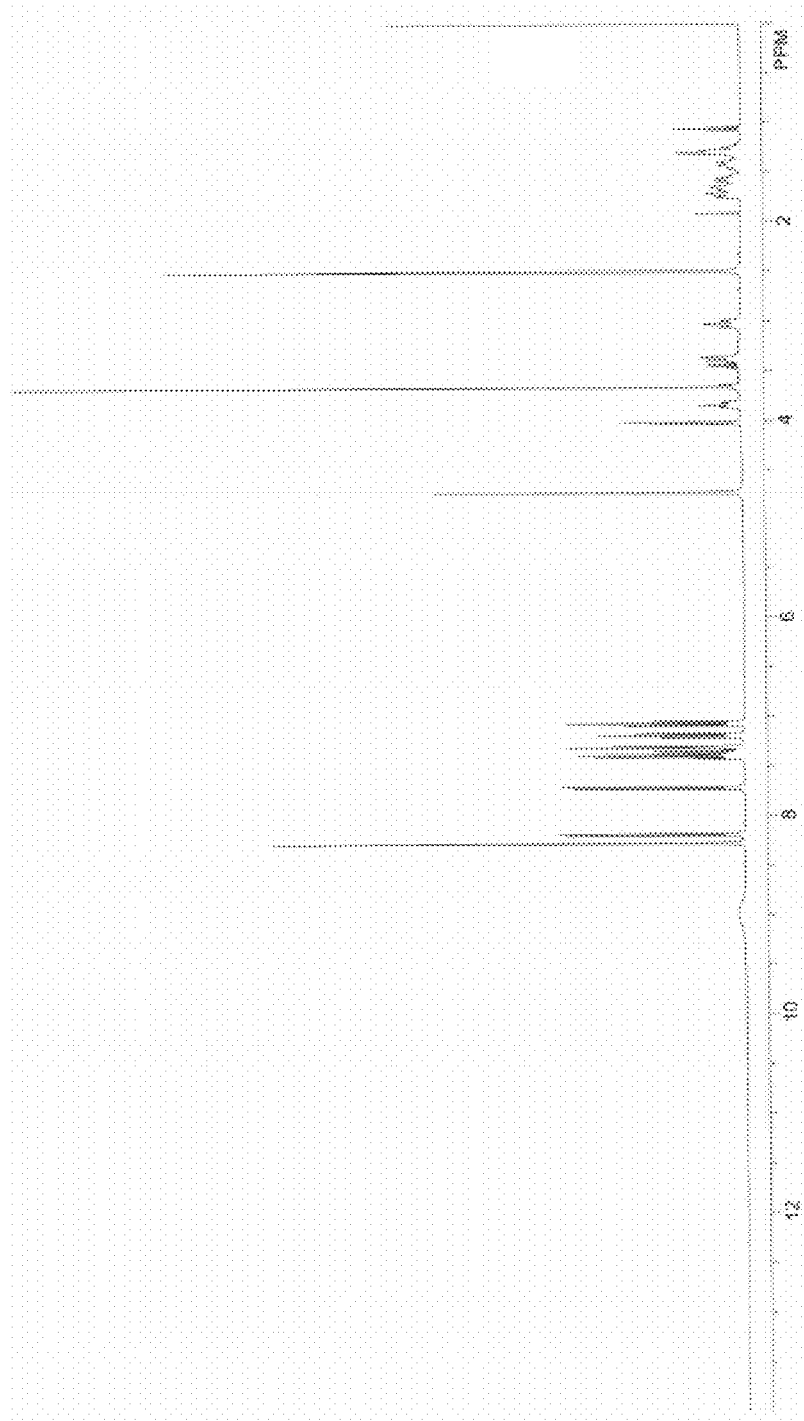
FIG. 44 is the proton nuclear magnetic resonance (¹H NMR) spectrum of polymorphic racemic methylphenidate pamoate 1:1 salt as a 1:1 mixture of mono-sodium salt and free carboxylic acid.

Example 11. Preparation of Polymorphic Racemic Methylphenidate Pamoate, (1:1) Salt To a 250 mL three-neck round-bottom flask equipped with a magnetic stir bar, thermowell, nitrogen inlet and addition funnel was charged disodium pamoate (1.50 g, 3.34 mmol) and 67 mL 75:25 ethanol/water, and the contents stirred at ambient temperature under a nitrogen atmosphere. A racemic-methylphenidate acetic acid salt solution was prepared according to the following procedure. To a 50 mL round-bottom flask equipped with a magnetic stir bar was charged racemic-methylphenidate base (779.2 mg, 3.34 mmol) and 13.4 mL 5% acetic acid/ethanol solution and the solution stirred at ambient temperature under a nitrogen atmosphere. The racemic-methylphenidate acetic acid solution was added to the disodium pamoate solution over a period of about one minute via an addition funnel with the pH of the combined solutions observed as about 6.3; the mixture was stirred for about an additional one hour at ambient temperature and under a nitrogen atmosphere. The solution was concentrated under reduced pressure (28.7 inches Hg and 22° C. water bath temperature) to provide the racemic-methylphenidate pamoate, (1:1) salt. The sample was triturated in water (about 34 g), the solids isolated by filtration through a medium frit filter, further washed with a small portion of water and dried under vacuum to provide 1.92 g (92% yield) of an off-white powder. The product was characterized by DSC (FIG. 41), FTIR (FIG. 42), PXRD (FIG. 43), and $^1$H-NMR (FIG. 44). The $^1$H-NMR spectrum was consistent with a 1:1 ratio of racemic-methylphenidate to pamoate moieties of the formed salt. The PXRD diffractogram indicated the product was crystalline.

Example 12. Preparation of Amorphous Naltrexone Pamoate, (1:1) Salt

Figure 45:
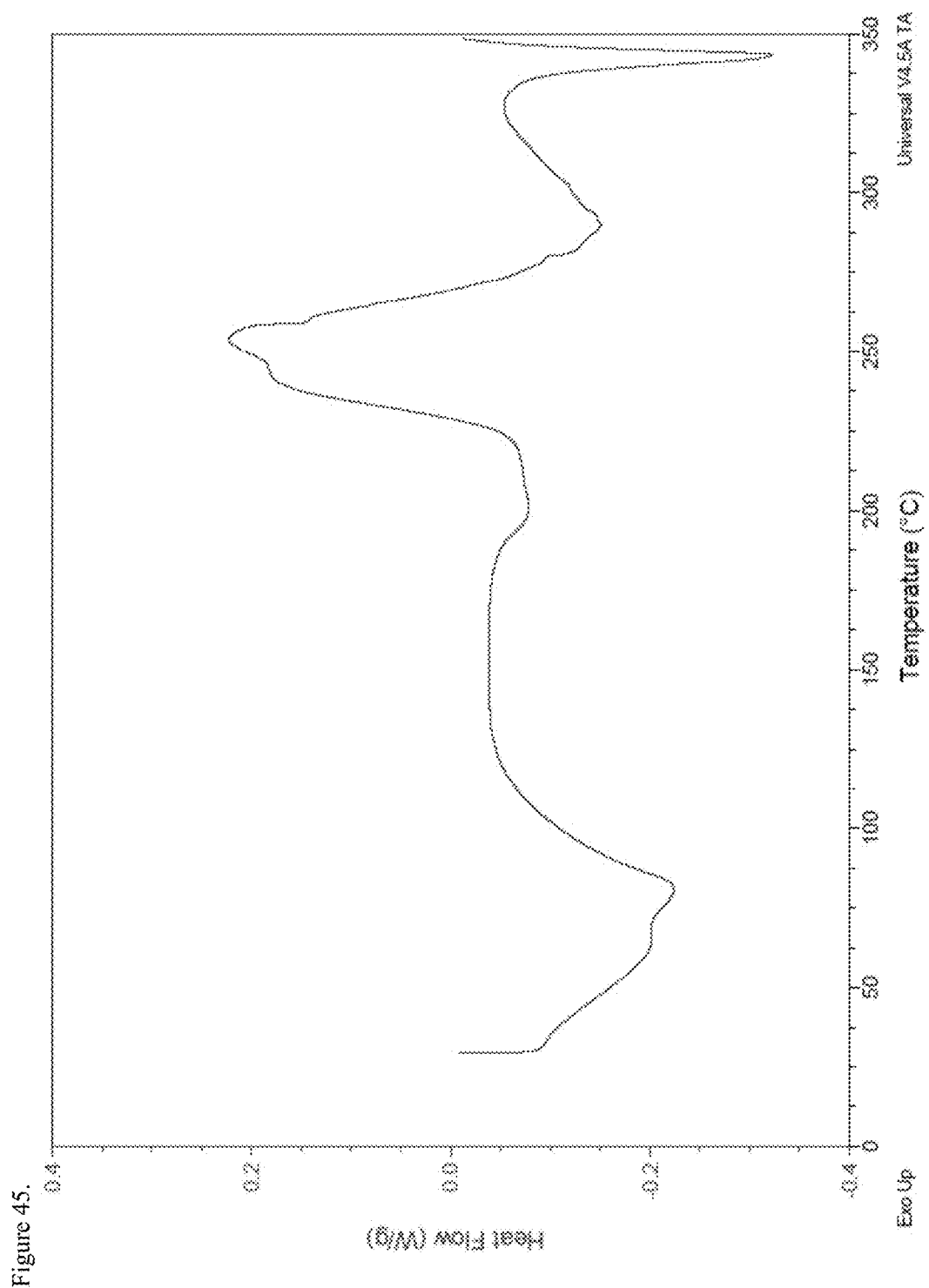
FIG. 45 is the differential scanning calorimetry (DSC) thermogram of amorphous naltrexone pamoate 1:1 salt as a 1:1 mixture of mono-sodium salt and free carboxylic acid.
Figure 46:
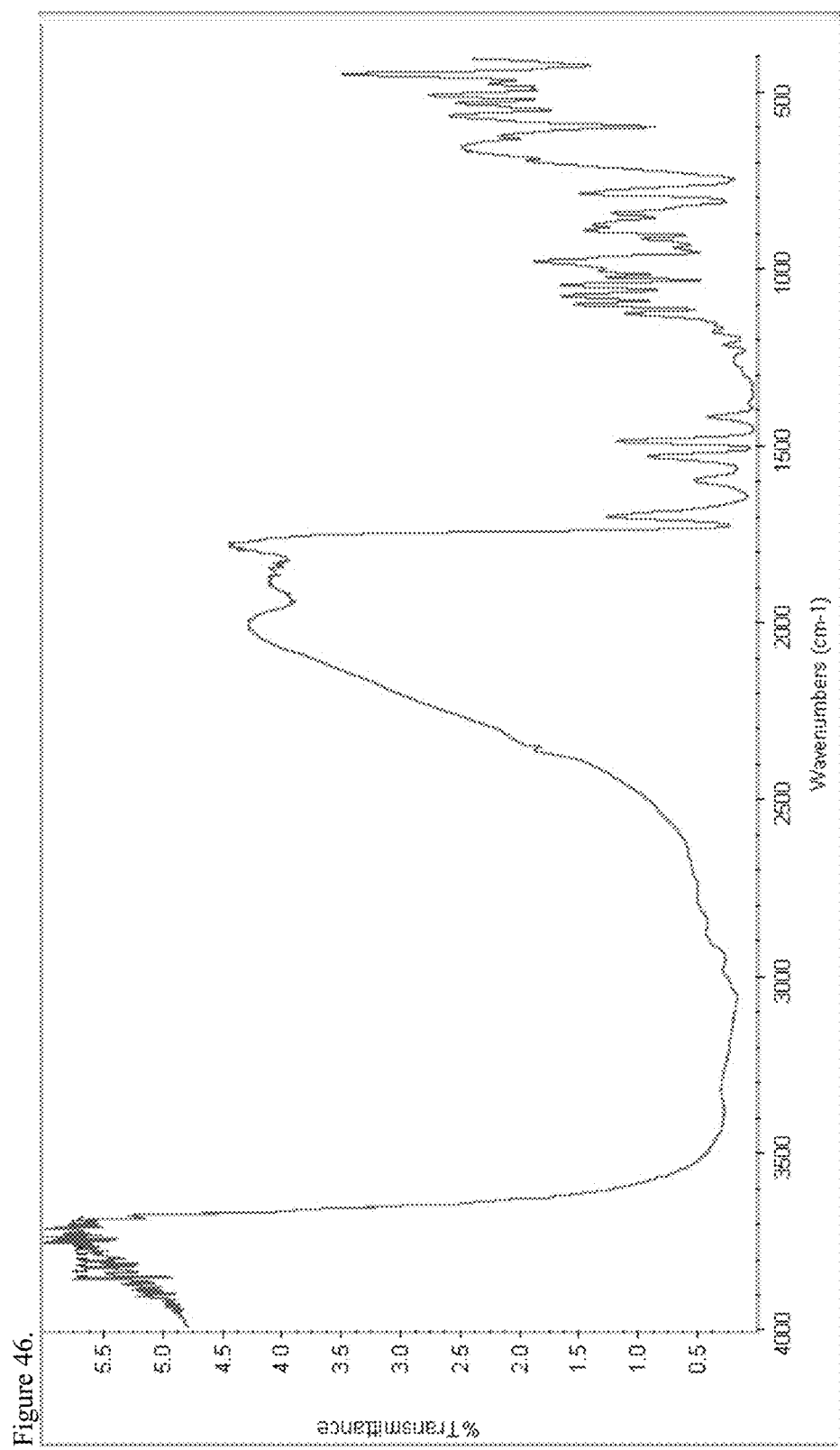
FIG. 46 is the Fourier transform infrared (FTIR) spectrum of amorphous naltrexone pamoate 1:1 salt as a 1:1 mixture of mono-sodium salt and free carboxylic acid.
Figure 47:
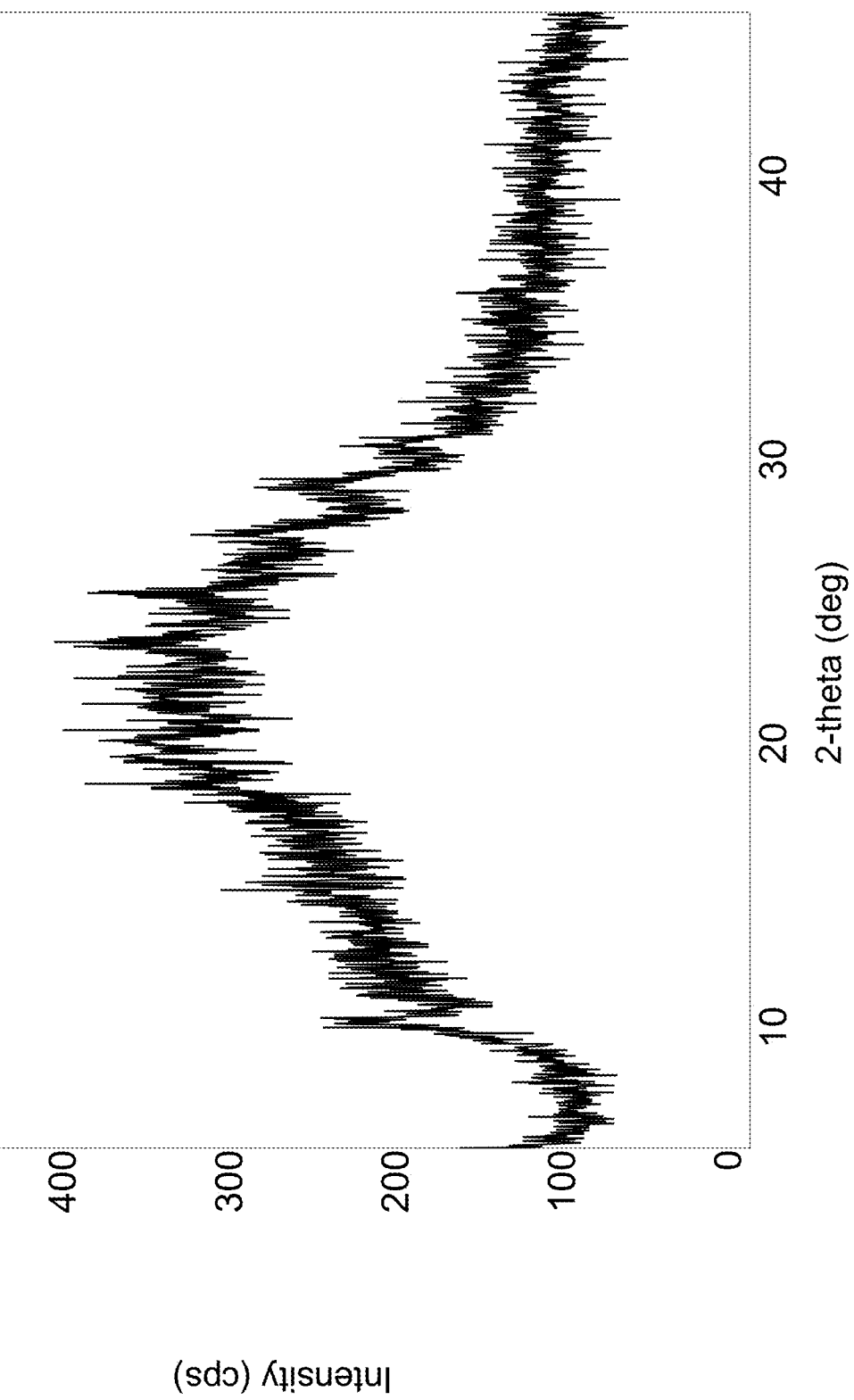
FIG. 47 is the powder X-ray diffraction (PXRD) diffractogram of amorphous naltrexone pamoate 1:1 salt as a 1:1 mixture of mono-sodium salt and free carboxylic acid.
Figure 48:
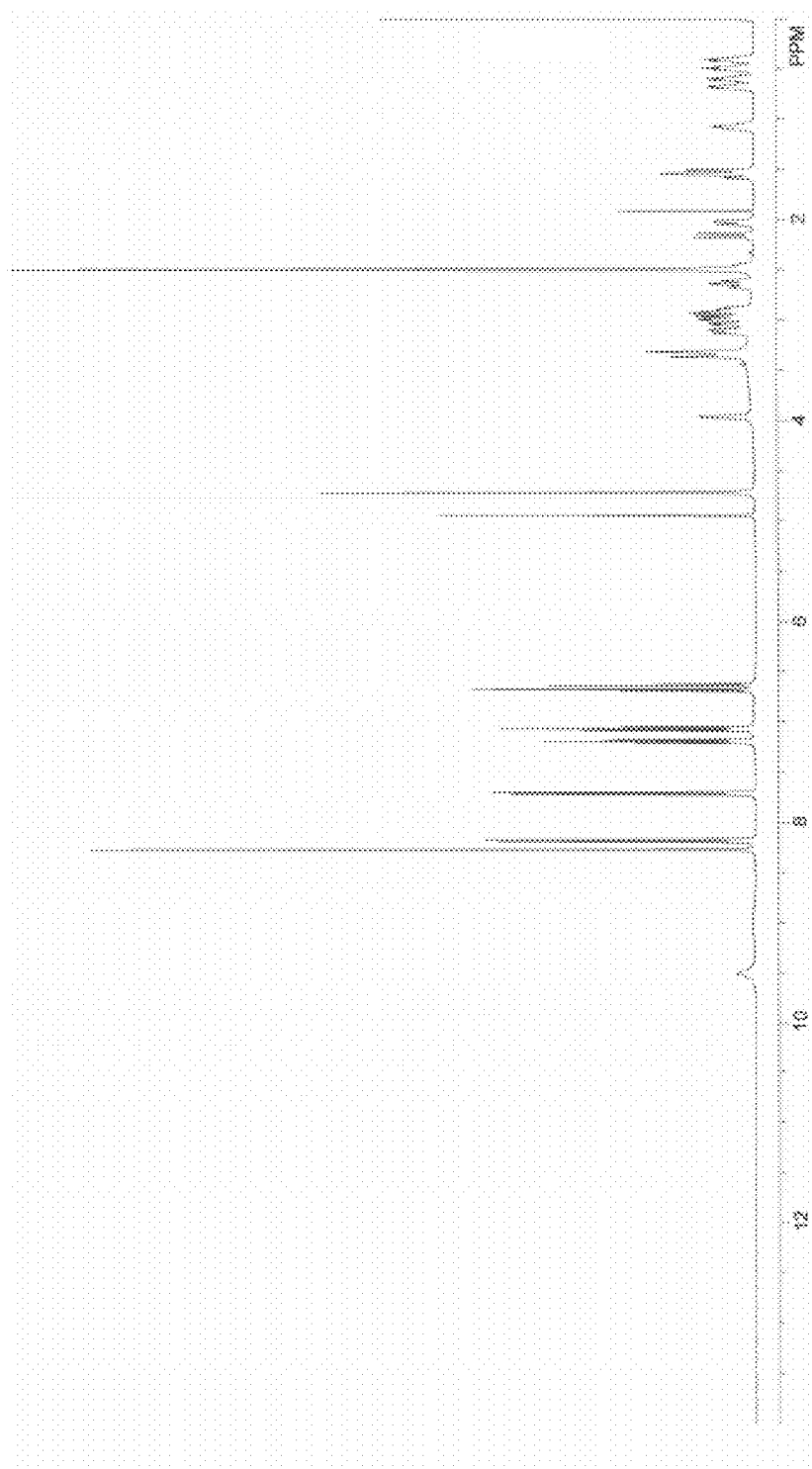
FIG. 48 is the proton nuclear magnetic resonance (¹H NMR) spectrum of amorphous naltrexone pamoate 1:1 salt as a 1:1 mixture of mono-sodium salt and free carboxylic acid.

To a 250 mL three-neck round-bottom flask equipped with a magnetic stir bar, thermowell, nitrogen inlet and addition funnel was charged disodium pamoate (1.50 g, 3.34 mmol) and 74 mL 75:25 ethanol/water, and the contents stirred at ambient temperature under a nitrogen atmosphere. A naltrexone acetic acid salt solution was prepared according to the following procedure. To a 50 mL round-bottom flask equipped with a magnetic stir bar was charged naltrexone base (1.14 g, 3.34 mmol), 13.4 mL 5% acetic acid/ethanol solution and 10 mL ethanol, and the solution stirred at ambient temperature under a nitrogen atmosphere. The naltrexone acetic acid solution was added to the disodium pamoate solution over a period of about one minute via an addition funnel with the pH of the combined solutions observed as about 6.4; the mixture was stirred for about an additional one hour at ambient temperature and under a nitrogen atmosphere. The solution was concentrated under reduced pressure (28.7 inches Hg and 22° C. water bath temperature) to provide naltrexone pamoate, (1:1) salt. The sample was triturated in water (about 34 g), the solids isolated by filtration through a medium frit filter, washed with a small portion of water and subsequently dried under vacuum to provide 2.35 g (96% yield) of a light yellow powder. The product was characterized by DSC (FIG. 45), FTIR (FIG. 46), PXRD (FIG. 47), $^1$H-NMR (FIG. 48), and sodium analysis. The $^1$H-NMR spectrum was consistent with a 1:1 ratio of naltrexone to pamoate moieties of the formed salt. The PXRD diffractogram indicated the product was predominantly amorphous. Sodium analysis indicated the remaining carboxyl functionality of the pamoate moiety of the 1:1 naltrexone pamoate to be a about a 50:50 mixture of sodium salt carboxylate and free carboxylic acid.

Example 13. Preparation of Polymorphic Naltrexone Pamoate, (1:1) Salt

Figure 49:
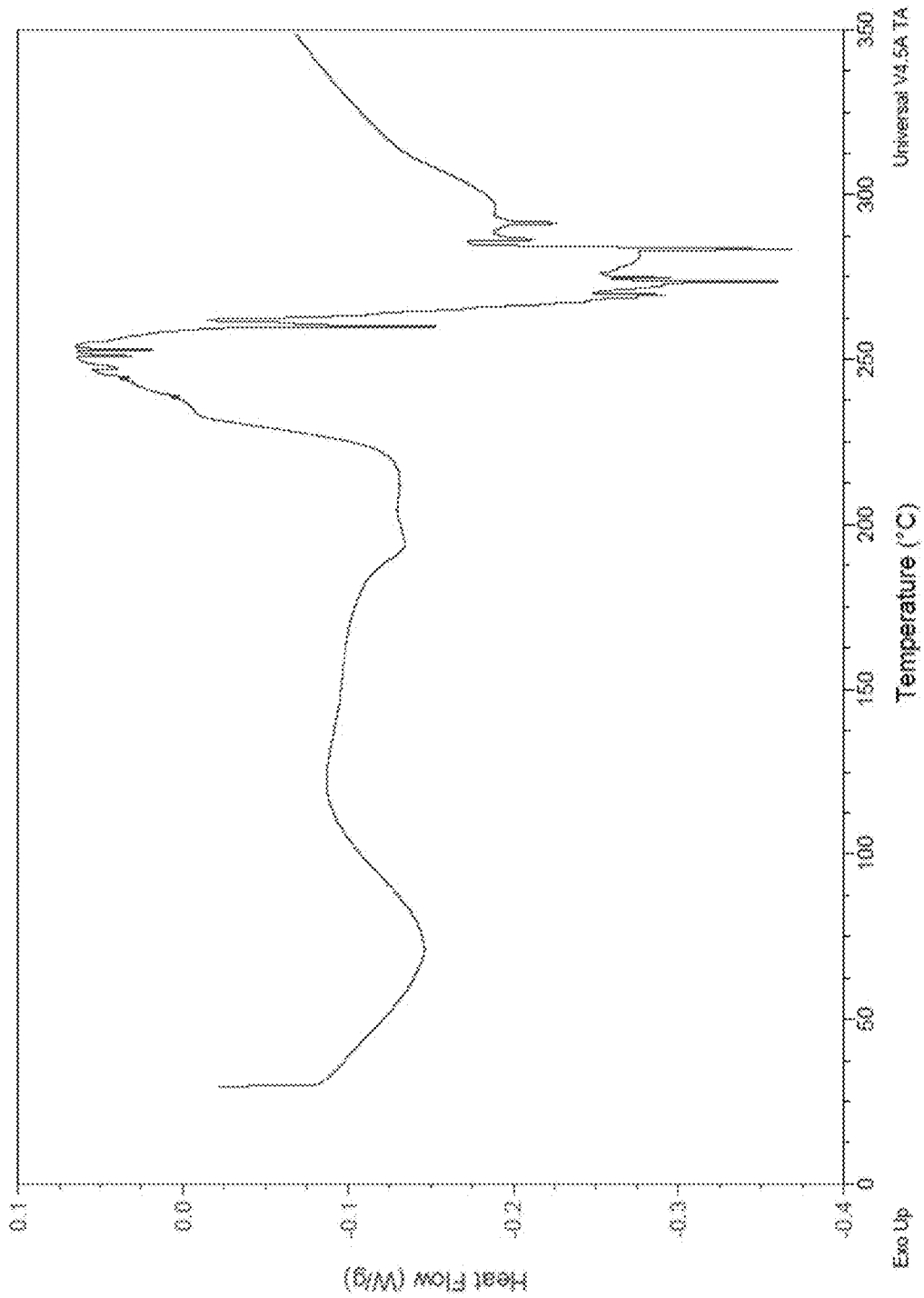
FIG. 49 is the differential scanning calorimetry (DSC) thermogram of polymorphic naltrexone pamoate 1:1 salt as the free carboxylic acid.
Figure 50:
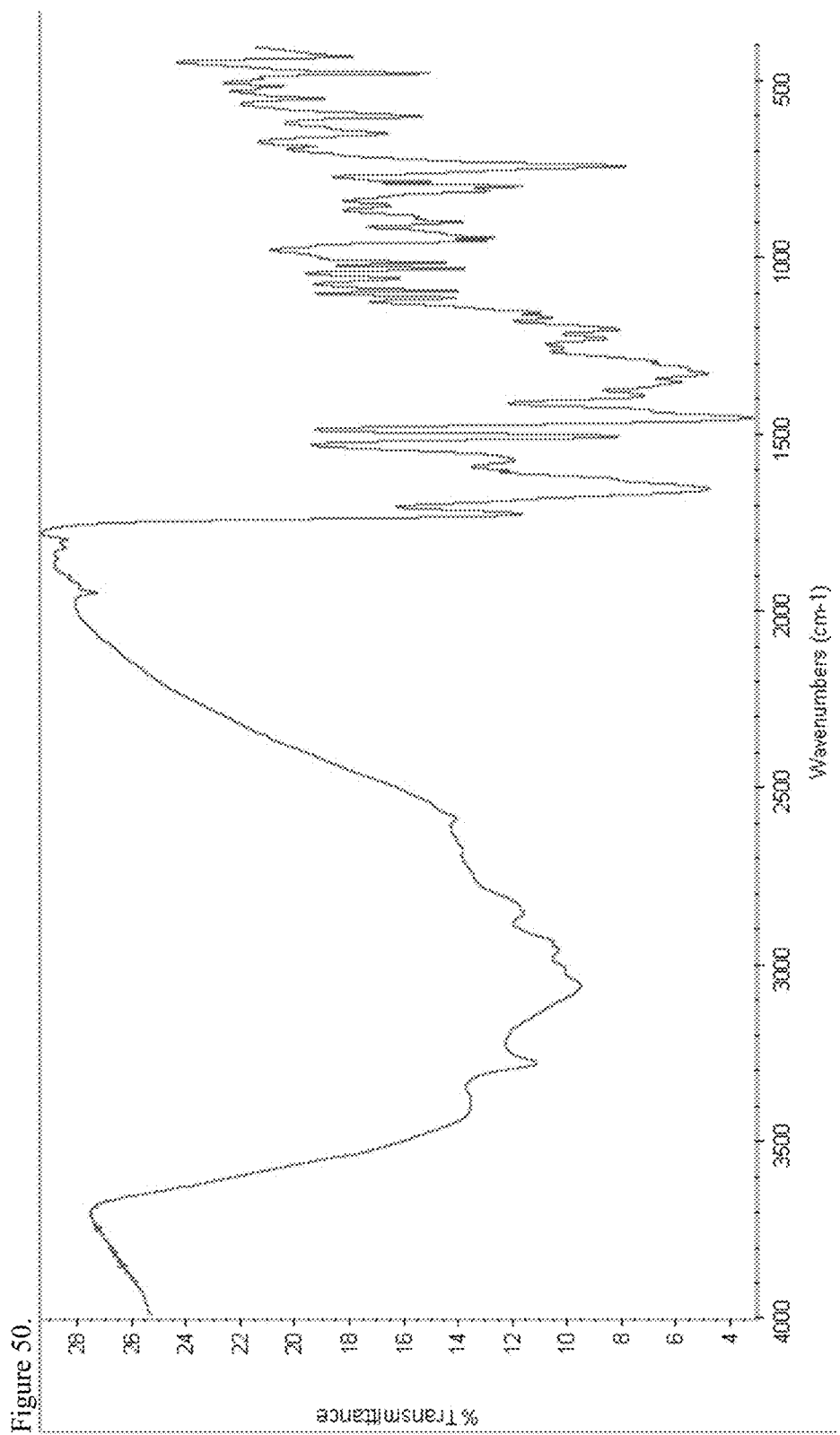
FIG. 50 is the Fourier transform infrared (FTIR) spectrum of polymorphic naltrexone pamoate 1:1 salt as the free carboxylic acid.
Figure 51:
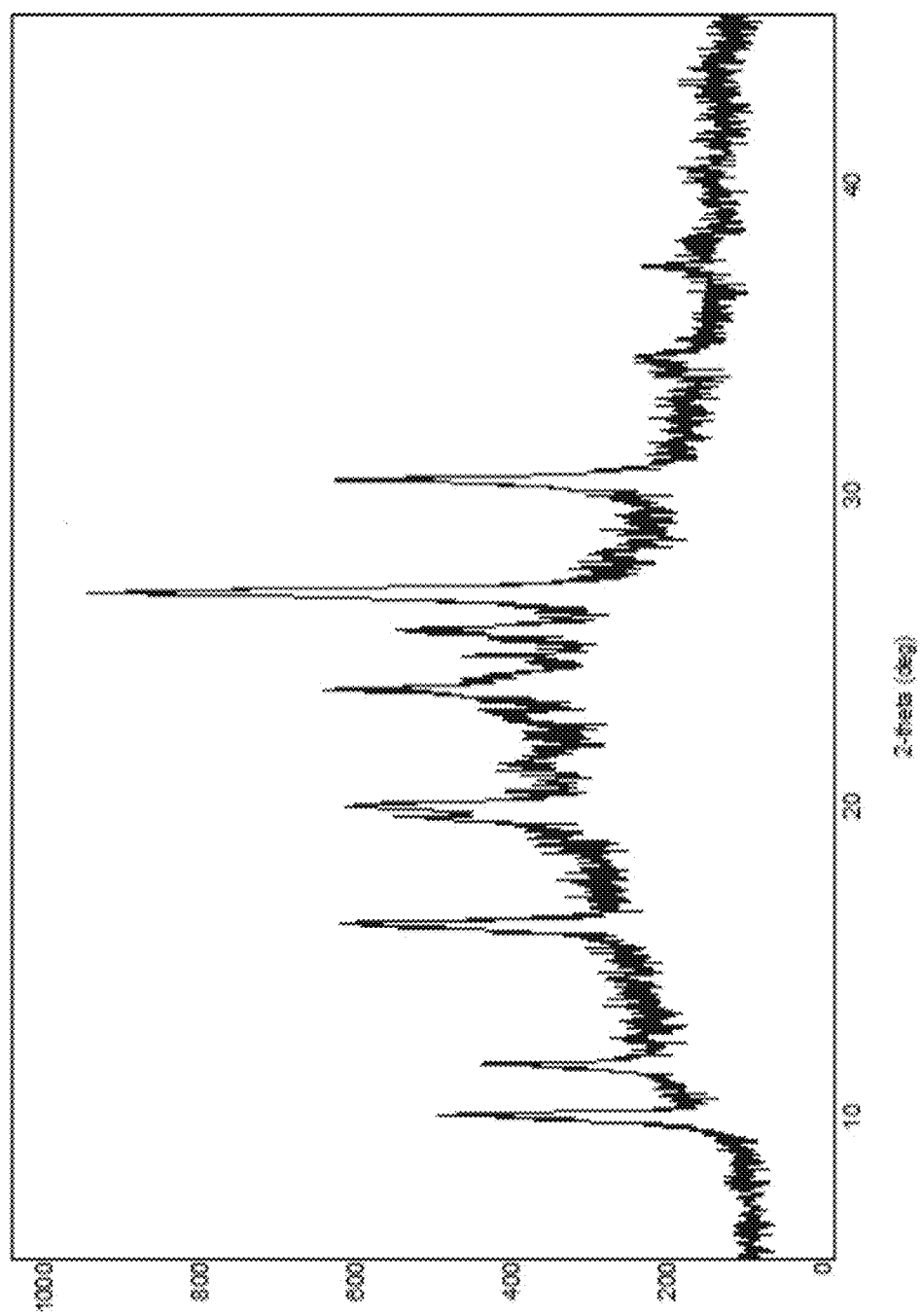
FIG. 51 is the powder X-ray diffraction (PXRD) diffractogram of polymorphic naltrexone pamoate 1:1 salt as the free carboxylic acid.
Figure 52:
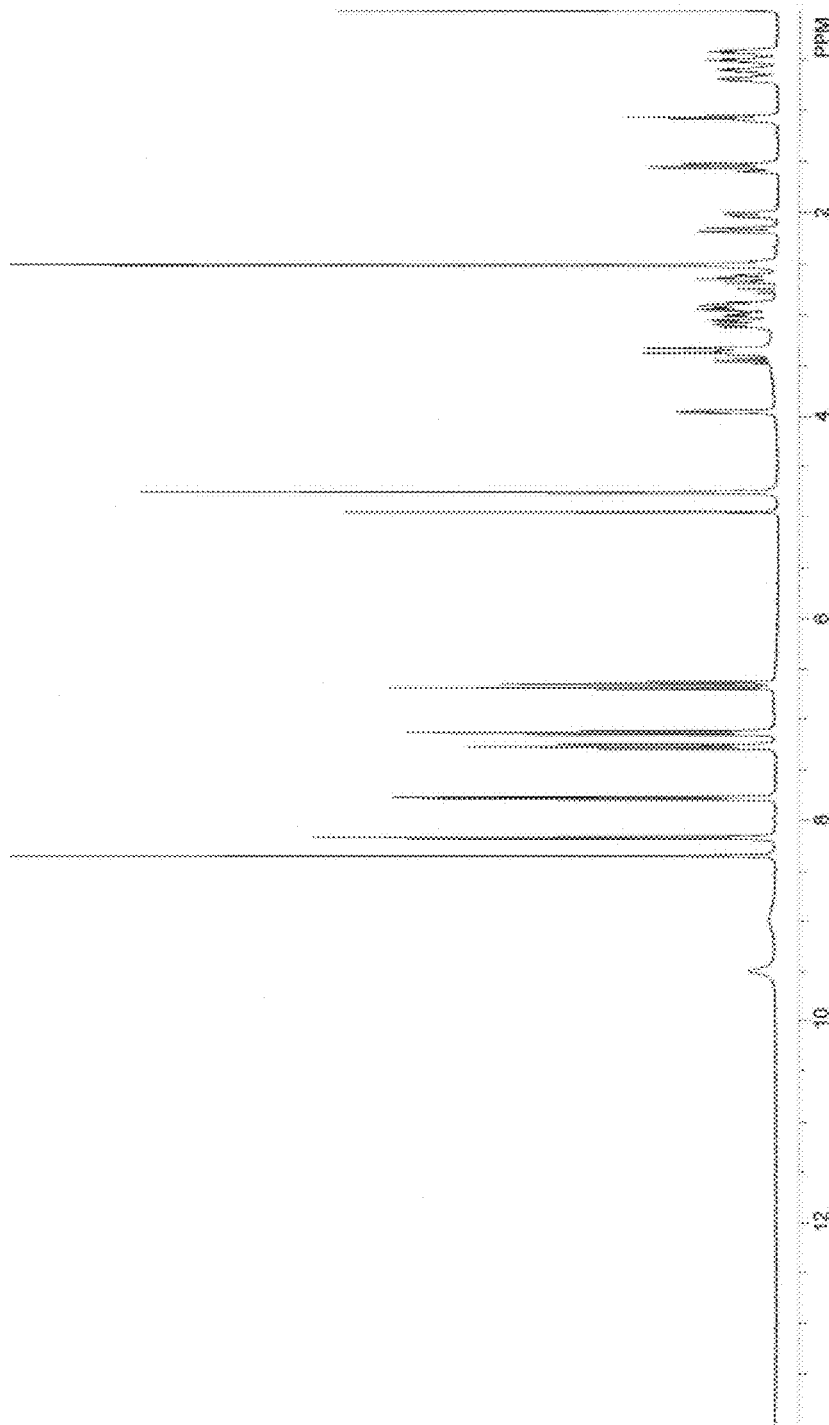
FIG. 52 is the proton nuclear magnetic resonance (¹H NMR) spectrum of polymorphic naltrexone pamoate 1:1 salt as the free carboxylic acid.

To a 100 mL three-neck round-bottom flask equipped with a magnetic stir bar, thermowell, nitrogen inlet and addition funnel was charged disodium pamoate (263 mg, 0.586 mmol) and 12 mL 75:25 ethanol/water, and the contents stirred at ambient temperature under a nitrogen atmosphere. A naltrexone formic acid salt solution was prepared according to the following procedure. To a 50 mL round-bottom flask equipped with a magnetic stir bar was charged naltrexone base (200 mg, 0.586 mmol), 1.75 mL ethanol and 1.75 mL 5% formic acid (88%)/ethanol solution and the solution stirred at room temperature under a nitrogen atmosphere. The naltrexone formic acid solution was added to the disodium pamoate solution over a period of about one minute via an addition funnel and the pH of the combined solutions was recorded as about 5.0. Citric acid (80 mg, 0.416 mmol) was immediately added to the reaction mixture with the pH dropping to about 4.7. The mixture was stirred for an additional about ten minutes at ambient temperature under a nitrogen atmosphere. The solution was concentrated under reduced pressure (28.7 inches Hg and 22° C. water bath temperature) to provide the naltrexone pamoate, (1:1) salt. The sample was triturated in water (about 34 g), the solids isolated by filtration through a medium frit filter and dried under vacuum to provide 370 mg g (87% yield) of a light yellow powder. The product was characterized by DSC (FIG. 49), FTIR (FIG. 50), PXRD (FIG. 51), $^1$H-NMR (FIG. 52) and sodium analysis. The $^1$H-NMR spectrum was consistent with a 1:1 ratio of naltrexone to pamoate moieties of the formed salt. The PXRD diffractogram indicated the product was crystalline. Sodium analysis indicated the carboxyl functionality of the pamoate moiety of the 1:1 naltrexone pamoate salt was present at about 94% as the free carboxylic acid.

Example 14. Preparation of Amorphous Imipramine Pamoate, (1:1) Salt

Figure 53:
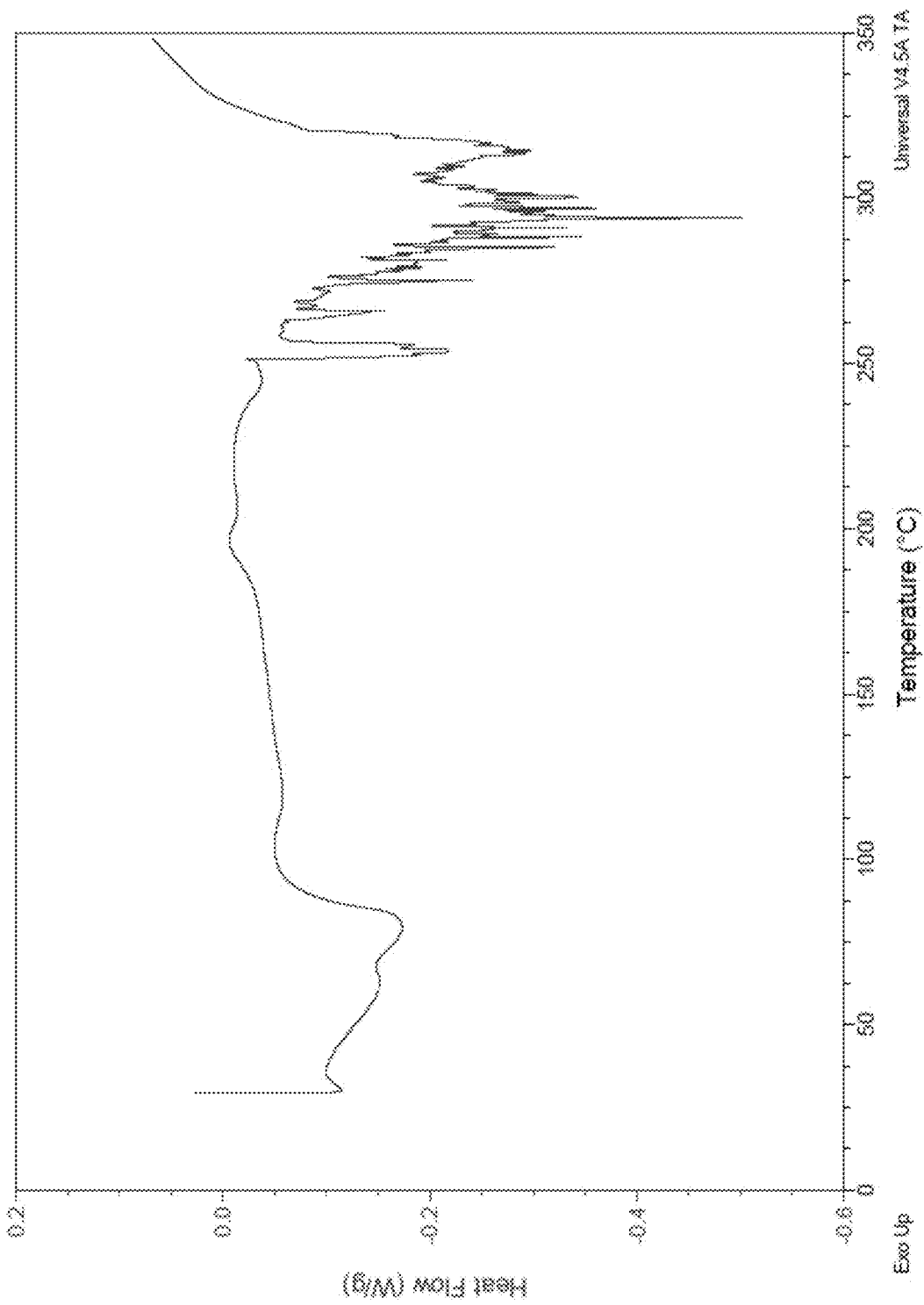
FIG. 53 is the differential scanning calorimetry (DSC) thermogram of amorphous imipramine pamoate 1:1 salt as a 1:1 mixture of mono-sodium salt and free carboxylic acid.
Figure 54:
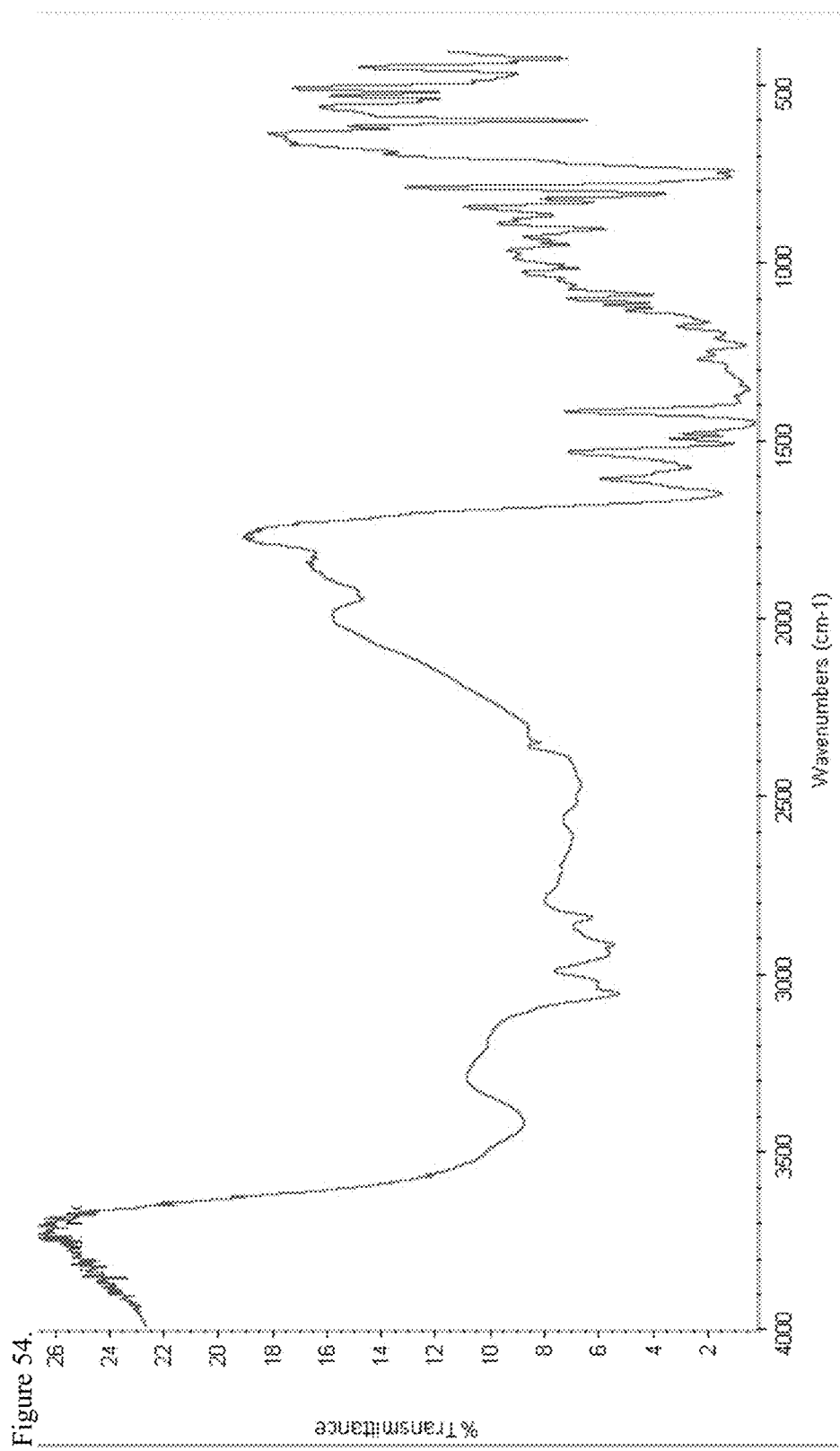
FIG. 54 is the Fourier transform infrared (FTIR) spectrum of amorphous imipramine pamoate 1:1 salt as a 1:1 mixture of mono-sodium salt and free carboxylic acid.
Figure 55:
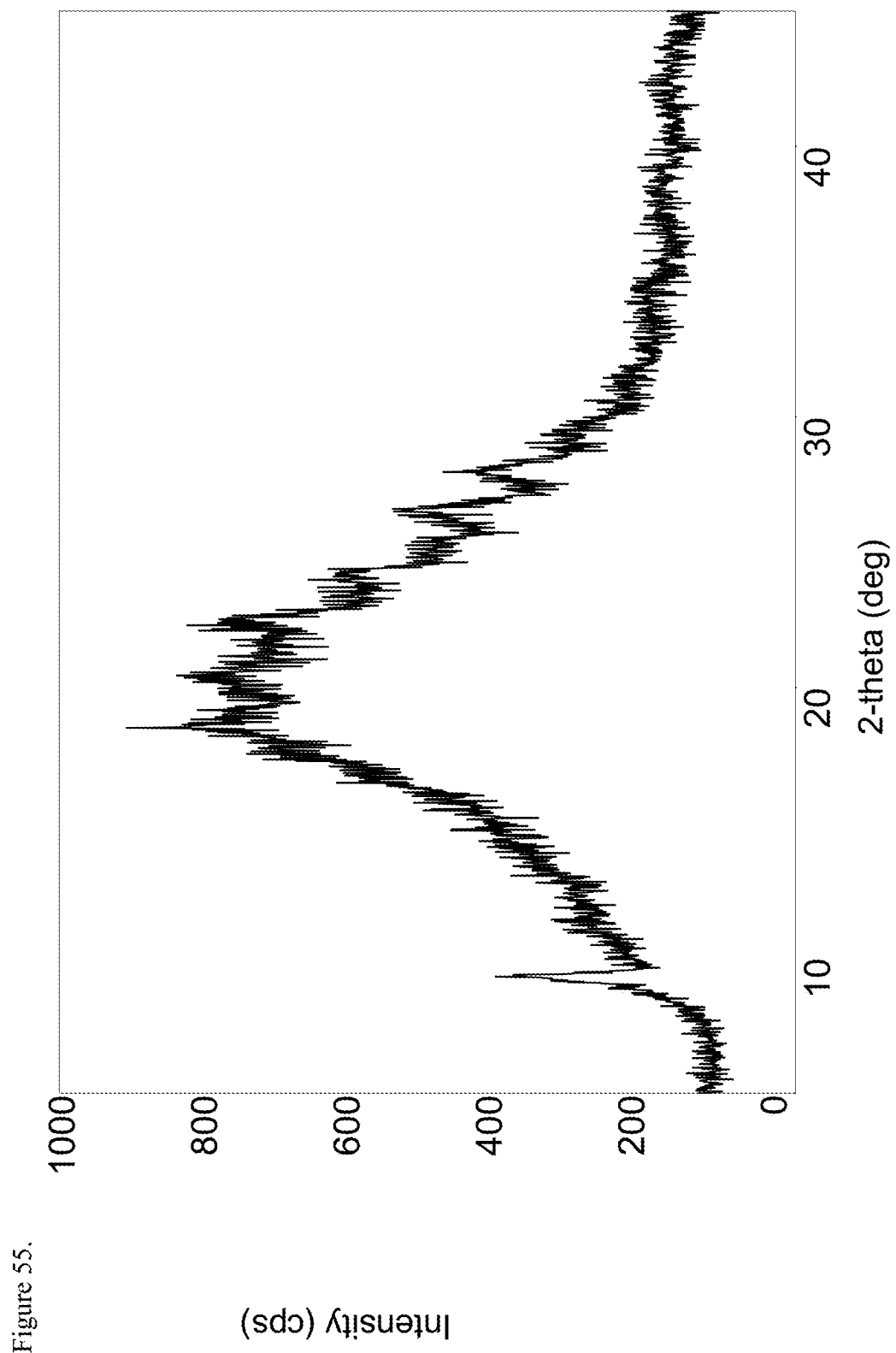
FIG. 55 is the powder X-ray diffraction (PXRD) diffractogram of amorphous imipramine pamoate 1:1 salt as a 1:1 mixture of mono-sodium salt and free carboxylic acid.
Figure 56:
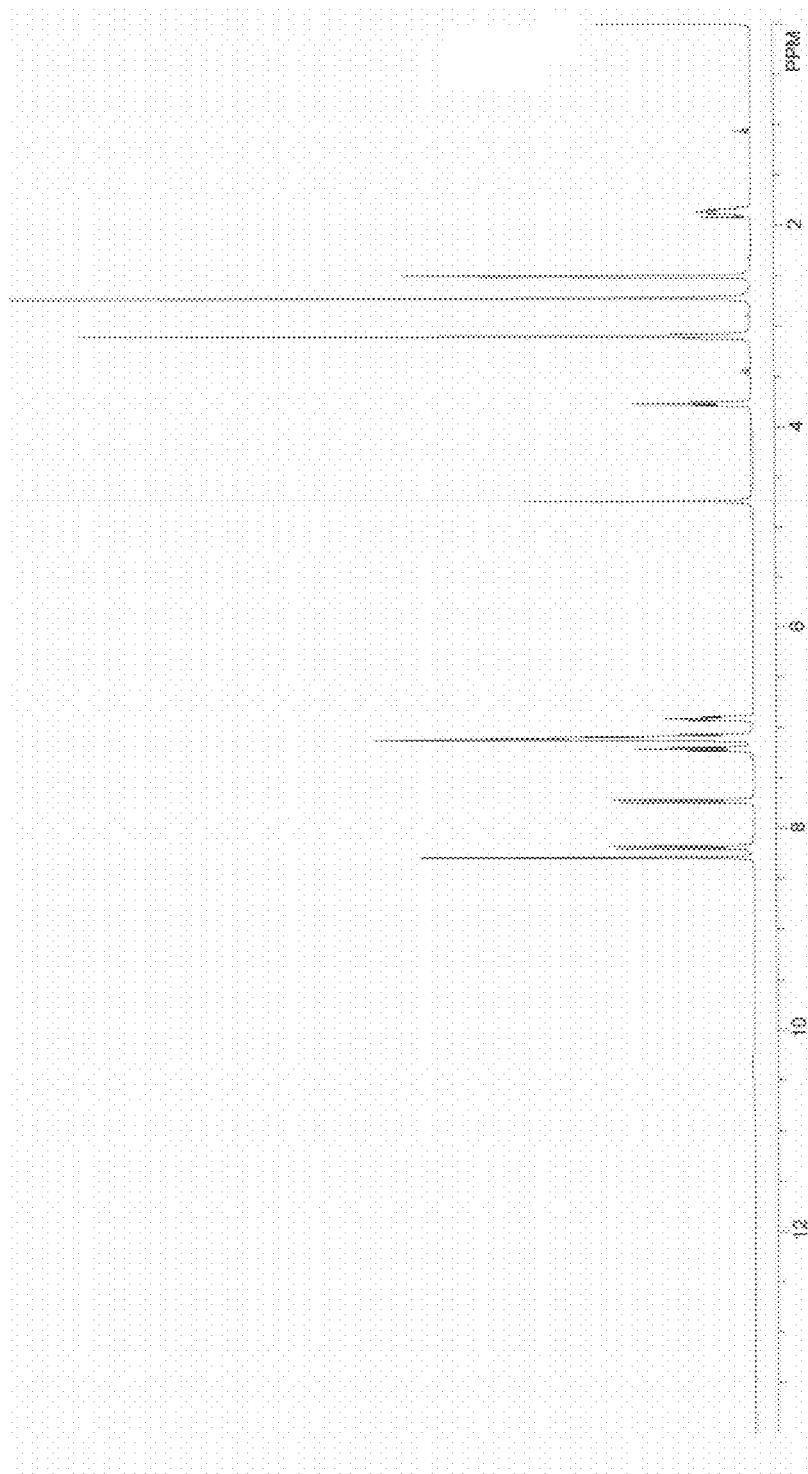
FIG. 56 is the proton nuclear magnetic resonance (¹H NMR) spectrum of amorphous imipramine pamoate 1:1 salt as a 1:1 mixture of mono-sodium salt and free carboxylic acid.

To a 250 mL one-neck round-bottom flask equipped with a magnetic stir bar, thermowell, nitrogen inlet and addition funnel was charged disodium pamoate (1.50 g, 3.34 mmol) and 67 mL 75:25 ethanol/water, and the contents stirred at ambient temperature under a nitrogen atmosphere. An imipramine acetic acid salt solution was prepared according to the following procedure. To a 50 mL round-bottom flask equipped with a magnetic stir bar was charged imipramine base (936.5 mg, 3.34 mmol) and 13.4 mL 5% acetic acid/ethanol solution and the solution stirred at ambient temperature under a nitrogen atmosphere. The imipramine acetic acid solution was added to the disodium pamoate solution over a period of about one minute via an addition funnel with the pH of the combined solutions recorded as about 6.0; the mixture was stirred for about an additional one hour at ambient temperature and under a nitrogen atmosphere. The solution was concentrated under reduced pressure (28.7 inches Hg and 22° C. water bath temperature) to provide imipramine pamoate, (1:1) salt. The sample was triturated in water (about 34 g), the solids isolated by filtration through a medium frit filter, further washed with a small portion of water and subsequently dried under vacuum to provide 2.08 g (93% yield) of a light-yellow powder. The product was characterized by DSC (FIG. 53), FTIR (FIG. 54), PXRD (FIG. 55), $^1$H-NMR (FIG. 56) and sodium analysis. The $^1$H-NMR spectrum was consistent with a 1:1 ratio of imipramine to pamoate moieties of the formed salt. The PXRD diffractogram indicated the product was predominantly amorphous. Sodium analysis indicated the carboxyl functionality of the pamoate moiety of the 1:1 imipramine pamoate salt was about a 50:50 mixture of sodium carboxylate and free carboxylic acid.

Example 15. Preparation of Amorphous Methadone Pamoate, (1:1) Salt

Figure 57:
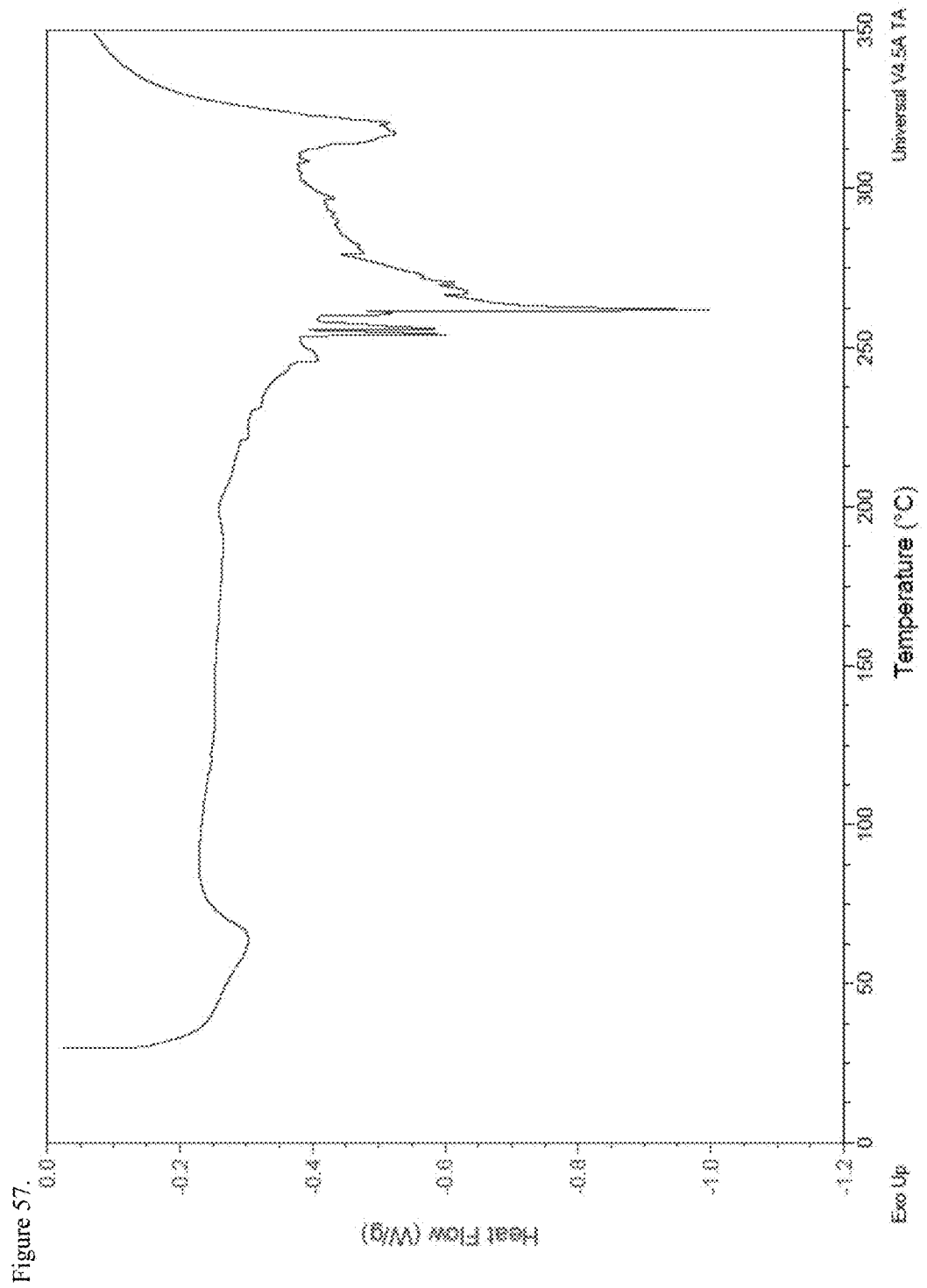
FIG. 57 is the differential scanning calorimetry (DSC) thermogram of amorphous methadone pamoate 1:1 salt as a 1:1 mixture of mono-sodium salt and free carboxylic acid.
Figure 58:
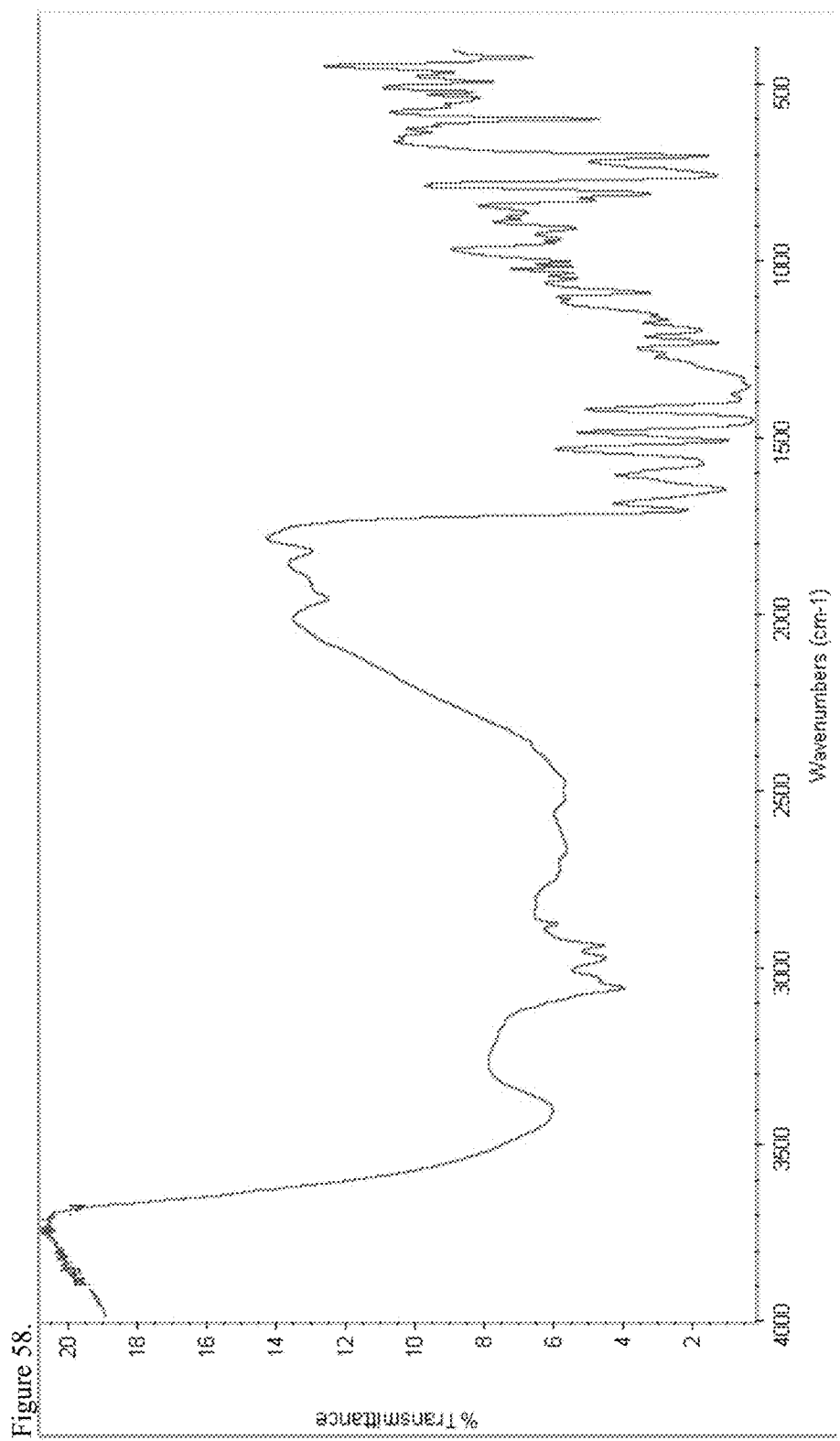
FIG. 58 is the Fourier transform infrared (FTIR) spectrum of amorphous methadone pamoate 1:1 salt as a 1:1 mixture of mono-sodium salt and free carboxylic acid.
Figure 59:
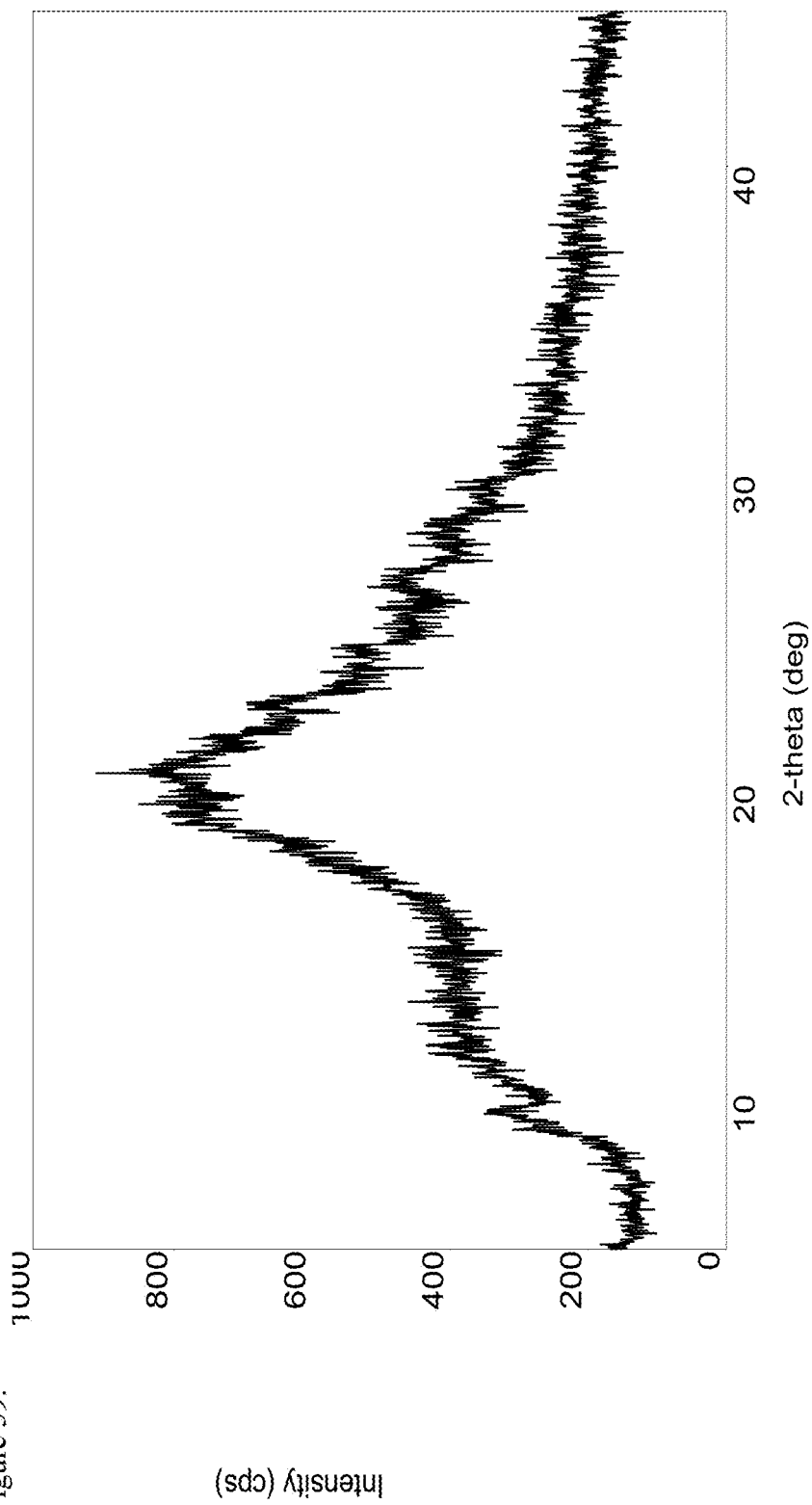
FIG. 59 is the powder X-ray diffraction (PXRD) diffractogram of amorphous methadone pamoate 1:1 salt as a 1:1 mixture of mono-sodium salt and free carboxylic acid.
Figure 60:
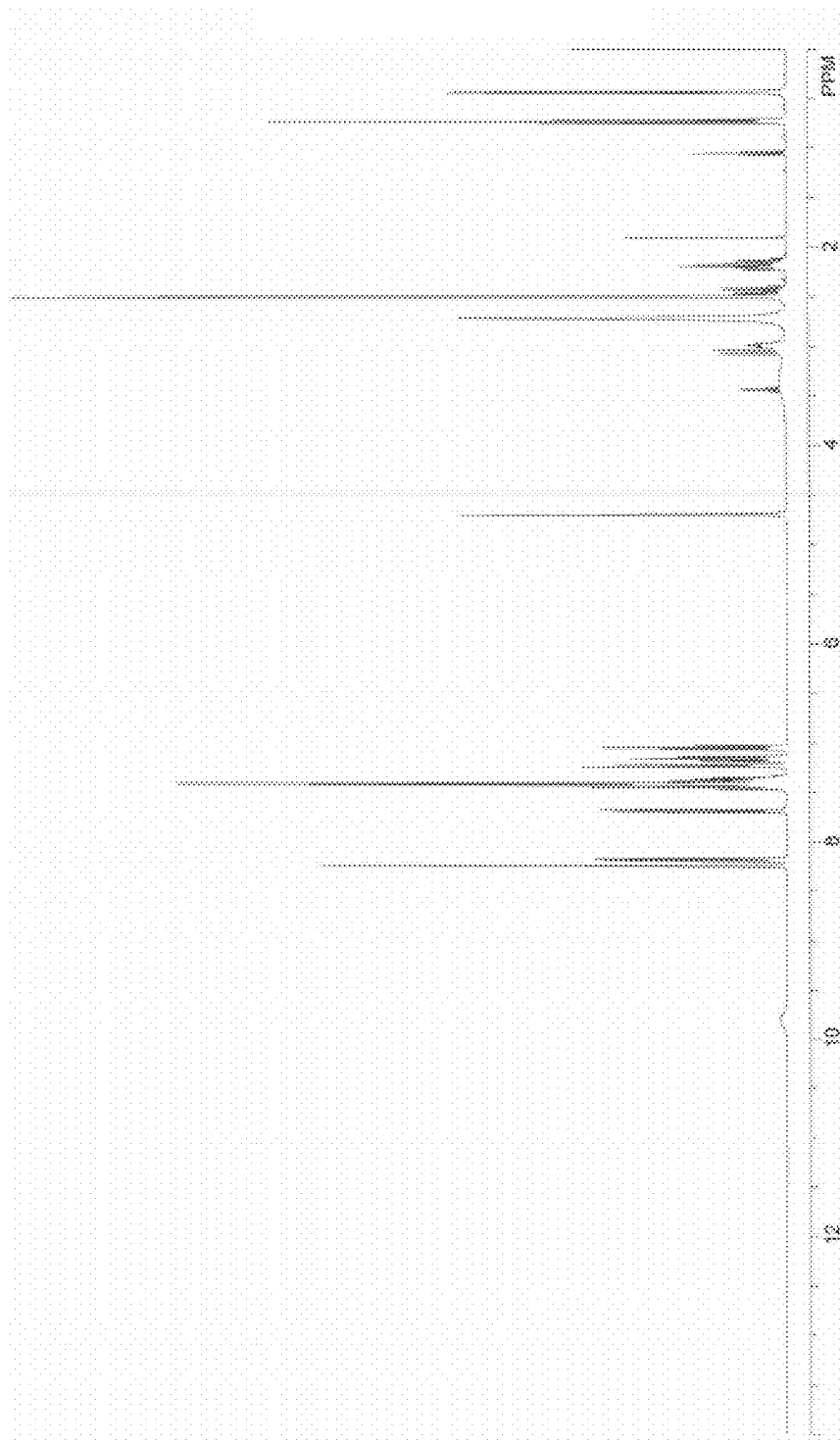
FIG. 60 is the proton nuclear magnetic resonance (¹H NMR) spectrum of amorphous methadone pamoate 1:1 salt as a 1:1 mixture of mono-sodium salt and free carboxylic acid.

To a 250 mL three-neck round-bottom flask equipped with a magnetic stir bar, thermowell, nitrogen inlet and addition funnel was charged disodium pamoate (1.50 g, 3.34 mmol) and 67 mL 75:25 ethanol/water, and the contents stirred at ambient temperature under a nitrogen atmosphere. A methadone acetic acid salt solution was prepared according to the following procedure. To a 50 mL round-bottom flask equipped with a magnetic stir bar was charged methadone base (1.03 g, 3.34 mmol) and 13.4 mL 5% acetic acid/ethanol solution, and the solution stirred at ambient temperature under a nitrogen atmosphere. The methadone acetic acid solution was added to the disodium pamoate solution over a period of about one minute via an addition funnel and the pH of the combined solutions was recorded as about 6.3; the mixture was stirred overnight at ambient temperature under a nitrogen atmosphere. The solution was concentrated under reduced pressure (28.7 inches Hg and 22° C. water bath temperature) to provide the methadone pamoate, (1:1) salt. The sample was triturated in water (about 34 g), the solids isolated by filtration through a medium frit filter, further washed with a small portion of water and subsequently dried under vacuum to provide 2.30 g (99% yield) of an off-white powder. The product was characterized by DSC (FIG. 57), FTIR (FIG. 58), PXRD (FIG. 59), $^1$H-NMR (FIG. 60), and sodium analysis. The $^1$H-NMR spectrum was consistent with a 1:1 ratio of methadone to pamoate moieties of the formed salt. The PXRD diffractogram indicated the product was predominantly amorphous. Sodium analysis indicated the carboxyl functionality of the pamoate moiety of the 1:1 methadone pamoate salt was present as about a 50:50 mixture of sodium carboxylate and free carboxylic acid.

Example 16. Characterization and Evaluation of Reaction Product Described in U.S. Pat. No. 6,897,111 [Greco et al.] Example 1 Alleging Preparation of 1:1 Haloperidol Pamoate Salt In Example 1 of Greco's '111 patent the assertion is made that, "Alternatively, other methods such as evaporation, slow or fast cooling or stirring solutions can be used to precipitate salt". This assertion was made in context of preparing "1:1 haloperidol pamoate salt". With the asserted experimental latitude of the Greco procedure(s) other findings were obtained from executing the Greco procedure.

Experimental Test Case A

Figure 61:
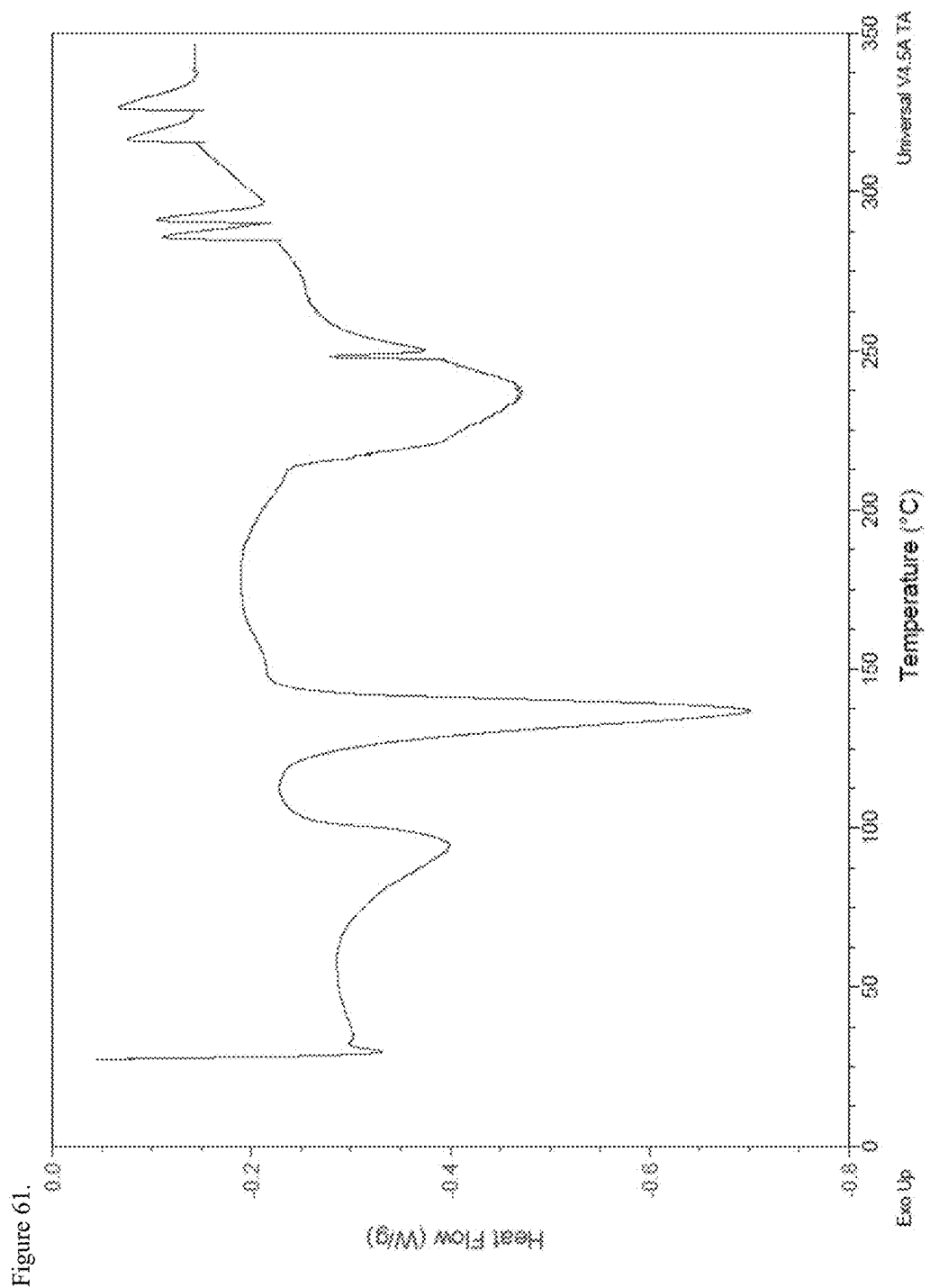
FIG. 61 is the differential scanning calorimetry (DSC) thermogram of polymorphic haloperidol pamoate 2:1 for attempting to reproduce Greco Patent Example 1 overnight stirring.
Figure 62:
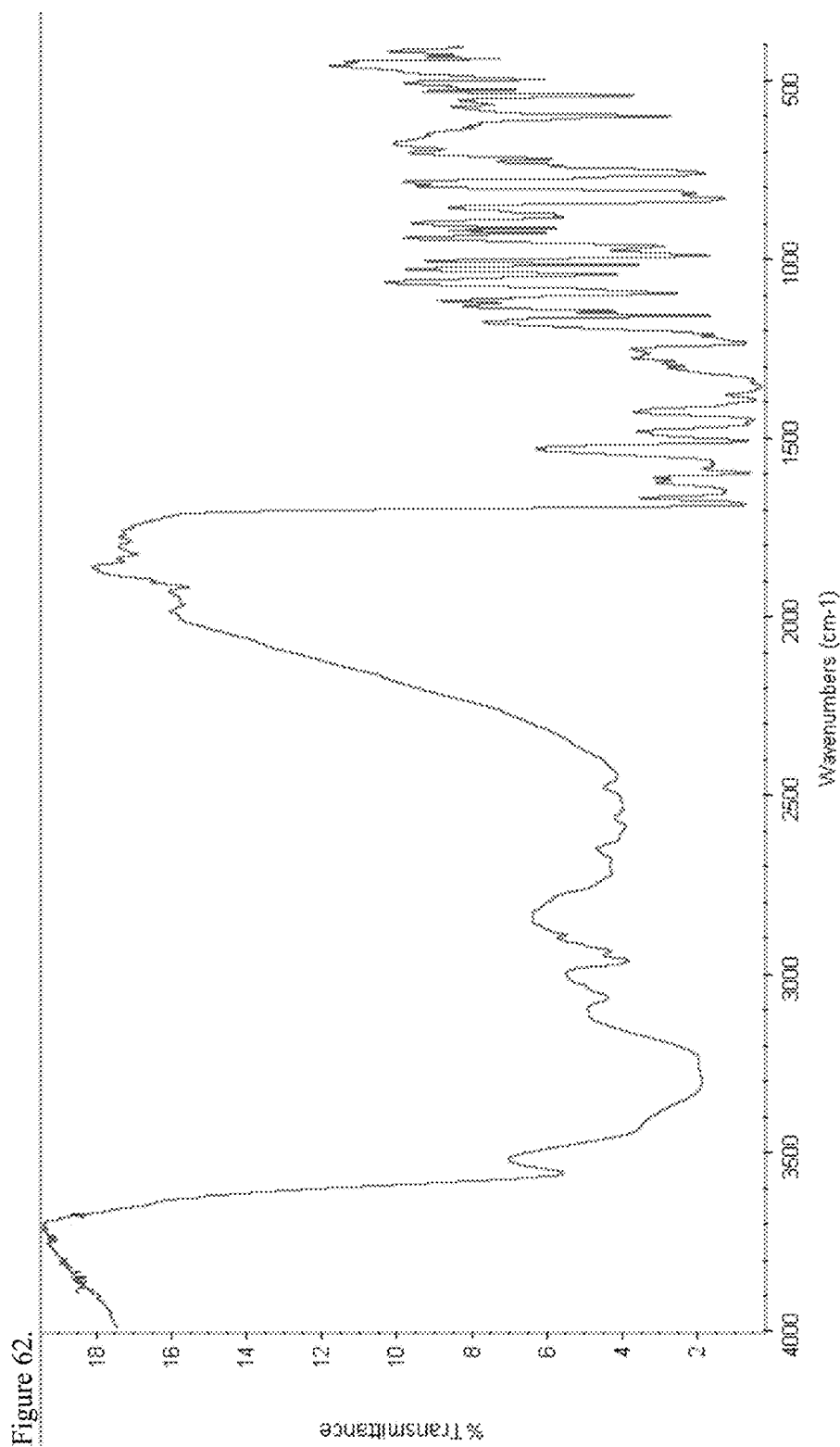
FIG. 62 is the Fourier transform infrared (FTIR) spectrum of polymorphic haloperidol pamoate 2:1 for attempting to reproduce Greco Patent Example 1 overnight stirring.
Figure 63:
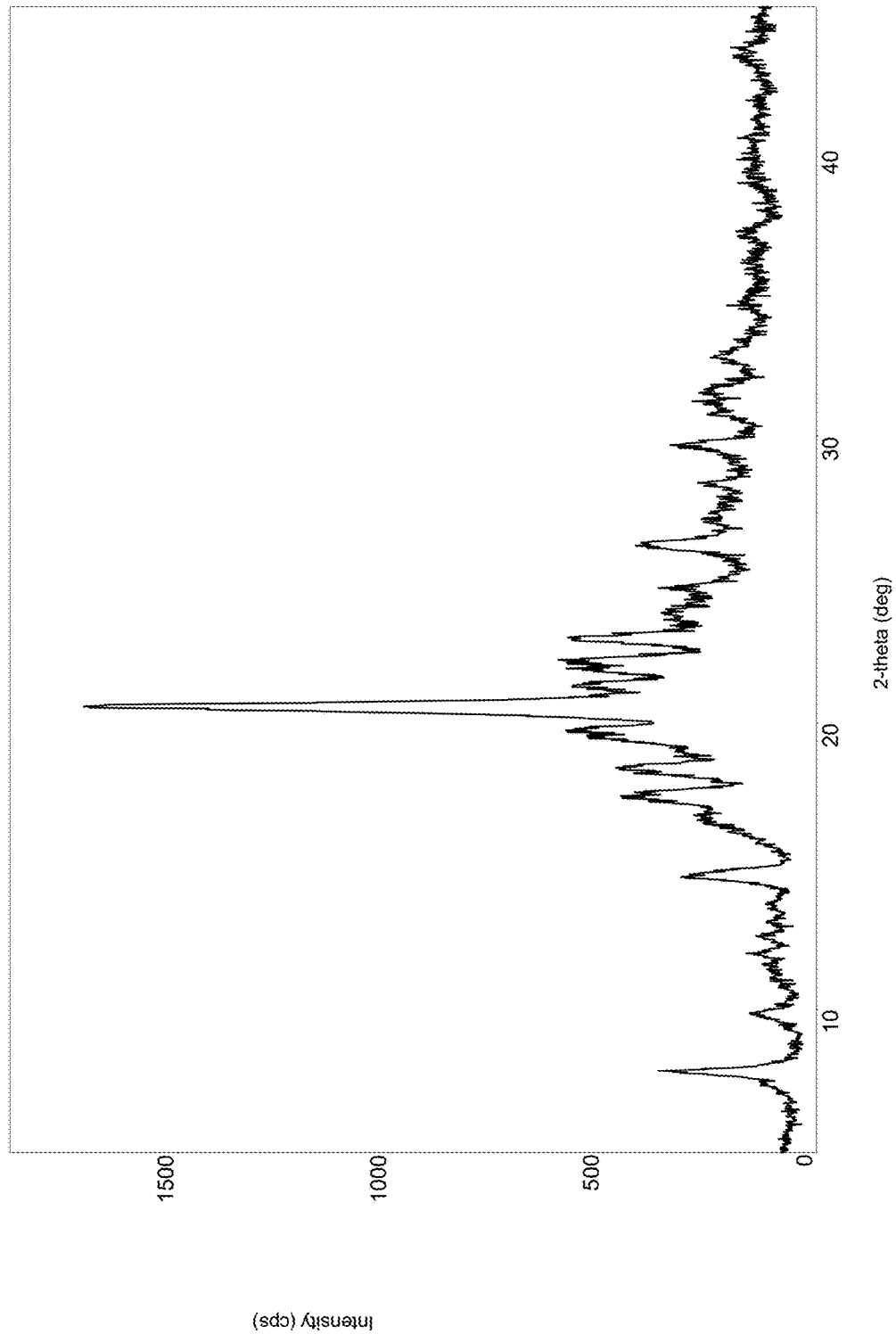
FIG. 63 is the powder X-ray diffraction (PXRD) diffractogram of polymorphic haloperidol pamoate 2:1 for attempting to reproduce Greco Patent Example 1 overnight stirring.
Figure 64:
FIG. 64 is the proton nuclear magnetic resonance (¹H NMR) spectrum of polymorphic haloperidol pamoate 2:1 for attempting to reproduce Greco Patent Example 1 overnight stirring.

To a 250 mL one-neck round-bottom flask equipped with a magnetic stir bar, thermowell, nitrogen inlet and addition funnel was charged disodium pamoate (1.50 g, 3.34 mmol) and 33 mL 50:50 ethanol/water and the contents stirred at ambient temperature under a nitrogen atmosphere. To a 50 mL round-bottom flask equipped with a magnetic stir bar was charged haloperidol (1.26 g, 3.34 mmol) and 33.4 mL 5% acetic acid/ethanol solution and the solution stirred at ambient temperature under a nitrogen atmosphere. The haloperidol acetic acid solution was added to the disodium pamoate solution over a period of about one minute via an addition funnel and the pH was recorded as about 5.4 with reaction occurring as simultaneous slurry formation ensued. The mixture was stirred overnight at ambient temperature while under a nitrogen atmosphere. The reaction mixture pH the following day had remained at about 5.4. The reaction mixture was filtered through a medium frit filter and the isolated solids washed with a small portion of ethanol and dried under vacuum to provide 1.63 g (86% yield based on 2:1 haloperidol pamoate) of an off-white powder. The product was characterized by DSC (FIG. 61), FTIR (FIG. 62), PXRD (FIG. 63) and $^1$H-NMR (FIG. 64). The $^1$H-NMR spectrum was consistent with a 2:1 ratio of haloperidol to pamoate moieties of the formed haloperidol pamoate salt and not the 1:1 salt asserted by Greco. The PXRD diffractogram indicated the reaction product was mostly crystalline.

Experimental Test Case B

Figure 65:
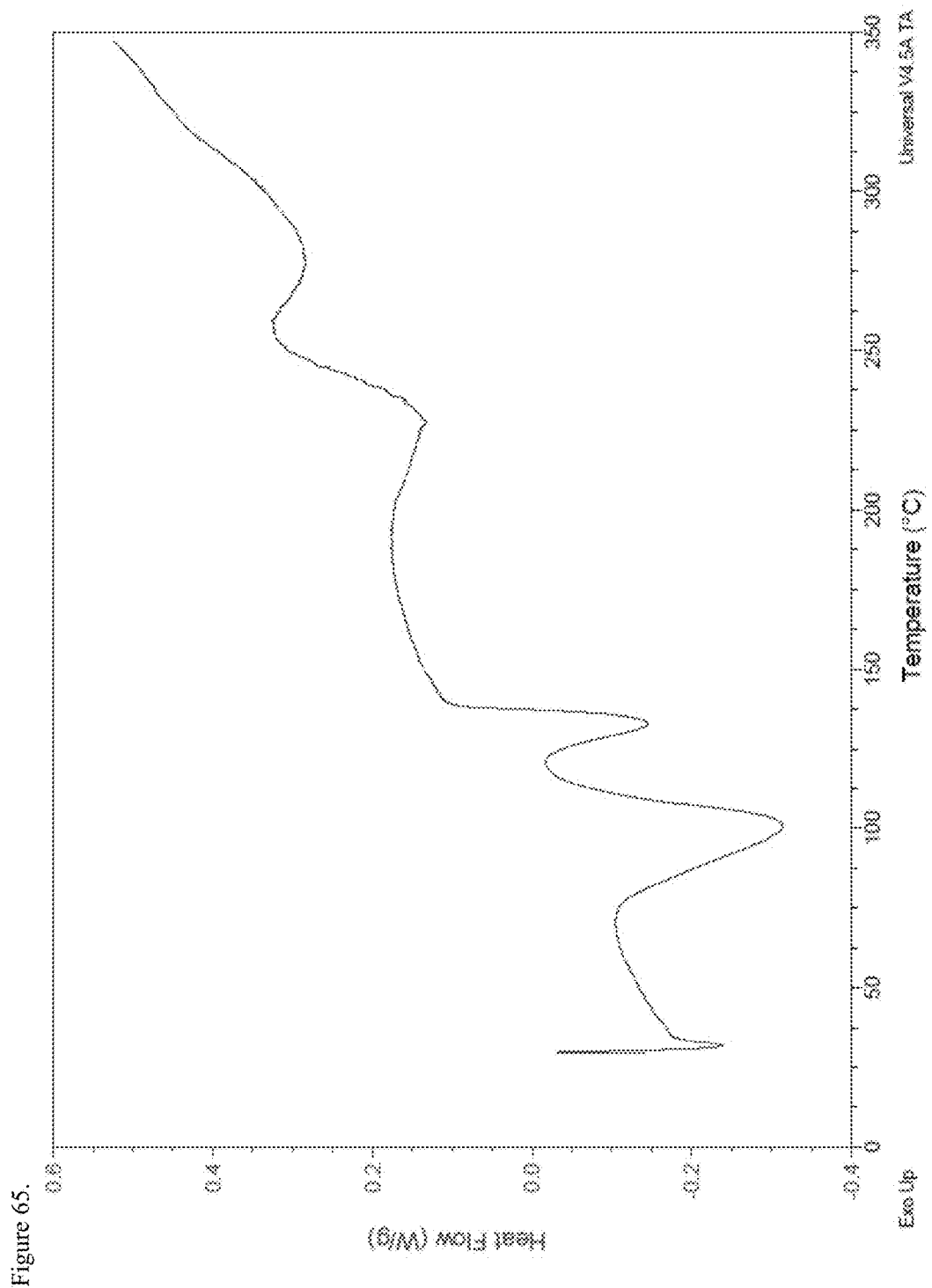
FIG. 65 is the differential scanning calorimetry (DSC) thermogram of polymorphic haloperidol pamoate 2:1 for attempting to reproduce Greco Patent Example 1 no stirring and sitting about three days.
Figure 66:
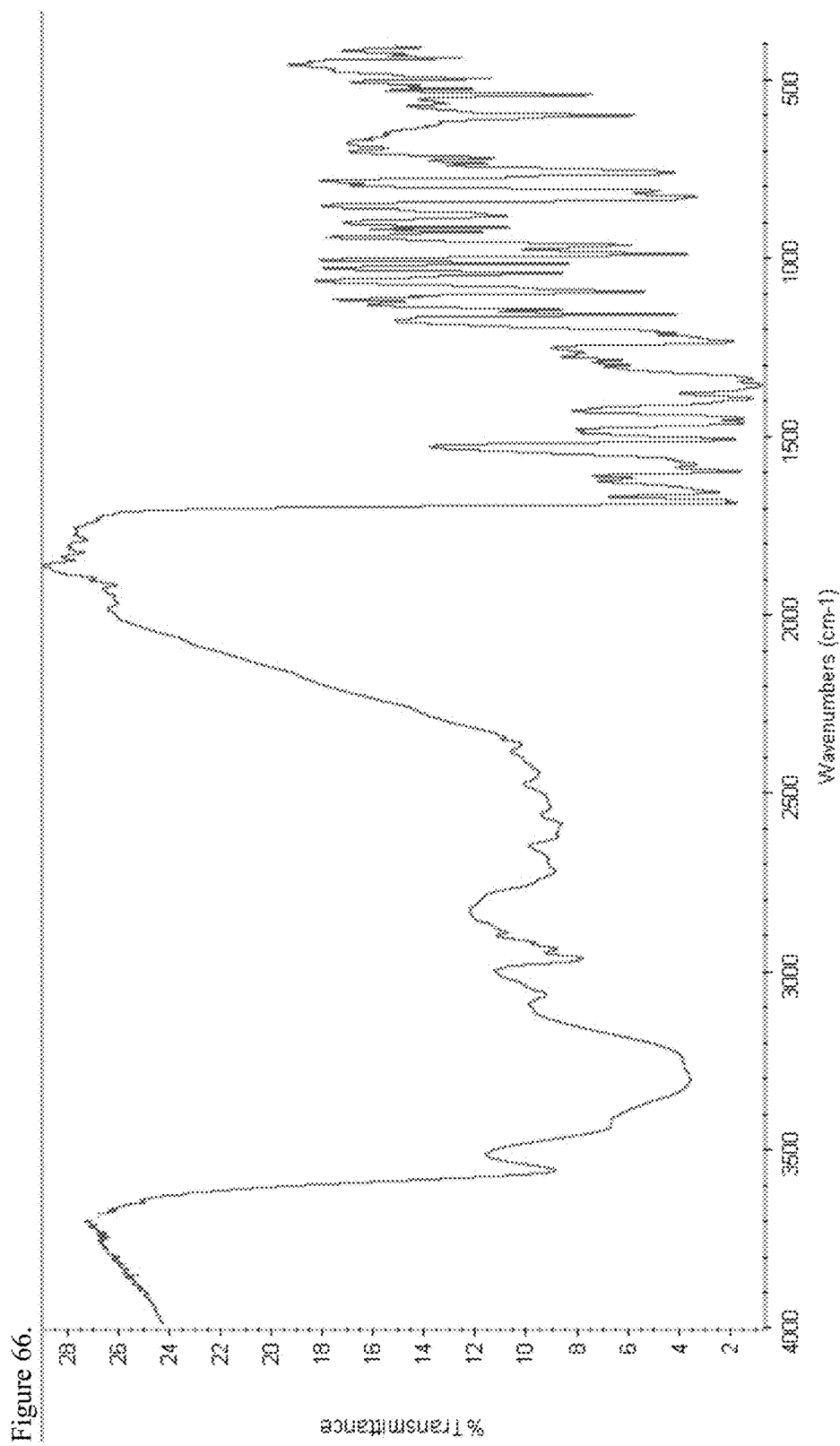
FIG. 66 is the Fourier transform infrared (FTIR) spectrum of polymorphic haloperidol pamoate 2:1 for attempting to reproduce Greco Patent Example 1 no stirring and sitting about three days.
Figure 67:
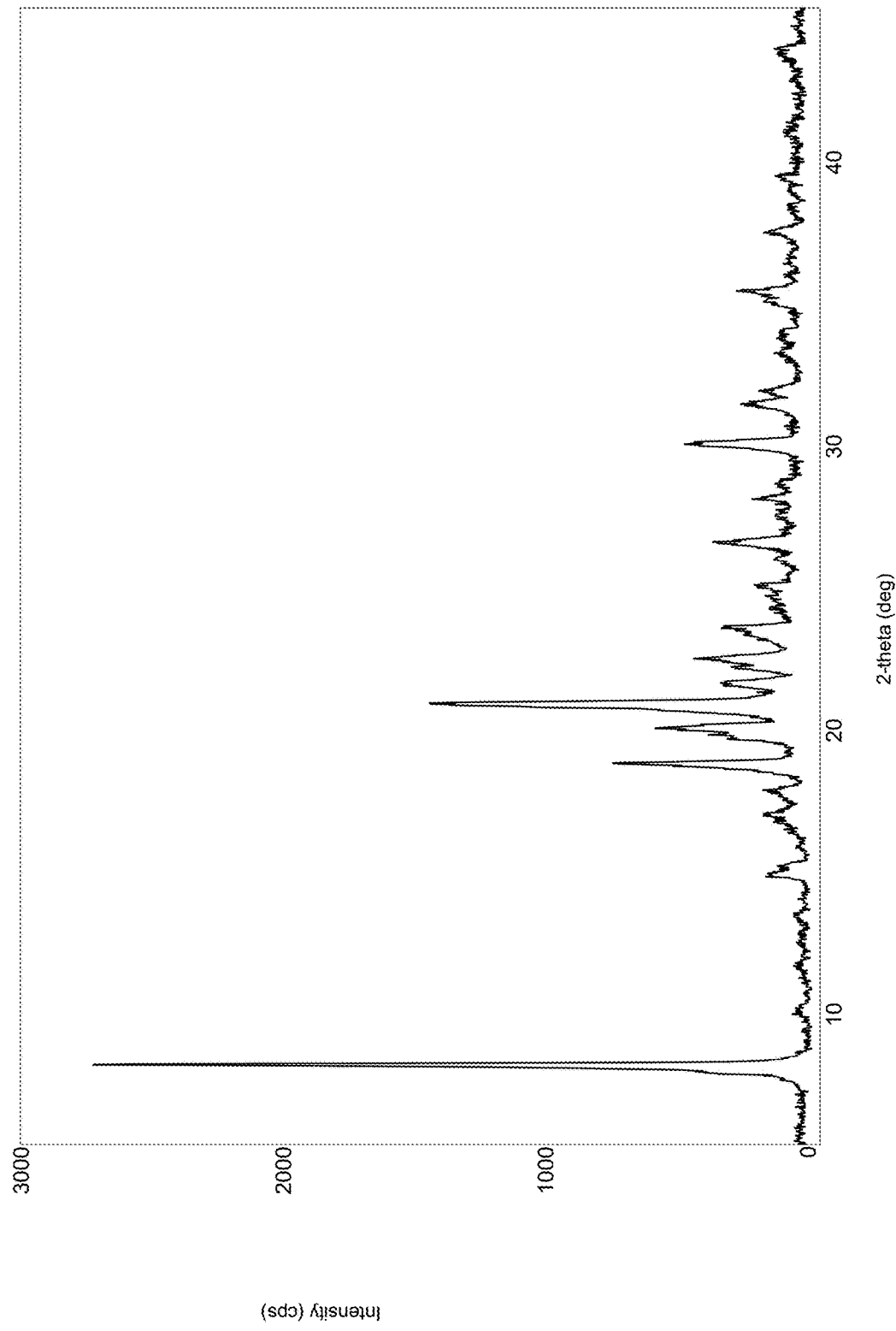
FIG. 67 is the powder X-ray diffraction (PXRD) diffractogram of polymorphic haloperidol pamoate 2:1 for attempting to reproduce Greco Patent Example 1 no stirring and sitting about three days.
Figure 68:
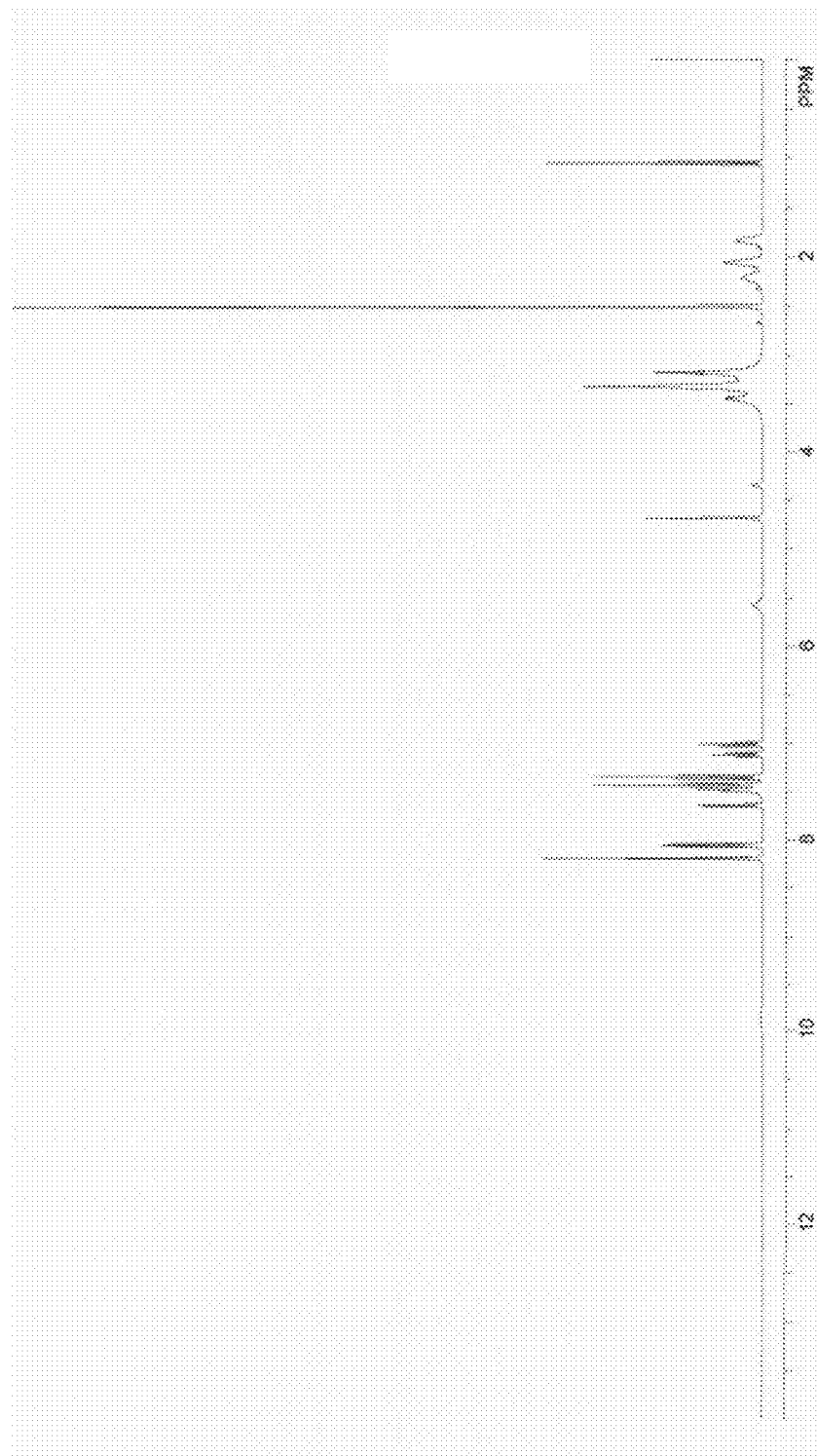
FIG. 68 is the proton nuclear magnetic resonance ($^1$H NMR) spectrum of polymorphic haloperidol pamoate 2:1 for attempting to reproduce Greco Patent Example 1 no stirring and sitting about three days.

Experimental Test Case A (op. cit.) was repeated using different experimental conditions allowed within the teaching of Greco in an effort to obtain the 1:1 haloperidol salt therein described. The changes evaluated the boundary conditions wherein stirring was omitted from the combined solutions and the reaction mixture was held at ambient temperature under a nitrogen atmosphere over a period of about three days. The formed solids were isolated in the same manner as those described above to yield 1.73 g (91% yield based on 2:1 haloperidol pamoate) of light-yellow needles. The product was characterized by DSC (FIG. 65), FTIR (FIG. 66), PXRD (FIG. 67) and $^1$H-NMR (FIG. 68). The $^1$H-NMR spectrum was consistent with a 2:1 ratio of haloperidol to pamoate moieties of the isolated salt and not the purported 1:1 ratio. The PXRD diffractogram indicated the reaction product was crystalline.

Figure 69:
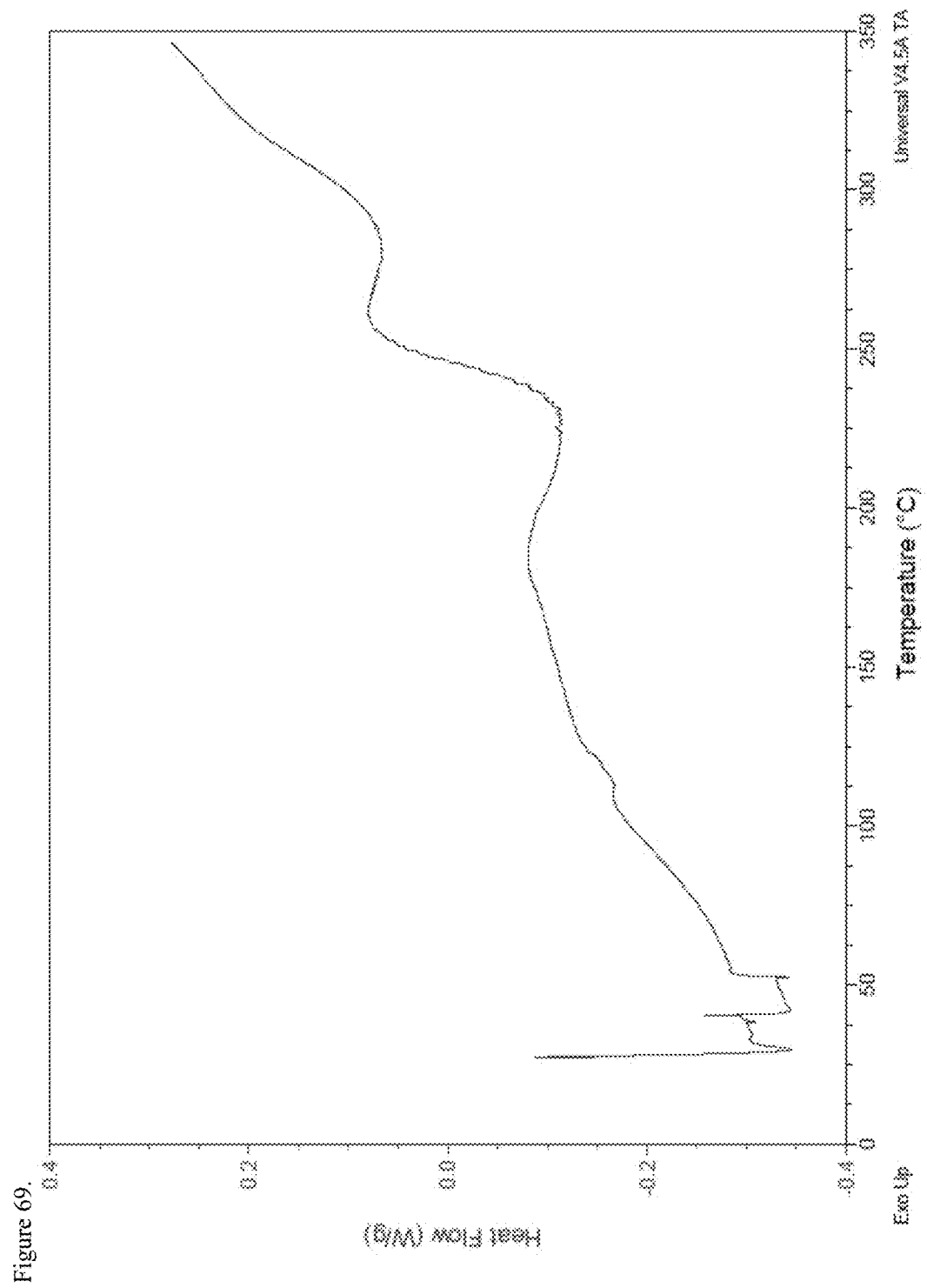
FIG. 69 is the differential scanning calorimetry (DSC) thermogram of amorphous haloperidol pamoate 2:1 for attempting to reproduce Greco Patent Example 2 overnight stirring.
Figure 70:
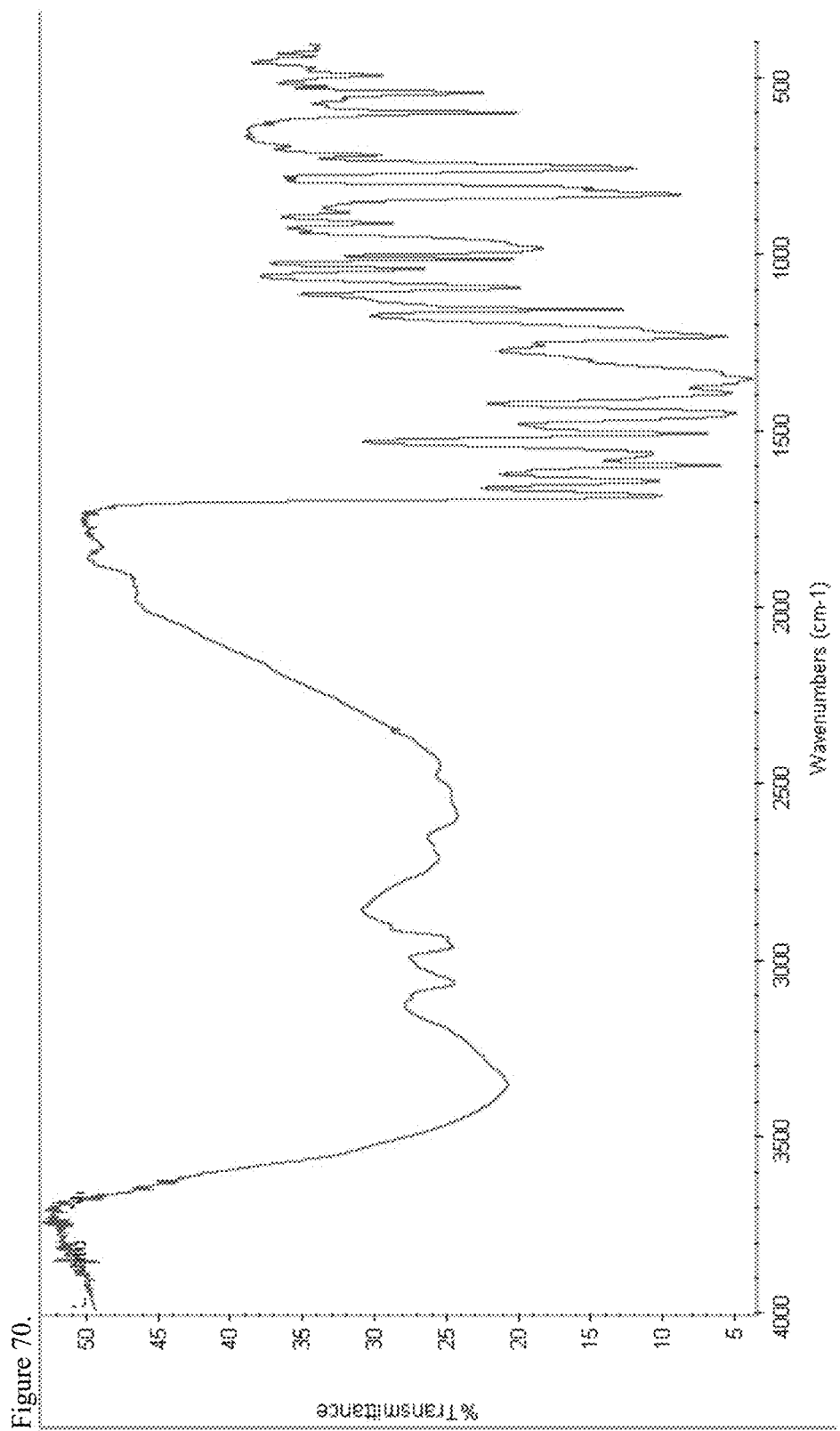
FIG. 70 is the Fourier transform infrared (FTIR) spectrum of amorphous haloperidol pamoate 2:1 for attempting to reproduce Greco Patent Example 2 overnight stirring.
Figure 71:
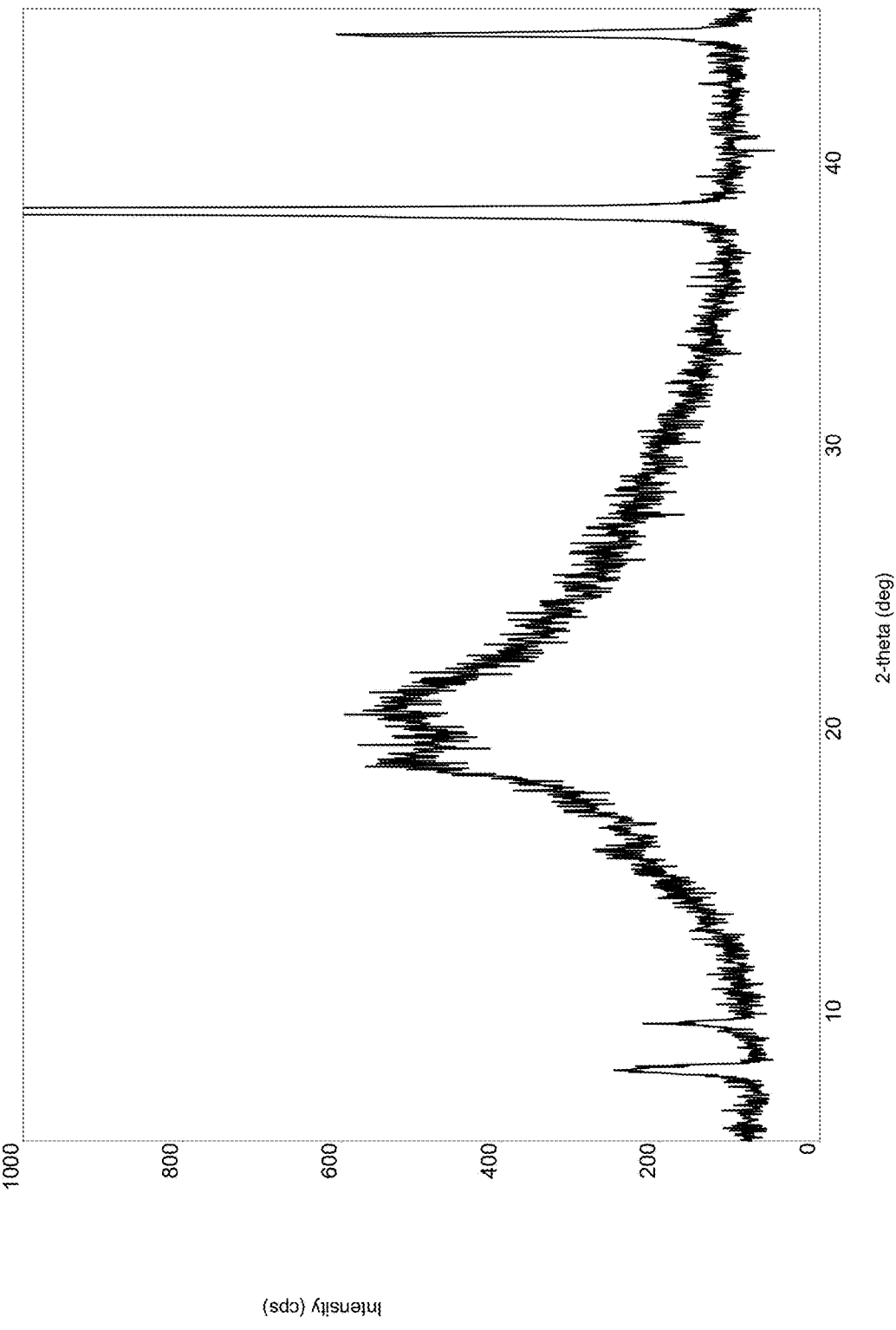
FIG. 71 is the powder X-ray diffraction (PXRD) diffractogram of amorphous haloperidol pamoate 2:1 for attempting to reproduce Greco Patent Example 2 overnight stirring.
Figure 72:
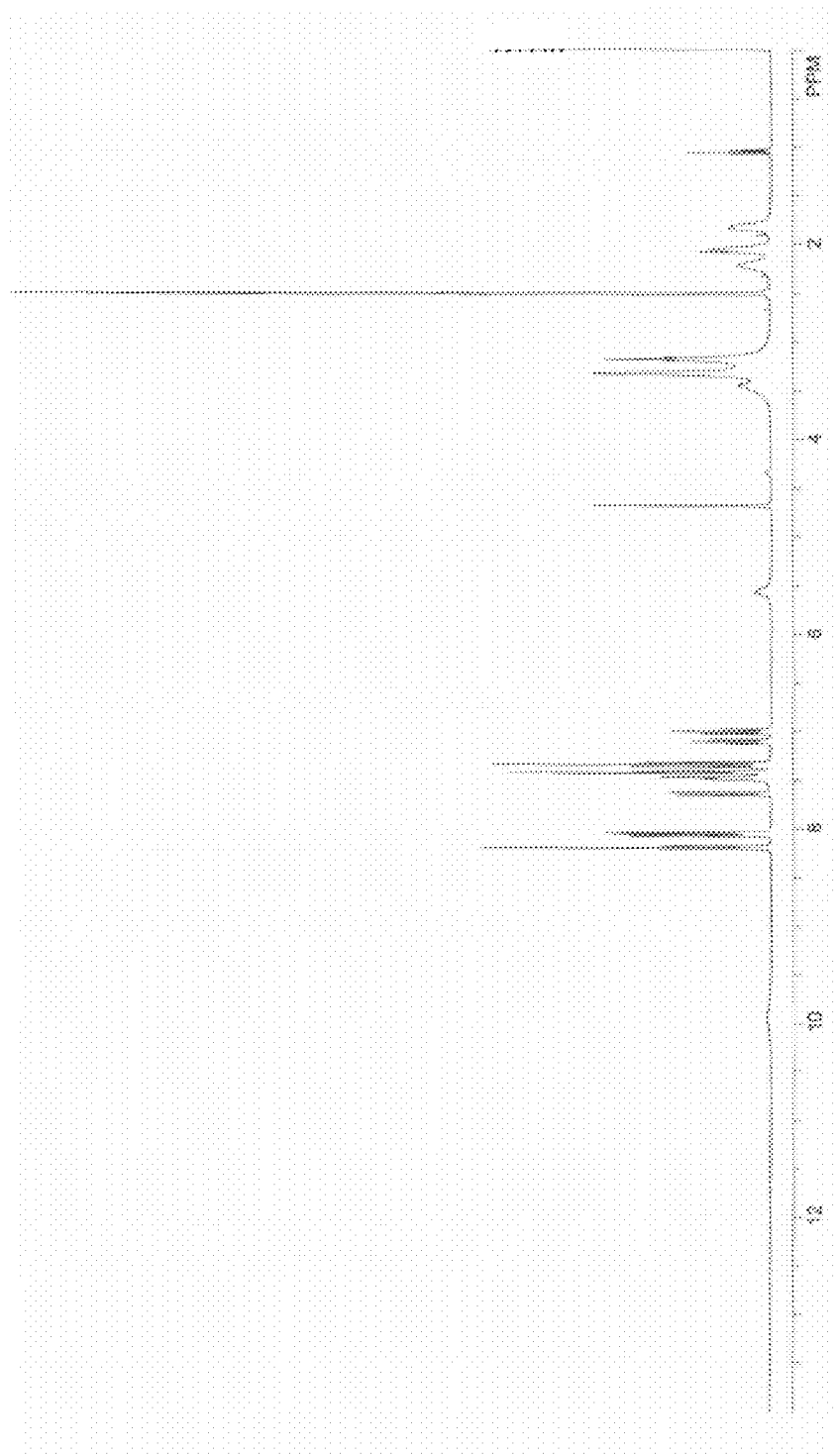
FIG. 72 is the proton nuclear magnetic resonance ($^1$H NMR) spectrum of amorphous haloperidol pamoate 2:1 for attempting to reproduce Greco Patent Example 2 overnight stirring.

Example 17. Characterization and Evaluation of Reaction Product Described in U.S. Pat. No. 6,897,111 [Greco et al.] Example 2 Alleging Preparation of 2:1 Haloperidol Pamoate Salt Experimental Test Case A To a 250 mL one-neck round-bottom flask equipped with a magnetic stir bar, thermowell, nitrogen inlet and addition funnel was charged disodium pamoate (1.50 g, 3.34 mmol) and 67 mL 75:25 ethanol/water and the contents stirred at ambient temperature under a nitrogen atmosphere. To a 50 mL round-bottom flask equipped with a magnetic stir bar was charged haloperidol (1.26 g, 3.34 mmol) and 13.4 mL 5% acetic acid/ethanol solution and the solution stirred at ambient temperature under a nitrogen atmosphere. The haloperidol acetic acid solution was added to the disodium pamoate solution over a period of about one minute via an addition funnel and the pH was recorded as about 6.1 with reaction occurring as simultaneous slurry formation ensued. The mixture was stirred overnight at ambient temperature while under a nitrogen atmosphere. The reaction mixture pH the following day had remained at about 6.1. The reaction mixture was filtered through a medium frit filter and the isolated solids washed with a small portion of ethanol and dried under vacuum to provide 0.89 g (47% yield based on 2:1 haloperidol pamoate) of a light yellow powder. The product was characterized by DSC (FIG. 69), FTIR (FIG. 70), PXRD (FIG. 71) and $^1$H-NMR (FIG. 72). The $^1$H-NMR spectrum was consistent with a 2:1 ratio of haloperidol to pamoate moieties of the formed haloperidol pamoate salt. The PXRD diffractogram indicated the reaction product was mostly amorphous.

Experimental Test Case B

Figure 73:
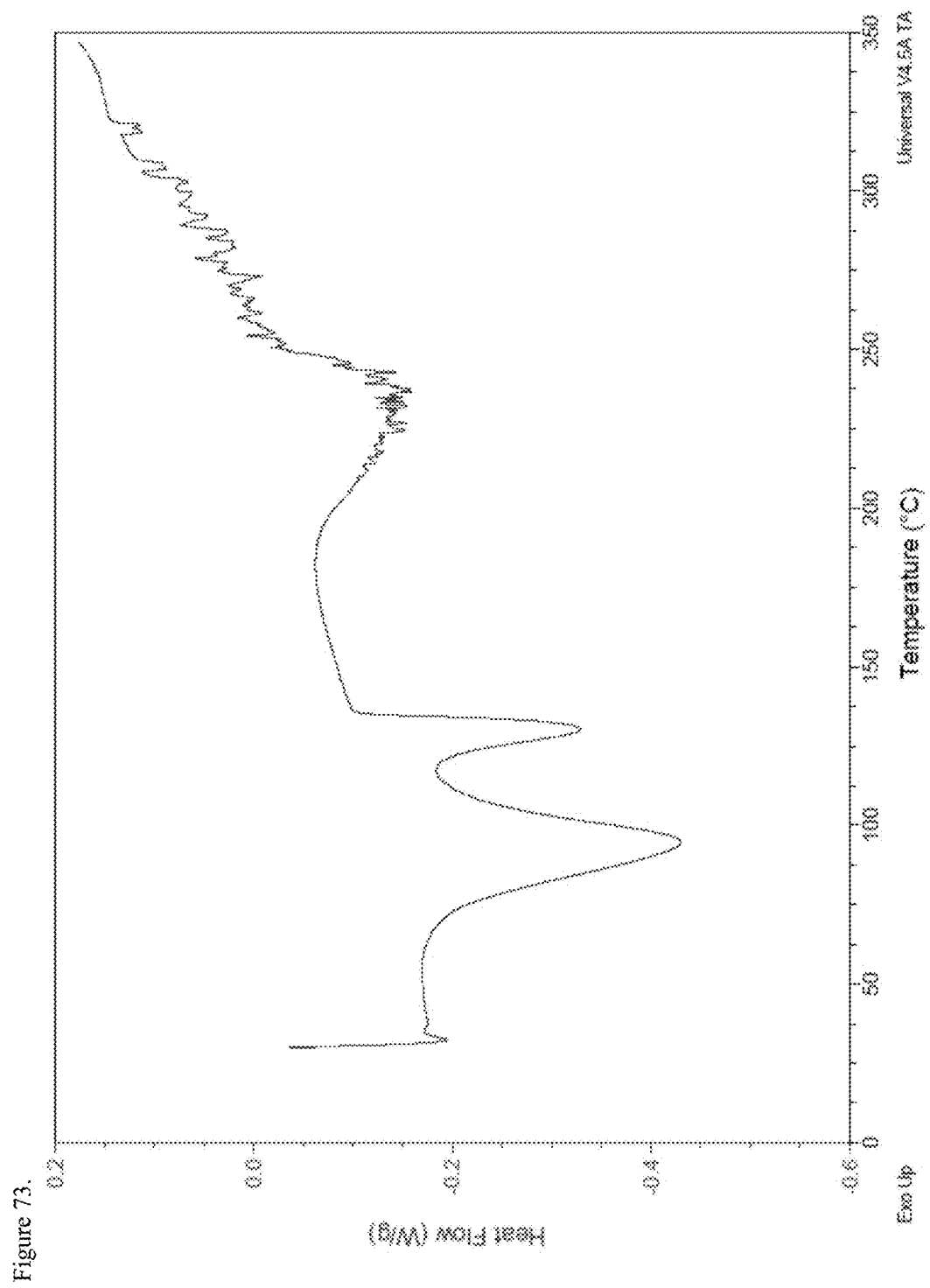
FIG. 73 is the differential scanning calorimetry (DSC) thermogram of polymorphic haloperidol pamoate 2:1 for attempting to reproduce Greco Patent Example 2 no stirring and sitting about three days.
Figure 74:
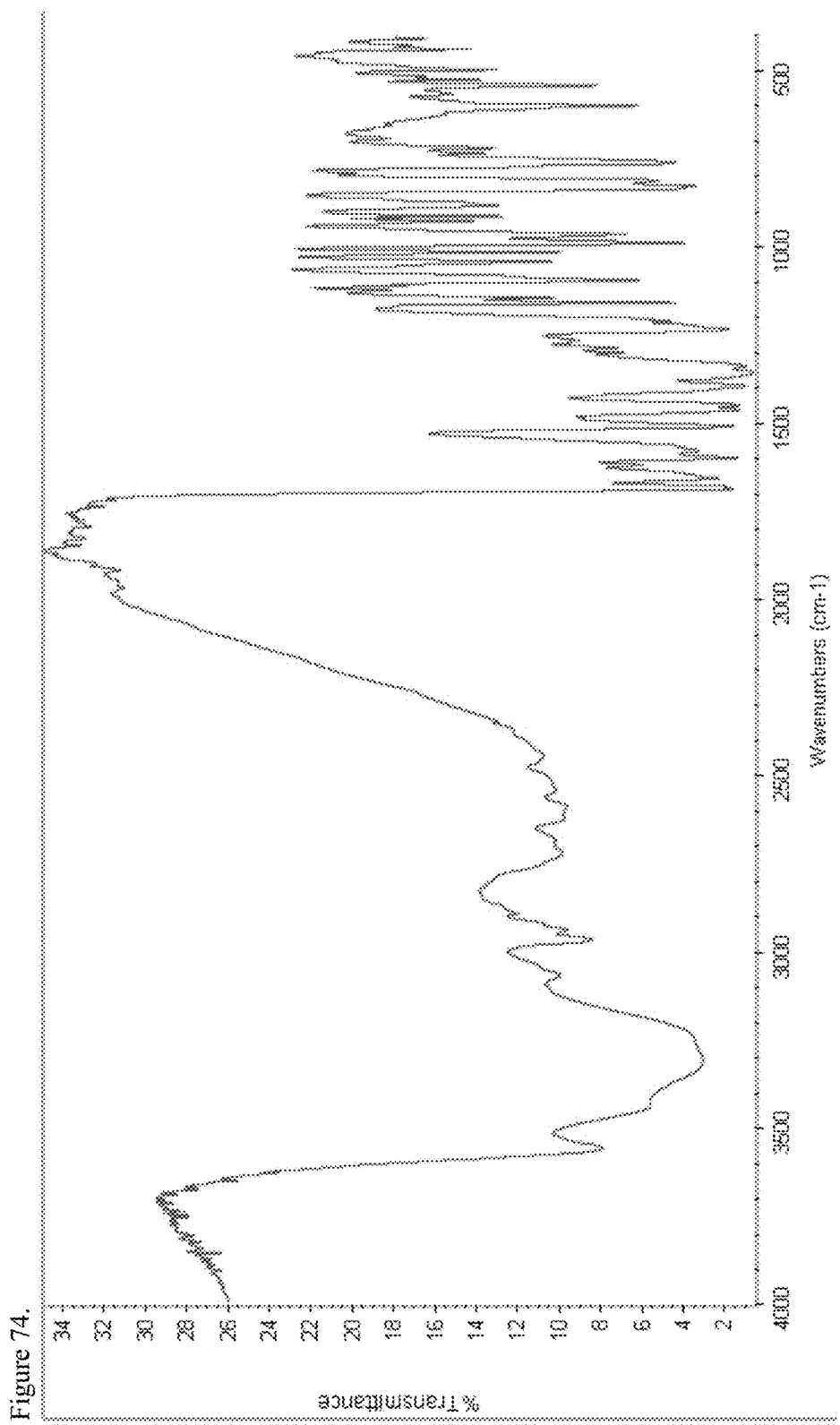
FIG. 74 is the Fourier transform infrared (FTIR) spectrum of polymorphic haloperidol pamoate 2:1 for attempting to reproduce Greco Patent Example 2 no stirring and sitting about three days.
Figure 75:
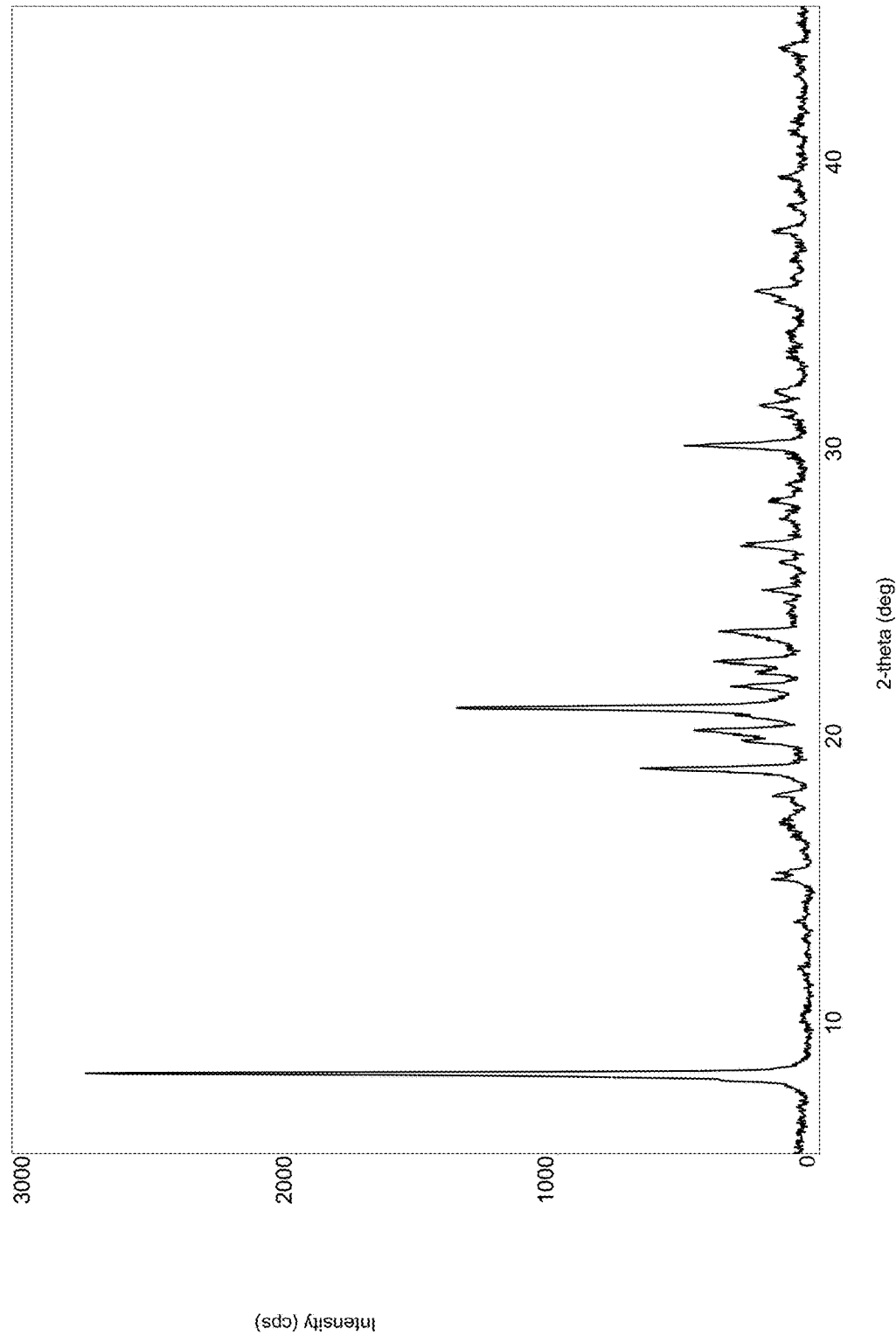
FIG. 75 is the powder X-ray diffraction (PXRD) diffractogram of polymorphic haloperidol pamoate 2:1 for attempting to reproduce Greco Patent Example 2 no stirring and sitting about three days.
Figure 76:
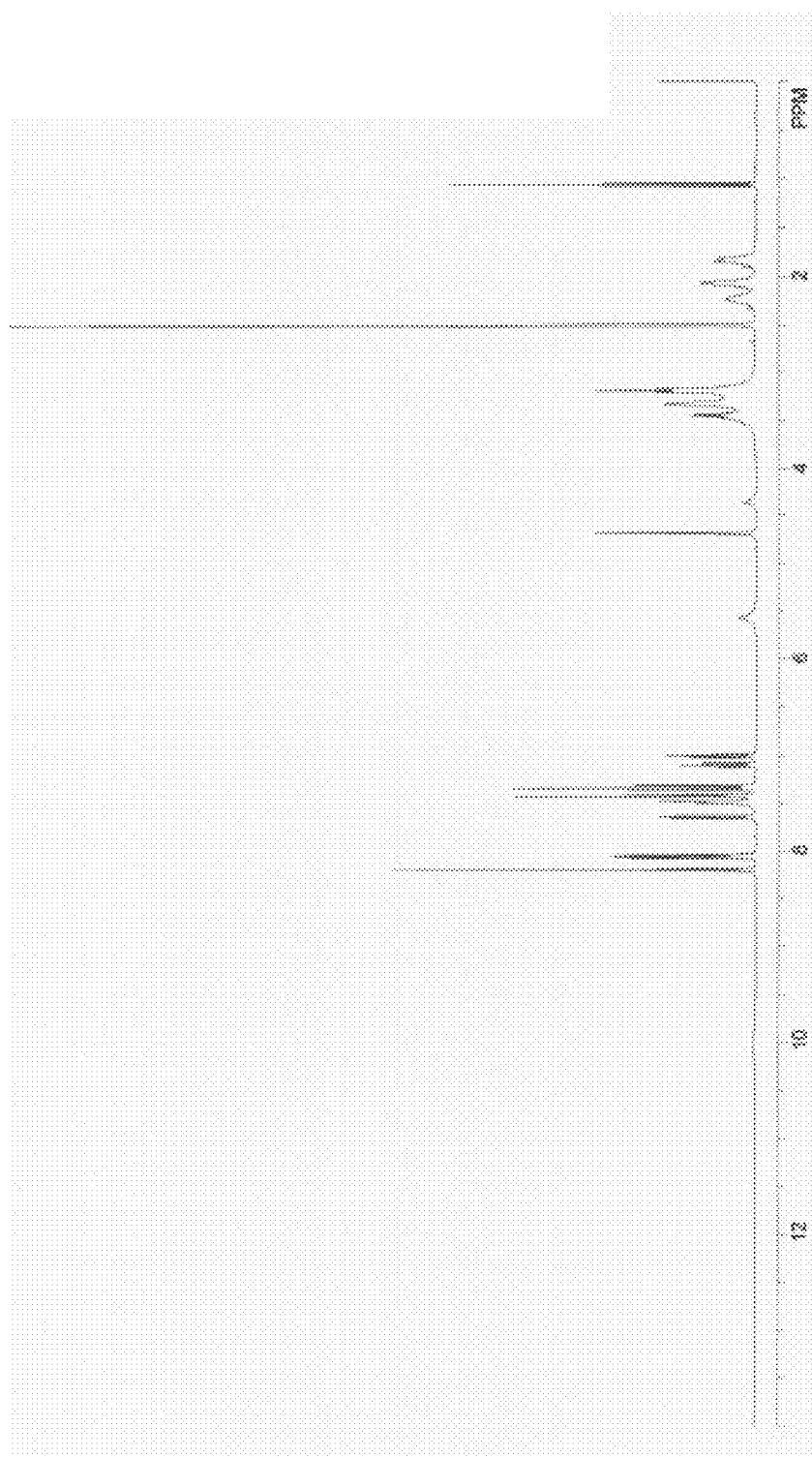
FIG. 76 is the proton nuclear magnetic resonance ($^1$H NMR) spectrum of polymorphic haloperidol pamoate 2:1 for attempting to reproduce Greco Patent Example 2 no stirring and sitting about three days.

Experimental Test Case A (op. cit.) was repeated using different experimental conditions allowed within the teaching of Greco. The changes evaluated the boundary conditions wherein stirring was omitted from the combined solutions and the reaction mixture was held at ambient temperature under a nitrogen atmosphere over a period of about three days. The formed solids were isolated in the same manner as those described above to yield 1.68 g (88% yield based on 2:1 haloperidol pamoate) of light-yellow needles. The product was characterized by DSC (FIG. 73), FTIR (FIG. 74), PXRD (FIG. 75) and $^1$H-NMR (FIG. 76). The $^1$H-NMR spectrum was consistent with a 2:1 ratio of haloperidol to pamoate moieties of the isolated salt. The PXRD diffractogram indicated the reaction product was crystalline.

Figure 113:
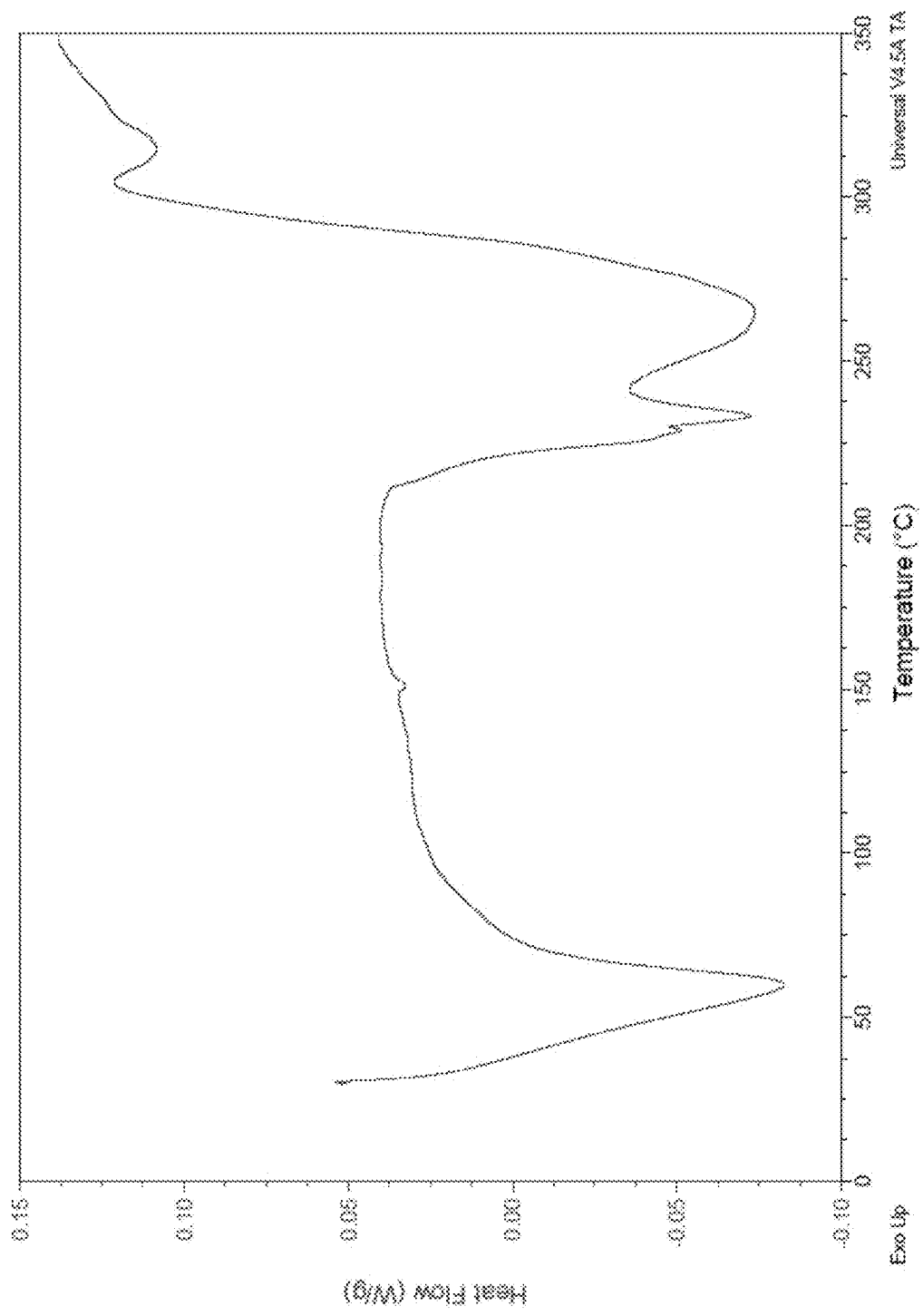
FIG. 113 is the differential scanning calorimetry (DSC) thermogram of L-thyroxine pamoate 1:1 salt as the mono-sodium carboxylate.
Figure 114:
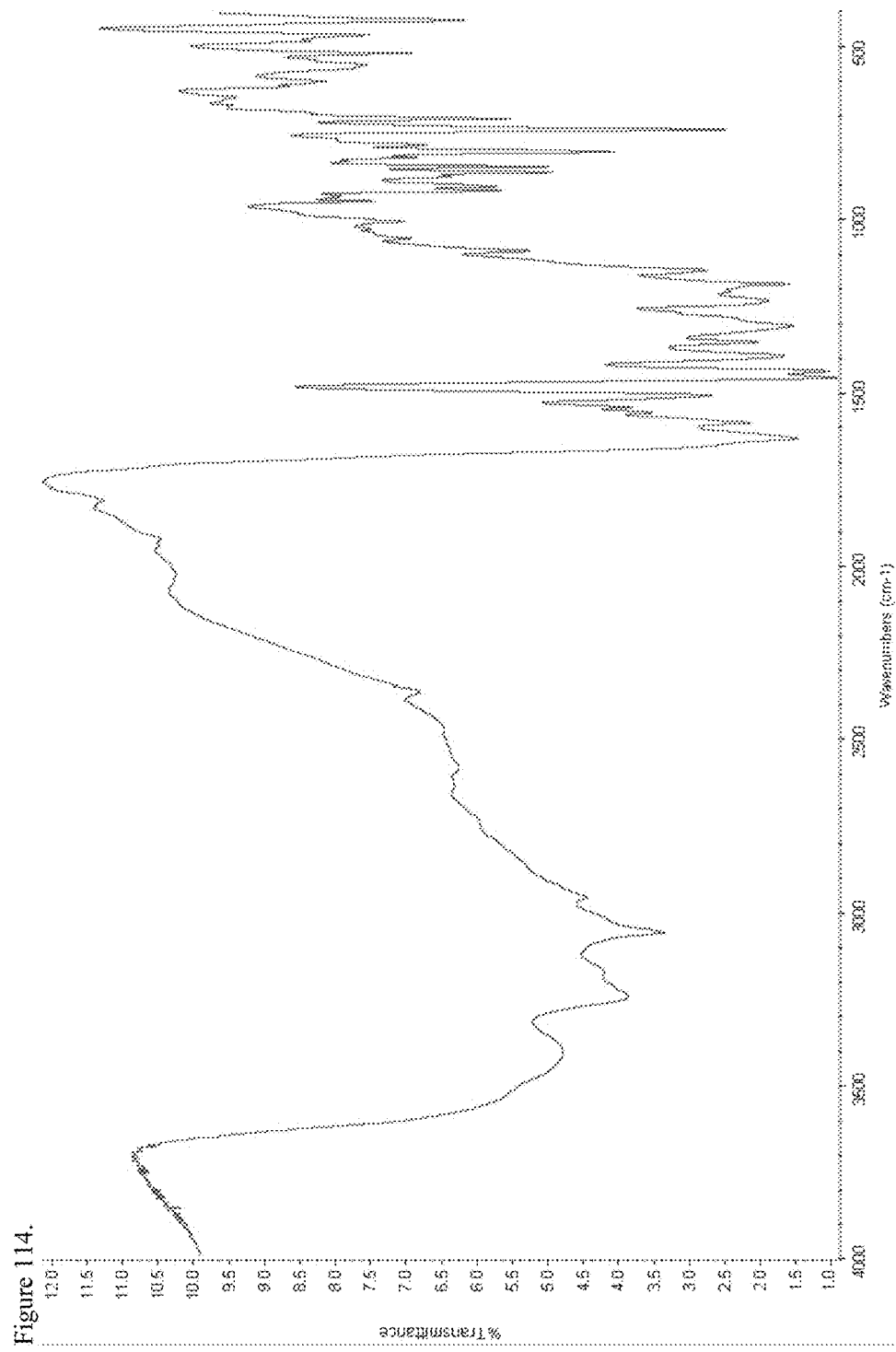
FIG. 114 is the Fourier transform infrared (FTIR) spectrum of polymorphic L-thyroxine pamoate 1:1 salt as the mono-sodium carboxylate.
Figure 115:
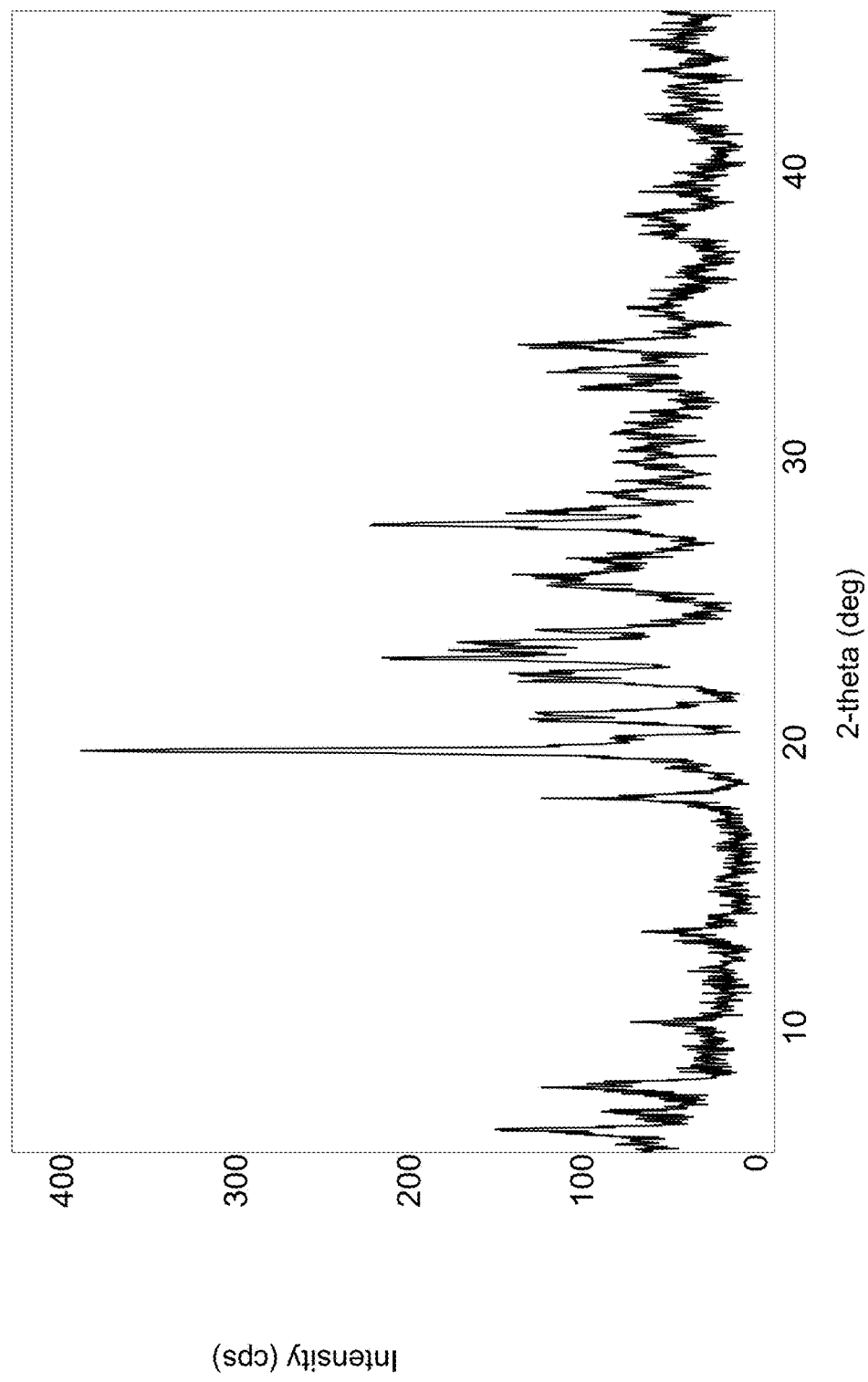
FIG. 115 is the powder X-ray diffraction (PXRD) diffractogram of polymorphic L-thyroxine pamoate 1:1 salt as the mono-sodium carboxylate.
Figure 116:
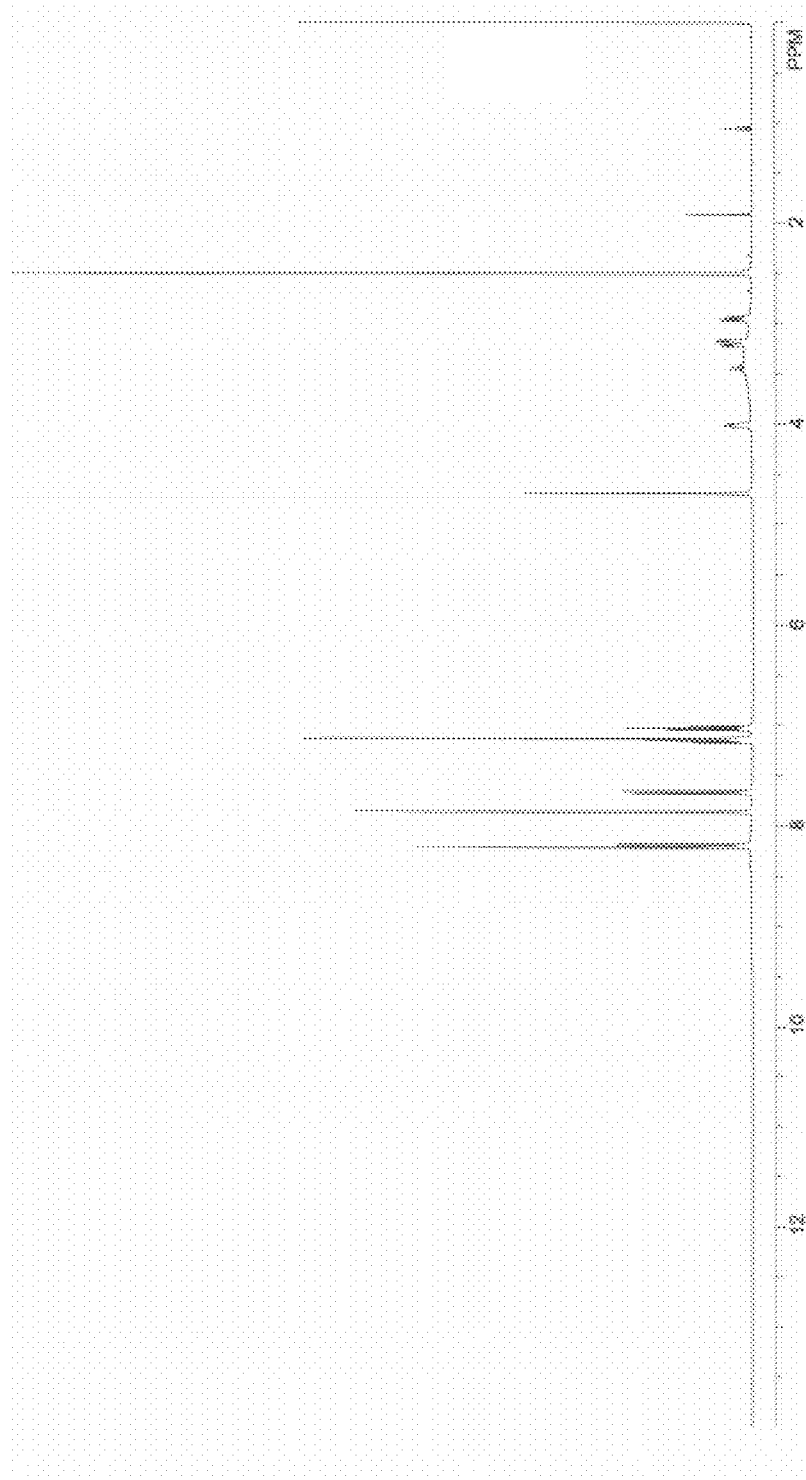
FIG. 116 is the proton nuclear magnetic resonance ($^1$H NMR) spectrum of polymorphic L-thyroxine pamoate 1:1 salt as the mono-sodium carboxylate.

Example 18. Preparation of Polymorphic L-Thyroxine pamoate, (1:1) Salt as the mono-Sodium Carboxylate To a 250 mL three-neck round-bottom flask equipped with a magnetic stir bar, thermowell, nitrogen inlet and addition funnel was charged disodium pamoate (1.5 g, 3.34 mmol) and 67 mL 75:25 ethanol/water, and the contents stirred at ambient temperature under a nitrogen atmosphere. A L-thyroxine acetic acid salt slurry was prepared according to the following procedure. To a 50 mL round-bottom flask equipped with a magnetic stir bar was charged L-thyroxine sodium salt pentahydrate (2.97 g, 3.34 mmol), 25 g ethanol and 13.4 mL 5% acetic acid/ethanol solution and the slurry stirred at room temperature under a nitrogen atmosphere. The L-thyroxine acetic acid slurry was added to the disodium pamoate solution (with an additional 44 g ethanol used for quantitative transfer of the slurry) over a period of about one minute via an addition funnel and the contents stirred for three days under a nitrogen atmosphere. The solution was concentrated under reduced pressure (28.7 inches Hg and 22° C. water bath temperature) to provide L-thyroxine pamoate, (1:1) salt. The sample was triturated in water (about 60 g), the solids isolated by filtration through a medium frit filter and dried under vacuum to provide 3.67 g (92% yield) of an off-white solid. The product was characterized by DSC (FIG. 113), FTIR (FIG. 114), PXRD (FIG. 115), $^1$H-NMR (FIG. 116), and sodium analysis. The $^1$H-NMR spectrum was consistent with a 1:1 ratio of L-thyroxine to pamoate moieties of the formed salt. The PXRD diffractogram indicated the product was crystalline. Sodium analysis indicated the carboxyl functionality of the pamoate moiety of the 1:1 L-thyroxine pamoate salt was present as the sodium carboxylate salt.

pH and Dose Dumping Dissolution Procedures

The amine containing organic acid addition salts of the present invention were tested to determine their dissolution profile as a function of pH, and as a function of ethanol concentration in acidic media (dose dumping). To perform these experiments the buffered dissolution media and acidic ethanol solutions were prepared as identified herein, "Preparation of Solutions". The test procedure was derived from the procedures cited in the United States Pharmacopeia and National Formulary (USP), numbers <1087> and <711>. The dose dumping procedure was adopted from the United States Food and Drug Administration's guidance regarding the dose dumping of oxymorphone. The sampling interval and regimen was defined and each sample analyzed by HPLC. Results from the HPLC analyses were plotted as a function of time and dissolution condition as illustrated in FIG. 77 through FIG. 112 inclusive. This procedure was used to obtain the pH and dose dumping dissolution profiles disclosed herein. Verb tense within the procedure description does not indicate a prospective condition but was used to facilitate the method's description herein. All activities within the procedure were conducted and executed for each of the compounds reported herein.

Dissolution Procedure

The analytical methodology described in detail in the Experimental section for determining the pH and dose dumping dissolution profiles relies on HPLC methodology to quantify the analytes. Typically, the principal analyte being monitored is the specific active ingredient, for example, hydrocodone. However, the separations methodology of HPLC also allows for quantification of the pamoate moiety too. Interestingly, the pamoate moiety provides an analysis and interpretation complication. Independently graphing the analytes, methadone and pamoate, to provide species-specific dissolution profiles may, at first, offer a conflicting result. Under acidic conditions, the methadone species may show significant release as a function of time whereas the corresponding pamoate dissolution profile indicates limited release. This is easily explained upon recognition that the pamoate moiety precipitates as pamoic acid and consequently its quantification within dissolution samples subjected to HPLC analysis is quite low despite correspondingly higher levels of the active ingredient. Conversely, the pamoate moiety in its ionic form, for instance at buffer pH 6.8 and greater, is reasonably soluble. Discernment is required to realize that methadone pamoate may have an inhibited dissolution profile in this pH range and indeed, monitoring the pamoate dissolution indicates only low levels of release.

The following is a general procedure for intrinsic dissolution experiments.

Preparation of Solutions

All reagents are ACS grade or equivalent. All solvents used are a minimal of HPLC grade. Water used in the preparations of all solutions is USP grade. These solution preparations have been taken directly from the USP.

Preparation of 0.1N HCl

To prepare 4 L of solution, add 33.3 mL of concentrated HCl to 977.7 mL of water, then add an additional 3000 mL of water.

Preparation of pH 4.5 Acetate Buffer

To prepare 1 L of solution add 2.99 g of sodium acetate tri-hydrate ($NaC_2H_3O_2 \cdot 3H_2O$) to a 1000 mL volumetric flask, then add 14.0 mLs of 2N acetic acid solution. Dissolve and dilute to volume with water.

Preparation of pH 6.8 Phosphate Buffer

To prepare 200 mL of solution first prepare a 0.2 M potassium phosphate solution by adding 27.22 g of monobasic potassium phosphate ($KH_2PO_4$) to a 1000 mL volumetric flask, then dissolve and dilute to volume with water. Add 50 mL of this solution to a 200 mL volumetric flask, then add 22.4 mL of 0.2M NaOH and dilute to volume with water.

Preparation of 5% Ethanol Solution for Dose Dumping Dissolution Profiles

To prepare 900 mL of media combine 45 mL of 200 proof ethanol with 855 mL of 0.1N HCl (see preparation procedure above).

Preparation of 20% Ethanol Solution for Dose Dumping Dissolution Profiles

To prepare 900 mL of media combine 180 mL of 200 proof ethanol with 720 mL of 0.1N HCl (see preparation procedure above).

Preparation of 40% Ethanol Solution for Dose Dumping Dissolution Profiles:

To prepare 900 mL of media combine 360 mL of 200 proof ethanol with 540 mL of 0.1N HCl (see preparation procedure above).

Preparation of Mobile Phase A (0.1% TFA in $H_2O$)

To prepare 1 L of mobile phase, add 1.0 mL of TFA (trifluoroacetic acid) to 1000 mL of $H_2O$. Mix well and filter this solution through a 0.45 μM nylon filter.

Preparation of Mobile Phase B (0.1% TFA in Acetonitrile)

To prepare 1 L of mobile phase, add 1.0 mL of TFA to 1000 mL acetonitrile. Mix well and filter this solution through a 0.45 μM nylon filter.

Preparation of Mobile Needle/Seal Wash Solution

To Prepare 1 L of Solution, Add 500 mL $H_2O$ to 500 mL Acetonitrile and Mix Well.

Procedures:

Intrinsic Dissolution Profiles:

Note: The following procedures were derived from USP <1087> Intrinsic Dissolution and USP <711> Dissolution methods, as well as manufacturer recommended procedures for use of the Distek Inc. intrinsic dissolution disks.

Preparation of API Pellet for Intrinsic Dissolution

The material which is to be subjected to dissolution is weighed using an analytical balance. 45.00-65.00 mgs of the analyte was weighed and transferred to a Distek Inc. fixed/static disk 316 stainless die with a 0.8 cm diameter die cavity. A hardened steel punch was then inserted into the cavity and the material was compressed at 2000 psi for 4-5 minutes using a bench top hydraulic press. A Viton gasket is then placed around the threaded shoulder of the die and a polypropylene cap is threaded onto the die. This process can be repeated to generate as many pellets as is necessary for the experiment. The die is placed in the dissolution vessel such that the 0.5 $cm^2$ pellet surface is exposed to the dissolution media.

Setup of Intrinsic Dissolution Apparatus

A Hansen Research SR8 Plus Dissolution Test Station was filled with water and set to a temperature of 37.2° C. The vessel cavities were then equipped with four 1 L flat-bottomed Distek dissolution vessels. Four vessels were then filled with 600 mL of the following media: 0.1N HCl, pH 4.5 acetate buffer, pH 6.8 phosphate buffer, and USP grade water. The solutions were allowed to warm in the water bath for approximately 1 hour, but not exceeding 3 hours, or until the temperature of the media matched that of the water bath. Paddles were then mounted to the Hansen Dissolution Test Station stirring apparatus above the four dissolution vessels such that the distance between the paddle and the die face is 1 inch. The paddle speed is then set to 50 RPM.

Intrinsic Dissolution Dose Dumping Profiles

Note: The following procedures were derived from the FDA Draft Guidance for Oxymorphone Hydrochloride (recommended in November, 2007).

Preparation of API Pellet for Intrinsic Dissolution Dose Dumping Profile

The material which is to be subjected to dissolution is weighed using an analytical balance. 45.00-65.00 mgs of the analyte was weighed and transferred to an Distek Inc. fixed/static disk 316 stainless die with a 0.8 cm diameter die cavity. A hardened steel punch was then inserted into the cavity and the material was compressed at 2000 psi for 4-5 minutes using a bench top hydraulic press. A Viton gasket is then placed around the threaded shoulder of the die and a polypropylene cap is threaded onto the die. This process can be repeated to generate as many pellets as is necessary for the experiment. The die is placed in the dissolution vessel such that the 0.5 $cm^2$ pellet surface is exposed to the dissolution media.

Setup of Intrinsic Dissolution Apparatus for Dose Dumping Profile

A Hansen Research SR8 Plus Dissolution Test Station was filled with water and set to a temperature of 37.2° C. The vessel cavities were then equipped with four 1 L flat-bottomed Distek dissolution vessels. The vessels were then filled with 900 mL of the following media: 0.1N HCl, 5% ethanol solution, 20% ethanol Solution, and 40% ethanol solution. The solutions were allowed to warm in the water bath for approximately 1 hour, but not exceeding 3 hours, or until the temperature of the media matched that of the water bath. Paddles were then mounted to the Hansen Dissolution Test Station stirring apparatus above the four dissolution vessels such that the distance between the paddle and the die face is 1 inch. The paddle speed is then set to 50 RPM.

Performing an Intrinsic Dissolution Experiment (Dose Dumping or pH Media)

The pellet prepared as described above is submerged into a vessel prepared as described above, with the pellet surface facing up (metal die up, polypropylene cap facing down). Forceps are used to aid this process so that the pellet apparatus can be gently placed into the bottom of the vessel. A timer is used to track the sampling intervals, and is started when the pellet is dropped into the solution. The lid to the dissolution apparatus is then lowered and the stirring apparatus is activated. Some planning is required in spacing out pellet drops such that each vessel can be sampled at the desired time intervals. Sampling is done by aspirating 5 mL of the solution using a Popper® Micro-Mate® Interchangeable Hypodermic Syringe equipped with a Vortex Pharma Group 10 micron cannula porous filter. This filter should be replaced after each use. Although sampling intervals can change from experiment to experiment, the following has been heavily utilized for the experiments described herein. Sampling occurring at t=1, 3, 5, 10, 15, 30, 45, 60, 90, 120 (in minutes).

HPLC Methodology

HPLC Procedure for Analyzing API Organic Acid Salts:

All samples should be analyzed with bracketing standard injections. The standard used should be from a qualified vendor with a known purity, (e.g. methadone hydrochloride, Mallinckrodt). Standard solutions should be prepared to have a concentration that is approximate to that of the samples being analyzed. All samples were run on a Waters Alliance 2695D Separations Module equipped with a Waters 2487 Dual Wavelength Detector detecting at 282 nm. The instrument was equipped with an Agilent 300 Extend-C18 5 μm 4.6×250 mm Zorbax column. The instrument was then plumbed with the proper solutions mentioned above in the section titled "Preparation of Solutions". The instrument is then set to initial column conditions (see gradient table below):

| Time (minutes) | %A | %B |
|---|---|---|
| 0.00 | 90 | 10 |
| 2.00 | 90 | 10 |
| 8.00 | 25 | 75 |
| 8.01 | 0 | 100 |
| 13.00 | 0 | 100 |
| 13.01 | 90 | 10 |
| 17.00 | 90 | 10 |

This method can be used to generate data which can be plotted to provide a dissolution profile of the analyte in question.

The invention has been described with reference to the preferred embodiments without limit thereto. One of skill in the art would realize additional embodiments and improvements which are not specifically set forth herein but which are within the scope of the invention as more specifically set forth in the claims appended hereto.

The invention claimed is:

1. A drug substance defined as a 1:1 salt of a pharmaceutically active compound and BNDO wherein said pharmaceutically active compound is selected from the group consisting of caffeine, acetorphine, acetylmethadol, allylprodine, alphacetylmethadol, bufotenine, dextromoramide, diethyltryptamine, etorphine, heroin, ibogaine, ketobemidone, lysergic acid diethylamide, mescaline, methaqualone, 3,4-methylenedioxyamphetamine, 3,4-methylenedioxymethamphetamine, N-ethyl-1-phenylcyclohexylamine, 1-(1-phenylcyclohexyl)pyrrolidine, psilocybin, psilocin, 1-{1-(2-thienyl)-cyclohexyl}-piperidine, alphaprodine, anileridine, cocaine, dextropropoxyphene, diphenoxylate, ethylmorphine, glutethimide, hydrocodone, hydromorphone, levorphanol, meperidine, morphine, opium, oxycodone, oxymorphone, thebaine, amphetamine, methamphetamine, methylphenidate, phencyclidine, codeine, benzphetamine, ketamine, alprazolam, chlorodiazepoxide, clorazepate, diethylpropion, fenfluramine, flurazepam, halazepam, lorazepam, mazindol, mebutamate, midazolam, oxazepam, pemoline, pentazocine, phentermine, prazepam, quazepam, temazepam, triazolam, zolpidem, buprenorphine, apomorphine, dihydrocodeine, codeinone, thebaine, morphothebaine, thebenine, metathebainone, phenyldihydrothebaine, thebainhydroquinone, flavothebanone, alpha-codeimethine, 14-hydroxycodeinone, sinomenine, dihydrosinomenine, hasubanonine, nalbuphine, nalmefene, naloxone, noscapine, oripavine, haloperidol, methadone, L-thyroxine and imipramine.

2. The drug substance of claim 1 selected from the group consisting of:
    amorphous hydrocodone pamoate 1:1 salt measured as a 1:1 mixture of mono-sodium salt and free carboxylic acid with a PXRD of FIG. 3;
    polymorphic hydrocodone pamoate 1:1 salt measured as the free carboxylic acid with a PXRD of FIG. 7;
    amorphous oxycodone pamoate 1:1 salt measured as a 1:1 mixture of mono-sodium salt and free carboxylic acid with a PXRD of FIG. 11;
    polymorphic haloperidol pamoate 1:1 salt measured as the free carboxylic acid with a PXRD of FIG. 15;
    polymorphic haloperidol pamoate 1:1 salt measured as the free carboxylic acid with a PXRD of FIG. 19;
    polymorphic haloperidol pamoate 1:1 salt measured as a 3:1 mixture of mono-sodium salt and free carboxylic acid with a PXRD of FIG. 23;
    amorphous morphine pamoate 1:1 salt measured as the 1:1 mixture of mono-sodium salt and free carboxylic acid with a PXRD of FIG. 27;
    amorphous oxymorphone pamoate 1:1 salt measured as the 1:1 mixture of mono-sodium salt and free carboxylic acid with a PXRD of FIG. 31;
    amorphous codeine pamoate 1:1 salt measured as a 1:1 mixture of mono-sodium salt and free carboxylic acid with a PXRD of FIG. 35;
    amorphous d-methylphenidate pamoate 1:1 salt measured as a 1:1 mixture of mono-sodium salt and the free carboxylic acid with a PXRD of FIG. 39;
    polymorphic racemic methylphenidate pamoate 1:1 measured as a 1:1 mixture of the mono-sodium salt and free carboxylic acid with a PXRD of FIG. 43;
    amorphous imipramine pamoate 1:1 salt measured as a 1:1 mixture of mono-sodium salt and free carboxylic acid with a PXRD of FIG. 55;
    amorphous methadone pamoate 1:1 salt measured as a 1:1 mixture of mono-sodium salt and free carboxylic acid with a PXRD of FIG. 59
and
    polymorphic L-thyroxine pamoate 1:1 salt measured as the mono-sodium carboxylate with a PXRD of FIG. 115.

3. The drug substance of claim 2 wherein said pharmaceutically active compound is selected from the group consisting of haloperidol, hydrocodone, oxycodone, codeine, oxymorphone, morphine, methylphenidate, imipramine, amphetamine, L-thyroxine and methadone.

4. The drug substance of claim 3 wherein said pharmaceutically active compound is selected from the group consisting of d-methylphenidate, racemic methylphenidate and dextro-amphetamine.

5. The drug substance of claim 2 wherein said drug substance is selected from the group consisting of hydrocodone pamoate 1:1; oxycodone pamoate 1:1; haloperidol pamoate 1:1; morphine pamoate 1:1; oxymorphone pamoate 1:1; codeine pamoate 1:1; d-methylphenidate pamoate 1:1; racemic methylphenidate pamoate 1:1; naltrexone pamoate 1:1; imipramine pamoate 1:1; methadone pamoate 1:1 and L-thyroxine pamoate 1:1.

6. The drug substance of claim 5 wherein said hydrocodone pamoate 1:1 is selected from amorphous hydrocodone pamoate 1:1 and polymorphic hydrocodone pamoate 1:1.

7. The drug substance of claim 6 wherein said amorphous hydrocodone pamoate 1:1 salt measured as a 1:1 mixture of mono-sodium salt and free carboxylic acid with a PXRD of FIG. 3 has a PXRD of FIG. 3.

8. The drug substance of claim 6 wherein said polymorphic hydrocodone pamoate 1:1 salt measured as a 1:1 mixture of mono-sodium salt and the free carboxylic acid has a PXRD of FIG. 7.

9. The drug substance of claim 5 wherein said oxycodone pamoate 1:1 is amorphous measured as the free carboxylic acid has a PXRD of FIG. 11.

10. The drug substance of claim 5 wherein said haloperidol pamoate 1:1 is polymorphic haloperidol pamoate 1:1.

11. The drug substance of claim 10 wherein said polymorphic haloperidol pamoate 1:1 as the free carboxylic acid has a PXRD selected from the group consisting of FIG. 15 and FIG. 19.

12. The drug substance of claim 10 wherein said polymorphic haloperidol pamoate 1:1 salt measured as a 3:1 mixture of mono-sodium slat and free carboxylic acid has a PXRD of FIG. 23.

13. The drug substance of claim 5 wherein said morphine pamoate 1:1 is amorphous morphine pamoate 1:1 measured as the 1:1 mixture of mono-sodium salt and free carboxylic acid has a PXRD of FIG. 27.

14. The drug substance of claim 5 wherein said oxymorphone pamoate 1:1 is amorphous oxymorphone pamoate 1:1 salt measured as the 1:1 mixture of mono-sodium salt and free carboxylic acid has a PXRD of FIG. 31.

15. The drug substance of claim 5 wherein said codeine pamoate 1:1 is amorphous codeine pamoate 1:1 salt measured as the 1:1 mixture of mono-sodium salt and free carboxylic acid has a PXRD of FIG. 35.

16. The drug substance of claim 5 wherein said d-methylphenidate pamoate 1:1 is amorphous d-methylphenidate pamoate 1:1 salt measured as the 1:1 mixture of mono-sodium salt and the free carboxylic acid has a PXRD of FIG. 39.

17. The drug substance of claim 5 wherein said racemic methylphenidate pamoate 1:1 is polymorphic racemic methylphenidate pamoate 1:1 salt measured as a 1:1 mixture of the mono-sodium salt and free carboxylic acid has a PXRD of FIG. 43.

18. The drug substance of claim 17 wherein said polymorphic racemic methylphenidate pamoate 1:1 measured as a 1:1 ratio of sodium salt and free carboxylic acid has a PXRD of FIG. 43.

19. The drug substance of claim 5 wherein said imipramine pamoate 1:1 is amorphous imipramine pamoate 1:1 salt measured as 1:1 mixture of mono-sodium salt and free carboxylic acid has a PXRD of FIG. 55.

20. The drug substance of claim 5 wherein said methadone pamoate 1:1 is amorphous methadone pamoate 1:1 salt measured as a 1:1 mixture of mono-sodium salt and free carboxylic acid has a PXRD of FIG. 59.

21. The drug substance of claim 5 wherein said L-thyroxine pamoate 1:1 is polymorphic L-thyroxine pamoate 1:1 salt measure as the mono-sodium carboxylate has a PXRD of FIG. 115.

22. The drug substance of claim 2 wherein said BNDO is defined by Structure A or B:

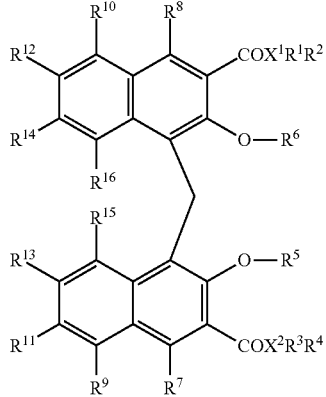

Structure A

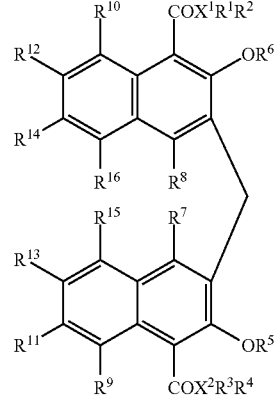

Structure B wherein:
$X^1$ and $X^2$ are selected from nitrogen, oxygen and sulfur;
$R^1$-$R^4$ are independently selected from H, an alkali metal alkyl or substituted alkyl of 1-6 carbons, aryl or substituted aryl of 6-12 carbons, alkylacyl, substituted alkylacyl, arylacyl or substituted arylacyl analogues sufficient to satisfy the valence of X, such as to provide a mixed anhydride or carbamate with the proviso that in the drug substance one of $R^1$-$R^4$ will be a pharmaceutically active compound;
$R^5$ and $R^6$ independently represent H, alkyl or substituted alkyl or 1-6 carbons, alkylacyl or substituted alkylacyl, arylacyl or substituted arylacyl;
$R^7$-$R^{16}$ are independently selected from H, alkyl or substituted alkyl of 1-6 carbons, adjacent groups may be taken together to form a cyclic alkyl or cyclic aryl moiety, either of which may be substituted; and
when X=O, one of $R^1$ or $R^2$ or one of $R^3$ or $R^4$ is not present and the other may represent H, an alkali metal cation or ammonium.

23. The drug substance of claim 22 wherein said $X^1$ or $X^2$ is oxygen.

24. The drug substance of claim 23 wherein one of said $R^1$ or $R^2$ or one of $R^3$ or $R^4$ is not present and the other represents H, an alkali metal cation or ammonium.

25. The drug substance of claim 22 wherein said $R^5$ and $R^6$ independently represent H, alkyl or substituted alkyl or 1-6 carbons.

26. The drug substance of claim 22 wherein said $R^7$-$R^{16}$ are independently selected from H, alkyl or substituted alkyl of 1-6 carbons.

27. The drug substance of claim 2 wherein said drug substance comprises a counterion.

28. The drug substance of claim 27 wherein said counterion is an alkali metal.

29. The drug substance of claim 28 wherein said counterion is sodium.

30. A drug product comprising a matrix and the drug substance of claim 2.

\* \* \* \* \*